US010973810B2

(12) United States Patent
Vincent et al.

(10) Patent No.: US 10,973,810 B2
(45) Date of Patent: Apr. 13, 2021

(54) METHODS FOR THE TREATMENT OF NEUROLOGICAL DISORDERS

(71) Applicant: Yumanity Therapeutics, Inc., Boston, MA (US)

(72) Inventors: Benjamin Vincent, Cambridge, MA (US); Daniel Tardiff, Arlington, MA (US); Jeff Piotrowski, Somerville, MA (US); Eric Solis, Milford, MA (US); Robert Scannevin, Hopkinton, MA (US); Chee-Yeun Chung, Brookline, MA (US); Rebecca Aron, Cambridge, MA (US); Bertrand Le Bourdonnec, Northborough, MA (US); Matthew Lucas, Lexington, MA (US); Kenneth Rhodes, Belmont, MA (US)

(73) Assignee: Yumanity Therapeutics, Inc., Boston, MA (US)

( * ) Notice: Subject to any disclaimer, the term of this patent is extended or adjusted under 35 U.S.C. 154(b) by 0 days.

(21) Appl. No.: 15/863,773

(22) Filed: Jan. 5, 2018

(65) Prior Publication Data

US 2018/0193325 A1    Jul. 12, 2018

Related U.S. Application Data

(60) Provisional application No. 62/443,066, filed on Jan. 6, 2017.

(51) Int. Cl.
| | |
|---|---|
| *A61K 31/454* | (2006.01) |
| *A61P 25/28* | (2006.01) |
| *G01N 33/68* | (2006.01) |
| *A61K 45/06* | (2006.01) |
| *A61K 31/4545* | (2006.01) |
| *A61P 25/14* | (2006.01) |
| *A61P 25/16* | (2006.01) |

(52) U.S. Cl.
CPC ........ *A61K 31/454* (2013.01); *A61K 31/4545* (2013.01); *A61K 45/06* (2013.01); *A61P 25/14* (2018.01); *A61P 25/16* (2018.01); *A61P 25/28* (2018.01); *G01N 33/6896* (2013.01); *G01N 2333/46* (2013.01); *G01N 2333/775* (2013.01); *G01N 2800/28* (2013.01); *G01N 2800/285* (2013.01); *G01N 2800/2814* (2013.01); *G01N 2800/2821* (2013.01); *G01N 2800/2828* (2013.01); *G01N 2800/2835* (2013.01)

(58) Field of Classification Search
CPC .................................................. A61K 31/454
USPC ........................................................... 514/1
See application file for complete search history.

(56) References Cited

U.S. PATENT DOCUMENTS

| | | |
|---|---|---|
| 7,790,408 B1 | 9/2010 | Ntambi et al. |
| 8,063,224 B2 | 11/2011 | Lachance et al. |
| 8,129,376 B2 | 3/2012 | Sundaresan et al. |
| 8,673,917 B2 | 3/2014 | Zoller et al. |
| 9,290,465 B2 | 3/2016 | Derryberry et al. |
| 9,296,711 B2 | 3/2016 | Erickson et al. |
| 2005/0119242 A1 | 6/2005 | DeLuca et al. |
| 2005/0256068 A1 | 11/2005 | McSwiggen et al. |
| 2007/0087363 A1 | 4/2007 | Bartel et al. |
| 2008/0132542 A1 | 6/2008 | Lachance et al. |
| 2008/0249100 A1 | 10/2008 | Chisholm et al. |
| 2008/0255130 A1 | 10/2008 | Koltun et al. |
| 2008/0255161 A1 | 10/2008 | Koltun et al. |
| 2009/0118296 A1* | 5/2009 | Black .................. C07D 401/04 514/252.02 |
| 2009/0149466 A1 | 6/2009 | Gillespie et al. |
| 2009/0170822 A1 | 7/2009 | DeLuca et al. |
| 2009/0253693 A1 | 10/2009 | Koltun et al. |
| 2009/0253738 A1 | 10/2009 | Koltun et al. |
| 2010/0022486 A1 | 1/2010 | Bouillot et al. |
| 2010/0160323 A1 | 6/2010 | Bischoff et al. |
| 2012/0252850 A1 | 10/2012 | Milne et al. |

FOREIGN PATENT DOCUMENTS

| | | |
|---|---|---|
| JP | 2005-213233 A | 8/2005 |
| JP | 2009-19013 A | 1/2009 |
| JP | 2010-43052 A | 2/2010 |
| KR | 10-2015-0014719 A | 2/2015 |
| KR | 10-2015-0015305 A | 2/2015 |
| WO | WO-99/63979 A2 | 12/1999 |
| WO | WO-03/070885 A2 | 8/2003 |
| WO | WO-2005/011654 A2 | 2/2005 |
| WO | WO-2005/011655 A2 | 2/2005 |
| WO | WO-2005/011656 A2 | 2/2005 |
| WO | WO-2005/011657 A2 | 2/2005 |
| WO | WO-2005/014607 A2 | 2/2005 |
| WO | WO-2006/014168 A1 | 2/2006 |
| WO | WO-2006/015621 A1 | 2/2006 |
| WO | WO-2006/034279 A1 | 3/2006 |
| WO | WO-2006/034312 A1 | 3/2006 |

(Continued)

OTHER PUBLICATIONS

Ponomarenko et al., Int. J. of Analytical Chem. (2016) V2016 p. 1-6. (Year: 2016).*

(Continued)

*Primary Examiner* — Yong L Chu

(74) *Attorney, Agent, or Firm* — Clark & Elbing LLP

(57) ABSTRACT

The present disclosure provides compounds and methods useful in the treatment of neurological disorders. The compounds of the invention, alone or in combination with other pharmaceutically active agents, can be used for treating or preventing neurological disorders.

10 Claims, 20 Drawing Sheets

Specification includes a Sequence Listing.

(56) References Cited

FOREIGN PATENT DOCUMENTS

| | | |
|---|---|---|
| WO | WO-2006/034315 A2 | 3/2006 |
| WO | WO-2006/034338 A1 | 3/2006 |
| WO | WO-2006/034341 A2 | 3/2006 |
| WO | WO-2006/034440 A2 | 3/2006 |
| WO | WO-2006/034441 A1 | 3/2006 |
| WO | WO-2006/034446 A2 | 3/2006 |
| WO | WO-2006/057902 A2 | 6/2006 |
| WO | WO-2006/086445 A2 | 8/2006 |
| WO | WO-2006/086447 A2 | 8/2006 |
| WO | WO-2006/125179 A1 | 11/2006 |
| WO | WO-2006/125181 A2 | 11/2006 |
| WO | WO-2006/125194 A2 | 11/2006 |
| WO | WO-2006/130986 A1 | 12/2006 |
| WO | WO-2007/009236 A1 | 1/2007 |
| WO | WO-2007/044085 A2 | 4/2007 |
| WO | WO-2007/046868 A2 | 4/2007 |
| WO | WO-2007/056846 A1 | 5/2007 |
| WO | WO-2007/130075 A1 | 11/2007 |
| WO | WO-2007/134457 A1 | 11/2007 |
| WO | WO-2007/136746 A2 | 11/2007 |
| WO | WO-2007/143597 A2 | 12/2007 |
| WO | WO-2007/143823 A1 | 12/2007 |
| WO | WO-2007/143824 A1 | 12/2007 |
| WO | WO-2008/003753 A1 | 1/2008 |
| WO | WO-2008/017161 A1 | 2/2008 |
| WO | WO-2008/024390 A2 | 2/2008 |
| WO | WO-2008/029266 A1 | 3/2008 |
| WO | WO-2008/036715 A1 | 3/2008 |
| WO | WO-2008/043087 A2 | 4/2008 |
| WO | WO-2008/044767 A1 | 4/2008 |
| WO | WO-2008/046226 A1 | 4/2008 |
| WO | WO-2008/056687 A1 | 5/2008 |
| WO | WO-2008/062276 A2 | 5/2008 |
| WO | WO-2008/074824 A2 | 6/2008 |
| WO | WO-2008/074832 A2 | 6/2008 |
| WO | WO-2008/074833 A2 | 6/2008 |
| WO | WO-2008/074834 A2 | 6/2008 |
| WO | WO-2008/074835 A1 | 6/2008 |
| WO | WO-2008/089580 A1 | 7/2008 |
| WO | WO-2008/096746 A1 | 8/2008 |
| WO | WO-2008/104524 A1 | 9/2008 |
| WO | WO-2008/116898 A1 | 10/2008 |
| WO | WO-2008/120744 A1 | 10/2008 |
| WO | WO-2008/120759 A1 | 10/2008 |
| WO | WO-2008/123469 A1 | 10/2008 |
| WO | WO-2008/127349 A2 | 10/2008 |
| WO | WO-2008/128335 A1 | 10/2008 |
| WO | WO-2008/139845 A1 | 11/2008 |
| WO | WO-2008/141455 A1 | 11/2008 |
| WO | WO-2008/157844 A1 | 12/2008 |
| WO | WO-2009/010560 A1 | 1/2009 |
| WO | WO-2009/012573 A1 | 1/2009 |
| WO | WO-2009/016216 A1 | 2/2009 |
| WO | WO-2009/019566 A1 | 2/2009 |
| WO | WO-2009/037542 A2 | 3/2009 |
| WO | WO-2009/056556 A1 | 5/2009 |
| WO | WO-2009/060053 A1 | 5/2009 |
| WO | WO-2009/060054 A1 | 5/2009 |
| WO | WO-2009/070533 A1 | 6/2009 |
| WO | WO-2009/073973 A1 | 6/2009 |
| WO | WO-2009/103739 A1 | 8/2009 |
| WO | WO-2009/106991 A2 | 9/2009 |
| WO | WO-2009/117659 A1 | 9/2009 |
| WO | WO-2009/124259 A1 | 10/2009 |
| WO | WO-2009/129625 A1 | 10/2009 |
| WO | WO-2009/150196 A1 | 12/2009 |
| WO | WO-2009/156484 A2 | 12/2009 |
| WO | WO-2010/006962 A1 | 1/2010 |
| WO | WO-2010/007482 A2 | 1/2010 |
| WO | WO-2010/025553 A1 | 3/2010 |
| WO | WO-2010/035052 A1 | 4/2010 |
| WO | WO-2010/037225 A1 | 4/2010 |
| WO | WO-2010/043052 A1 | 4/2010 |
| WO | WO-2010/045371 A1 | 4/2010 |
| WO | WO-2010/045374 A1 | 4/2010 |
| WO | WO-2010/056230 A1 | 5/2010 |
| WO | WO-2010/094120 A1 | 8/2010 |
| WO | WO-2010/094126 A1 | 8/2010 |
| WO | WO-2010/108268 A1 | 9/2010 |
| WO | WO-2010/112520 A1 | 10/2010 |
| WO | WO-2011/011506 A1 | 1/2011 |
| WO | WO-2011/011508 A1 | 1/2011 |
| WO | WO-2011/011872 A1 | 2/2011 |
| WO | WO-2011/015629 A1 | 2/2011 |
| WO | WO-2011/030312 A1 | 3/2011 |
| WO | WO-2011/039358 A1 | 4/2011 |
| WO | WO-2011/047481 A1 | 4/2011 |
| WO | WO-2011/131593 A1 | 10/2011 |
| WO | WO-2012/046681 A1 | 4/2012 |
| WO | WO-2013/085954 A1 | 6/2013 |
| WO | WO-2013/085957 A1 | 6/2013 |
| WO | WO-2013/134546 A1 | 9/2013 |
| WO | WO-2013/160811 A1 | 10/2013 |
| WO | WO-2014/116386 A1 | 7/2014 |
| WO | WO-2015/132610 A1 | 9/2015 |
| WO | WO-2015/137385 A1 | 9/2015 |
| WO | WO-2016/040794 A1 | 3/2016 |
| WO | WO-2019/084157 A1 | 5/2019 |

OTHER PUBLICATIONS

Astarte et al. PLos One, (2011), 6(10), p. 1-9. (Year: 2011).*
Larson et al. Journal of Neuroscience (2012), 32(30), p. 10253-10266. (Year: 2012).*
Simon et al. Molecular & Cellular Proteomics (2012), 11(11), p. 1389-1403. (Year: 2012).*
Wikipedia "list of neurological conditions and disorders" (2018).*
Hamilton et al. Cell Stem Cell, (2015), v.17, p. 397-411.*
Zhang et al., Current Neuropharmacology, (2016), V14, p. 356-363.*
Pankratz et al. Movement Disorder, (2006), 21(1), p. 45-49.*
Friedrich et al., "Mechanism of amyloid plaque formation suggests an intracellular basis of Abeta pathogenicity," Proc Natl Acad Sci U.S.A. 107(5):1942-7 (2010).
International Search Report and Written Opinion for International Application No. PCT/US2018/012697, dated May 7, 2018 (16 pages).
Larson et al., "Soluble α-synuclein is a novel modulator of Alzheimer's disease pathophysiology," Available in PMC Jan. 25, 2013, published in final edited form as: J Neurosci. 32(30):10253-66 (2012) (28 pages).
Simon et al., "Total ApoE and ApoE4 isoform assays in an Alzheimer's disease case-control study by targeted mass spectrometry (n=669): a pilot assay for methionine-containing proteotypic peptides," Mol Cell Proteomics. 11(11):1389-403 (2012).
Bähler et al., "Heterologous modules for efficient and versatile PCR-based gene targeting in Schizosaccharomyces pombe," Yeast. 14(10):943-51 (1998).
Berge et al., "Pharmaceutical salts," J Pharm Sci. 66(1):1-19 (1977).
Black et al., "Advances and limitations in the evaluation of analgesic combination therapy," Neurology. 65(12 Suppl 4):S3-6 (2005) (14 pages).
Chung et al., "Identification and rescue of alpha-synuclein toxicity in Parkinson patient-drived neurons," available in PMC Nov. 22, 2014, published in final edited form as: Science. 342(6161):983-7 (2013) (12 pages).
Cingolani et al., "A program for annotating and predicting the effects of single nucleotide polymorphisms, SnpEff: SNPs in the genome of Drosophila melanogaster strain w1118; iso-2; iso-3," Fly(Austin). 6(2):80-92 (2012).
Cooper et al., "Alpha-synuclein blocks ER-Golgi traffic and Rab1 rescues neuron loss in Parkinson's models," available in PMC Sep. 19, 2007, published in final edited form as: Science. 313(5785):324-8 (2006) (12 pages).
Dillon et al., "Development of a novel LC/MS method to quantitate cellular stearoyl-CoA desaturase activity," Anal Chim Acta. 627(1):99-104 (2008).

(56) References Cited

OTHER PUBLICATIONS

Gietz, "Yeast transformation by the LiAc/SS carrier DNA/PEG method," Methods Mol Biol. 1205:1-12 (2014).

Kamboh et al., "A novel mutation in the apolipoprotein E gene (APOE*4 Pittsburgh) is associated with the risk of late-onset Alzheimer's disease," Neurosci Lett. 263(2-3):129-32 (1999).

Li et al., "Fast and accurate long-read alignment with Burrows-Wheeler transform," Bioinformatics. 26(5):589-95 (2010).

Li et al., "Fast and accurate short read alignment with Burrows-Wheeler transform," Bioinformatics. 25(14):1754-60 (2009).

Li et al., "The sequence alignment/map format and SAMtools," Bioinformatics. 25(16):2078-9 (2009).

Longtine et al., "Additional modules for versatile and economical PCR-based gene deletion and modification in *Saccharomyces cerevisiae*," Yeast. 14(10):953-61 (1998).

Miyazaki et al., "The biosynthesis of hepatic cholesterol esters and triglycerides is impaired in mice with a disruption of the gene for stearoyl-CoA desaturase 1," J Biol Chem. 275(39):30132-8 (2000).

Piotrowski et al., "Plant-derived antifungal agent poacic acid targets beta-1,3-glucan," Proc Natl Acad Sci U S A. 112(12):E1490-7 (2015).

Shanklin et al., "Stearoyl-acyl-carrier-protein desaturase from higher plants is structurally unrelated to the animal and fungal homologs," Proc Natl Acad Sci U S A. 88(6):2510-4 (1991).

Soulard et al., "Development of a high-throughput screening assay for stearoyl-CoA desaturase using rat liver microsomes, deuterium labeled stearoyl-CoA and mass spectrometry," Anal Chim Acta. 627(1):105-11 (2008).

Su et al., "Compounds from an unbiased chemical screen reverse both ER-to-Golgi trafficking defects and mitochondrial dysfunction in Parkinson's disease models," Dis Model Mech. 3(3-4):194-208 (2010).

Suzuki et al., "Knocking out multi-gene redundancies via cycles of sexual assortment and fluorescence selection," available in PMC Aug. 1, 2011, published in final edited form as: Nat Methods. 8(2):159-64 (2011) (15 pages).

Tafesse et al., "Disruption of Sphingolipid Biosynthesis Blocks Phagocytosis of Candida albicans," PLoS Pathog. 11(10):e1005188 (2015) (27 pages).

Tindale et al., "Rare and common variants in the Apolipoprotein E gene in healthy oldest old," Neurobiol Aging. 35(3):727.e1-3 (2014) (3 pages).

Wang et al., "Characterization of HSCD5, a novel human stearoyl-CoA desaturase unique to primates," Biochem Biophys Res Commun. 332(3):735-42 (2005).

Garrison et al., "Haplotype-based variant detection from short-read sequencing," <https://arxiv.org/pdf/1207.3907.pdf>, retrieved Apr. 23, 2018 (2012) (9 pages).

Extended European Search Report for European Patent Application No. 18735798.3, dated Nov. 4, 2020 (10 pages).

\* cited by examiner

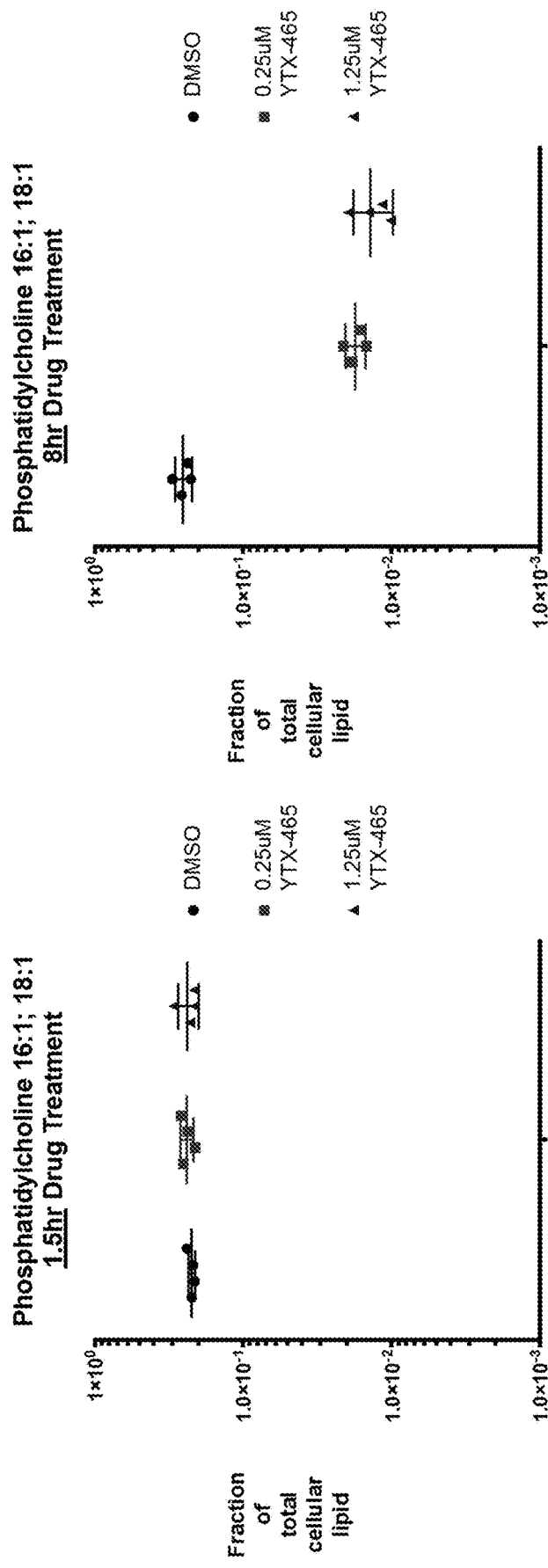

SEQUENCE LISTING

<160> NUMBER OF SEQ ID NOS: 1

<210> SEQ ID NO 1

-continued

```
<211> LENGTH: 510
<212> TYPE: PRT
<213> ORGANISM: Saccharomyces cerevisiae

<400> SEQUENCE: 1

Met Pro Thr Ser Gly Thr Thr Ile Glu Leu Ile Asp Asp Gln Phe Pro
1               5                   10                  15

Lys Asp Asp Ser Ala Ser Ser Gly Ile Val Asp Glu Val Asp Leu Thr
            20                  25                  30

Glu Ala Asn Ile Leu Ala Thr Gly Leu Asn Lys Lys Ala Pro Arg Ile
        35                  40                  45

Val Asn Gly Phe Gly Ser Leu Met Gly Ser Lys Glu Met Val Ser Val
    50                  55                  60

Glu Phe Asp Lys Lys Gly Asn Glu Lys Lys Ser Asn Leu Asp Arg Leu
65                  70                  75                  80

Leu Glu Lys Asp Asn Gln Glu Lys Glu Glu Ala Lys Thr Lys Ile His
                85                  90                  95

Ile Ser Glu Gln Pro Trp Thr Leu Asn Asn Trp His Gln His Leu Asn
            100                 105                 110

Trp Leu Asn Met Val Leu Val Cys Gly Met Pro Met Ile Gly Trp Tyr
        115                 120                 125

Phe Ala Leu Ser Gly Lys Val Pro Leu His Leu Asn Val Phe Leu Phe
    130                 135                 140

Ser Val Phe Tyr Tyr Ala Val Gly Gly Val Ser Ile Thr Ala Gly Tyr
145                 150                 155                 160

His Arg Leu Trp Ser His Arg Ser Tyr Ser Ala His Trp Pro Leu Arg
                165                 170                 175

Leu Phe Tyr Ala Ile Phe Gly Cys Ala Ser Val Glu Gly Ser Ala Lys
            180                 185                 190

Trp Trp Gly His Ser His Arg Ile His His Arg Tyr Thr Asp Thr Leu
        195                 200                 205

Arg Asp Pro Tyr Asp Ala Arg Arg Gly Leu Trp Tyr Ser His Met Gly
    210                 215                 220

Trp Met Leu Leu Lys Pro Asn Pro Lys Tyr Lys Ala Arg Ala Asp Ile
225                 230                 235                 240

Thr Asp Met Thr Asp Asp Trp Thr Ile Arg Phe Gln His Arg His Tyr
                245                 250                 255

Ile Leu Leu Met Leu Leu Thr Ala Phe Val Ile Pro Thr Leu Ile Cys
            260                 265                 270

Gly Tyr Phe Phe Asn Asp Tyr Met Gly Gly Leu Ile Tyr Ala Gly Phe
        275                 280                 285

Ile Arg Val Phe Val Ile Gln Gln Ala Thr Phe Cys Ile Asn Ser Leu
    290                 295                 300

Ala His Tyr Ile Gly Thr Gln Pro Phe Asp Asp Arg Arg Thr Pro Arg
305                 310                 315                 320

Asp Asn Trp Ile Thr Ala Ile Val Thr Phe Gly Glu Gly Tyr His Asn
                325                 330                 335

Phe His His Glu Phe Pro Thr Asp Tyr Arg Asn Ala Ile Lys Trp Tyr
            340                 345                 350

Gln Tyr Asp Pro Thr Lys Val Ile Ile Tyr Leu Thr Ser Leu Val Gly
        355                 360                 365

Leu Ala Tyr Asp Leu Lys Lys Phe Ser Gln Asn Ala Ile Glu Glu Ala
    370                 375                 380

Leu Ile Gln Gln Glu Gln Lys Lys Ile Asn Lys Lys Lys Ala Lys Ile
```

-continued

```
                385                 390                 395                 400
Asn Trp Gly Pro Val Leu Thr Asp Leu Pro Met Trp Asp Lys Gln Thr
                    405                 410                 415

Phe Leu Ala Lys Ser Lys Glu Asn Lys Gly Leu Val Ile Ile Ser Gly
                420                 425                 430

Ile Val His Asp Val Ser Gly Tyr Ile Ser Glu His Pro Gly Gly Glu
            435                 440                 445

Thr Leu Ile Lys Thr Ala Leu Gly Lys Asp Ala Thr Lys Ala Phe Ser
        450                 455                 460

Gly Gly Val Tyr Arg His Ser Asn Ala Ala Gln Asn Val Leu Ala Asp
465                 470                 475                 480

Met Arg Val Ala Val Ile Lys Glu Ser Lys Asn Ser Ala Ile Arg Met
                485                 490                 495

Ala Ser Lys Arg Gly Glu Ile Tyr Glu Thr Gly Lys Phe Phe
                500                 505                 510
```

METHODS FOR THE TREATMENT OF NEUROLOGICAL DISORDERS

BACKGROUND OF THE INVENTION

An incomplete understanding of the molecular perturbations that cause disease, as well as a limited arsenal of robust model systems, has contributed to a failure to generate successful disease-modifying therapies against common and progressive neurological disorders, such as Parkinson's Disease (PD) and Alzheimer's Disease (AD). Progress is being made on many fronts to find agents that can arrest the progress of these disorders. However, the present therapies for most, if not all, of these diseases provide very little relief. Accordingly, a need exists to develop therapies that can alter the course of neurological diseases (e.g., neurodegenerative diseases). More generally, a need exists for better methods and compositions for the treatment of neurological disorders in order to improve the quality of the lives of those afflicted by such diseases.

Stearoyl-CoA desaturases (SCDs) introduce a double bond in the C9-C10 position of saturated fatty acids such as palmitoyl-CoA and stearoyl-CoA which are converted to palmitoleoyl-CoA and oleoyl-CoA, respectively. One SCD gene, SCD1, has been characterized in humans for which there are two isoforms, SCD1 and SCD5. In turn, there are two forms of SCD5, SCD5a and SCD5b, which differ at the C-terminus. The present inventors have discovered that inhibition of SCDs is capable of suppressing toxicity in cells related to protein misfolding and/or aggregation. Accordingly, inhibition of SCDs may provide new methods for the treatment of diseases and disorders related to toxicity caused by protein misfolding and/or aggregation.

SUMMARY OF THE INVENTION

This disclosure provides compounds that modulate the activity of SCDs (e.g., SCD1 and/or SCD5), pharmaceutical compositions including such compounds, and methods of utilizing such compounds and compositions for modulating the activity of SCDs for the treatment of diseases and disorders related to toxicity caused by proteins such as toxicity related to misfolding and/or aggregation of proteins. In some embodiments, the disease or disorder is a neurological disorders.

In one aspect, the disclosure provides a method of treating a neurological disorder in a subject in need thereof. This method includes administering an effective amount of an SCD inhibitor.

In another aspect, the disclosure provides a method of treating a neurological disorder in a subject in need thereof. The method includes administering an SCD inhibitor in an amount sufficient to suppress toxicity in a cell (e.g., in a mammalian neural cell) related to a protein (e.g., toxicity related to misfolding and/or aggregation of a protein such as α-synuclein or ApoE4). In some embodiments, the toxicity is α-synuclein-related toxicity. In some embodiments, the toxicity is ApoE4-related toxicity.

In another aspect, the disclosure provides a method of suppressing toxicity in a cell (e.g., a neural cell) related to a protein (e.g., toxicity related to misfolding and/or aggregation of a protein such as α-synuclein or ApoE4). This method includes contacting a cell with an SCD inhibitor.

In another aspect, the disclosure provides a method of treating a neurological disorder in a subject in need thereof. This method includes (a) determining the level (e.g., in a neural cell) of a protein or a particular form of a protein (e.g., a misfolded form of a protein) related to a neurological disorder (e.g., α-synuclein, ApoE4, or an undesired form thereof) in the subject; and (b) administering an effective amount of an SCD inhibitor to the subject if the level of the protein or the particular form of the protein (e.g., a misfolded form of the protein) related to a neurological disorder is greater than a predetermined level (e.g., the level in a sample from a subject that does not have a neurological disorder).

In another aspect, the disclosure provides a method of treating a neurological disorder in a subject in need thereof, wherein the subject has an elevated level, or is predicted to have an elevated level (e.g., based on genetic markers) of a protein or a particular form of a protein related to a neurological disorder (e.g., α-synuclein, ApoE4, or an undesired form thereof). This method includes administering an effective amount of an SCD inhibitor to the subject. In some embodiments, the subject has an elevated level of the protein or the particular form of the protein (e.g., a misfolded form of the protein) related to a neurological disorder compared to a predetermined reference value (e.g., a value in a sample from a healthy subject).

In another aspect, the disclosure provides a method of treating a neurological disorder in a subject, wherein the subject has an elevated level (e.g., the subject has a level about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more greater as compared to a reference such as the level in a sample from a healthy subject) of a protein or a particular form of a protein (e.g., a misfolded form of a protein) related to a neurological disorder (e.g., α-synuclein, ApoE4, or an undesired form thereof), the method including administering an effective amount of an SCD inhibitor.

In another aspect, the disclosure provides a method of treating a neurological disorder in a subject in need thereof. This method includes (a) administering an effective amount of an SCD inhibitor to the subject; and (b) determining the level (e.g., in a neural cell) of a protein or a particular form of a protein related to a neurological disorder (e.g., α-synuclein, ApoE4, or an undesired form thereof) in the subject.

In another aspect, the disclosure provides a method of treating a neurological disorder in a subject in need thereof. This method includes (a) administering an effective amount of an SCD inhibitor to the subject; and (b) determining the level of neurite degeneration (e.g., by determining the level of a marker of neurite degeneration) in the subject.

In another aspect, the disclosure provides a method of suppressing neurite degeneration in a subject. This method includes administering an SCD inhibitor to the subject in an amount sufficient to suppress neurite degeneration.

In some embodiments of any of the foregoing methods, the SCD inhibitor is an SCD1 inhibitor. In some embodiments of any of the foregoing methods, the SCD inhibitor is an SCD5 inhibitor. In some embodiments, the SCD inhibitor is selective for SCD1 over SCD5. In some embodiments of any of the foregoing methods, the SCD inhibitor has activity for SCD1 that is at least 2.5-fold greater (e.g., at least 5-fold greater, at least 10-fold greater, at least 20-fold greater) than the activity of the inhibitor for SCD5. In some embodiments, the SCD inhibitor is selective for SCD5 over SCD1. In some embodiments of any of the foregoing methods, the SCD inhibitor has activity for SCD5 that is at least 2.5-fold greater (e.g., at least 5-fold greater, at least 10-fold greater, at least 20-fold greater) than the activity of the inhibitor for SCD1. In some embodiments, the SCD inhibitor is a nonselective SCD inhibitor.

In some embodiments of any of the foregoing methods, administering includes contacting a cell with an effective amount of an SCD inhibitor.

In some embodiments of any of the foregoing methods, the SCD inhibitor is any compound described herein (e.g., any compound having the structure of any one of Formula I-LXI). In some embodiments of any of the foregoing methods, the SCD inhibitor is a compound of Formula I. In some embodiments of any of the foregoing methods, the SCD inhibitor is a compound of Formula II. In some embodiments of any of the foregoing methods, the SCD inhibitor is a compound of Formula III. In some embodiments of any of the foregoing methods, the SCD inhibitor is a compound of Formula IV. In some embodiments of any of the foregoing methods, the SCD inhibitor is a compound of Formula V. In some embodiments of any of the foregoing methods, the SCD inhibitor is a compound of Formula VI. In some embodiments of any of the foregoing methods, the SCD inhibitor is a compound of Formula VII. In some embodiments of any of the foregoing methods, the SCD inhibitor is a compound of Formula VIII. In some embodiments of any of the foregoing methods, the SCD inhibitor is a compound of Formula IX. In some embodiments of any of the foregoing methods, the SCD inhibitor is a compound of Formula X. In some embodiments of any of the foregoing methods, the SCD inhibitor is a compound of Formula XI. In some embodiments of any of the foregoing methods, the SCD inhibitor is a compound of Formula XII. In some embodiments of any of the foregoing methods, the SCD inhibitor is a compound of Formula XIII. In some embodiments of any of the foregoing methods, the SCD inhibitor is a compound of Formula XIV. In some embodiments of any of the foregoing methods, the SCD inhibitor is a compound of Formula XV. In some embodiments of any of the foregoing methods, the SCD inhibitor is a compound of Formula XVI. In some embodiments of any of the foregoing methods, the SCD inhibitor is a compound of Formula XVII. In some embodiments of any of the foregoing methods, the SCD inhibitor is a compound of Formula XVIII. In some embodiments of any of the foregoing methods, the SCD inhibitor is a compound of Formula XIX. In some embodiments of any of the foregoing methods, the SCD inhibitor is a compound of Formula XX. In some embodiments of any of the foregoing methods, the SCD inhibitor is a compound of Formula XXI. In some embodiments of any of the foregoing methods, the SCD inhibitor is a compound of Formula XXII. In some embodiments of any of the foregoing methods, the SCD inhibitor is a compound of Formula XXIII. In some embodiments of any of the foregoing methods, the SCD inhibitor is a compound of Formula XXIV. In some embodiments of any of the foregoing methods, the SCD inhibitor is a compound of Formula XXV. In some embodiments of any of the foregoing methods, the SCD inhibitor is a compound of Formula XXVI. In some embodiments of any of the foregoing methods, the SCD inhibitor is a compound of Formula XXVII. In some embodiments of any of the foregoing methods, the SCD inhibitor is a compound of Formula XXVIII. In some embodiments of any of the foregoing methods, the SCD inhibitor is a compound of Formula XXIX. In some embodiments of any of the foregoing methods, the SCD inhibitor is a compound of Formula XXX. In some embodiments of any of the foregoing methods, the SCD inhibitor is a compound of Formula XXXI. In some embodiments of any of the foregoing methods, the SCD inhibitor is a compound of Formula XXXII. In some embodiments of any of the foregoing methods, the SCD inhibitor is a compound of Formula XXXIII. In some embodiments of any of the foregoing methods, the SCD inhibitor is a compound of Formula XXXIV. In some embodiments of any of the foregoing methods, the SCD inhibitor is a compound of Formula XXXV. In some embodiments of any of the foregoing methods, the SCD inhibitor is a compound of Formula XXXVI. In some embodiments of any of the foregoing methods, the SCD inhibitor is a compound of Formula XXXVII. In some embodiments of any of the foregoing methods, the SCD inhibitor is a compound of Formula XXXVIII. In some embodiments of any of the foregoing methods, the SCD inhibitor is a compound of Formula XXXIX. In some embodiments of any of the foregoing methods, the SCD inhibitor is a compound of Formula XL. In some embodiments of any of the foregoing methods, the SCD inhibitor is a compound of Formula XLI. In some embodiments of any of the foregoing methods, the SCD inhibitor is a compound of Formula XLII. In some embodiments of any of the foregoing methods, the SCD inhibitor is a compound of Formula XLIII. In some embodiments of any of the foregoing methods, the SCD inhibitor is a compound of Formula XLIV. In some embodiments of any of the foregoing methods, the SCD inhibitor is a compound of Formula XLV. In some embodiments of any of the foregoing methods, the SCD inhibitor is a compound of Formula XLVI. In some embodiments of any of the foregoing methods, the SCD inhibitor is a compound of Formula XLVII. In some embodiments of any of the foregoing methods, the SCD inhibitor is a compound of Formula XLVIII. In some embodiments of any of the foregoing methods, the SCD inhibitor is a compound of Formula XLIX. In some embodiments of any of the foregoing methods, the SCD inhibitor is a compound of Formula L. In some embodiments of any of the foregoing methods, the SCD inhibitor is a compound of Formula LI. In some embodiments of any of the foregoing methods, the SCD inhibitor is a compound of Formula LII. In some embodiments of any of the foregoing methods, the SCD inhibitor is a compound of Formula LIII. In some embodiments of any of the foregoing methods, the SCD inhibitor is a compound of Formula LIV. In some embodiments of any of the foregoing methods, the SCD inhibitor is a compound of Formula LV. In some embodiments of any of the foregoing methods, the SCD inhibitor is a compound of Formula LVI. In some embodiments of any of the foregoing methods, the SCD inhibitor is a compound of Formula LVII. In some embodiments of any of the foregoing methods, the SCD inhibitor is a compound of Formula LVIII. In some embodiments of any of the foregoing methods, the SCD inhibitor is a compound of Formula LIX. In some embodiments of any of the foregoing methods, the SCD inhibitor is a compound of Formula LX. In some embodiments of any of the foregoing methods, the SCD inhibitor is a compound of Formula LXI.

In some embodiments of any of the foregoing methods, the SCD inhibitor is not a compound of Formula I. In some embodiments of any of the foregoing methods, the SCD inhibitor is not a compound of Formula II. In some embodiments of any of the foregoing methods, the SCD inhibitor is not a compound of Formula III. In some embodiments of any of the foregoing methods, the SCD inhibitor is not a compound of Formula IV. In some embodiments of any of the foregoing methods, the SCD inhibitor is not a compound of Formula V. In some embodiments of any of the foregoing methods, the SCD inhibitor is not a compound of Formula VI. In some embodiments of any of the foregoing methods, the SCD inhibitor is not a compound of Formula VII. In some embodiments of any of the foregoing methods, the SCD inhibitor is not a compound of Formula VIII. In some embodiments of any of the foregoing methods, the SCD inhibitor is not a compound of Formula IX. In some embodiments of any of the foregoing methods, the SCD inhibitor is not a compound of Formula X. In some embodiments of any of the foregoing methods, the SCD inhibitor is not a compound of Formula XI. In some embodiments of any of the foregoing methods, the SCD inhibitor is not a compound of Formula XII. In some embodiments of any of the foregoing methods, the SCD inhibitor is not a compound of Formula XIII. In some embodiments of any of the foregoing methods, the SCD inhibitor is not a compound of Formula XIV. In some embodiments of any of the foregoing methods, the SCD inhibitor is not a compound of Formula XV. In some embodiments of any of the foregoing methods, the SCD inhibitor is not a compound of Formula XVI. In some embodiments of any of the foregoing methods, the SCD inhibitor is not a compound of Formula XVII. In some embodiments of any of the foregoing methods, the SCD inhibitor is not a compound of Formula XVIII. In some embodiments of any of the foregoing methods, the SCD inhibitor is not a compound of Formula XIX. In some embodiments of any of the foregoing methods, the SCD inhibitor is not a compound of Formula XX. In some embodiments of any of the foregoing methods, the SCD inhibitor is not a compound of Formula XXI. In some embodiments of any of the foregoing methods, the SCD inhibitor is not a compound of Formula XXII. In some embodiments of any of the foregoing methods, the SCD inhibitor is not a compound of Formula XXIII. In some embodiments of any of the foregoing methods, the SCD inhibitor is not a compound of Formula XXIV. In some embodiments of any of the foregoing methods, the SCD inhibitor is not a compound of Formula XXV. In some embodiments of any of the foregoing methods, the SCD inhibitor is not a compound of Formula XXVI. In some embodiments of any of the foregoing methods, the SCD inhibitor is not a compound of Formula XXVII. In some embodiments of any of the foregoing methods, the SCD inhibitor is not a compound of Formula XXVIII. In some embodiments of any of the foregoing methods, the SCD inhibitor is not a compound of Formula XXIX. In some embodiments of any of the foregoing methods, the SCD inhibitor is not a compound of Formula XXX. In some embodiments of any of the foregoing methods, the SCD inhibitor is not a compound of Formula XXXI. In some embodiments of any of the foregoing methods, the SCD inhibitor is not a compound of Formula XXXII. In some embodiments of any of the foregoing methods, the SCD inhibitor is not a compound of Formula XXXIII. In some embodiments of any of the foregoing methods, the SCD inhibitor is not a compound of Formula XXXIV. In some embodiments of any of the foregoing methods, the SCD inhibitor is not a compound of Formula XXXV. In some embodiments of any of the foregoing methods, the SCD inhibitor is not a compound of Formula XXXVI. In some embodiments of any of the foregoing methods, the SCD inhibitor is not a compound of Formula XXXVII. In some embodiments of any of the foregoing methods, the SCD inhibitor is not a compound of Formula XXXVIII. In some embodiments of any of the foregoing methods, the SCD inhibitor is not a compound of Formula XXXIX. In some embodiments of any of the foregoing methods, the SCD inhibitor is not a compound of Formula XL. In some embodiments of any of the foregoing methods, the SCD inhibitor is not a compound of Formula XLI. In some embodiments of any of the foregoing methods, the SCD inhibitor is not a compound of Formula XLII. In some embodiments of any of the foregoing methods, the SCD inhibitor is not a compound of Formula XLIII. In some embodiments of any of the foregoing methods, the SCD inhibitor is not a compound of Formula XLIV. In some embodiments of any of the foregoing methods, the SCD inhibitor is not a compound of Formula XLV. In some embodiments of any of the foregoing methods, the SCD inhibitor is not a compound of Formula XLVI. In some embodiments of any of the foregoing methods, the SCD inhibitor is not a compound of Formula XLVII. In some embodiments of any of the foregoing methods, the SCD inhibitor is not a compound of Formula XLVIII. In some embodiments of any of the foregoing methods, the SCD inhibitor is not a compound of Formula XLIX. In some embodiments of any of the foregoing methods, the SCD inhibitor is not a compound of Formula L. In some embodiments of any of the foregoing methods, the SCD inhibitor is not a compound of Formula LI. In some embodiments of any of the foregoing methods, the SCD inhibitor is not a compound of Formula LII. In some embodiments of any of the foregoing methods, the SCD inhibitor is not a compound of Formula LIII. In some embodiments of any of the foregoing methods, the SCD inhibitor is not a compound of Formula LIV. In some embodiments of any of the foregoing methods, the SCD inhibitor is not a compound of Formula LV. In some embodiments of any of the foregoing methods, the SCD inhibitor is not a compound of Formula LVI. In some embodiments of any of the foregoing methods, the SCD inhibitor is not a compound of Formula LVII. In some embodiments of any of the foregoing methods, the SCD inhibitor is not a compound of Formula LVIII. In some embodiments of any of the foregoing methods, the SCD inhibitor is not a compound of Formula LIX. In some embodiments of any of the foregoing methods, the SCD inhibitor is not a compound of Formula LX. In some embodiments of any of the foregoing methods, the SCD inhibitor is not a compound of Formula LXI.

In some embodiments of any of the foregoing methods, the SCD inhibitor is a compound of any one of Formula I-XXX. In some embodiments of any of the foregoing methods, the SCD inhibitor is a compound of any one of Formula XXXI-XLII. In some embodiments of any of the foregoing methods, the SCD inhibitor is a compound of any one of Formula XLIII-XLIV. In some embodiments of any of the foregoing methods, the SCD inhibitor is a compound of any one of Formula XLVI-XLVII. In some embodiments of any of the foregoing methods, the SCD inhibitor is a compound of any one of Formula L-LX.

In some embodiments of any of the foregoing methods, the SCD inhibitor is not a compound of any one of Formula I-XXX. In some embodiments of any of the foregoing methods, the SCD inhibitor is not a compound of any one of Formula XXXI-XLII. In some embodiments of any of the foregoing methods, the SCD inhibitor is not a compound of any one of Formula XLIII-XLIV. In some embodiments of any of the foregoing methods, the SCD inhibitor is not a compound of any one of Formula XLVI-XLVII. In some embodiments of any of the foregoing methods, the SCD inhibitor is not a compound of any one of Formula L-LX.

In some embodiments of any of the foregoing methods, a cell expresses α-synuclein and/or a human apolipoprotein E (ApoE) protein (e.g., ApoE2, ApoE3, or ApoE4).

In some embodiments of any of the foregoing methods, the subject carries one or two copies of the ApoE4 allele).

In some embodiments of any of the foregoing methods, the subject is a human.

In some embodiments of any of the foregoing methods, the cell is a neural cell (e.g., a neuron or glial cell).

In some embodiments of any of the foregoing methods, the method includes inhibition of neurite degeneration or cell death.

Neurological disorders include, but are not limited to Alexander disease, Alpers' disease, Alzheimer's disease (AD), amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, PD, Pelizaeus-Merzbacher disease, Pick's disease, primary lateral sclerosis, Refsum's disease, Sandhoff disease, Schilder's disease, Steele-Richardson-Olszewski disease, tabes dorsalis, frontal temporal dementia, vascular dementia, Down's syndrome, and Guillain-Barre Syndrome.

In some embodiments of any of the foregoing methods, the neurological disorder is a proteopathy (e.g., a synucleinopathy, AD, Alexander disease, amyotrophic lateral sclerosis (ALS), a prion disease (e.g., Creutzfeldt-Jakob disease), Huntington's disease, Machado-Joseph disease, Pick's disease, or frontotemporal dementia). In some embodiments of any of the foregoing methods, the neurological disorder is a synucleinopathy such as Parkinson's disease (PD), dementia with Lewy bodies, pure autonomic failure, multiple system atrophy, incidental Lewy body disease, pantothenate kinase-associated neurodegeneration, Alzheimer's disease, Down's Syndrome, Gaucher disease, or the Parkinsonism-dementia complex of Guam. In some embodiments of any of the foregoing methods, the neurological disorder is a progressive neurodegenerative disorder (e.g. Alpers' disease, ataxia telangectsia, Canavan disease, Cockayne syndrome, corticobasal degeneration, Kennedy's disease, Krabbe disease, Pelizaeus-Merzbacher disease, primary lateral sclerosis, Refsum's disease, Sandhoff disease, Schilder's disease, Steele-Richardson-Olszewski disease, tabes dorsalis, vascular dementia, or Guillain-Barre Syndrome). In some embodiments of any of the foregoing methods, the neurological disorder is an ApoE-associated neurodegenerative disorder (e.g., AD, vascular cognitive impairment, cerebral amyloid angiopathy, traumatic brain injury, or multiple sclerosis).

In some embodiments of any of the foregoing methods, the method further includes administering an additional therapeutic agent (e.g., a small molecule, an antibody or fragment thereof, or a nucleic acid) to the subject. In some embodiments of any of the foregoing methods, the method further includes administering to the subject a cognition-enhancing agent, an antidepressant agent, an anxiolytic agent, an antipsychotic agent, a sedative, a dopamine promoter, or an anti-tremor agent. In some embodiments, the additional therapeutic agent and the SCD inhibitor are administered within 28 days of each other (e.g., within 21, 14, 10, 7, 5, 4, 3, 2, or 1 days) or within 24 hours (e.g., 12, 6, 3, 2, or 1 hours; or concomitantly) in amounts that together are effective to treat the subject.

In some embodiments of any of the foregoing methods, the SCD inhibitor is a compound of Formula Ia-Id:

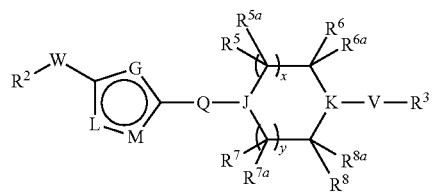

(Ia)

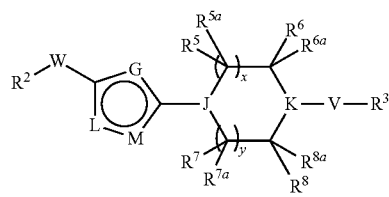

(Ib)

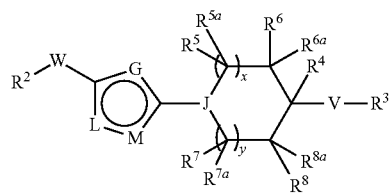

(Ic)

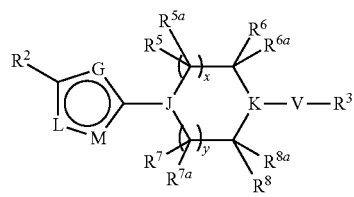

(Id)

wherein:

x and y are each independently 0, 1, 2 or 3;

each $R^1$ is independently selected from the group consisting of hydrogen, $C_1$-$C_{12}$alkyl, $C_2$-$C_{12}$ hydroxyalkyl, $C_4$-$C_{12}$cycloalkylalkyl and $C_7$-$C_{19}$aralkyl;

each $R^4$ is independently selected from hydrogen, fluoro, chloro, $C_1$-$C_{12}$alkyl, $C_1$-$C_{12}$alkoxy, haloalkyl, cyano, nitro or —N($R^9$)$_2$;

or two adjacent $R^4$ groups, together with the carbons to which they are attached, may form an aryl, heteroaryl or heterocyclyl ring system;

$R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or $R^5$ and $R^{5a}$ together, $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or one of $R^5$, $R^{5a}$, $R^6$ and $R^{6a}$ together with one of $R^7$, $R^{7a}$, $R^8$ and $R^{8a}$ forms a direct bond or an alkylene bridge, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl; and each $R^9$ is independently selected from hydrogen or $C_1$-$C_6$alkyl.

In some embodiments of the compound of Formula Ia, G is —N($R^4$)—, —O—, —S(O)$_t$— (where t is 0, 1 or 2), —C($R^4$)= or —C($R^4$)=C($R^4$)—;

J and K are each independently N or C($R^{10}$);

L and M are each independently —N= or —C($R^4$)=, provided that when G is —C($R^4$)= or —C($R^4$)=C($R^4$)—, L and M cannot both be —C($R^4$)=;

Q is —N(R⁴)—, —O—, —S(O)$_t$ (where t is 0, 1 or 2), —C(O)—, —C(S)—, an alkylene chain or an alkenylene chain;

V is a direct bond, —N(R¹)—, —N(R¹)C(O)—, —O—, —C(O)—, —C(O)O—, —C(S)—, —C(O)N(R¹)—, —S(O)$_t$— (where t is 0, 1 or 2) or —S(O)$_p$N(R¹)— (where p is 1 or 2);

W is a direct bond, —N(R¹)C(O)—, —C(O)N(R¹)—, —OC(O)N(R¹)—, —N(R¹)C(O)N(R¹)—, —O—, —N(R¹)—, —S(O)$_t$— (where t is 0, 1 or 2), —N(R¹)S(O)$_p$— (where p is 1 or 2), —S(O)$_p$N(R¹)— (where p is 1 or 2), —C(O)—, —OS(O)₂N(R¹)—, —OC(O)—, —C(O)O—, —N(R¹)C(O)O— or —C(R¹)₂—;

R² is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or R² is a multi-ring structure having 2 to 4 rings wherein the rings are independently selected from the group consisting of cycloalkyl, heterocyclyl, aryl and heteroaryl and where some or all of the rings may be fused to each other;

R³ is selected from the group consisting of hydrogen, $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_9$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or R³ is a multi-ring structure having 2 to 4 rings wherein the rings are independently selected from the group consisting of cycloalkyl, heterocyclyl, aryl and heteroaryl and where some or all of the rings may be fused to each other;

R¹⁰ is independently selected from hydrogen, fluoro, chloro, $C_1$-$C_{12}$alkyl or $C_1$-$C_{12}$alkoxy; or as a stereoisomer, enantiomer or tautomer thereof, as a mixture of stereoisomers, as a pharmaceutically acceptable salt thereof, or as a prodrug thereof.

In some embodiments of the compound of Formula Ib,
G is —N(R⁴)—, —O—, or —S(O)$_t$— (where t is 0, 1 or 2);

J and K are each independently N or C(R¹¹);

L and M are each independently —N= or —C(R⁴)=;

V is —C(O)—, —C(O)O—, —C(S)—, —C(O)N(R¹)—, —S(O)$_t$— (where t is 0, 1 or 2), —S(O)$_p$N(R¹)— (where p is 1 or 2), —C(R¹⁰)H—, —N(R¹)—, —O—;

W is a direct bond, —N(R¹)C(O)—, —C(O)N(R¹)—, —OC(O)N(R¹)—, —N(R¹)C(O)N(R¹)—, —O—, —N(R¹)—, —S(O)$_t$— (where t is 0, 1 or 2), —N(R¹)S(O)$_p$— (where p is 1 or 2), —S(O)$_p$N(R¹)— (where p is 1 or 2), —C(O)—, —OS(O)₂N(R¹)—, —OC(O)—, —C(O)O—, —N(R¹)C(O)—;

R² is selected from the group consisting of hydrogen, $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or R² is a multi-ring structure having 2 to 4 rings wherein the rings are independently selected from the group consisting of cycloalkyl, heterocyclyl, aryl and heteroaryl and where some or all of the rings may be fused to each other;

R³ is selected from the group consisting of hydrogen, $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or R³ is a multi-ring structure having 2 to 4 rings wherein the rings are independently selected from the group consisting of cycloalkyl, heterocyclyl, aryl and heteroaryl and where some or all of the rings may be fused to each other;

R¹⁰ is a hydrogen or $C_1$-$C_3$alkyl; and

R¹¹ is independently selected from hydrogen, fluoro, chloro, $C_1$-$C_{12}$alkyl or $C_1$-$C_{12}$alkoxy; or a stereoisomer, enantiomer or tautomer thereof, a pharmaceutically acceptable salt thereof, a pharmaceutical composition thereof or a prodrug thereof.

In some embodiments of the compound of Formula Ic,
G is —N(R⁴)—, —O—, —S(O)$_t$ (where t is 0, 1 or 2), —C(R⁴)= or —C(R⁴)=C(R⁴)—;

J is N or C(R¹⁰);

L and M are each independently —N= or —C(R⁴)=, provided that when G is —C(R⁴)= or —C(R⁴)=C(R⁴)—, L and M cannot both be —C(R⁴)=;

V is a direct bond, —N(R¹)—, —N(R¹)C(O)—, —O—, —C(O)—, —C(O)O—, —C(S)—, —C(O)N(R¹)—, —S(O)$_p$— (where p is 1 or 2), or —S(O)$_p$N(R¹)— (where p is 1 or 2);

W is —N(R¹)C(O)—, —C(O)N(R¹)—, —OC(O)N(R¹)—, —N(R¹)C(O)N(R¹)—, —O—, —N(R¹)—, —S(O)$^t$— (where t is 0, 1 or 2), —N(R¹)S(O)$_p$— (where p is 1 or 2), —S(O)$_p$N(R¹)— (where p is 1 or 2), —C(O)—, —OS(O)₂N(R¹)—, —OC(O)—, —C(O)O—, —N(R¹)C(O)O— or —C(R¹)₂—;

R² is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or R² is a multi-ring structure having 2 to 4 rings wherein the rings are independently selected from the group consisting of cycloalkyl, heterocyclyl, aryl and heteroaryl and where some or all of the rings may be fused to each other;

R³ is selected from the group consisting of hydrogen, $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or R³ is a multi-ring structure having 2 to 4 rings wherein the rings are independently selected from the group consisting of cycloalkyl, heterocyclyl, aryl and heteroaryl and where some or all of the rings may be fused to each other;

R¹⁰ is independently selected from hydrogen, fluoro, chloro, $C_1$-$C_{12}$alkyl or $C_1$-$C_{12}$alkoxy; or as a stereoisomer, enantiomer or tautomer thereof, as a pharmaceutically acceptable salt thereof, or as a prodrug thereof.

In some embodiments of the compound of Formula Id,
G is —N(R⁴)—, —O—, —S(O)$_t$ (where t is 0, 1 or 2), —C(R⁴)= or —C(R⁴)=C(R⁴)—;

J and K are each independently N or C(R¹⁰);

L and M are each independently —N= or —C(R⁴)=, provided that when G is —C(R⁴)= or —C(R⁴)=C(R⁴)—, L and M cannot both be —C(R⁴)=;

V is direct bond, —N(R¹)—, —N(R¹)C(O)—, —O—, —C(O)—, —C(O)O—, —C(S)—, —C(O)N(R¹)—, —S(O)$_p$— (where p is 1 or 2), or —S(O)$_p$N(R¹)— (where p is 1 or 2);

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^{10}$ is independently selected from hydrogen, fluoro, chloro, $C_1$-$C_{12}$alkyl or $C_1$-$C_{12}$alkoxy; or as a stereoisomer, enantiomer or tautomer thereof, as a mixture of stereoisomers, as a pharmaceutically acceptable salt thereof, or as a prodrug thereof.

In some embodiments, the invention provides compounds of Formula Ib having the following Formula Iba:

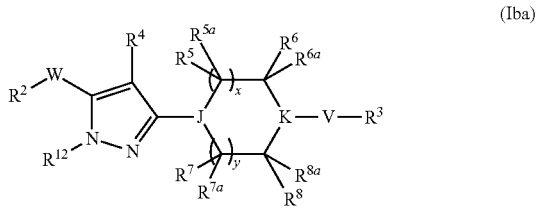

(Iba)

wherein:

x and y are each independently 1, 2 or 3;

M is —C($R^4$)═ or —N═;

$R^{12}$ is hydrogen, —C(O)O$R^{13}$, —C(O)N($R^{13}$)$_2$, $C_1$-$C_{12}$alkyl, $C_2$-$C_{12}$hydroxyalkyl, $C_4$-$C_{12}$cycloalkylalkyl or $C_7$-$C_{19}$aralkyl; and each $R^{13}$ is independently selected from hydrogen, $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; or as a stereoisomer, enantiomer or tautomer thereof, as a mixture of stereoisomers, as a pharmaceutically acceptable salt thereof, or as a prodrug thereof.

Compounds of Formula (I) may be synthesized by methods known in the art, e.g., those described in International Patent Publications No. WO2006/034341, WO2006/034315, WO2006/034338, and WO2006/034440. In some embodiments, the SCD inhibitor is a compound disclosed in International Patent Publications No. WO2006/034341, WO2006/034315, WO2006/034338, and WO2006/034440, the compounds of which are herein incorporated by reference.

In some embodiments of any of the foregoing methods, the SCD inhibitor is a compound of Formula II:

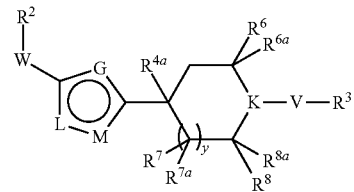

(II)

wherein:

y is 0, 1, 2, or 3;

G is —N($R^4$)—, —O—, —S(O)$_t$— (where t is 0, 1 or 2), —C($R^4$)═ or —C($R^4$)═C($R^4$)—;

K is N or C($R^{10}$);

L and M are each independently —N═ or —C($R^4$)═, provided that when G is —C($R^4$)═ or —C($R^4$)═C($R^4$)—, L and M cannot both be —C($R^4$)═;

V is —N($R^1$)—, —O—, —C($R^{10}$)$_2$—, —C(O)—, —C(O)O—, —C(S)—, —C(O)N($R^1$)—, —S(O)$_t$— (where t is 0, 1 or 2) or —S(O)$_p$N($R^1$)— (wherein p is 1 or 2), provided that when K is N, V cannot be —S—;

W is a direct bond, —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_p$— (where p is 1 or 2), —S(O)$_p$N($R^1$)— (where p is 1 or 2), —C(O)—, —OS(O)$_2$N($R^1$)—, —OC(O)—, —C(O)O—, or —N($R^1$)C(O)O—;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

each $R^4$ is independently selected from hydrogen, fluoro, chloro, $C_1$-$C_{12}$alkyl, $C_1$-$C_{12}$alkoxy, haloalkyl, cyano, nitro or —N($R^9$)$_2$;

or two adjacent $R^4$ groups, together with the carbons to which they are attached, may form an aryl, heteroaryl or heterocyclyl ring system;

$R^{4a}$ is hydrogen, fluoro, chloro, $C_1$-$C_{12}$alkyl, $C_1$-$C_{12}$alkoxy, haloalkyl, cyano, nitro or —N($R^9$)$_2$;

or $R^{4a}$ is a direct bond to an adjacent carbon;

$R^6$, $R^{6a}$, $R^7$, $R^{7a}$, $R^8$ and $R^{8a}$ are each independently selected from hydrogen or $C_1$-$C_3$alkyl;

or $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^6$, $R^{6a}$, $R^7$, $R^{7a}$, $R^8$ and $R^{8a}$ are each independently selected from hydrogen or $C_1$-$C_3$alkyl;

or one of $R^6$ and $R^{6a}$ together with one of $R^7$, $R^{7a}$, $R^8$ and $R^{8a}$ forms a direct bond or an alkylene bridge, while the remaining $R^6$, $R^{6a}$, $R^7$, $R^{7a}$, $R^8$ and $R^{8a}$ are each independently selected from hydrogen or $C_1$-$C_3$alkyl;

each $R^9$ is independently selected from hydrogen or $C_1$-$C_6$alkyl; and $R^{10}$ is independently selected from hydrogen, fluoro, chloro, $C_1$-$C_{12}$alkyl or $C_1$-$C_{12}$alkoxy; or as a stereoisomer, enantiomer or tautomer thereof, as a mixture of stereoisomers, as a pharmaceutically acceptable salt thereof, or as a prodrug thereof.

Compounds of Formula (II) may be synthesized by methods known in the art, e.g., those described in International Patent Publication No. WO2006/034279. In some embodiments, the SCD inhibitor is a compound disclosed in International Patent Publication No. WO2006/034279, the compounds of which are herein incorporated by reference.

In some embodiments of any of the foregoing methods, the SCD inhibitor is a compound of Formula III:

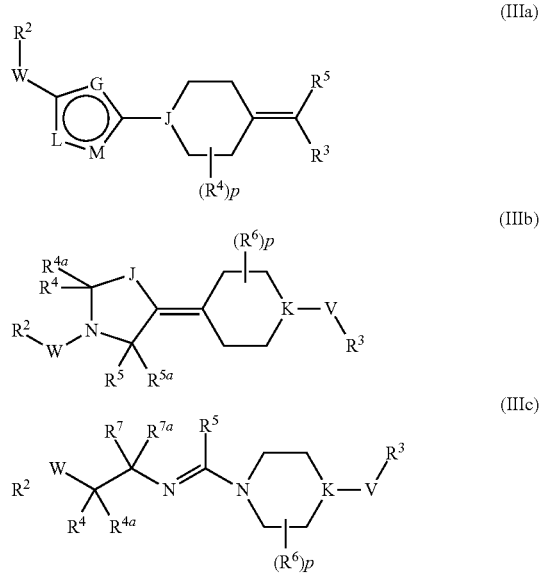

(IIIa)

(IIIb)

(IIIc)

wherein:
p is 0 to 8;
each $R^1$ is independently selected from the group consisting of hydrogen, alkyl, hydroxyalkyl, cycloalkylalkyl and aralkyl;

each $R^{1a}$ is selected from the group consisting of hydrogen, $C_1$-$C_6$alkyl, cycloalkylalkyl, —$OR^1$, and cyano;

$R^2$ is selected from the group consisting of alkyl, alkenyl, hydroxyalkyl, hydroxyalkenyl, alkoxyalkyl, cycloalkyl, cycloalkylalkyl, aryl, aralkyl, heterocyclyl, heterocyclylalkyl, heteroaryl, and heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of alkyl, alkenyl, hydroxyalkyl, hydroxyalkenyl, alkoxyalkyl, cycloalkyl, cycloalkylalkyl, aryl, aralkyl, heterocyclyl, heterocyclylalkyl, heteroaryl and heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

or a stereoisomer, enantiomer or tautomer thereof, or a racemic or non-racemic mixture thereof, or a pharmaceutically acceptable salt or prodrug thereof.

In some embodiments of the compound of Formula IIIa, W is —$N(R^1)C(O)$—, —$C(O)N(R^1)$—, —$OC(O)N(R^1)$—, —$N(R^1)C(O)N(R^1)$—, —$O$—, —$N(R^1)$—, —$S(O)_t$— (where t is 0, 1 or 2), —$C(O)$—, —$N(R^1)S(O)_2$—, —$S(O)_2N(R^1)$—, —$OS(O)_2N(R^1)$—, —$OC(O)$—, —$C(O)O$—, —$N(R^1)C(O)O$—, —$N(R^1)C(NR^{1a})N(R^1)$—, —$N(R^1)C(S)N(R^1)$—, —$N(R^1)C(NR^{1a})$—, —$C(NR^{1a})N(R^1)$—, heteroaryl, heterocyclyl or a direct bond;

L and M are independently selected from —N═ or —$C(R^4)$═;

G is selected from —$C(R^4)$═$C(R^4)$—, —$C(R^4)$═N—, —N═$C(R^4)$—, —N═N—, —$N(R^4)$—, —O— or —$S(O)_t$-(where t is 0, 1 or 2);

J is selected from N or $C(R^6)$;
each $R^4$ is alkyl;
or one of $R^4$ together with another one of $R^4$ on a different carbon atom forms an alkylene bridge, while the remaining $R^4$'s are each alkyl;

$R^5$ is independently selected from hydrogen, alkyl, fluoro, chloro, or —$C(O)OR^7$;

$R^6$ is selected from hydrogen, alkyl, fluoro, or chloro; and
$R^7$ is hydrogen, alkyl, aryl or aralkyl.

In some embodiments of the compound of Formula IIIb, W is —$N(R^1)C(O)$—$R^9$—, —$S(O)_t$—$R^9$— (where t is 1, 2), —$C(O)$—$R^9$—, —$OC(O)$—$R^9$—, —$N(R^1)C(NR^{1a})$—$R^9$—, —$C(NR^{1a})$—$R^9$—, —$N(R^1)C(S)$—$R^9$—, heteroaryl, heteroarylalkyl, heterocyclyl, heterocyclylalkyl or a direct bond;

K is selected from N or $C(R^7)$;
when K is N, V is —$C(O)$—, —$C(O)O$—, —$C(S)$—, —$C(O)N(R^1)$—, —$S(O)_t$ (where t is 0, 1 or 2), —$S(O)_qN(R^1)$— (where q is 1 or 2), —$C(R^8)H$— or —$C(NR^{1a})$—;

when K is $C(R^7)$, V is —O—, —$C(O)$—, —$C(O)O$—, —$OC(O)$—, —$C(S)$—, —$C(O)N(R^1)$—, —$N(R^1)C(O)$—, —$S(O)_t$-(where t is 0, 1 or 2), —$S(O)_qN(R^1)$— (where q is 1 or 2), —$N(R^1)S(O)_q$— (where q is 1 or 2), —$C(R^8)H$— or —$C(NR^{1a})$—;

J is selected from —O—, —$N(R^1)$—, —$S(O)_t$— (where t is 0, 1 or 2) or —$C(R^6)_2$—;

$R^4$ and $R^{4a}$ are each independently selected from hydrogen or alkyl,
or $R^4$ and $R^{4a}$ together form an oxo group;

$R^5$ and $R^{5a}$ are each independently selected from a hydrogen or alkyl,
or $R^5$ and $R^{5a}$ together form an oxo group;
each $R^6$ is alkyl;
or one of $R^6$ together with another $R^6$ on different carbon atom from an alkylene bridge and the other $R^6$'s are each alkyl;

$R^7$ is selected from hydrogen, alkyl, fluoro, or chloro;
$R^8$ is selected from hydrogen, alkyl, fluoro, chloro, methoxy, trifluoromethyl, cyano, nitro or —$N(R^1)_2$; and each $R^9$ is independently a direct bond, a straight or branched alkylene chain or a straight or branched alkenylene chain.

In some embodiments of the compound of Formula IIIc, W is —$N(R^1)C(O)$—, —$C(O)N(R^1)$—, —$OC(O)N(R^1)$—, —$N(R^1)C(O)N(R^1)$—, —$O$—, —$N(R^1)$—, —$S(O)_t$— (where t is 0, 1 or 2), —$C(O)$—, —$N(R^1)S(O)_2$—, —$S(O)_2N(R^1)$—, —$OS(O)_2N(R^1)$—, —$OC(O)$—, —C(O)O—, —N(R$^1$)C(O)O—, —N(R$^1$)C(NR$^{1a}$)N(R$^1$)—, —N(R$^1$)C(S)N(R$^1$)—, —N(R$^1$)C(NR$^{1a}$)—, —C(NR$^{1a}$)N(R$^1$)—, heteroaryl, heterocyclyl or a direct bond;

K is selected from N or C(R$^9$);

when K is N, V is —C(O)—, —C(O)O—, —C(S)—, —C(O)N(R$^1$)—, —S(O)$_t$ (where t is 0, 1 or 2), —S(O)$_q$N(R$^1$)— (where q is 1 or 2), —C(R$^8$)H— or —C(NR$^{1a}$)—;

when K is C(R$^9$), V is —O—, —C(O)—, —C(O)O—, —OC(O)—, —C(S)—, —C(O)N(R$^1$)—, —N(R$^1$)C(O)—, —S(O)$_t$-(where t is 0, 1 or 2), —S(O)$_q$N(R$^1$)— (where q is 1 or 2), —N(R$^1$)S(O)$_q$— (where q is 1 or 2), —C(R$^8$)H— or —C(NR$^{1a}$)—;

R$^4$ and R$^{4a}$ are each independently selected from the group consisting of hydrogen, alkyl, aryl, fluoro or chloro;

or R$^4$ and R$^{4a}$ together form an oxo group;

R$^5$ is selected from alkyl, aryl, heteroaryl, cyano or —N(R$^1$)$_2$;

each R$^6$ is alkyl;

or one of R$^6$ together with another R$^6$ on different carbon atom from an alkylene bridge and the other R$^6$'s are each alkyl;

R$^7$ and R$^{7a}$ are independently selected from hydrogen and alkyl;

R$^8$ is selected from hydrogen, alkyl, fluoro, chloro, methoxy, trifluoromethyl, cyano, nitro or —N(R$^1$)$_2$; and R$^9$ is selected from hydrogen, alkyl, fluoro or chloro.

Compounds of Formula (III) may be synthesized by methods known in the art, e.g., those described in International Patent Publications No. WO2006/125181, WO2007/046868, and WO2006/125194. In some embodiments, the SCD inhibitor is a compound disclosed in International Patent Publications No. WO2006/125181, WO2007/046868, and WO2006/125194, the compounds of which are herein incorporated by reference.

In some embodiments of any of the foregoing methods, the SCD inhibitor is a compound of Formula IVa-IVb:

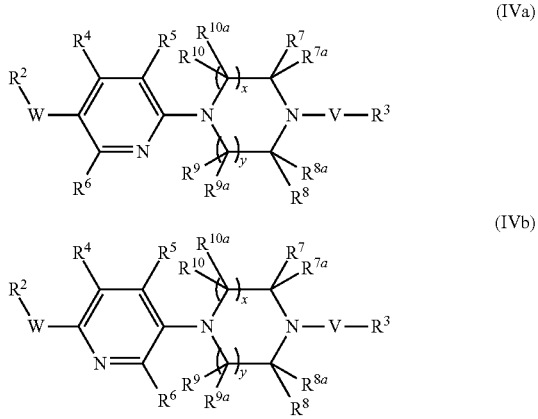

wherein:

each R$^1$ is independently selected from the group consisting of hydrogen, C$_1$-C$_{12}$alkyl, C$_2$-C$_{12}$hydroxyalkyl, C$_4$-C$_{12}$cycloalkylalkyl and C$_7$-C$_{19}$aralkyl;

R$^2$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl, and C$_3$-C$_{12}$heteroarylalkyl;

or R$^2$ is a multi-ring structure having 2 to 4 rings wherein the rings are independently selected from the group consisting of cycloalkyl, heterocyclyl, aryl and heteroaryl and where some or all of the rings may be fused to each other;

R$^3$ is selected from the group consisting of C$_1$-C$_{12}$alkyl, C$_2$-C$_{12}$alkenyl, C$_2$-C$_{12}$hydroxyalkyl, C$_2$-C$_{12}$hydroxyalkenyl, C$_2$-C$_{12}$alkoxyalkyl, C$_3$-C$_{12}$cycloalkyl, C$_4$-C$_{12}$cycloalkylalkyl, aryl, C$_7$-C$_{19}$aralkyl, C$_3$-C$_{12}$heterocyclyl, C$_3$-C$_{12}$heterocyclylalkyl, C$_1$-C$_{12}$heteroaryl and C$_3$-C$_{12}$heteroarylalkyl;

or R$^3$ is a multi-ring structure having 2 to 4 rings wherein the rings are independently selected from the group consisting of cycloalkyl, heterocyclyl, aryl and heteroaryl and where some or all of the rings may be fused to each other;

R$^7$, R$^{7a}$, R$^8$, R$^{8a}$, R$^9$, R$^{9a}$, R$^{10}$, and R$^{10a}$ are each independently selected from hydrogen or C$_1$-C$_3$alkyl;

or R$^7$ and R$^{7a}$ together, or R$^8$ and R$^{8a}$ together, or R$^9$ or R$^{9a}$ together, or R$^{10}$ and R$^{10a}$ together are an oxo group, provided that when V is —C(O)—, R$^7$ and R$^{7a}$ together or R$^8$ and R$^{8a}$ together do not form an oxo group, while the remaining R$^7$, R$^{7a}$, R$^8$, R$^{8a}$, R$^9$, R$^{9a}$, R$^{10}$ and R$^{10a}$ are each independently selected from hydrogen or C$_1$-C$_3$alkyl;

or one of R$^{10}$, R$^{10a}$, R$^7$ and R$^{7a}$ together with one of R$^8$, R$^{8a}$, R$^9$ and R$^{9a}$ form an alkylene bridge, while the remaining R$^{10}$, R$^{10a}$, R$^7$, R$^{7a}$, R$^8$, R$^{8a}$, R$^9$ and R$^{9a}$ are each independently selected from hydrogen or C$_1$-C$_3$alkyl;

R$^{11}$ is a hydrogen or C$_1$-C$_3$alkyl; and each R$^{13}$ is independently selected from hydrogen or C$_1$-C$_6$alkyl; or a stereoisomer, enantiomer or tautomer thereof, a pharmaceutically acceptable salt thereof, a pharmaceutical composition thereof or a prod rug thereof.

In some embodiments of the compound of Formula IVa,

W is —O—, —N(R$^1$)—, —C(R$^1$)$_2$—, —C(O)—, —OC(O)—, —S(O)$_t$— (where t is 0, 1 or 2), —N(R$^1$)S(O)$_t$— (where t is 1 or 2), —S(O)$_2$N(R$^1$)—, —C(O)N(R$^1$)—, —C(S)N(R$^1$)—, —OS(O)$_2$N(R$^1$)—, —OC(O)N(R$^1$)—, —OC(S)N(R$^1$)—, —N(R$^1$)C(O)N(R$^1$)— or —N(R$^1$)C(S)N(R$^1$)—;

V is —C(O)—, —C(S)—, —C(O)N(R$^1$)—, —C(O)O—, —C(S)O—, —S(O)$_t$— (where t is 1 or 2), —S(O)$_t$N(R$^1$)— (where t is 1 or 2) or —C(R$^{11}$)H;

R$^4$, R$^5$, and R$^6$ are each independently selected from hydrogen, bromo, fluoro, chloro, methyl, methoxy, trifluoromethyl, cyano, nitro, or —N(R$^{13}$)$_2$;

In some embodiments of the compound of Formula IVb,

W is —O—, —N(R$^1$)—, —C(O)—, —S(O)$_t$— (where t is 0, 1 or 2), —N(R$^1$)S(O)$_2$—, —S(O)$_2$N(R$^1$)—, —OS(O)$_2$N(R$^1$)—, —C(O)N(R$^1$)—, —OC(O)N(R$^1$)—, —C(S)N(R$^1$)—, —OC(S)N(R$^1$)—, —N(R$^1$)C(O)—, —N(R$^1$)C(O)N(R$^1$)—;

V is —C(O)—, —C(S)—, —C(O)N(R$^1$)—, —C(O)O—, —S(O)$_2$—, —S(O)$_2$N(R$^1$)— or —C(R$^1$)H—;

R$^4$, R$^5$, and R$^6$ are each independently selected from hydrogen, fluoro, chloro, methyl, methoxy, trifluoromethyl, cyano, nitro, or —N(R$^{13}$)$_2$;

In some embodiments, the invention provides compounds of Formula (IVa) having the following Formula (IVca):

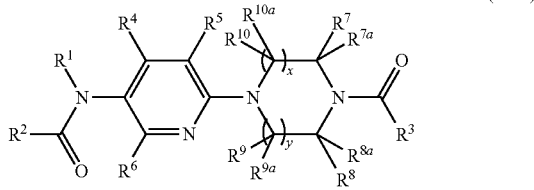

(IVca)

wherein:

$R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_1$-$C_{12}$heteroaryl, $C_3$-$C_{12}$heterocyclylalkyl, $C_3$-$C_{12}$heterocyclyl, and $C_3$-$C_{12}$heteroarylalkyl, provided that $R^2$ is not pyrazinyl, pyridinonyl, pyrrolidinonyl or imidazolyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

or $R^9$ or $R^{9a}$ together, or $R^{10}$ and $R^{10a}$ together form an oxo group, while the remaining $R^7$, $R^{7a}$, $R^8$, $R^{8a}$, $R^9$, $R^{9a}$, $R^{10}$ and $R^{10a}$ are each independently selected from hydrogen or $C_1$-$C_3$alkyl;

In some embodiments, the invention provides compounds of Formula IVa having the following Formula IVcb:

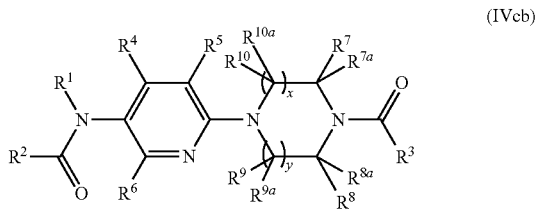

(IVcb)

wherein:

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl;

or $R^9$ or $R^{9a}$ together, or $R^{10}$ and $R^{10a}$ together form an oxo group, while the remaining $R^7$, $R^{7a}$, $R^8$, $R^{8a}$, $R^9$, $R^{9a}$, $R^{10}$ and $R^{10a}$ are each independently selected from hydrogen or $C_1$-$C_3$alkyl; and each $R^{12}$ is independently selected from hydrogen, $C_1$-$C_6$alkyl, $C_3$-$C_6$cycloalkyl, aryl or aralkyl.

In some embodiments, the invention provides compounds of Formula IVa having the following Formula IVd:

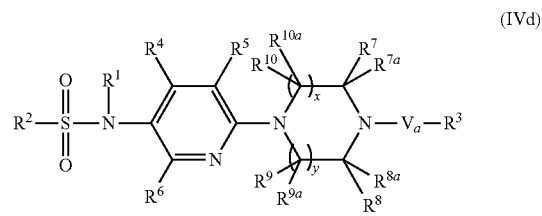

(IVd)

wherein:

$V_a$ is —C(O)—, —C(S)—, —C(O)N($R^1$)—, —C(S)N($R^1$)—, —C(O)O—, —C(S)O—, —S(O)$_t$— (where t is 1 or 2), or —S(O)$_t$N($R^1$)— (where t is 1 or 2);

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other.

In some embodiments, the invention provides compounds of Formula IVa having the following Formula IVe:

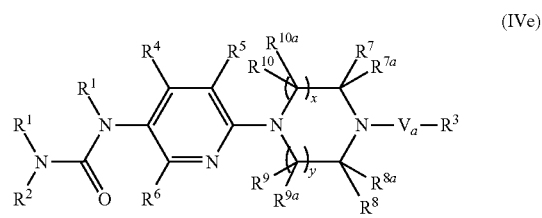

(IVe)

wherein:

$V_a$ is —C(O)—, —C(S)—, —C(O)N($R^1$)—, —C(S)N($R^1$)—, —C(O)O—, —C(S)O—, —S(O)$_t$— (where t is 1 or 2), or —S(O)$_t$N($R^1$)— (where t is 1 or 2);

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other.

In some embodiments, the invention provides compounds of Formula IVa having the following Formula IVf:

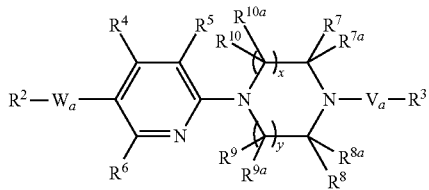

(IVf)

wherein:
$W_a$ is —O—, —N($R^1$)—, —S(O)$_t$— (where t is 0, 1 or 2);
$V_a$ is —C(O)—, —C(S)—, —C(O)N($R^1$)—, —C(S)N($R^1$)—, —C(O)O—, —C(S)O—, —S(O)$_t$— (where t is 1 or 2), or —S(O)$_t$N($R^1$)— (where t is 1 or 2);
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other.

In some embodiments, the invention provides compounds of Formula IVa having the following Formula IVaa:

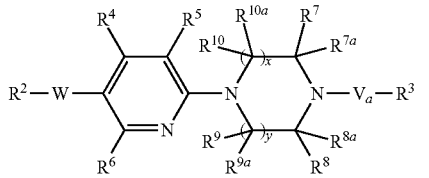

(IVaa)

wherein:
W is —N($R^1$)S(O)$_t$— (where t is 1 or 2);
V is —C(O)—, —C(S)—, —C(O)N($R^1$)—, —C(S)N($R^1$)—, —C(O)O—, —C(S)O—, —S(O)$_t$— (where t is 1 or 2), —S(O)$_t$N($R^1$)— (where t is 1 or 2) or —C($R^{11}$)H.

In some embodiments, the invention provides compounds of Formula IVb having the following Formula IVha:

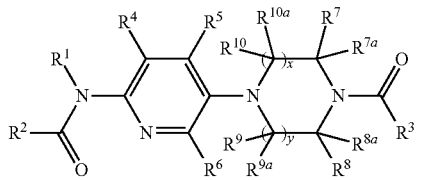

(IVha)

wherein:
$R^2$ is selected from the group consisting of $C_7$-$C_{12}$alkyl, $C_3$-$C_{12}$alkenyl, $C_7$-$C_{12}$hydroxyalkyl, $C_1$-$C_{12}$alkoxy, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_1$-$C_{12}$heteroaryl, $C_3$-$C_{12}$heterocyclylalkyl and $C_3$-$C_{12}$heteroarylalkyl, provided that $R^2$ is not pyrazinyl, pyridinonyl, pyrrolidinone or imidazolyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^9$ or $R^{9a}$ together, or $R^{10}$ and $R^{10a}$ together form an oxo group, while the remaining $R^7$, $R^{7a}$, $R^8$, $R^{8a}$, $R^9$, $R^{9a}$, $R^{10}$ and $R^{10a}$ are each independently selected from hydrogen or $C_1$-$C_3$alkyl.

In some embodiments, the invention provides compounds of Formula IVb having the following Formula IVhb:

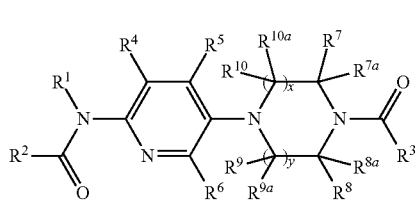

(IVhb)

wherein:
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^2$ is phenyl optionally substituted with one or more substituents selected from halo and $C_1$-$C_6$trihaloalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is phenyl optionally substituted by one or more substituents selected from the group consisting of halo, cyano, nitro, hydroxyl, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl;

or $R^9$ or $R^{9a}$ together, or $R^{10}$ and $R^{10a}$ together form an oxo group, while the remaining $R^7$, $R^{7a}$, $R^8$, $R^{8a}$, $R^9$, $R^{9a}$, $R^{10}$ and $R^{10a}$ are each independently selected from hydrogen or $C_1$-$C_3$alkyl;

each $R^{12}$ is independently selected from hydrogen, $C_1$-$C_6$alkyl, $C_3$-$C_6$cycloalkyl, aryl or aralkyl.

In some embodiments, the invention provides compounds of Formula IVb having the following Formula IVi:

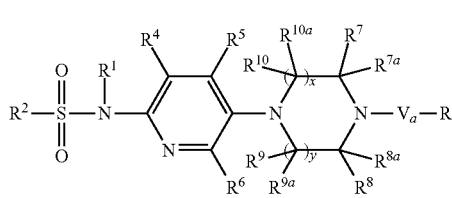

(IVi)

wherein:

$V_a$ is —C(O)—, —C(S)—, —C(O)N($R^1$)—, —C(O)O—, —S(O)$_2$— or —S(O)$_2$N($R^1$)—;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other.

In some embodiments, the invention provides compounds of Formula IVb having the following Formula IVj:

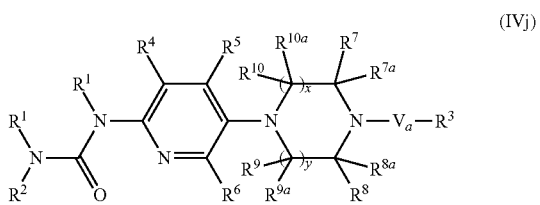

(IVj)

wherein:

$V_a$ is —C(O)—, —C(S)—, —C(O)N($R^1$)—, —C(O)O—, —S(O)$_2$— or —S(O)$_2$N($R^1$)—;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other.

In some embodiments, the invention provides compounds of Formula IVb having the following Formula IVk:

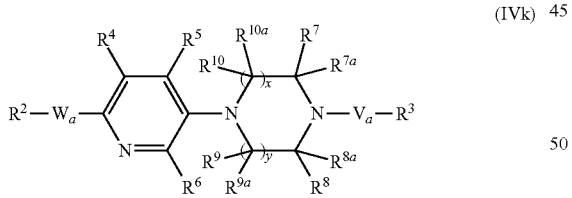

(IVk)

wherein:

$W_a$ is —O—, —N($R^1$)— or —S(O)$_t$— (where t is 0, 1 or 2);

$V_a$ is —C(O)—, —C(S)—, —C(O)N($R^1$)—, —C(O)O—, —S(O)$_2$— or —S(O)$_2$N($R^1$)—;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consist-ing of cycloalkyl, heterocyclyl, aryl and heteroaryl and where some or all of the rings may be fused to each other.

In some embodiments, the invention provides compounds of Formula IVb having the following Formula IVIa:

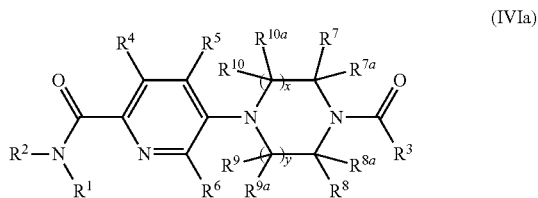

(IVIa)

wherein:

$R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl;

or $R^2$ is a multi-ring structure having 2 to 4 rings wherein the rings are independently selected from the group consist-ing of cycloalkyl, heterocyclyl, aryl and heteroaryl, where some or all of the rings may be fused to each other;

$R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_5$-$C_{12}$heteroaryl and $C_3$-$C_{12}$heteroarylalkyl;

or $R^3$ is a multi-ring structure having 2 to 4 rings wherein the rings are independently selected from the group consist-ing of cycloalkyl, heterocyclyl, aryl and heteroaryl and where some or all of the rings may be fused to each other.

In some embodiments, the invention provides compounds of Formula IVb having the following Formula IVIb:

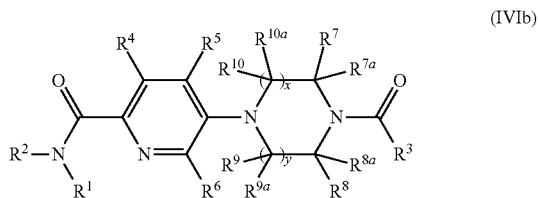

(IVIb)

wherein:

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consist-ing of cycloalkyl, heterocyclyl, aryl and heteroaryl and where some or all of the rings may be fused to each other;

$R^3$ is naphthyl or phenyl, each optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl, and provided that when $R^3$ is naphthyl, $R^2$ cannot be $C_1$-$C_6$alkyl, $C_2$-$C_6$hydroxyalkyl or phenyl substituted by amino;

each $R^{12}$ is independently selected from hydrogen, $C_1$-$C_6$alkyl, $C_3$-$C_6$cycloalkyl, aryl or aralkyl.

Compounds of Formula (IV) may be synthesized by methods known in the art, e.g., those described in International Patent Publications No. WO2005/011656 and WO2005/011654. In some embodiments, the SCD inhibitor is a compound disclosed in International Patent Publications No. WO2005/011656 and WO2005/011654, the compounds of which are herein incorporated by reference.

In some embodiments of any of the foregoing methods, the SCD inhibitor is a compound of Formula V:

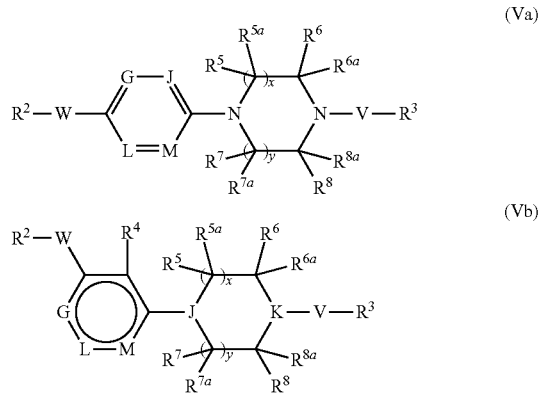

wherein:
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

each $R^5$, $R^{5a}$, $R^6$, $R^{6a}$, $R^7$, $R^{7a}$, $R^8$ and $R^{8a}$ is independently selected from hydrogen or $C_1$-$C_3$alkyl;

or $R^5$ and $R^{5a}$ together, or $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

each $R^9$ is independently selected from hydrogen or $C_1$-$C_6$alkyl.

In some embodiments of the compound of Formula $V_a$, x and y are each independently 1, 2 or 3;

G, J, L and M are each independently selected from —N= or —C($R^4$)=; provided that at most two of G, J, L and M are —N=;

V is —C(O)—, —C(O)O—, —C(S)—, —C(O)N($R^1$)—, —S(O)$_t$— (where t is 0, 1 or 2), —S(O)$_p$N($R^1$)— (where p is 1 or 2), —C($R^{10}$)H—, —N($R^1$)—, —C(=N$R^{1a}$)—, or —O—;

W is a direct bond, —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_p$— (where p is 1 or 2), —S(O)$_p$N($R^1$)— (where p is 1 or 2), —C(O)—, —OS(O)$_2$N($R^1$)—, —OC(O)—, —C(O)O—, —N($R^1$)C(O)O—, —NR$^1$C(=NR$^{1a}$)NR$^1$—, —NR$^1$C(=S)NR$^1$—, or —C(=NR$^{1a}$)NR$^1$—;

each $R^{1a}$ is independently selected from the group consisting of hydrogen, $C_1$-$C_{12}$alkyl, $C_4$-$C_{12}$cycloalkylalkyl, $C_7$-$C_{19}$aralkyl, OR$^1$, and cyano;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

each $R^4$ is independently selected from hydrogen, fluoro, chloro, methyl, methoxy, trifluoromethyl, cyano, nitro or —N($R^9$)$_2$;

or one of $R^5$, $R^{5a}$, $R^6$, and $R^{6a}$ together with one of $R^7$, $R^{7a}$, $R^8$ and $R^{8a}$ form an alkylene bridge, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is hydrogen or $C_1$-$C_3$alkyl;

provided that when G, J and L are each —C($R^4$) where each $R^4$ is hydrogen, and M is —N=, and x is 1 or 2 and y is 1; W cannot be —N($R^1$)C(O)—;

a stereoisomer, enantiomer or tautomer thereof, a pharmaceutically acceptable salt thereof.

In some embodiments of the compound of Formula Vb, x and y are each independently 0, 1, 2 or 3;

G is —N= or —C($R^4$)=;

J and K are each independently N or C($R^{10}$);

L and M are each independently —N= or —C($R^4$)=; provided that L and M cannot both be —C($R^4$)= when G is —C($R^4$)= and provided that L and M cannot both be —N= when G is —N=;

V is a direct bond, —N($R^1$)—, —N($R^1$)C(O)—, —O—, —C(O)—, —C(O)O—, —C(S)—, —C(O)N($R^1$)—, —S(O)$_p$— (where p is 0, 1 or 2) or —S(O)$_p$N($R^1$)— (where p is 1 or 2);

W is a direct bond, —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_p$— (where p is 1 or 2), —S(O)$_p$N($R^1$)— (where p is 1 or 2), —C(O)—, —OS(O)$_2$N($R^1$)—, —OC(O)—, —C(O)O—, —N($R^1$)C(O)O—;

$R^3$ is selected from the group consisting of hydrogen, $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

each $R^4$ is independently selected from hydrogen, fluoro, chloro, $C_1$-$C_{12}$alkyl, $C_1$-$C_{12}$alkoxy, haloalkyl, cyano, nitro or —N($R^9$)$_2$;

or one of $R^5$, $R^{5a}$, $R^6$, and $R^{6a}$ together with one of $R^7$, $R^{7a}$, $R^8$ and $R^{8a}$ forms a direct bridge or an alkylene bridge, while the remaining $R^5$, $R^{5a}$, $R^6$, $R^{6a}$, $R^7$, $R^{7a}$, $R^8$, and $R^{8a}$ are each independently selected from hydrogen or $C_1$-$C_3$alkyl;

$R^{10}$ is independently selected from hydrogen, fluoro, chloro, $C_1$-$C_{12}$alkyl or $C_1$-$C_{12}$alkoxy;

as a stereoisomer, enantiomer or tautomer thereof, as a mixture of stereoisomers, as a pharmaceutically acceptable salt thereof, or as a prodrug thereof.

In some embodiments, the invention provides compounds of Formula Va having the following Formula Vc:

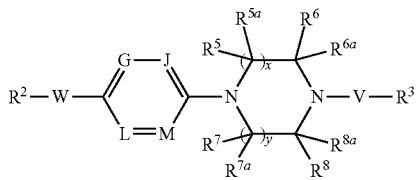

(Vc)

wherein:

W is —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_2$—, —S(O)$_2$N($R^1$)—, —C(O)—, —OS(O)$_2$N($R^1$)—, —OC(O)—, —C(O)O— or —N($R^1$)C(O)O—;

V is —C(O)—, —C(O)O—, —C(S)—, —C(O)N($R^1$)—, —S(O)$_2$—, —S(O)$_2$N($R^1$)—, —C($R^{10}$)H—;

G, J, L and M are each independently selected from —N= or —C($R^4$)=; provided that at least two of G, J, L and M are —N=, and provided that when G and J are both —C($R^4$)=, L and M cannot both be —N=, and when L and M are both —C($R^4$)=, G and J cannot both be —N=;

a stereoisomer, enantiomer or tautomer thereof, a pharmaceutically acceptable salt thereof, a pharmaceutical composition thereof or a prodrug thereof.

In some embodiments, the invention provides compounds of Formula Va having the following Formula Vd:

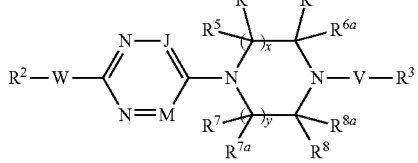

(Vd)

wherein:

W is —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_2$—, —S(O)$_2$N($R^1$)—, —C(O)—, —OS(O)$_2$N($R^1$)—, —OC(O)—, —C(O)O— or —N($R^1$)C(O)O—;

V is —C(O)—, —C(O)O—, —C(S)—, —C(O)N($R^1$)—, —S(O)$_2$—, —S(O)$_2$N($R^1$)—, —C($R^{10}$)H—;

J and M are each independently selected from —N= or —C($R^4$)=;

a stereoisomer, enantiomer or tautomer thereof, a pharmaceutically acceptable salt thereof, a pharmaceutical composition thereof or a prodrug thereof.

In some embodiments, the invention provides compounds of Formula Va having the following Formula Ve:

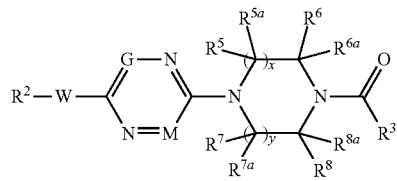

(Ve)

wherein:

W is —N($R^1$)C(O)—, —C(O)N($R^1$)— or —OC(O)N($R^1$)—;

G and M are each —C($R^4$)=;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is phenyl optionally substituted by one or more substituents selected from the group of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl;

each $R^5$, $R^{5a}$, $R^{6a}$, $R^7$, $R^{7a}$, $R^8$ and $R^{8a}$ is independently selected from hydrogen or $C_1$-$C_3$alkyl;

or $R^5$ and $R^{5a}$ together or $R^7$ and $R^{7a}$ together form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

each $R^{12}$ is independently selected from hydrogen, $C_1$-$C_6$alkyl, $C_3$-$C_6$cycloalkyl, aryl or aralkyl;

a stereoisomer, enantiomer or tautomer thereof, a pharmaceutically acceptable salt thereof, a pharmaceutical composition thereof or a prodrug thereof.

In some embodiments, the invention provides compounds of Formula Va having the following Formula Vf:

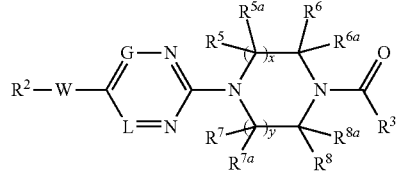

(Vf)

wherein:

W is —N($R^1$)C(O)—, —C(O)N($R^1$)— or —OC(O)N($R^1$)—;

G and L are each —C($R^4$)=;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is phenyl optionally substituted by one or more substituents selected from the group of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl;

each $R^5$, $R^{5a}$, $R^6$, $R^{6a}$, $R^7$, $R^{7a}$, $R^8$ and $R^{8a}$ is independently selected from hydrogen or $C_1$-$C_3$alkyl;

or $R^5$ and $R^{5a}$ together or $R^7$ and $R^{7a}$ together form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

each $R^{12}$ is independently selected from hydrogen, $C_1$-$C_6$alkyl, $C_3$-$C_6$cycloalkyl, aryl or aralkyl;

a stereoisomer, enantiomer or tautomer thereof, a pharmaceutically acceptable salt thereof, a pharmaceutical composition thereof or a prodrug thereof.

In some embodiments, the invention provides compounds of Formula Va having the following Formula Vca:

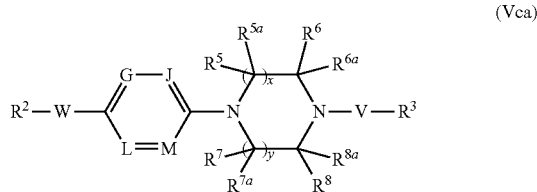

(Vca)

wherein:
W is —N($R^1$)C(O)N($R^1$)—, —O—, —N($R^1$)—, —S(O)$_t$— (where t is 0, 1 or 2), —N($R^1$)S(O)$_2$—, —S(O)$_2$N($R^1$)—, —C(O)O— or —N($R^1$)C(O)O—;

V is —C(O)—, —C(O)O—, —C(S)—, —C(O)N($R^1$)—, —S(O)$_2$—, —S(O)$_2$N($R^1$)—;

G, J, L and M are each independently selected from —N= or —C($R^4$)=; provided that at least two of G, J, L and M are —N=, and provided that when G and J are both —C($R^4$)=, L and M cannot both be —N=, and when L and M are both —C($R^4$)=, G and J cannot both be —N=;

a stereoisomer, enantiomer or tautomer thereof, a pharmaceutically acceptable salt thereof, a pharmaceutical composition thereof or a prodrug thereof.

Compounds of Formula (V) may be synthesized by methods known in the art, e.g., those described in International Patent Publications No. WO2006/086445, WO2006/034446 and WO2005/011657. In some embodiments, the SCD inhibitor is a compound disclosed in International Patent Publications No. WO2006/086445, WO2006/034446 and WO2005/011657, the compounds of which are herein incorporated by reference.

In some embodiments of any of the foregoing methods, the SCD inhibitor is a compound of Formula VI:

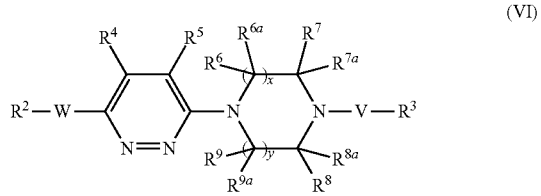

(VI)

wherein:
x and y are each independently 1, 2 or 3;
W is —C(O)N($R^1$)—, —C(O)N[C(O)$R^{1a}$]—, —N($R^1$)C(O)N($R^1$)— or —N($R^1$)C(O)—;
V is —C(O)—, —C(S)—, —C($R^{10}$)H—;
each $R^1$ is independently selected form the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl;
$R^{1a}$ is selected from the group consisting of hydrogen, $C_1$-$C_6$alkyl and cycloalkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
or $R^2$ is a multi-ring structure having 2 to 4 rings wherein the rings are independently selected from the group consisting of cycloalkyl, heterocyclyl, aryl and heteroaryl and where some or all of the rings may be fused to each other;
$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
or $R^3$ is a multi-ring structure having 2 to 4 rings wherein the rings are independently selected from the group consisting of cycloalkyl, heterocyclyl, aryl and heteroaryl and where some or all of the rings may be fused to each other;
$R^4$ and $R^5$ are each independently selected from hydrogen, fluoro, chloro, methyl, methoxy, trifluoromethyl, cyano, nitro or —N($R^{12}$)$_2$;
$R^6$, $R^{6a}$, $R^7$, $R^{7a}$, $R^8$, $R^{8a}$, $R^9$ and $R^{9a}$ are each independently selected from hydrogen or $C_1$-$C_3$alkyl;
or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$ and $R^{9a}$ are each independently selected from hydrogen or $C_1$-$C_3$alkyl;
or one of $R^6$, $R^{6a}$, $R^7$ and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$ and $R^{9a}$ are each independently selected from hydrogen or $C_1$-$C_3$alkyl;
$R^{10}$ is hydrogen or $C_1$-$C_3$alkyl; and
each $R^{12}$ is independently selected from hydrogen or $C_1$-$C_6$alkyl;
a stereoisomer, enantiomer or tautomer thereof, a pharmaceutically acceptable salt thereof, a pharmaceutical composition thereof or a prodrug thereof.

In some embodiments, the invention provides compounds of Formula VI having the following Formula VIa:

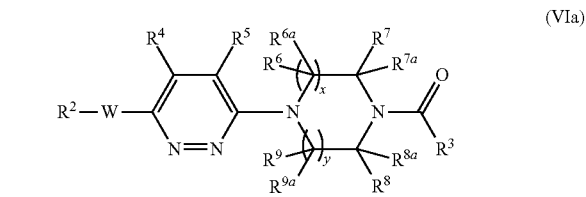

(VIa)

wherein:

W is —C(O)N($R^1$)— or —N($R^1$)C(O)—;

$R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_5$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, and trifluoromethyl.

In some embodiments, the invention provides compounds of Formula VI having the following Formula VIb:

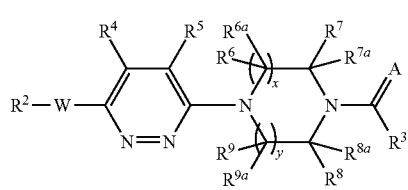

(VIb)

wherein:

A is oxygen or sulfur;

W is —C(O)N($R^1$)— or —N($R^1$)C(O)—;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{11}$)$_2$, —OC(O)$R^{11}$, —C(O)O$R^{11}$, —S(O)$_2$N($R^{11}$)$_2$, cycloalkyl, heterocyclyl, heteroaryl and heteroarylcycloalkyl, provided that $R^3$ is not phenyl substituted with optionally substituted thienyl;

$R^4$ and $R^5$ are each independently selected from hydrogen, fluoro, chloro, methyl, methoxy, and trifluoromethyl.

each $R^{11}$ is independently selected from hydrogen, $C_1$-$C_6$alkyl, $C_3$-$C_6$cycloalkyl, aryl or aralkyl.

In some embodiments, the invention provides compounds of Formula VI having the following Formula VIc:

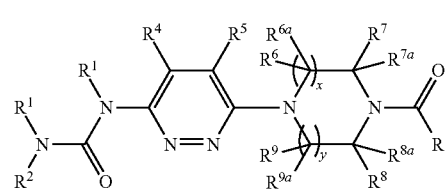

(VIc)

wherein:

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, aryl, $C_7$-$C_{19}$aralkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, and trifluoromethyl.

In some embodiments, the invention provides compounds of Formula VI having the following Formula VIda:

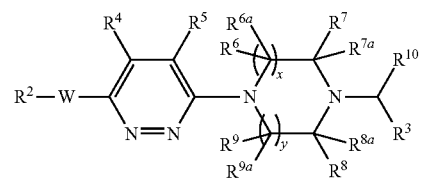

(VIda)

wherein:

W is —C(O)N($R^1$)—, —N($R^1$)C(O)N($R^1$)— or —N($R^1$)C(O)—;

$R^2$ is selected from the group consisting of $C_7$-$C_{12}$alkyl, $C_2$-$C_{12}$alkenyl, $C_7$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, $C_{13}$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^{10}$ is hydrogen or $C_1$-$C_3$alkyl; and each $R^{12}$ is independently selected from hydrogen or $C_1$-$C_6$alkyl;

provided, however, that $R^2$ cannot be pyrazinyl, pyridinonyl, pyrrolidinonyl or imidazolyl.

In some embodiments, the invention provides compounds of Formula VI having the following Formula VIdb:

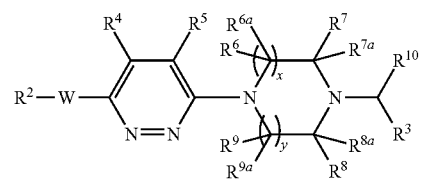

(VIdb)

wherein:

W is —C(O)N($R^1$)—, —N($R^1$)C(O)N($R^1$)— or —N($R^1$)C(O)—;

$R^3$ is selected from the group consisting of $C_7$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy or $C_2$-$C_{12}$alkoxyalkyl.

In some embodiments, the invention provides compounds of Formula VI having the following Formula VIe:

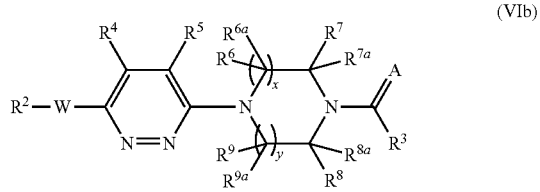

(VIb)

wherein:

W is a direct bond, —C(O)N($R^1$)—, —C(O)N[C(O)$R^{1a}$]—, —N($R^1$)C(O)N($R^1$)—, —N($R^1$)C(O)—, —OC(O)N($R^1$)—, —N($R^1$)S(O)$_p$— (where p is 1 or 2), —S(O)$_p$N($R^1$)— (where p is 1 or 2), —C(O)—, —OS(O)$_2$N($R^1$)—, —O(C)O—, —C(O)O—, —N($R^1$)C(O)O—, —N($R^1$)C(=N$R^{1a}$)N($R^1$)—, —N($R^1$)C(=S)N($R^1$)—, —N($R^1$)C(=N$R^{1a}$)—, or —C(=N$R^{1a}$)N($R^1$)—;

V is —C(O)—, —C(O)O—, —C(S)—, —C(O)N($R^1$), —S(O)$_t$— (where t is 0, 1, or 2), —S(O)$_p$N($R^1$)— (where p is 1 or 2), —C($R^{10}$)H— or —C(=N$R^{1a}$)—;

$R^{1a}$ is selected from the group consisting of hydrogen, —O$R^1$, cyano, $C_1$-$C_6$alkyl and cycloalkylalkyl.

Compounds of Formula (VI) may be synthesized by methods known in the art, e.g., those described in International Patent Publications No. WO2005/011655, WO2006/086447 and WO2009/106991. In some embodiments, the SCD inhibitor is a compound disclosed in International Patent Publications No. WO2005/011655, WO2006/086447 and WO2009/106991, the compounds of which are herein incorporated by reference.

In some embodiments of any of the foregoing methods, the SCD inhibitor is a compound of Formula VII:

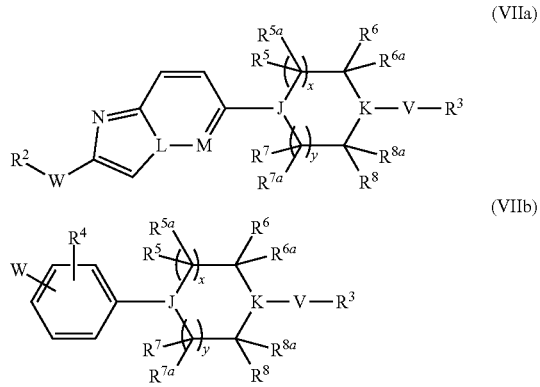

wherein:

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or $R^5$ and $R^{5a}$ together, $R^6$ and $R^{6a}$ together, or $R^7$ and $R^{7a}$ together, or $R^8$ and $R^{8a}$ together are an oxo group, provided that when V is —C(O)—, $R^6$ and $R^{6a}$ together or $R^8$ and $R^{8a}$ together do not form an oxo group, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

or one of $R^5$, $R^{5a}$, $R^6$ and $R^{6a}$ together with one of $R^7$, $R^{7a}$, $R^8$ and $R^{8a}$ forms a direct bond or an alkylene bridge, while the remaining $R^5$, $R^{5a}$, $R^6$, $R^{6a}$, $R^7$, $R^{7a}$, $R^8$ and $R^{8a}$ are each independently selected from hydrogen or $C_1$-$C_3$alkyl;

each $R^9$ is independently selected from hydrogen or $C_1$-$C_6$alkyl;

as a stereoisomer, enantiomer or tautomer thereof, as a mixture of stereoisomers, as a pharmaceutically acceptable salt thereof, or as a prodrug thereof.

In some embodiments of the compound of Formula VIIa, x and y are each independently 1, 2 or 3;

J and K are each independently N or C($R^{11}$);

L is N or C($R^4$);

M is —N= or —C($R^4$)=;

W is a direct bond, —N($R^1$)C(O)—, —C(O)N($R^1$)—, —OC(O)N($R^1$)—, —N($R^1$)C(O)N($R^1$)—, —O—, —N($R^1$)—, —S(O)$_t$— (where t is 0, 1 or 2), —N($R^1$)S(O)$_p$— (where p is 1 or 2), —S(O)$_p$N($R^1$)— (where p is 1 or 2), —C(O)—, —OS(O)$_2$N($R^1$)—, —OC(O)—, —C(O)O—, —N($R^1$)C(O)O— or —C($R^1$)$_2$—;

V is —N($R^1$)—, —N($R^1$)C(O)—, —C(O)—, —C(O)O—, —C(S)—, —C(O)N($R^1$)—, —S(O)$_p$— (where p is 0, 1 or 2) or —S(O)$_p$N($R^1$)— (wherein p is 1 or 2) or —C($R^{10}$)H;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

each $R^4$ is independently selected from hydrogen, fluoro, chloro, $C_1$-$C_{12}$alkyl, $C_1$-$C_{12}$alkoxy, haloalkyl, cyano, nitro or —N($R^9$)$_2$;

$R^{10}$ is a hydrogen or $C_1$-$C_3$alkyl; and $R^{11}$ is independently selected from hydrogen, fluoro, chloro, $C_1$-$C_{12}$alkyl or $C_1$-$C_{12}$alkoxy;

In some embodiments of the compound of Formula VIIb, x and y are each independently 0, 1, 2 or 3;

J and K are each independently N or C($R^{01}$);

V is a direct bond, —N($R^1$)—, —N($R^1$)C(O)—, —O—, —C(O)—, —C(O)O—, —C(S)—, —C(O)N($R^1$)—, —S(O)$_p$— (where p is 0, 1 or 2) or —S(O)$_p$N($R^1$)— (where p is 1 or 2);

W is $R^2$—N($R^1$)C(O)—, $R^2$—C(O)N($R^1$)—, $R^2$—OC(O)N($R^1$)—, $R^2$—N($R^1$)C(O)N($R^1$)—, $R^2$—O—, $R^2$—N($R^1$)—, $R^2$—S(O)$_t$— (where t is 0, 1 or 2), $R^2$—N($R^1$)S(O)$_p$— (where p is 1 or 2), $R^2$—S(O)$_p$N($R^1$)— (where p is 1 or 2), $R^2$—C(O)—, $R^2$—OS(O)$_2$N($R^1$)—, $R^2$—OC(O)—, $R^2$—C(O)O—, $R^2$—N($R^1$)C(O)O— or $R^2$—C($R^1$)$_2$—;

$R^3$ is selected from the group consisting of hydrogen, $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl, provided that $R^3$ is not optionally substituted cyclopentyl or an optionally substituted 5-membered heterocyclic ring;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ is hydrogen, fluoro, chloro, hydroxyl, $C_1$-$C_{12}$alkyl, $C_1$-$C_{12}$alkoxy, haloalkyl, cyano, nitro or —N($R^9$)$_2$;

each $R^{o1}$ is independently selected from hydrogen, fluoro, chloro, $C_1$-$C_{12}$alkyl or $C_1$-$C_{12}$alkoxy.

In some embodiments, the invention provides compounds of Formula VIIa having the following Formula VIIc:

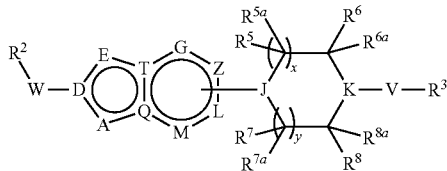

(VIIc)

A, D, E, G, Z, L, and M are each independently N, NH or C($R^4$);

T and Q are each independently C or N.

In some embodiments, the invention provides compounds of Formula VIIb having the following Formula VIId:

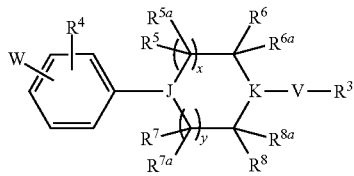

(VIId)

W is —CN, $R^2$—N($R^1$)C(O)—, $R^2$—C(O)N($R^1$)—, $R^2$—OC(O)N($R^1$)—, $R^2$—N($R^1$)C(O)N($R^1$)—, $R^2$—O—, $R^2$—N($R^1$)—, $R^2$—S(O)$_t$— (where t is 0, 1 or 2), $R^2$—N($R^1$)S(O)$_p$— (where p is 1 or 2), $R^2$—S(O)$_p$N($R^1$)— (where p is 1 or 2), $R^2$—C(O)—, $R^2$—OS(O)$_2$N($R^1$)—, $R^2$—OC(O)—, $R^2$—C(O)O—, $R^2$—N($R^1$)C(O)O— or $R^2$—C($R^1$)$_2$—.

Compounds of Formula (VII) may be synthesized by methods known in the art, e.g., those described in International Patent Publications No. WO2006/034312 and WO2006/034441. In some embodiments, the SCD inhibitor is a compound disclosed in International Patent Publications No. WO2006/034312 and WO2006/034441, the compounds of which are herein incorporated by reference.

In some embodiments of any of the foregoing methods, the SCD inhibitor is a compound of Formula VIII:

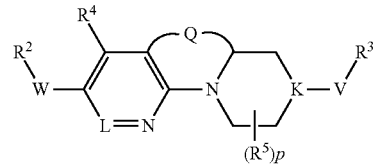

(VIIIa)

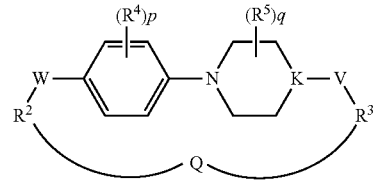

(VIIIb)

wherein:

K is selected from N or C($R^6$);

L is —N= or —C($R^4$)=;

each $R^1$ is independently selected from the group consisting of hydrogen, alkyl, hydroxyalkyl, cycloalkylalkyl and aralkyl;

each $R^5$ is alkyl;

or one of $R^5$ together with one of $R^5$ on a different carbon atom form an alkylene bridge, while the remaining $R^5$'s are each alkyl;

$R^6$ is hydrogen, alkyl, fluoro or chloro; and $R^7$ is hydrogen, alkyl, fluoro, chloro, methoxy, trifluoromethyl, cyano, nitro or —N($R^1$)$_2$;

or a stereoisomer, enantiomer or tautomer thereof, or a racemic or non-racemic mixture thereof, or a pharmaceutically acceptable salt or prodrug thereof.

In some embodiments of the compound of Formula VIIIa, p is 0 to 7;

Q is an optionally substituted alkylene bridge or —(CH$_2$)$_x$A(CH$_2$)$_y$— where x and y are independently selected from 0, 1, 2, or 3 and A is selected from —O—, —C(O)—, —N($R^1$)—, —N($R^1$)C(O)—, —C(O)N($R^1$)—, —S(O)$_t$- (where t is 0, 1 or 2);

W is —N($R^1$)C(O)—, —C(O)N($R^1$)—, —OC(O)N ($R^1$)—, —N($R^1$)C(O)N($R^1$)—, —O—, —N($R^1$)—, —S(O)$_t$— (where t is 0, 1 or 2), —C(O)—, —N($R^1$)S(O)$_2$—, —S(O)$_2$N($R^1$)—, —OS(O)$_2$N($R^1$)—, —OC(O)—, —C(O)O—, —N($R^1$)C(O)O—, —N($R^1$)C(N$R^{1a}$)N($R^1$)—, —N($R^1$)C(S)N($R^1$)—, —N($R^1$)C(N$R^{1a}$)—, —C(N$R^{1a}$)N ($R^1$)—, heteroaryl, heterocyclyl or a direct bond;

when K is C($R^6$), V is —O—, —C(O)—, —C(O)O—, —OC(O)—, —C(S)—, —C(O)N($R^1$)—, —N($R^1$)C(O)—, —S(O)$_t$-(where t is 0, 1 or 2), —S(O)$_q$N($R^1$)— (where q is 1 or 2), —N($R^1$)S(O)$_q$— (where q is 1 or 2), —C($R^7$)H— or —C(N$R^{1a}$)—;

each $R^{1a}$ is selected from the group consisting of hydrogen, $C_1$-$C_6$alkyl, cycloalkylalkyl, —O$R^1$ and cyano;

$R^2$ is selected from the group consisting of alkylene, cycloalkyl, aryl, heterocyclyl, and heteroaryl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is alkyl, alkenyl, hydroxyalkyl, hydroxyalkenyl, alkoxyalkyl, cycloalkyl, cycloalkylalkyl, aryl, aralkyl, heterocyclyl, heterocyclylalkyl, heteroaryl and heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ is hydrogen, fluoro, chloro, methyl, methoxy, trifluoromethyl, cyano, nitro or —N(R$^1$)$_2$.

In some embodiments of the compound of Formula VIIIb,
p is 0 to 2;
q is 0 to 8;
W is —N(R$^1$)C(O)—, —C(O)N(R$^1$)—, —OC(O)N(R$^1$)—, —N(R$^1$)C(O)N(R$^1$)—, —O—, —N(R$^1$)—, —S(O)$_t$— (where t is 0, 1 or 2), —C(O)—, —N(R$^1$)S(O)$_2$—, —S(O)$_2$N(R$^1$)—, —OS(O)$_2$N(R$^1$)—, —OC(O)—, —C(O)O—, —N(R$^1$)C(O)O—, —NR$^1$C(=NR$^{1a}$)NR$^1$—, —NR$^1$C(=S)NR$^1$—, —NR$^1$(R$^{1a}$N)C—, or —C=(NR$^{1a}$)NR$^1$—, a heteroaryl group, a heterocyclyl group or a direct bond;

V is —C(O)—, —C(O)O—, —C(S)—, —C(O)N(R$^1$)—, —S(O)$_t$ (where t is 0, 1 or 2), —S(O)$_p$N(R$^1$)— (where p is 1 or 2), —C(R$^7$)H— or —C(=NR$^{1a}$)—;

Q is an optionally substituted C$_8$-C$_{20}$alkylene bridge, or —(CH$_2$)$_x$A(CH$_2$)$_y$— where x and y are independently selected from 0 to 10 provided that the sum of x and y is 8 to 20, and A is selected from —O—, —C(O)—, —N(R$^1$)C(O)—, —C(O)N(R$^1$)—, —N(R$^1$)—, —S(O)$_t$— (where t is 0, 1 or 2), —S(O)$_p$N(R$^1$)— (where p is 1 or 2), aryl, heterocyclyl, or heteroaryl;

$R^{1a}$ is selected from the group consisting of hydrogen, C$_1$-C$_6$alkyl and cycloalkylalkyl, —OR$^1$, nitro, —S(O)$_2$R$^{1b}$, and cyano;

$R^{1b}$ is C$_1$-C$_6$alkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of cycloalkyl, aryl, heterocyclyl, heterocyclylalkyl, heteroaryl, heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

each $R^4$ is independently selected from alkyl, fluoro, chloro, methyl, methoxy, trifluoromethyl, cyano, nitro or —N(R$^1$)$_2$.

Compounds of Formula (VIII) may be synthesized by methods known in the art, e.g., those described in International Patent Publications No. WO2006/125179 and WO2007/136746. In some embodiments, the SCD inhibitor is a compound disclosed in International Patent Publications No. WO2006/125179 and WO2007/136746, the compounds of which are herein incorporated by reference.

In some embodiments of any of the foregoing methods, the SCD inhibitor is a compound of Formula IX:

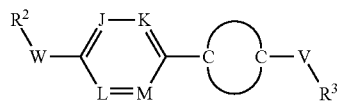

wherein:
W is —N(R$^1$)C(O)—, —C(O)N(R$^1$)—, —OC(O)N(R$^1$)—, —N(R$^1$)C(O)N(R$^1$)—, —O—, —N(R$^1$)—, —S(O)$_t$— (where t is 0, 1 or 2), —C(O)—, —N(R$^1$)S(O)$_2$—, —S(O)$_2$N(R$^1$)—, —OS(O)$_2$N(R$^1$)—, —OC(O)—, —C(O)O—, —N(R$^1$)C(O)O—, —N(R$^1$)C(NR$^{1a}$)N(R$^1$)—, —N(R$^1$)C(S)N(R$^1$)—, —N(R$^1$)C(NR$^{1a}$)—, —C(NR$^{1a}$)N(R$^1$)—, heteroaryl, heterocyclyl or a direct bond;

V is —O—, —C(O)—, —C(O)O—, —OC(O)—, —C(S)—, —C(O)N(R$^1$)—, —N(R$^1$)C(O)—, —S(O)$_t$— (where t is 0, 1 or 2), —S(O)$_q$N(R$^1$)— (where q is 1 or 2), —N(R$^1$)S(O)$_q$— (where q is 1 or 2), —C(R$^5$)H— or —C(NR$^{1a}$)—;

is selected from cycloalkyl, aryl, heterocyclyl, or heteroaryl;

J, K, L and M are independently selected from —N= or —C(R$^4$)=;

each $R^1$ is independently selected from the group consisting of hydrogen, alkyl, hydroxyalkyl, cycloalkylalkyl and aralkyl;

each $R^{1a}$ is selected from the group consisting of hydrogen, C$_1$-C$_6$alkyl, cycloalkylalkyl, —OR$^1$, and cyano;

$R^2$ is selected from the group consisting of alkyl, alkenyl, hydroxyalkyl, hydroxyalkenyl, alkoxyalkyl, cycloalkyl, cycloalkylalkyl, aryl, aralkyl, heterocyclyl, heterocyclylalkyl, heteroaryl, and heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of alkyl, alkenyl, hydroxyalkyl, hydroxyalkenyl, alkoxyalkyl, cycloalkyl, cycloalkylalkyl, aryl, aralkyl, heterocyclyl, heterocyclylalkyl, heteroaryl and heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other; and $R^4$ is selected from hydrogen, alkyl, fluoro, chloro, methoxy, trifluoromethyl, cyano, nitro or —N(R$^1$)$_2$;

or a stereoisomer, enantiomer or tautomer thereof, or a racemic or non-racemic mixture thereof, or a pharmaceutically acceptable salt or prodrug thereof.

Compounds of Formula (IX) may be synthesized by methods known in the art, e.g., those described in International Patent Publication No. WO2007/044085. In some embodiments, the SCD inhibitor is a compound disclosed in International Patent Publication No. WO2007/044085, the compounds of which are herein incorporated by reference.

In some embodiments of any of the foregoing methods, the SCD inhibitor is a compound of Formula X,

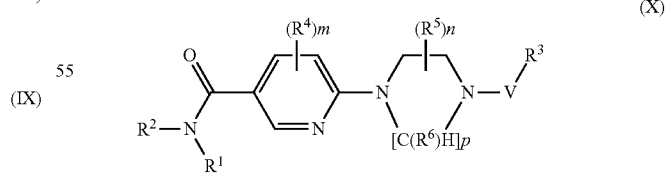

wherein:
m is 1, 2 or 3;
n is 1, 2, 3 or 4;
p is 2, 3 or 4;
V is —C(O)—, —S(O)— or —S(O)$_2$;
$R^1$ is hydrogen, alkyl, alkenyl, aryl, heteroaryl, aralkyl, aralkenyl or cycloalkyl;

R² is selected from the group consisting of hydrogen, —R⁷—OR⁸, —R⁷—N(R⁸)₂, —R⁷—S(O)ₜR¹⁰ (where t is 0, 1 or 2), alkyl, alkenyl, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl and optionally substituted heteroarylalkenyl;

R³ is selected from the group consisting of hydrogen, —R⁹—OR⁸, —R⁹—N(R⁸)₂, alkyl, alkenyl, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl and optionally substituted heteroarylalkenyl;

each R⁴ is independently hydrogen, alkyl, alkenyl, halo, haloalkyl, aryl, cyano, nitro, —R⁹—OR⁸, —R⁹—N(R⁸)₂ or —S(O)ₜR¹⁰ (where t is 0, 1 or 2);

each R⁵ and R⁶ is independently hydrogen, oxo, alkyl, alkenyl, halo, haloalkyl or aryl;

or one R⁵ and one R⁶ may together form an straight or branched alkylene bridge;

each R⁷ is independently a straight or branched alkylene or alkenylene chain;

each R⁸ is independently hydrogen, alkyl, alkenyl, haloalkyl, cycloalkyl, cycloalkylalkyl, aryl, aralkyl, heterocyclyl, heterocylylalkyl, heteroaryl or heteroarylalkyl;

each R⁹ is independently a direct bond or a straight or branched alkylene or alkenylene chain; and R¹⁰ is alkyl, alkenyl, haloalkyl, cycloalkyl, cycloalkylalkyl, aryl, aralkyl, heterocyclyl, heterocylylalkyl, heteroaryl or heteroarylalkyl;

as a single stereoisomer, a mixture of stereoisomers, a racemic mixture thereof of stereoisomers, or as a tautomer.

Compounds of Formula (X) may be synthesized by methods known in the art, e.g., those described in International Patent Publication No. WO2006/014168. In some embodiments, the SCD inhibitor is a compound disclosed in International Patent Publication No. WO2006/014168, the compounds of which are herein incorporated by reference.

In some embodiments of any of the foregoing methods, the SCD inhibitor is a compound of Formula XI,

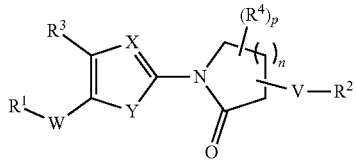

(XI)

wherein:
X is CH or N;
Y is NH, N—CH₃, O or S;
W is selected from —N(R⁵)C(O)—, —C(O)N(R⁵)—, —OC(O)N(R⁵)—, —N(R⁵)C(O)O—, —N(R⁵)C(O)N(R⁵)—, —O—, —S—, —N(R⁵)—, —S(O)ₜ—, —N(R⁵)S(O)ₜ—, —S(O)ₜN(R⁵)—, —OS(O)ₜN(R⁵)—, C(O)—, —OC(O)—, —C(O)O—, —N(R⁵)C(═N(R⁵ᵃ))NR⁵—, —N(R⁵)((R⁵ᵃ)N═)C—, —C(═N(R⁵ᵃ))N(R⁵)—, or a direct bond;

V is selected from —N(R⁵)C(O)—, —C(O)N(R⁵)—, —OC(O)N(R⁵)—, —N(R⁵)C(O)O—, —N(R⁵)C(O)N(R⁵)—, —O—, —S—, —N(R⁵)—, —S(O)ₜ—, —N(R⁵)S(O)ₜ—, —S(O)ₜN(R⁵)—, —OS(O)ₜN(R⁵)—, C(O)—, —OC(O)—, —C(O)O—, —N(R⁵)C(═N(R⁵ᵃ))NR⁵—, —N(R⁵)((R⁵ᵃ)N═)C—, —C(═N(R⁵ᵃ))N(R⁵)—, ═C(R⁵)— or a direct bond;

n is 0, 1, 2 or 3;
p is an integer from 0 to 9;
t is 1 or 2;

R¹ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;

or R¹ is a multi-ring structure having 2 to 4 rings wherein the rings are independently selected from the group consisting of cycloalkyl, heterocyclyl, aryl and heteroaryl and where some or all of the rings may be fused to each other;

R² is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;

or R² is a multi-ring structure having 2 to 4 rings wherein the rings are independently selected from the group consisting of cycloalkyl, heterocyclyl, aryl and heteroaryl and where some or all of the rings may be fused to each other;

R³ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, haloalkyl, haloalkoxy, cyano and —N(R⁵)₂;

each R⁴ is independently selected from the group consisting of alkyl, halo, haloalkyl, haloalkoxy, hydroxyl, hydroxyalkyl, alkoxy, —N(R⁵)₂, cycloalkylalkyl and aralkyl;

or two R⁴s attached to the same carbon form an oxo while each of the remaining R⁴s are as described above;

each R⁵ is independently selected from the group consisting of hydrogen, alkyl, aryl, heteroaryl, cycloalkyl, hydroxyalkyl, cycloalkylalkyl and aralkyl; and R⁵ᵃ is selected from the group consisting of hydrogen, alkyl, cycloalkylalkyl and cyano; or a stereoisomer, enantiomer or tautomer thereof, a pharmaceutically acceptable salt thereof, a pharmaceutical composition thereof or a prodrug thereof.

Compounds of Formula (XI) may be synthesized by methods known in the art, e.g., those described in International Patent Publication No. WO2008/036715. In some embodiments, the SCD inhibitor is a compound disclosed in International Patent Publication No. WO2008/036715, the compounds of which are herein incorporated by reference.

In some embodiments of any of the foregoing methods, the SCD inhibitor is a compound of Formula XII,

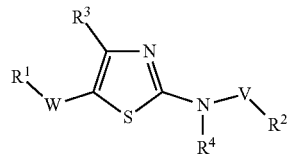

(XII)

wherein:
W is selected from —O—, —OC(O)—, —OC(O)N(R⁵)—, —OS(O)₂N(R⁵)—, —C(O)—, —C(O)O—, —C(O)

—N(R$^5$)—, —N(R$^5$)—, —N(R$^5$)C(O)—, —N(R$^5$)C(O)O—, —N(R$^5$)C(O)N(R$^5$)—, —N(R$^5$)S(O)$_2$, —S(O)$_t$— (where t is 0, 1 or 2), or —S(O)$_2$N(R$^5$)—;

V is selected from —C(O)—, —C(O)N(R$^5$)—, —C(O)O—, —S(O)$_t$— (where t is 1 or 2) or a direct bond;

R$^1$ is selected from the group consisting of alkyl, alkenyl, —R$^6$—OR$^7$, hydroxyalkenyl, cycloalkyl, cycloalkylalkyl, aryl, aralkyl, aralkenyl, heterocyclyl, heterocyclylalkyl, heteroaryl, and heteroarylalkyl;

or R$^1$ is a multi-ring structure having 2 to 4 rings wherein the rings are independently selected from the group consisting of cycloalkyl, heterocyclyl, aryl and heteroaryl and where some or all of the rings may be fused to each other;

R$^2$ is selected from the group consisting of alkyl, alkenyl, —R$^6$—OR$^7$, hydroxyalkenyl, cycloalkyl, cycloalkylalkyl, aryl, aralkyl, aralkenyl, heterocyclyl, heterocyclylalkyl, heteroaryl and heteroarylalkyl;

or R$^2$ is a multi-ring structure having 2 to 4 rings wherein the rings are independently selected from the group consisting of cycloalkyl, heterocyclyl, aryl and heteroaryl and where some or all of the rings may be fused to each other;

R$^3$ is selected from hydrogen, alkyl, alkenyl, hydroxyalkyl, hydroxyalkenyl, alkoxyalkyl, cycloalkyl, cycloalkylalkyl, heterocyclyl, aryl, aralkyl, heteroaryl, fluoro, chloro, bromo, trihaloalkyl, trihaloalkoxy, cyano, nitro, —OR$^4$, —OC(O)R$^2$, —N(R$^5$)C(O)OR$^5$, —N(R$^5$)C(O)N(R$^4$)(R$^5$) or —N(R$^5$)S(O)$_2$R$^2$;

each R$^4$ and R$^5$ is independently selected from the group consisting of
R$^6$—N(R$^7$)$_2$, —R$^6$—OR$^7$, —R$^6$—C(O)OR$^7$, hydrogen, alkyl, cycloalkylalkyl and aralkyl;

each R$^6$ is a straight or branched alkylene chain; and each R$^7$ is hydrogen, alkyl, aryl or aralkyl;

or a stereoisomer, enantiomer or tautomer thereof, or a racemic or non-racemic mixture thereof, or a pharmaceutically acceptable salt or prodrug thereof.

Compounds of Formula (XII) may be synthesized by methods known in the art, e.g., those described in International Patent Publication No. WO2007/130075. In some embodiments, the SCD inhibitor is a compound disclosed in International Patent Publication No. WO2007/130075, the compounds of which are herein incorporated by reference.

In some embodiments of any of the foregoing methods, the SCD inhibitor is a compound of Formula XIII,

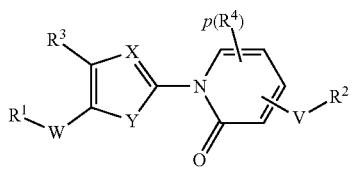

(XIII)

wherein:
V is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —N(R$^5$)—, —S—, —S(O)$_t$—, —N(R$^5$)S(O)$_t$—, —S(O)$_t$N(R$^5$)—, —OS(O)$_2$, —OS(O)$_2$N(R$^5$)—, —C(O)—, —OC(O)—, —C(O)O—, —N(R$^5$)C(=N(R$^{5a}$))NR$^5$—, —N(R$^5$)C(=S)NR$^5$—, —N(R$^5$)((R$^{5a}$)N=)C—, —C(=N(R$^{5a}$))N(R$^5$)—, alkylene, alkenylene, alkynylene, aryl, heteroaryl, a cycloalkyl, a heterocyclyl, or a direct bond;

W is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —N(R$^5$)—, —S—, —S(O)$_t$—, —N(R$^5$)S(O)$_t$—, —S(O)$_t$N(R$^5$)—, —OS(O)$_2$N(R$^5$)—, —C(O)—, —OC(O)—, —C(O)O—, —N(R$^5$)C(=N(R$^{5a}$))NR$^5$—, —N(R$^5$)((R$^{5a}$)N=)C—, —C(=N(R$^{5a}$))N(R$^5$)—, aryl, a heteroaryl, heterocyclyl, alkynylene, alkenylene, alkylene or direct bond;

X is selected from C(H) or N;

Y is selected from S, O, N(H) or N(CH$_3$);

p is 0, 1, 2, or 3;

t is 1 or 2;

R$^1$ is selected from the group consisting of hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl, and heteroarylalkyl;

or R$^1$ is a multi-rins structure having 2 to 4 rings wherein the rings are independently selected from the group consisting of cycloalkyl, heterocyclyl, aryl and heteroaryl and where some or all of the rings may be fused to each other;

R$^2$ is selected from the group consisting of hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl and heteroarylalkyl;

or R$^2$ is a multi-ting structure having 2 to 4 rings wherein the rings are independently selected from the group consisting of cycloalkyl, heterocyclyl, aryl and heteroaryl and where some or all of the rings may be fused to each other;

R$^3$ is selected from the group consisting of hydrogen, alkyl, alkenyl, alkoxy, hydroxyalkyl, alkoxyalkyl, cycloalkyl, cycloalkylalkyl, heterocyclyl, aryl, aralkyl, heteroaryl, halo, haloalkyl, trihaloalkoxyl, cyano and —N(R$^5$)$_2$;

R$^4$ is selected from the group consisting of alkyl, hydroxyalkyl, cycloalkylalkyl, aralkyl, halo, haloalkyl, —OCF$_3$, —OC(H)F$_2$, and cyano;

or two adjacent R$^4$ groups, together with the carbon atoms to which they are attached, may form a cycloalkyl, heterocyclyl, aryl or heteroaryl and the remaining R$^4$ groups, if present, are as described above;

R$^5$ is selected from the group consisting of hydrogen, aryl, alkyl, heteroaryl, heterocyclyl, haloalkyl, hydroxyalkyl, cycloalkylalkyl and aralkyl;

R$^{5a}$ is selected from the group consisting of hydrogen, alkyl, cycloalkylalkyl and cyano; a stereoisomer, enantiomer or tautomer thereof, a pharmaceutically acceptable salt thereof, a pharmaceutical composition thereof or a prodrug thereof.

Compounds of Formula (XIII) may be synthesized by methods known in the art, e.g., those described in International Patent Publication No. WO2007/143597. In some embodiments, the SCD inhibitor is a compound disclosed in International Patent Publication No. WO2007/143597, the compounds of which are herein incorporated by reference.

In some embodiments of any of the foregoing methods, the SCD inhibitor is a compound of Formula XIV,

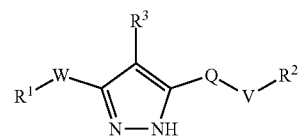

(XIV)

wherein:
Q is

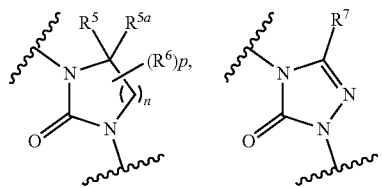

W is —N(R$^8$)C(O)—, —C(O)N(R$^8$)—, C$_1$-C$_6$alkylene, C$_2$-C$_6$alkeneylene, C$_2$-C$_6$alkynylene or a direct bond;

V is selected from a C$_1$-C$_6$alkylene;

n is 1, 2, or 3;

p is 1, 2, 3, 5, or 6;

R$^1$ is hydrogen, an optionally substituted C$_1$-C$_7$alkyl, C$_2$-C$_6$alkenyl, C$_2$-C$_6$alkynyl, C$_1$-C$_7$alkoxy, hydroxyC$_1$-C$_4$alkyl, C$_1$-C$_7$alkoxyC$_1$-C$_4$alkyl, an optionally substituted C$_3$-C$_7$cycloalkyl, an optionally substituted C$_3$-C$_7$cycloalkylC$_1$-C$_4$alkyl, an optionally substituted C$_6$-C$_{10}$aryl, haloC$_1$-C$_4$alkyl, an optionally substituted C$_6$-C$_{10}$arylC$_1$-C$_4$alkyl, an optionally substituted C$_2$-C$_{10}$heterocyclyl, an optionally substituted C$_2$-C$_{10}$heterocyclylC$_1$-C$_4$alkyl, an optionally substituted C$_1$-C$_{10}$heteroaryl, or an optionally substituted C$_1$-C$_{10}$heteroarylC$_1$-C$_4$alkyl;

R$^2$ is C$_3$-C$_7$alkyl, haloC$_1$-C$_4$alkyl, C$_2$-C$_6$alkenyl, C$_2$-C$_6$alkynyl, C$_1$-C$_7$alkoxy, hydroxyl, hydroxyC$_1$-C$_4$alkyl, C$_1$-C$_6$alkoxyC$_1$-C$_4$alkyl, an optionally substituted C$_3$-C$_7$cycloalkyl, an optionally substituted C$_6$-C$_{10}$aryl, an optionally substituted C$_2$-C$_{10}$heterocyclyl, or an optionally substituted C$_1$-C$_{10}$heteroaryl, provided that V—R$^2$ is not quinolin-4-ylmethyl when R$^1$ is an alkyl;

R$^3$ is hydrogen, C$_1$-C$_6$alkyl, C$_2$-C$_6$alkenyl, C$_2$-C$_6$alkynyl, C$_1$-C$_6$alkoxy, hydroxyC$_1$-C$_4$alkyl, C$_1$-C$_6$alkoxyC$_1$-C$_4$alkyl, C$_3$-C$_7$cycloalkyl, C$_3$-C$_7$cycloalkylC$_1$-C$_4$alkyl, C$_2$-C$_{10}$heterocyclyl, C$_6$-C$_{10}$aryl, C$_6$-C$_{10}$arylC$_1$-C$_4$alkyl, C$_1$-C$_{10}$ heteroaryl, halo, haloC$_1$-C$_4$alkyl, trifluoromethoxy, cyano, hydroxy, or —N(R$^8$)$_2$;

R$^5$ and R$^{5a}$ are independently selected from hydrogen, C$_1$-C$_6$alkyl, haloC$_1$-C$_4$alkyl, hydroxy, hydroxyC$_1$-C$_4$alkyl, C$_1$-C$_6$alkoxy, C$_3$-C$_7$cycloalkylC$_1$-C$_4$alkyl and C$_6$-C$_{10}$arylC$_1$-C$_4$alkyl;

or R$^5$ and R$^{5a}$ are together to form an oxo (=O) group, or to form a C$_3$-C$_7$cycloalkyl;

R$^6$, for each occurrence, is independently selected from C$_1$-C$_6$alkyl, C$_6$-C$_{10}$aryl, C$_3$-C$_7$cycloalkyl, C$_1$-C$_{10}$heteroaryl, C$_2$-C$_{10}$heterocyclyl, hydroxyC$_1$-C$_4$alkyl, haloC$_1$-C$_4$alkyl, C$_1$-C$_6$alkoxy, C$_3$-C$_7$cycloalkylC$_1$-C$_4$alkyl, C$_6$-C$_{10}$arylC$_1$-C$_4$alkyl-N(R$^8$)C(O)R$^{12}$, —C(O)N(R$^8$)R$^{12}$, —OC(O)N(R$^8$)R$^{12}$, —N(R$^8$)C(O)OR$^{12}$, —N(R$^8$)C(O)N(R$^8$)R$^{12}$, —OR$^{12}$, —SR$^{12}$, —N(R$^8$)R$^{12}$, —S(O)$_t$R$^{12}$, —N(R$^8$)S(O)$_2$R$^{12}$, —S(O)$_2$N(R$^8$)R$^{12}$, —OS(O)$_2$N(R$^8$)R$^{12}$, —C(O)R$^{12}$, —OC(O)R$^{12}$, —N(R$^8$)C(=N(R$^{8a}$))N(R$^8$)R$^{12}$, —N(R$^8$)C(=S)N(R$^8$)R$^{12}$, —N(R$^8$)((R$^{8a}$)N=)CR$^{12}$, and —C(=N(R$^{8a}$))N(R$^8$)R$^{12}$;

or R$^5$ and R$^8$ on adjacent carbons together to form a C$_3$-C$_7$cycloalkyl or C$_6$-C$_{10}$aryl;

R$^7$ is hydrogen, C$_1$-C$_7$alkyl, haloC$_1$-C$_4$alkyl, C$_8$-C$_{10}$aryl, C$_3$-C$_7$cycloalkyl, C$_1$-C$_{10}$heteroaryl, C$_2$-C$_{10}$heterocyclyl, hydroxyC$_1$-C$_4$alkyl, C$_3$-C$_7$cycloalkylC$_1$-C$_4$alkyl or aralkyl;

R$^8$, for each occurrence, is independently selected from hydrogen, C$_1$-C$_7$alkyl, hydroxyC$_1$-C$_4$alkyl, C$_3$-C$_7$cycloalkyl, C$_3$-C$_7$cycloalkylC$_1$-C$_4$alkyl, C$_6$-C$_{10}$aryl, C$_1$-C$_{10}$heteroaryl, C$_2$-C$_{10}$heterocyclyl and aralkyl; and R$^{8a}$, for each occurrence, is independently selected from hydrogen, C$_1$-C$_7$alkyl, C$_3$-C$_7$cycloalkyl, C$_3$-C$_7$cycloalkylC$_1$-C$_4$alkyl, and cyano;

R$^{12}$, for each occurrence, is independently selected from hydrogen, C$_3$-C$_7$alkyl, C$_2$-C$_6$alkenyl, C$_2$-C$_6$alkynyl, C$_1$-C$_7$alkoxy, hydroxy, hydroxyC$_1$-C$_4$alkyl, C$_1$-C$_6$alkoxyC$_1$-C$_4$alkyl, C$_3$-C$_7$cycloalkyl, C$_3$-C$_7$cycloalkylC$_1$-C$_4$alkyl, C$_6$-C$_{10}$aryl, haloC$_1$-C$_4$alkyl, aralkyl, aralkyloxy, C$_2$-C$_{10}$heterocyclyl, C$_2$-C$_{10}$ heterocyclylC$_1$-C$_4$alkyl, C$_1$-C$_{10}$heteroaryl, and C$_1$-C$_{10}$heteroarylC$_1$-C$_4$alkyl;

or a pharmaceutically acceptable salt thereof.

Compounds of Formula (XIV) may be synthesized by methods known in the art, e.g., those described in International Patent Publication No. WO2011/039358. In some embodiments, the SCD inhibitor is a compound disclosed in International Patent Publication No. WO2011/039358, the compounds of which are herein incorporated by reference.

In some embodiments of any of the foregoing methods, the SCD inhibitor is a compound of Formula XV,

(XV)

X is N or CH;
Y is NH, O, S or N—CH$_3$;
Q is

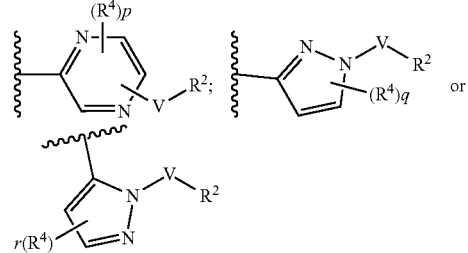

wherein when Q is

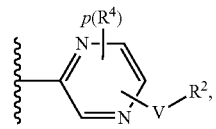

W is selected from —N(R$^6$)C(O)—, —C(O)N(R$^6$)—, —OC(O)N(R$^6$)—, —N(R$^6$)C(O)O—, —N(R$^6$)C(O)N(R$^6$)—, —O—, —N(R$^6$)—, —S—, —S(O)$_t$—, —N(R$^6$)S(O)$_t$—, —S(O)$_t$N(R$^6$)—, —OS(O)$_t$N(R$^6$)—, —C(O)—, —O(C)O, —C(O)O—, —N(R$^6$)C(=N(R$^{6a}$))N(R$^6$)—, —N(R$^6$)((R$^{6a}$)N=)C—, —C(=N(R$^{6a}$))N(R$^6$)—, an aryl, a heteroaryl, a heterocyclyl, an alkynylene, am alkenylene, alkylene or a direct bond;

V is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —N(R$^5$)—, —S—, —S(O)$_t$—, —N(R$^5$)S(O)$_2$—, —S(O)$_2$N(R$^5$)—, —OS(O)$_2$N(R$^5$)—, —C(O)—, —O(C)O, —C(O)O—, —CR$^5$C(O)N(R$^5$)—, —(CR$^5{}_2$)$_n$C (O)—, —(CR⁵)ₙO—, —(CR⁵₂)ₙN(R⁶)—, —(CR⁵₂)ₙN(R⁵)C(O)—, —(CR⁵₂)ₙN(R⁵)C(O)O—, —(CR⁵₂)ₙN(R⁵)S(O)ₜ—, —N(R⁵)C(=N(R⁵ᵃ))NR⁵—, —N(R⁵)((R⁵ᵃ)N=)C—, —C(=N(R⁵ᵃ))N(R⁵)—, —(CR⁵)ₙCR⁵=CR⁵, an alkynylene, an alkenylene, an alkynyl, and alkylene or a direct bond;

t is 1 or 2;
p is 0, 1 or 2;
n is an integer from 1 to 6;
R¹ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R¹ is a multi-ring structure having 2 to 4 rings wherein the rings are independently selected from the group consisting of cycloalkyl, heterocyclyl, aryl and heteroaryl and where some or all of the rings may be fused to each other;
R² is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R² is a multi-ring structure having 2 to 4 rings wherein the rings are independently selected from the group consisting of cycloalkyl, heterocyclyl, aryl and heteroaryl and where some or all of the rings may be fused to each other;
R³ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, trifluoromethyl, trifluoromethoxy, cyano and —N(R⁶)₂;
R⁴ is selected from the group consisting of alkyl, halo, —N(R⁶)₂, haloalkyl, hydroxyl, alkoxy, —N(R²)₂, cycloalkylalkyl and aralkyl;
R⁵ and R⁶ are independently selected from the group consisting of hydrogen, alkyl, halo, aryl, heteroaryl, cycloalkyl, hydroxyalkyl, cycloalkylalkyl and aralkyl;
R⁵ᵃ and R⁶ᵃ are independently selected from the group consisting of hydrogen, alkyl, cycloalkylalkyl and cyano.
or as a stereoisomer, enantiomer or tautomer thereof, a pharmaceutically acceptable salt thereof, a pharmaceutical composition thereof or a prodrug thereof.

In some embodiments of the compound of Formula XVa:
wherein when Q is

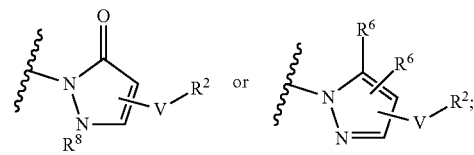

V is selected from —C(O)N(R⁵)—, —S(O)ₜ—, —S(O)₂N(R⁵)—, —C(O)—, —C(C)O, —CR⁵₂C(O)N(R⁵)—, —(CR⁵₂)ₙC(O)—, —(CR⁵₂)ₙO—, —(CR⁵₂)ₙN(R⁶)—, —(CR⁵₂)ₙN(R⁵)C(O)—, —(CR⁵₂)ₙN(R⁵)C(O)O—, —(CR⁵₂)ₙN(R⁵)S(O)ₜ—, an aryl, a heteroaryl, a heterocyclyl, an alkynylene, an alkenylene, an alkylene or a direct bond;
r is 0, 1 or 2;
R⁴ is selected from the group consisting of alkyl, haloalkyl, hydroxyl, alkoxy, —N(R²)₂, cycloalkylalkyl and aralkyl;
R⁵ᵃ and R⁶ᵃ are independently selected from the group consisting of hydrogen, alkyl, cycloalkylalkyl and cyano.

Compounds of Formula (XV) may be synthesized by methods known in the art, e.g., those described in International Patent Publication No. WO2008/024390. In some embodiments, the SCD inhibitor is a compound disclosed in International Patent Publication No. WO2008/024390, the compounds of which are herein incorporated by reference.

In some embodiments of any of the foregoing methods, the SCD inhibitor is a compound of Formula XVI,

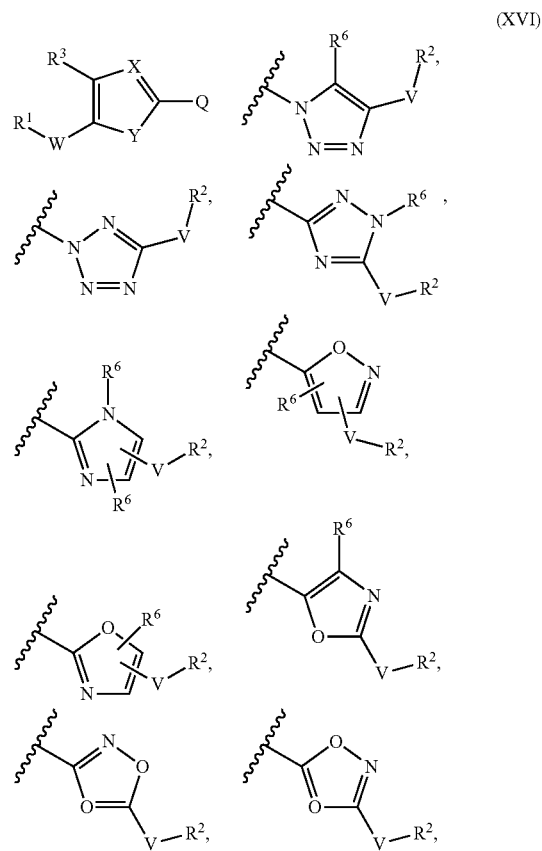

wherein when Q is

W is —N(R⁷)C(O)—, —C(O)N(R⁷)—, —OC(O)N(R⁷)—, —N(R⁷)C(O)O—, —N(R⁷)C(O)N(R⁷)—, —N(R⁷)—, —O—, —S—, —S(O)ₜ—, —N(R⁷)S(O)ₜ—, —S(O)ₜN(R⁷)—, —OS(O)ₜN(R⁷)—, —C(O)—, —O(C)O, —C(O)O—, —N(R⁷)C(=N(R⁷ᵃ))N(R⁷)—, —N(R⁷)C(=S)N(R⁷)—, —N(R⁷)((R⁷ᵃ)N=)C—, —C(=N(R⁷ᵃ))N(R⁷)—, an alkenylene group, an alkynylene group or a direct bond;
V is —N(R⁷)C(O)—, —N(R⁷)C(O)O—, —N(R⁷)C(O)N(R⁷)—, —N(R⁷)—, —N(R⁷)S(O)₂—, —O—, —S—, —S(O)ₜ, —N(R⁷)S(O)ₜ, —S(O)₂N(R⁷)—, —C(O)—, —OC(O)—, —C(O)O—, —C(O)N(R⁷)—, —OC(O)N(R⁷)—, —C(R⁷₂)ₙC(O)N(R⁷)—, —(R⁷₂)ₙC(O)—, —(CR⁷₂)ₙO—, —(CR⁷₂)ₙN(R⁷)—, —(CR⁷₂)ₙN(R⁷)C(O)—, —(CR⁷₂)ₙN(R⁷)C(O)N(R⁷)—, —C(=N(R⁷ᵃ))N(R⁷)—, an alkenylene group, an alkynylene group or a direct bond;

X is N or CH;
Y is NH, O, S or N—CH$_3$;
t is 1 or 2;
n is an integer from 1 to 6;
R$^1$ is selected from the group consisting of hydrogen, alkyl, alkenyl, hydroxyalkyl, alkoxy, alkoxyalkyl, cycloalkyl, cycloalkylalkyl, aryl, aralkyl, heterocyclyl, heterocyclylalkyl, heteroaryl and heteroarylalkyl;
or R$^1$ is a multi-ring structure having 2 to 4 rings wherein the rings are independently selected from the group consisting of cycloalkyl, heterocyclyl, aryl and heteroaryl and where some or all of the rings may be fused to each other;
R$^2$ is selected from the group consisting of hydrogen, alkyl, alkenyl, hydroxyalkyl, alkoxy, alkoxyalkyl, cycloalkyl, cycloalkylalkyl, aryl, aralkyl, heterocyclyl, heterocyclylalkyl, heteroaryl and heteroarylalkyl;
or R$^2$ is a multi-ring structure having 2 to 4 rings wherein the rings are independently selected from the group consisting of cycloalkyl, heterocyclyl, aryl and heteroaryl and where some or all of the rings may be fused to each other;
R$^3$ is selected from the group consisting of hydrogen, alkyl, alkenyl, hydroxyalkyl, alkoxy, alkoxyalkyl, cycloalkyl, cycloalkylalkyl, heterocyclyl, aryl, aralkyl, heteroaryl, halo, trifluoromethyl, trifluoromethoxyl, cyano, nitro and —N(R$^7$)$_2$;
R$^6$ is selected from the group consisting of hydrogen, alkyl, cycloalkyl, cycloalkylalkyl and aralkyl; each R$^7$ is the same or different and independently selected from the group consisting of hydrogen, halo, hydroxy, alkyl, alkenyl, alkynyl, aryl, alkoxyalkyl, haloalkyl, heteroaryl, heteroarylalkyl, heterocyclyl, heterocyclylalkyl, hydroxyalkyl, cycloalkyl, cycloalkylalkyl and aralkyl;
R$^{7a}$ is selected from the group consisting of hydrogen, alkyl, cycloalkylalkyl and cyano; and
R$^8$ is hydrogen or alkyl; or
a stereoisomer, enantiomer or tautomer thereof, a pharmaceutically acceptable salt thereof, a pharmaceutical composition thereof or a prodrug thereof.
or
wherein when Q is

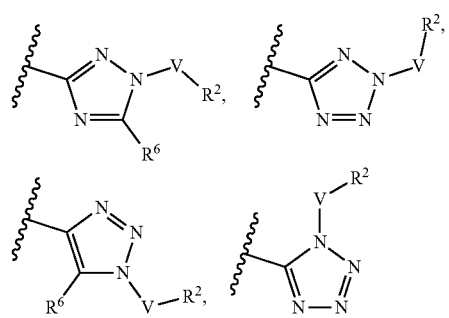

W is —N(R$^7$)C(O)—, —C(O)N(R$^7$)—, —OC(O)N(R$^7$)—, —N(R$^7$)C(O)O—, —N(R$^7$)C(O)N(R$^7$)—, —O—, —S—, —S(O)$_t$—, —N(R$^7$)S(O)$_t$—, —S(O)$_t$N(R$^7$)—, —OS(O)$_t$N(R$^7$)—, —C(O)—, —O(C)O, —C(O)O—, —N(R$^7$)C(=N(R$^{7a}$))N(R$^7$)—, —N(R$^7$)C(=S)N(R$^7$)—, —N(R$^7$)((R$^{7a}$)N=)C—, —C(=N(R$^{7a}$))N(R$^7$)—, an alkenylene group, an alkynylene group or a direct bond;
V is —S(O)$_t$—, —S(O)$_2$N(R$^7$)—, —C(O)—, —C(O)O—, —C(O)N(R$^7$)—, —C(R$^7$$_2$)$_n$C(O)N(R$^7$)—, —(CR$^7$$_2$)$_n$C(O)—, —(CR$^7$$_2$)$_n$O, —(CR$^7$$_2$)$_n$—, —(CR$^7$$_2$)$_n$N(R$^7$)—, —(CR$^7$$_2$)$_n$N(R$^7$)C(O)—, —(CR$^7$$_2$)$_n$N(R$^7$)C(O)N(R$^7$)—, —C(=N(R$^{7a}$))N(R$^7$)—, an alkenylene group, an alkynylene group or a direct bond.

Compounds of Formula (XVI) may be synthesized by methods known in the art, e.g., those described in International Patent Publication No. WO2008/074835. In some embodiments, the SCD inhibitor is a compound disclosed in International Patent Publication No. WO2008/074835, the compounds of which are herein incorporated by reference.

In some embodiments of any of the foregoing methods, the SCD inhibitor is a compound of Formula XVII,

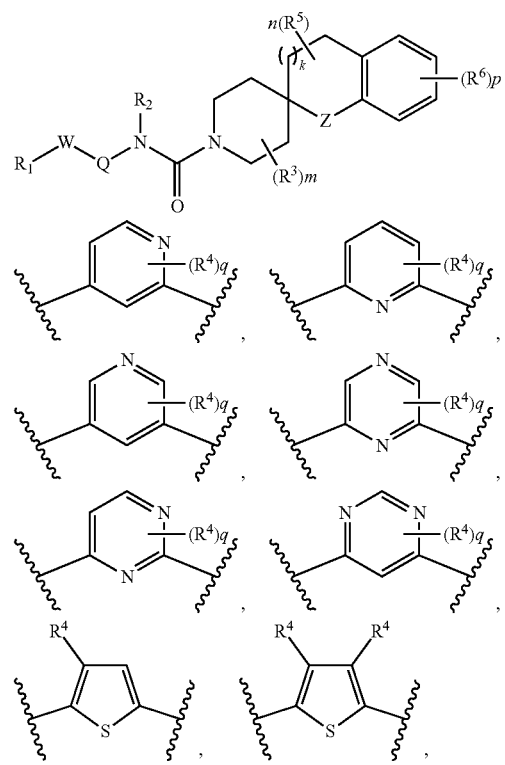

(XVII)

wherein Q is

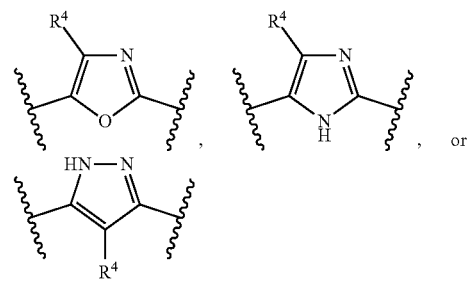

W is —N(R$^7$)C(O)—, —C(O)N(R$^7$)—, —N(R$^7$)C(O)N(R$^7$)—, —N(R$^7$)S(O)$_t$—, —S(O)$_t$N(R$^7$)—, or a direct bond;
Z is —C(R$^4$)$_u$—, —C(O)—, —O—, —N(R$^7$)—, —S(O)$_t$—, —O— or —S—;
k is 0 or 1;
m is 0 to 8;
n is 0, 1, 2, 3 or 4;
p is 0, 1, 2, 3 or 4;

q is 1, 2, or 3;

t is 1 or 2;

u is 1 or 2;

$R^1$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl, or heteroarylalkyl;

or $R^1$ is a multi-ring structure having 2 to 4 rings wherein the rings are independently cycloalkyl, heterocyclyl, aryl or heteroaryl and where some or all of the rings may be fused to each other;

$R^2$ is hydrogen, or alkyl;

$R^3$ is independently alkyl, halo, haloalkyl, hydroxy, or $-N(R^7)_2$;

$R^4$ is independently alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, haloalkoxy, cyano, hydroxy or $-N(R^7)_2$;

$R^5$ is independently alkyl, halo, haloalkyl, hydroxy, cycloalkyl or $-N(R^7)_2$;

or two $R^5$'s on the same carbon atom form an oxo (=O);

$R^6$ is independently alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, haloalkoxy, cyano, hydroxy or $-N(R^7)_2$; and $R^7$ is independently hydrogen, alkyl, alkenyl, hydroxyalkyl, cycloalkylalkyl, aryl, heteroaryl, heterocyclyl, aralkyl;

or a pharmaceutically acceptable salt thereof or a prodrug thereof.

Compounds of Formula (XVII) may be synthesized by methods known in the art, e.g., those described in International Patent Publication No. WO2010/112520. In some embodiments, the SCD inhibitor is a compound disclosed in International Patent Publication No. WO2010/112520, the compounds of which are herein incorporated by reference.

In some embodiments of any of the foregoing methods, the SCD inhibitor is a compound of Formula XVIII, (XVIII)

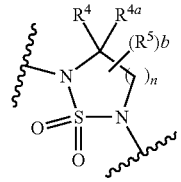

wherein:

X is N or CH:

Y is NH, O, S or N—CH$_3$;

Q is

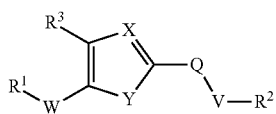

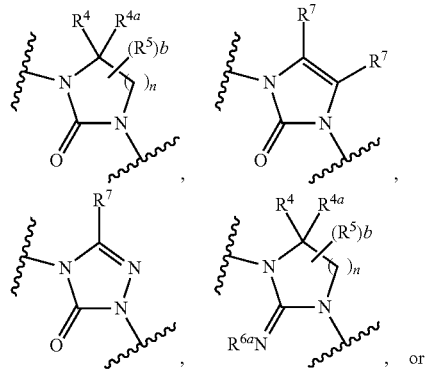

W is selected from $-N(R^6)C(O)-$, $-C(O)N(R^6)-$, $-OC(O)N(R^6)-$, $-N(R^6)C(O)O-$, $-N(R^6)C(O)N(R^6)-$, $-O-$, $-S-$, $-N(R^6)-$, $-S(O)_t-$, $-N(R^6)S(O)_t-$, $-S(O)_tN(R^6)-$, $-OS(O)_tN(R^6)-$, $-C(O)-$, $-O(C)O$, $-C(O)O-$, $-N(R^6)C(=N(R^{6a}))N(R^6)-$, $-N(R^6)((R^{6a})N=)C-$, $-C(=N(R^{6a}))N(R^6)-$, or a direct bond;

V is selected from $-R^8-C(O)N(R^6)-$, $-R^8-OC(O)N(R^6)-$, $-S(O)_t-$, $-S(O)_2N(R^6)-$, $-R^8-C(O)-$, $-R^8-O(C)O-$, $-C(=N(R^{6a}))N(R^6)-$, or a direct bond;

n is 1, 2, or 3;

p is 0, 1, 2, to 2n:

t is 1 or 2;

$R^1$ is selected from the group consisting of halo, hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl, or heteroarylalkyl;

or $R^1$ is a multi-ring structure having 2 to 4 rings wherein the rings are independently selected from the group consisting of cycloalkyl, heterocyclyl, aryl and heteroaryl and where some or all of the rings may be fused to each other;

$R^2$ is selected from the group consisting of hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of hydrogen, alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, haloalkoxyl, cyano, or $-N(R^6)_2$;

each of $R^4$ and $R^{4a}$ are independently selected from the group consisting of hydrogen, alkyl, haloalkyl, hydroxyl, hydroxyalkyl, alkoxy, cycloalkylalkyl or aralkyl;

or $R^4$ and $R^{4a}$ are together to form an oxo (=O) group or a cycloaklyl;

$R^5$ is selected from the group consisting of alkyl, aryl, cycloalkyl, heteroaryl, heterocyclyl, hydroxyalkyl, alkoxy, cycloalkylalkyl, aralkyl, $-N(R^6)C(O)R^2-$, $-C(O)N(R^6)R^2-$, $-OC(O)N(R^6)R^2-$, $-N(R^6)C(O)OR^2-$, $-N(R^6)C(O)N(R^6)R^2-$, $-OR^2-$, $-SR^2-$, $-N(R^6)R^2-$, $-S(O)_tR^2-$, $-N(R^6)S(O)_2R^2-$, $-S(O)_2N(R^6)R^2-$, $-OS(O)_2N(R^6)R^2-$, $-C(O)R^2-$, $-O(C)OR^2-$, $-C(O)OR^2-$, $-N(R^6)C(=N(R^{6a}))N(R^6)R^2-$, $-N(R^6)C(=S)N(R^6)R^2-$, $-N(R^6)((R^{6a})N=)CR^2-$, or $-C(=N(R^{6a}))N(R^6)R^2-$;

each $R^6$ is independently selected from the group consisting of hydrogen, alkyl, hydroxyalkyl, cycloalkylalkyl, aryl, heteroaryl, heterocyclyl or aralkyl;

each $R^{6a}$ is independently selected from the group consisting of hydrogen, alkyl, cycloalkylalkyl, or cyano;

each $R^7$ is independently selected from the group consisting of hydrogen, alkyl, trifluoromethyl, aryl, cycloalkyl, heteroaryl, heterocyclyl, hydroxyalkyl, cycloalkylalkyl or aralkyl; and each $R^8$ is independently a direct bond, an optionally substituted straight or branched alkylene chain, an optionally substituted straight or branched alkenylene chain or an optionally substituted straight or branched alkynylene chain; or as a stereoisomer, enantiomer or tautomer thereof; a pharmaceutically acceptable salt thereof, a pharmaceutical composition thereof or a prod rug thereof.

Compounds of Formula (XVIII) may be synthesized by methods known in the art, e.g., those described in International Patent Publication No. WO2008/127349. In some embodiments, the SCD inhibitor is a compound disclosed in International Patent Publication No. WO2008/127349, the compounds of which are herein incorporated by reference.

In some embodiments of any of the foregoing methods, the SCD inhibitor is a compound of Formula XIX,

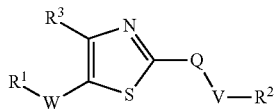

(XIX)

wherein:
Q is

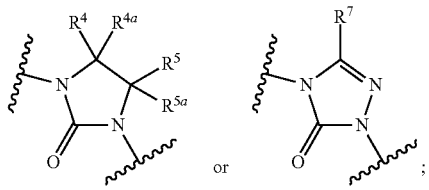

W is —N($R^6$)C(O)—, —$R^8$—C(O)N($R^6$)—, —$R^8$—OC(O)N($R^6$)—, —N($R^6$)C(O)O—, —N($R^6$)C(O)N($R^6$)—, —O—, —S—, —N($R^6$)—, —S(O)$_t$—, —N($R^6$)S(O)$_t$—, —S(O)$_t$N($R^6$)—, —OS(O)$_t$N($R^6$)—, —$R^8$—C(O)—, —O(C)O, —C(O)O—, —N($R^6$)C(=N($R^{6a}$))N($R^6$)—, —N($R^6$)(($R^{6a}$)N=)C—, —C(=N($R^{6a}$))N($R^6$)—, or a direct bond;

V is selected from —C(O)N($R^6$)—, —S(O)$_t$—, —S(O)$_2$N($R^6$)—, —C(O)—, —$R^8$—C(O)O—, $R^8$—OC(O)N($R^6$)—, $R^8$—C(O)N($R^6$)—, —$R^8$—C(O)—, —C(=N($R^{6a}$))N($R^6$)—, or a direct bond;

t is 1 or 2;

$R^1$ is halo, hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl, or heteroarylalkyl;

or $R^1$ is a multi-ring structure having 2 to 4 rings wherein the rings are independently selected from the group consisting of cycloalkyl, heterocyclyl, aryl and heteroaryl and where some or all of the rings may be fused to each other;

$R^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is hydrogen or alkyl;

$R^4$ and $R^{4a}$ are independently hydrogen, alkyl, haloalkyl, hydroxyl, hydroxyalkyl, alkoxy, cycloalkylalkyl or aralkyl;

or $R^4$ and $R^{4a}$ are taken together to form an oxo (=O) group, cycloaklyl or heterocyclyl;

$R^5$ and $R^{5a}$ are independently hydrogen, alkyl or haloalkyl;

$R^4$ and $R^5$ are taken from a cycloalkyl, aryl, heteroaryl or heterocyclyl, and the remaining $R^{4a}$ and $R^{5a}$ are as described above;

$R^6$ is independently hydrogen, alkyl, hydroxyalkyl, cycloalkylalkyl, aryl, heteroaryl, heterocyclyl or aralkyl;

$R^{6a}$ are independently hydrogen, alkyl cycloalkylalkyl, or cyano;

$R^7$ is hydrogen, alkyl, trifluoromethyl, aryl, cycloalkyl, heteroaryl, heterocyclyl, hydroxyalkyl, cycloalkylalkyl or aralkyl; and $R^8$ is independently a direct bond, an optionally substituted straight or branched alkylene chain, an optionally substituted straight or branched alkenylene chain or an optionally substituted straight or branched alkynylene chain; or as a stereoisomer, enantiomer or tautomer thereof, a pharmaceutically acceptable salt thereof, a pharmaceutical composition thereof or as a prodrug thereof.

Compounds of Formula (XIX) may be synthesized by methods known in the art, e.g., those described in International Patent Publication No. WO2009/103739. In some embodiments, the SCD inhibitor is a compound disclosed in International Patent Publication No. WO2009/103739, the compounds of which are herein incorporated by reference.

In some embodiments of any of the foregoing methods, the SCD inhibitor is a compound of Formula XX, $R^1$—W—P-Q-$R^2$  (XX)

wherein P is

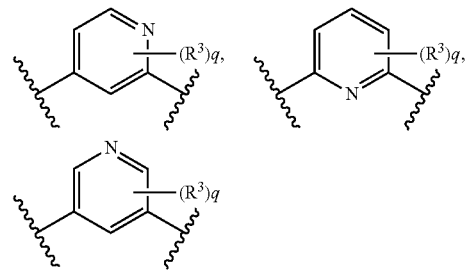

wherein P is
Q is

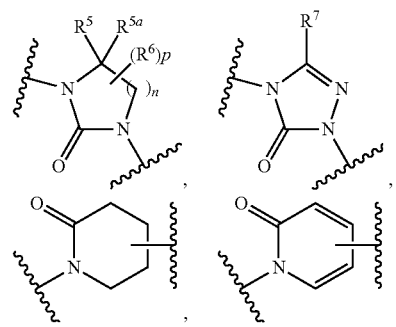

W is selected from —N(R$^8$)C(O)—, —C(O)N(R$^8$)— or a direct bond;

n is 1, 2, or 3;

p is 0, 1, 2, to 2n;

q is 0, 1, 2, or 3;

R$^1$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl, or heteroarylalkyl;

R$^2$ is hydrogen, alkyl, alkenyl, alkynyl, alkoxy, hydroxy, hydroxyalkyl, alkoxyalkyl, cycloalkyl, cycloalkylalkyl, aryl, haloalkyl, aralkyl, aralkyloxy, heterocyclyl, heterocyclylalkyl, heteroaryl or heteroarylalkyl;

R$^3$ is alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, trifluoromethoxy, cyano, hydroxy, or —N(R$^6$)$_2$;

R$^5$ and R$^{5a}$ are independently hydrogen, alkyl, haloalkyl, hydroxyl, hydroxyalkyl, alkoxy, cycloalkylalkyl or aralkyl; or R$^5$ and R$^{5a}$ are together to form an oxo (═O) group, or to form a cycloaklyl;

R$^6$ is alkyl, aryl, cycloalkyl, heteroaryl, heterocyclyl, hydroxyalkyl, haloalkyl, alkoxy, cycloalkylalkyl, or aralkyl; or R$^5$ and R$^6$ on adjacent carbons are together to form a cycloalkyl, or to form an aryl;

R$^7$ is hydrogen, alkyl, haloalkyl, aryl, cyclolkyl, heteroaryl, heterocyclyl, hydroxyalkyl, cycloalkylalkyl or aralkyl; and R$^8$ is hydrogen, alkyl, hydroxyalkyl, cycloalkylalkyl, aryl, heteroaryl, heterocyclyl, or aralkyl; or a stereoisomer, enantiomer or tautomer thereof, a pharmaceutically acceptable salt thereof, a pharmaceutical composition thereof or a prodrug thereof.

Compounds of Formula (XX) may be synthesized by methods known in the art, e.g., those described in International Patent Publication No. WO2009/156484. In some embodiments, the SCD inhibitor is a compound disclosed in International Patent Publication No. WO2009/156484, the compounds of which are herein incorporated by reference.

In some embodiments of any of the foregoing methods, the SCD inhibitor is a compound of Formula XXI,

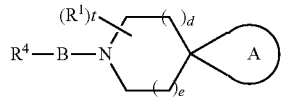

(XXIa, XXIb)

or a pharmaceutically acceptable salt thereof; wherein
A is selected from the group consisting of:

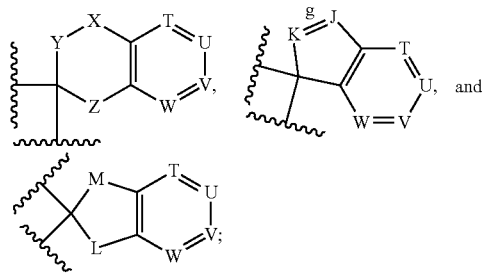

g is a single bond or a double bond;

J and K are each independently selected from the group consisting of: S, O, NH, CH and CH$_2$, wherein each NH is unsubstituted or substituted with R$^9$, and wherein each CH and CH$_2$ is unsubstituted or substituted with R$^2$, provided that when g is a single bond at least one of J and K is CH$_2$ unsubstituted or substituted with R$^2$, and further provided that when g is a double bond then both J and K are CH;

L and M are each independently selected from the group consisting of: S, O, NH and CH$_2$, wherein each NH is unsubstituted or substituted with R$^9$, and wherein each CH$_2$ is unsubstituted or substituted with R$^2$;

T, U, V and W are each independently selected from N and CH, wherein each CH is unsubstituted or substituted with R$^3$, provided that at least two of T, U, V and W are CH;

X is CH$_2$, wherein CH$_2$ is unsubstituted or substituted with R$^2$;

Y is independently selected from the group consisting of: O, NH and CH$_2$, wherein each NH is unsubstituted or substituted with R$^9$, and wherein each CH$_2$ is unsubstituted or substituted with R$^2$;

Z is independently selected from the group consisting of: S, S(O), S(O)$_2$, O, NH and CH$_2$, wherein each NH is unsubstituted or substituted with R$^9$, and wherein each CH$_2$ is unsubstituted or substituted with R$^2$;

each R$^1$ is independently selected from the group consisting of: hydrogen, halogen, and C$_{1-3}$alkyl, wherein alkyl is unsubstituted or substituted with one to three substituents independently selected from halogen and hydroxy;

each R$^2$ is independently selected from the group consisting of: hydrogen, halogen, oxo, C$_{1-6}$alkyl, (CH$_2$)$_n$OR$^e$, (CH$_2$)$_n$N(R$^e$)$_2$, (CH$_2$)$_n$C≡N, (CH$_2$)$_n$COR$^e$, and (CH$_2$)$_n$S(O)$_q$R$^e$, wherein alkyl is unsubstituted or substituted with hydroxy or one to three halogens, and wherein any CH$_2$ in R$^2$ is unsubstituted or substituted with one to two groups independently selected from halogen, hydroxy, and C$_{1-4}$alkyl unsubstituted or substituted with one to five fluorines;

each R$^a$ is independently selected from the group consisting of:

hydrogen, halogen, cyano,

C$_{1-4}$alkyl, unsubstituted or substituted with one to five fluorines,

C$_{1-4}$alkoxy, unsubstituted or substituted with one to five fluorines,

C$_{1-4}$alkylthio, unsubstituted or substituted with one to five fluorines,

C$_{1-4}$alkylsulfonyl,

—CO$_2$H,

C$_{1-4}$alkyloxycarbonyl, and

C$_{1-4}$alkylcarbonyl;

each R$^b$ is independently selected from the group consisting of: hydrogen, and C$_{1-4}$alkyl, wherein alkyl is unsubstituted or substituted with one to five fluorines;

each R$^c$ is independently selected from the group consisting of: —(CH$_2$)$_m$CO$_2$H, —(CH$_2$)$_m$CO$_2$C$_{1-3}$ alkyl, —(CH$_2$)$_m$—NR$^b$—(CH$_2$)$_p$CO$_2$H, —(CH$_2$)$_m$—NR$^b$—(CH$_2$)$_p$CO$_2$C$_{1-3}$alkyl, —(CH$_2$)$_m$—O—(CH$_2$)$_p$CO$_2$H, —(CH$_2$)$_m$—O—(CH$_2$)$_p$CO$_2$C$_{1-3}$alkyl, —(CH$_2$)$_m$—S—(CH$_2$)$_p$CO$_2$H, and —(CH$_2$)$_m$—S—(CH$_2$)$_p$CO$_2$C$_{1-3}$ alkyl, wherein any CH$_2$ in R$^c$ is unsubstituted or substituted with one to two groups independently selected from halogen, hydroxy, and C$_{1-4}$alkyl unsubstituted or substituted with one to five fluorines;

each $R^d$ is independently selected from the group consisting of: —(CH$_2$)$_n$CO$_2$H, —(CH$_2$)$_n$CO$_2$C$_{1-3}$alkyl, —(CH$_2$)$_n$—NR$^b$—(CH$_2$)$_p$CO$_2$H, —(CH$_2$)$_n$—NR$^b$—(CH$_2$)$_p$CO$_2$C$_{1-3}$alkyl, —(CH$_2$)$_n$—O—(CH$_2$)$_p$CO$_2$H, —(CH$_2$)$_n$—O—(CH$_2$)$_p$CO$_2$C$_{1-3}$alkyl, —(CH$_2$)$_n$—S—(CH$_2$)$_p$CO$_2$H, and —(CH$_2$)$_n$—S—(CH$_2$)$_p$CO$_2$C$_{1-3}$alkyl, wherein any CH$_2$ in $R^d$ is unsubstituted or substituted with one to two groups independently selected from the group consisting of: halogen, hydroxy, and C$_{1-4}$alkyl unsubstituted or substituted with one to five fluorines;

each $R^e$ is independently selected from the group consisting of: hydrogen, and C$_{1-6}$alkyl, wherein alkyl is unsubstituted or substituted with one to three substituents independently selected from the group consisting of: halogen, cyano, —C$_{1-4}$alkoxy, —C$_{1-4}$alkylthio, —C$_{1-4}$alkylsulfonyl, —CO$_2$H, and —CO$_2$C$_{1-4}$alkyl;

each $R^g$ is independently selected from the group consisting of: hydrogen, and C$_{1-6}$alkyl, m is an integer from 1 to 3;
n is an integer from 0 to 3;
p is an integer from 1 to 3;
q is an integer from 1 to 2;
t is an integer from 0 to 8;
d is an integer from 0 to 2; and
e is an integer from 0 to 2,
provided that d+e is 2.

In some embodiments of the compound of Formula XXIa,

B is a 5 membered heteroaryl ring containing 1, 2 or 3 heteroatoms selected from NH, O and S, wherein any CH is unsubstituted or substituted with one substituent selected from $R^a$, and wherein any NH is unsubstituted or substituted with one substituent selected from $R^b$;

each $R^3$ is independently selected from the group consisting of: hydrogen, halogen, —C$_{1-6}$alkyl, —C$_{1-6}$alkenyl, —OC$_{1-6}$alkyl, (CH$_2$)$_n$OR$^e$, (CH$_2$)$_n$N(R$^e$)$_2$, (CH$_2$)$_n$C≡N, (CH$_2$)$_n$COR$^e$, and (CH$_2$)$_n$S(O)$_q$R$^e$, wherein alkyl is unsubstituted or substituted with one to three substituents selected from: hydroxy, halogen, C$_{1-4}$alkyl, C$_{3-6}$cycloalkyl, C$_{2-5}$cycloheteroalkyl, aryl, and heteroaryl, wherein alkyl, cycloalkyl, cycloheteroalkyl, aryl and heteroaryl are unsubstituted or substituted with one to three substituents selected from: halogen, hydroxy, and C$_{1-4}$alkyl unsubstituted or substituted with one to five fluorines, and wherein any CH$_2$ in $R^3$ is unsubstituted or substituted with one to two groups independently selected from halogen, hydroxy, and C$_{1-4}$alkyl unsubstituted or substituted with one to five fluorines;

$R^4$ is selected from the group consisting of:

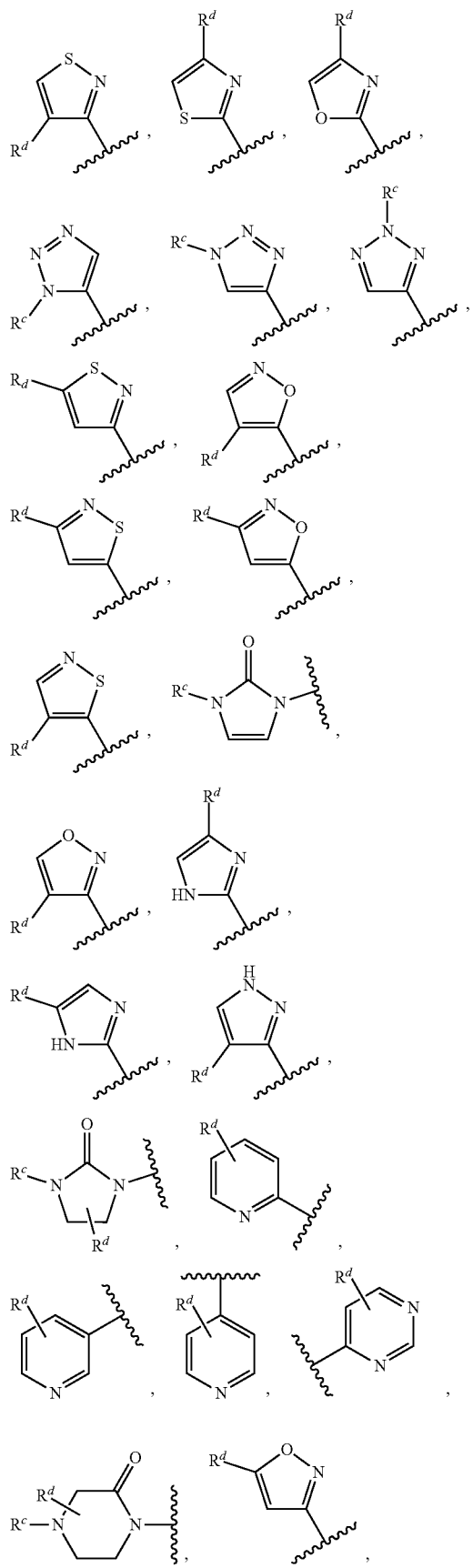

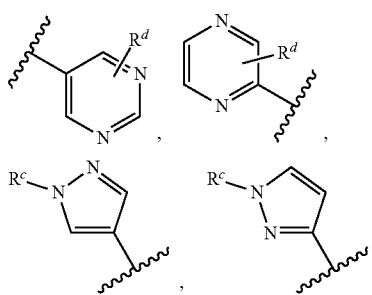

In some embodiments of the compound of Formula XXIb, B is selected from the group consisting of:

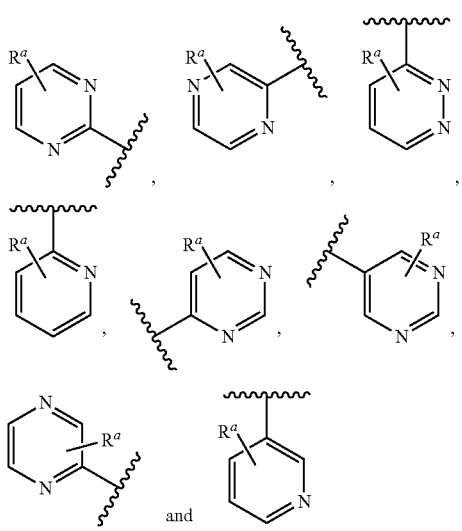

each $R^3$ is independently selected from the group consisting of: hydrogen, halogen, —$C_{1-6}$alkyl, —$OC_{1-6}$alkyl, $(CH_2)_nOR^e$, $(CH_2)_nN(R^e)_2$, $(CH_2)_nC\equiv N$, $(CH_2)_nCOR^e$, and $(CH_2)_nS(O)_qR^e$, wherein alkyl is unsubstituted or substituted with hydroxy or one to three halogens, and wherein any $CH_2$ in $R^3$ is unsubstituted or substituted with one to two groups independently selected from halogen, hydroxy, and $C_{1-4}$alkyl unsubstituted or substituted with one to five fluorines;

$R^4$ is selected from the group consisting of:

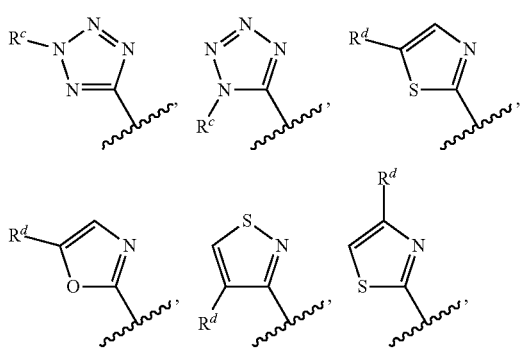

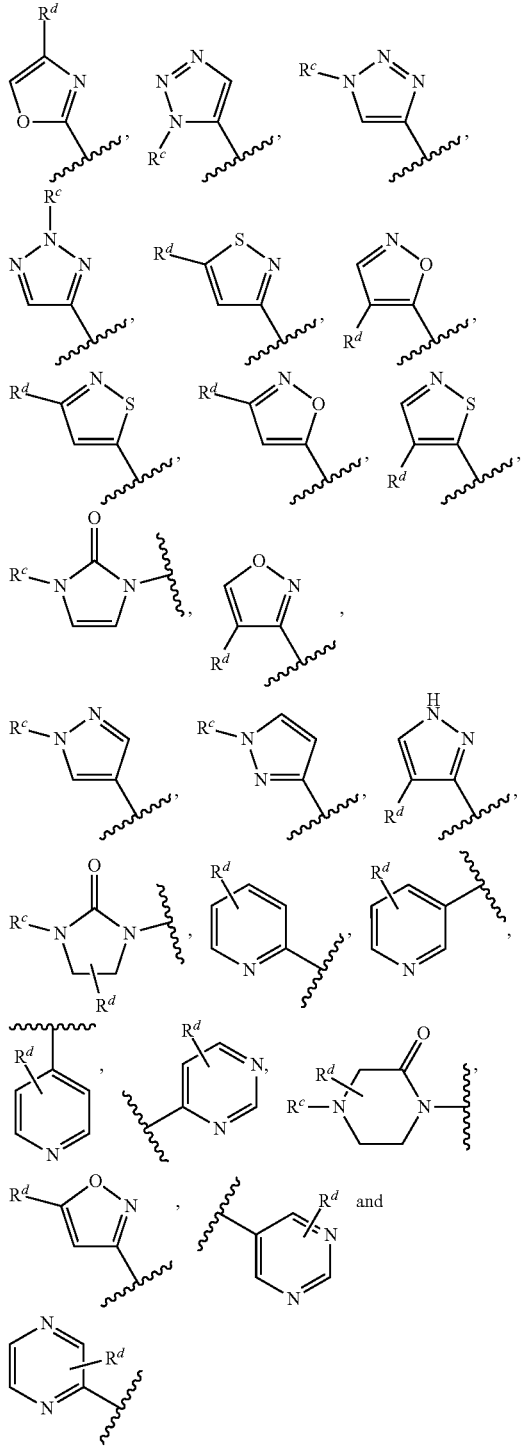

Compounds of Formula (XXI) may be synthesized by methods known in the art, e.g., those described in International Patent Publications No. WO2010/094120 and WO2011/047481. In some embodiments, the SCD inhibitor is a compound disclosed in International Patent Publications No. WO2010/094120 and WO2011/047481, the compounds of which are herein incorporated by reference.

In some embodiments of any of the foregoing methods, the SCD inhibitor is a compound of Formula XXII,

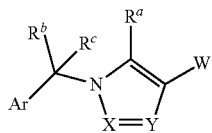
(XXII)
or a pharmaceutically acceptable salt thereof;
wherein X and Y are each independently CH or N;
W is heteroaryl selected from the group consisting of:
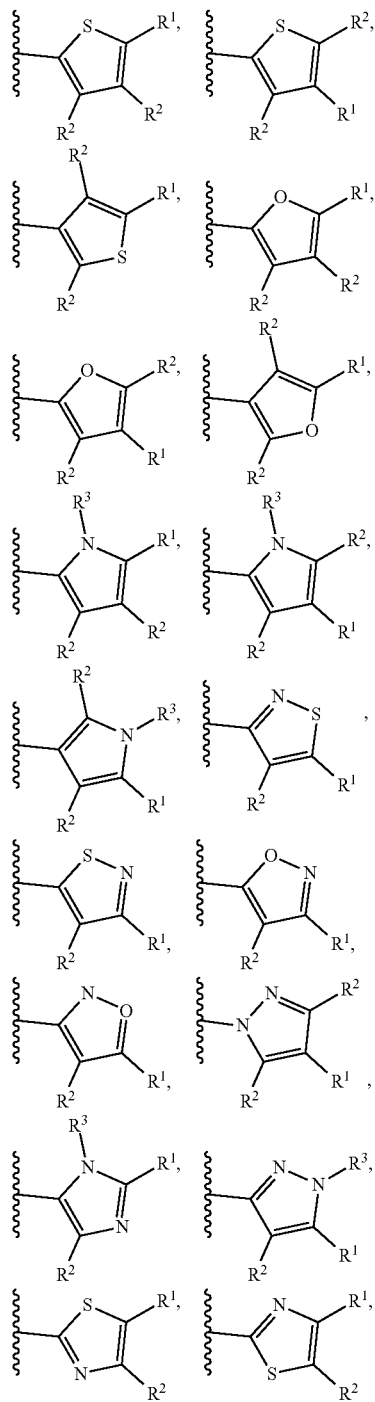
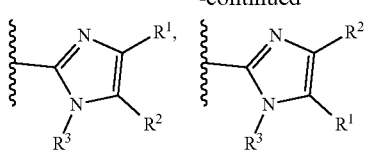
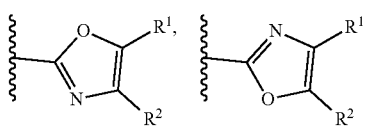
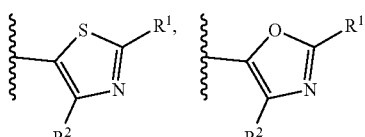
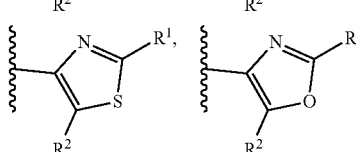
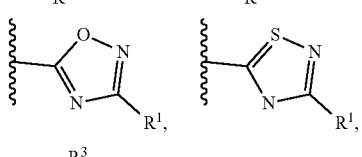
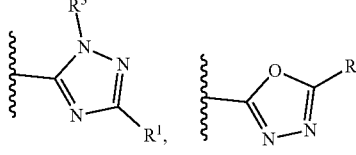
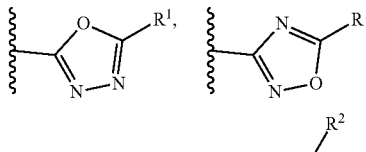
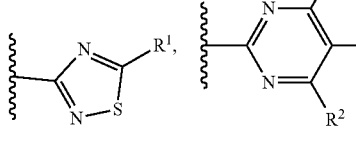
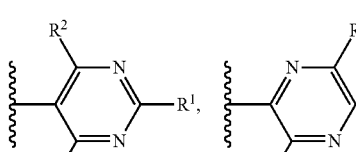
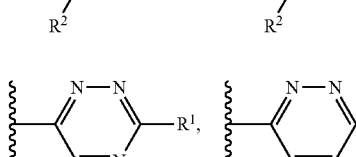
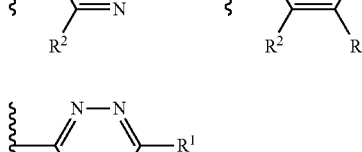
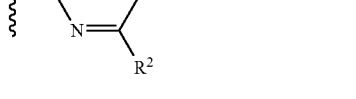

$R^1$ is heteroaryl selected from the group consisting of:

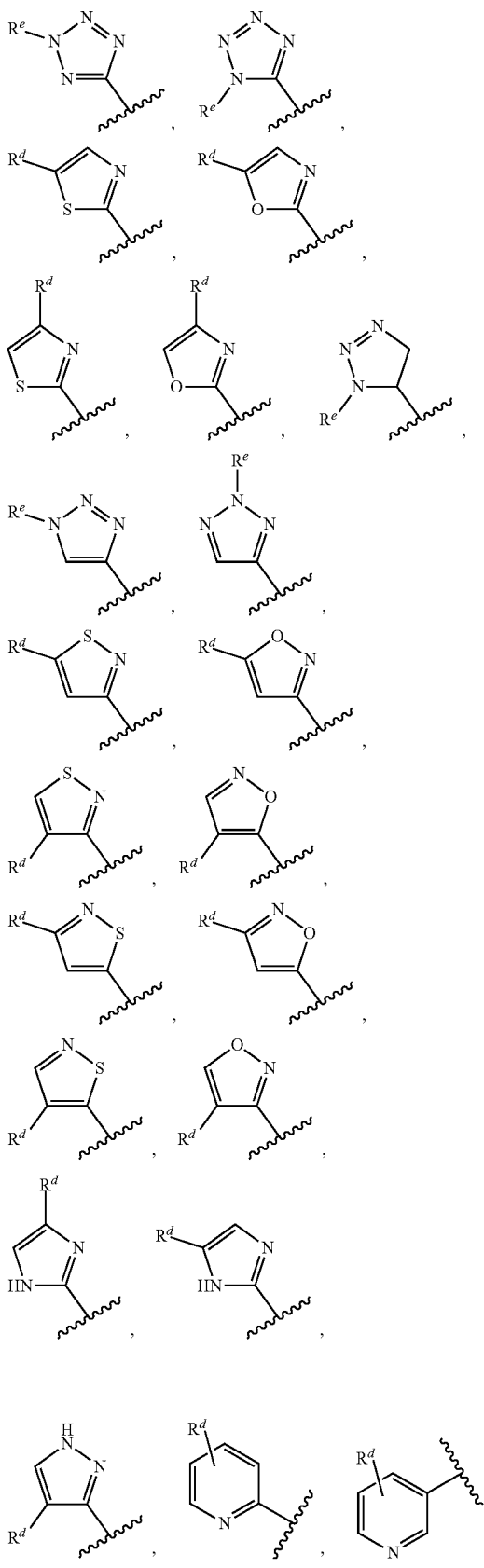

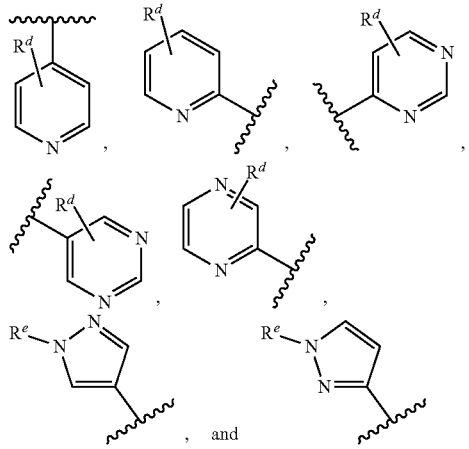

wherein
$R^d$ is $-(CH_2)_nCO_2H$, $-(CH_2)_nCO_2C_{1-3}$alkyl, $-(CH_2)_n-Z-(CH_2)_pCO_2H$, or $-(CH_2)_nZ-(CH_2)_p CO_2C_{1-3}$alkyl;
$R^e$ is $-(CH_2)_mCO_2H$, $-(CH_2)_mCO_2C_{1-3}$alkyl, $-(CH_2)_m-Z-(CH_2)_pCO_2H$, or $-(CH_2)_m-Z-(CH_2)_p CO_2C_{1-3}$ alkyl;
m is an integer from 1 to 3;
p is an integer from 1 to 3;
n is an integer from 0 to 3;
Z is O or S;
each $R^2$ is independently selected from the group consisting of:
hydrogen,
halogen,
cyano,
$C_{1-4}$alkyl, optionally substituted with one to five fluorines,
$C_{1-4}$alkoxy, optionally substituted with one to five fluorines,
$C_{1-4}$alkylthio, optionally substituted with one to five fluorines,
$C_{1-4}$alkylsulfonyl,
carboxy,
$C_{1-4}$alkyloxycarbonyl, and
$C_{1-4}$alkylcarbonyl;
$R^3$ is hydrogen or $C_{1-4}$ alkyl wherein alkyl is optionally substituted with one to five fluorines;
Ar is phenyl or pyridyl each of which is optionally substituted with one to five substituents independently selected from the group consisting of:
halogen,
$C_{1-6}$alkyl optionally substituted with one to five fluorines,
$C_{2-6}$alkenyl,
$C_{2-6}$alkynyl,
$C_{1-6}$alkylthio, optionally substituted with one to five fluorines,
$C_{1-6}$alkoxy, optionally substituted with one to five fluorines, and
$C_{3-6}$cycloalkyl;
$R^a$ is hydrogen or $C_{1-4}$ alkyl wherein alkyl is optionally substituted with one to five fluorines; and
$R^b$ and $R^c$ are each independently hydrogen, fluorine, or $C_{1-4}$ alkyl wherein alkyl is optionally substituted with one to five fluorines;
or $R^b$ and $R^c$ are taken together to form a 3- to 6-membered saturated carbocyclic ring optionally containing a heteroatom selected from the group consisting of O, S, and N.

Compounds of Formula (XXII) may be synthesized by methods known in the art, e.g., those described in International Patent Publication No. WO2010/025553. In some embodiments, the SCD inhibitor is a compound disclosed in International Patent Publication No. WO2010/025553, the compounds of which are herein incorporated by reference.

In some embodiments of any of the foregoing methods, the SCD inhibitor is a compound of Formula XXIII,

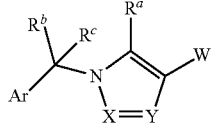

(XXIII)

or a pharmaceutically acceptable salt thereof; wherein X and Y are each independently CH or N;
W is heteroaryl selected from the group consisting of:

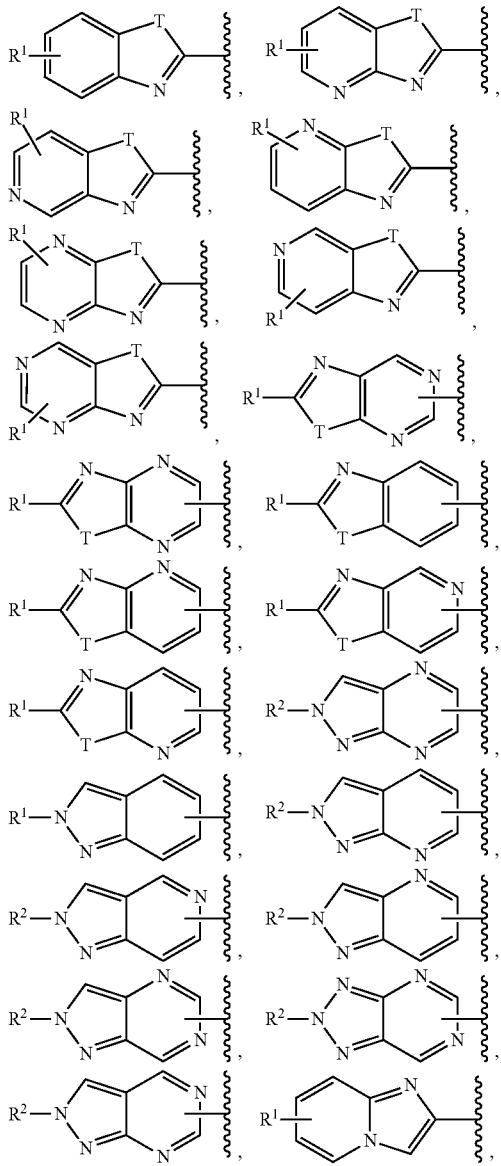

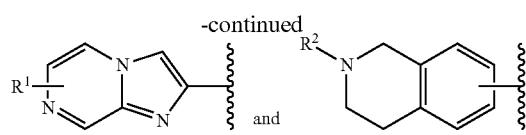

wherein W is further optionally substituted with one to two substituents independently selected from $R^4$;

$R^1$ is selected from the group consisting of: $-(CH_2)_p CO_2H$, $-(CH_2)_p CO_2 C_{1-4}alkyl$, $-Z(CH_2)_m CO_2H$, $-Z(CH_2)_m CO_2 C_{1-4}alkyl$, $-(CH_2)_n OR^6$, $-(CH_2)_n-CONR^6R^7$, $-(CH_2)_n-OCONR^6R^7$, $-(CH_2)_n-SO_2NR^6R^7$, $-(CH_2)_n-SO_2R^8$, $-(CH_2)_n-NR^9SO2R^8$, $-(CH_2)_n-NR^9CONR^6R^7$, $-(CH_2)_n-NR^9COR^9$, and $-(CH_2)_n-NR^9CO_2R^8$;

$R^2$ is $-(CH_2)_m CO_2H$ or $-(CH_2)_m CO_2 C_{1-3}alkyl$;
each m is independently an integer from 1 to 3;
each n is independently an integer from 0 to 3;
each p is independently an integer from 0 to 3;
T is O, S, or $NR^5$;
Z is O, S, or $NR^5$;
each $R^4$ is independently selected from the group consisting of:
hydrogen,
halogen,
cyano,
$C_{1-4}$alkyl, optionally substituted with one to five fluorines,
$C_{1-4}$alkoxy, optionally substituted with one to five fluorines,
$C_{1-4}$alkylthio, optionally substituted with one to five fluorines,
$C_{1-4}$alkylsulfonyl,
carboxy,
$C_{1-4}$alkyloxycarbonyl, and
$C_{1-4}$alkylcarbonyl;
$R^5$ is hydrogen or $C_{1-4}$alkyl wherein alkyl is optionally substituted with one to five fluorines;
$R^6$ and $R^7$ are each independently selected from the group consisting of hydrogen,
$(CH_2)_n$-phenyl,
$(CH_2)_n-C_{3-6}$cycloalkyl, and
$C_{1-6}$ alkyl, wherein alkyl is optionally substituted with one to five substituents independently selected from fluorine and hydroxy and wherein phenyl and cycloalkyl are optionally substituted with one to five substituents independently selected from halogen, hydroxy, $C_{1-6}$alkyl, and $C_{1-6}$alkoxy, wherein alkyl and alkoxy are optionally substituted with one to five fluorines;
or $R^6$ and $R^7$ together with the nitrogen atom to which they are attached form a heterocyclic ring selected from azetidine, pyrrolidine, piperidine, piperazine, and morpholine wherein said heterocyclic ring is optionally substituted with one to three substituents independently selected from halogen, hydroxy, $C_{1-6}$alkyl, and $C_{1-6}$alkoxy, wherein alkyl and alkoxy are optionally substituted with one to five fluorines;
each $R^8$ is independently $C_{1-6}$alkyl, wherein alkyl is optionally substituted with one to five substituents independently selected from fluorine and hydroxyl;
$R^9$ is hydrogen or $R^8$;
Ar is phenyl or pyridyl each of which is optionally substituted with one to five substituents independently selected from the group consisting of:
halogen,
$C_{1-6}$alkyl optionally substituted with one to five fluorines,
$C_{2-6}$alkenyl, $C_{2-6}$alkynyl,
$C_{1-6}$alkylthio, optionally substituted with one to five fluorines,
$C_{1-6}$alkoxy, optionally substituted with one to five fluorines, and
$C_{3-6}$cycloalkyl;
$R^a$ is hydrogen or $C_{1-4}$alkyl wherein alkyl is optionally substituted with one to five fluorines; and
$R^b$ and $R^c$ are each independently hydrogen, fluorine, or $C_{1-4}$alkyl wherein alkyl is optionally substituted with one to five fluorines;
or $R^b$ and $R^c$ are taken together to form a 3- to 6-membered saturated carbocyclic ring optionally containing a heteroatom selected from the group consisting of O, S, and N.

Compounds of Formula (XXIII) may be synthesized by methods known in the art, e.g., those described in International Patent Publication No. WO2010/037225. In some embodiments, the SCD inhibitor is a compound disclosed in International Patent Publication No. WO2010/037225, the compounds of which are herein incorporated by reference.

In some embodiments of any of the foregoing methods, the SCD inhibitor is a compound of Formula XXIV, (XXIV)

or a pharmaceutically acceptable salt thereof; wherein
X is NH, Y is C, and Z is N or $CR^5$;
or X and Z are each $CR^5$, and Y is N;
W is a residue selected from the group consisting of:

wherein each $R^a$ is independently selected from the group consisting of:
hydrogen,
halogen,
$C_{1-4}$alkyl, optionally substituted with one to five fluorines, and
$C_{1-4}$alkoxy, optionally substituted with one to five fluorines;
$R^3$, $R^4$, and each $R^5$ are each independently selected from the group consisting of:
hydrogen,
halogen,
$C_{1-4}$alkyl, optionally substituted with one to five fluorines, and
$C_{1-4}$alkoxy, optionally substituted with one to five fluorines;
$R^2$ is selected from the group consisting of:
$SO_2$cyclopropyl,
$SC_{1-3}$alkyl, optionally substituted with one to five fluorines,
$S(O)C_{1-3}$alkyl, optionally substituted with one to five fluorines,
$SO_2C_{1-3}$alkyl, optionally substituted with one to five fluorines, and
$SO_2NR^bR^b$, wherein each $R^b$ is independently hydrogen or $C_{1-3}$alkyl; and
$R^1$ is selected from the group consisting of: cyclopentenyl, cyclohexenyl, phenyl, and heteroaryl selected from the group consisting of: pyridyl, pyrimidinyl, pyridazinyl, pyrazinyl, furyl, thienyl, thiazolyl, oxazolyl, isoxazolyl, isothiazolyl, imidazolyl, and pyrazolyl;
wherein aryl and heteroaryl are optionally substituted with one to three substituents independently selected from the group consisting of halogen, hydroxy, cyano, and $C_{1-3}$alkyl wherein alkyl is optionally substituted with one to five fluorines.

Compounds of Formula (XXIV) may be synthesized by methods known in the art, e.g., those described in International Patent Publication No. WO2009/129625. In some embodiments, the SCD inhibitor is a compound disclosed in International Patent Publication No. WO2009/129625, the compounds of which are herein incorporated by reference.

In some embodiments of any of the foregoing methods, the SCD inhibitor is a compound of Formula XXV, (XXV)

or a pharmaceutically acceptable salt thereof, wherein:
Z is independently selected from the group consisting of: S, S(O), $S(O)_2$, O, NH and $CH_2$, wherein each NH is unsubstituted or substituted with $R^9$, and wherein $CH_2$ is unsubstituted or substituted with $R^2$;
B is a 5 membered heteroaryl ring containing 1, 2 or 3 heteroatoms selected from NH, O and S, wherein any CH is unsubstituted or substituted with one substituent selected from $R^a$, and wherein any NH is unsubstituted or substituted with one substituent selected from $R^b$;
each $R^1$ is independently selected from the group consisting of: hydrogen, halogen, and $C_{1-3}$alkyl, wherein alkyl is unsubstituted or substituted with one to three substituents independently selected from halogen and hydroxy;

each $R^2$ is independently selected from the group consisting of: hydrogen, halogen, aryl, heteroaryl, biphenyl, $C_{1-6}$alkyl, $(CH_2)_nOR^e$, $(CH_2)_nN(R^e)_2$, $(CH_2)_nC\equiv N$, $(CH_2)_nCOR^e$, and $(CH_2)_nS(O)_qR^e$, wherein $CH_2$, alkyl, phenyl, aryl and heteroaryl are unsubstituted or substituted with one to three substituents independently selected from $R^f$;

each $R^3$ is independently selected from the group consisting of: hydrogen, halogen, $-C_{1-6}$alkyl, $-OC_{1-6}$alkyl, $(CH_2)_nOR^e$, $(CH_2)_nN(R^e)_2$, $(CH_2)_nC\equiv N$, $(CH_2)_nCOR^e$, and $(CH_2)_nS(O)_qR^e$, wherein alkyl is unsubstituted or substituted with hydroxy or one to three halogens, and wherein any $CH_2$ in $R^3$ is unsubstituted or substituted with one to two groups independently selected from halogen, hydroxy, and $C_{1-4}$ alkyl unsubstituted or substituted with one to five fluorines;

$R^4$ is selected from the group consisting of:

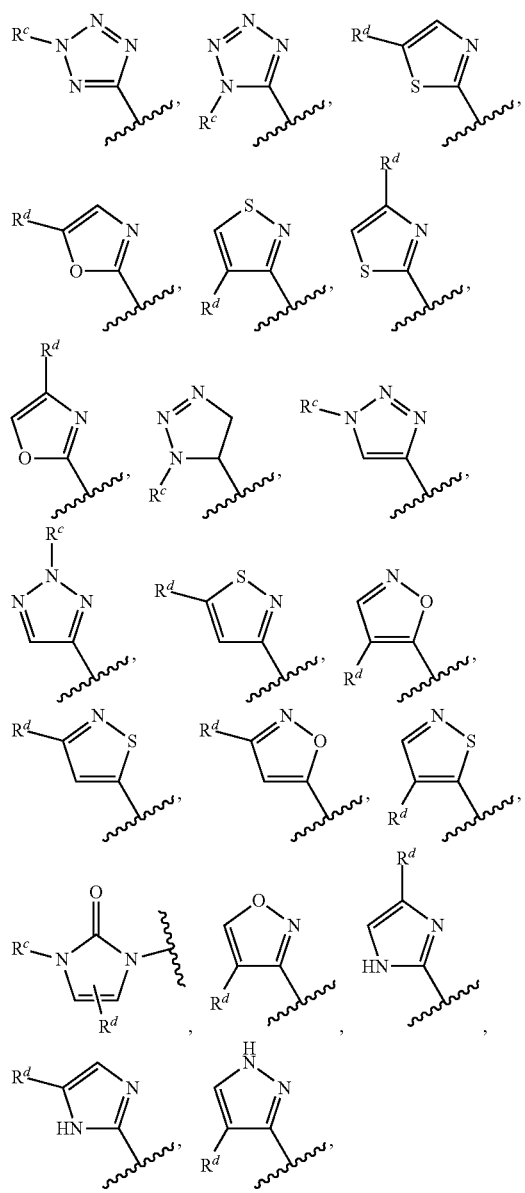

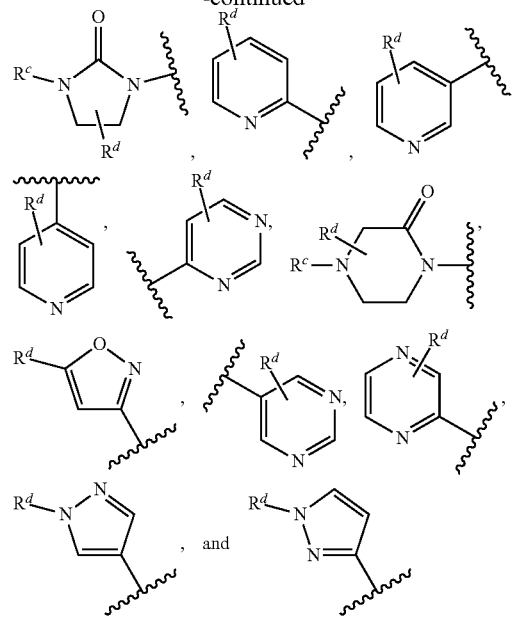

, and each $R^a$ is independently selected from the group consisting of:
hydrogen,
halogen,
cyano,
$C_{1-4}$alkyl, unsubstituted or substituted with one to five fluorines,
$C_{1-4}$alkoxy, unsubstituted or substituted with one to five fluorines,
$C_{1-4}$alkylthio, unsubstituted or substituted with one to five fluorines,
$C_{1-4}$alkylsulfonyl,
$-CO_2H$,
$C_{1-4}$alkyloxycarbonyl, and
$C_{1-4}$alkylcarbonyl;

each $R^b$ is independently selected from the group consisting of: hydrogen, and $C_{1-4}$alkyl,
wherein alkyl is unsubstituted or substituted with one to five fluorines;

each $R^c$ is independently selected from the group consisting of: $-(CH_2)_mCO_2H$, $-(CH_2)_mCO_2C_{1-3}$alkyl, $-(CH_2)_m-NR^b-(CH_2)_pCO_2H$, $-(CH_2)_m-NR^b-(CH_2)_pCO_2C_{1-3}$alkyl, $-(CH_2)_m-O-(CH_2)_pCO_2H$, $-(CH_2)_m-O-(CH_2)_pCO_2C_{1-3}$alkyl, $-(CH_2)_m-S-(CH_2)_pCO_2H$, and $-(CH_2)_m-S-(CH_2)_pCO_2C_{1-3}$alkyl, wherein any $CH_2$ in $R^c$ is unsubstituted or substituted with one to two groups independently selected from halogen, hydroxy, and $C_{1-4}$alkyl unsubstituted or substituted with one to five fluorines;

each $R^d$ is independently selected from the group consisting of: $-(CH_2)_nCO_2H$, $-(CH_2)_nCO_2C_{1-3}$alkyl, $-(CH_2)_n-NR^b-(CH_2)_pCO_2H$, $-(CH_2)_n-NR^b-(CH_2)_pCO_2C_{1-3}$alkyl, $-(CH_2)_n-O-(CH_2)_pCO_2H$, $-(CH_2)_n-O-(CH_2)_pCO_2C_{1-3}$alkyl, $-(CH_2)_n-S-(CH_2)_pCO_2H$, and $-(CH_2)_n-S-(CH_2)_pCO_2C_{1-3}$alkyl, where in any $CH_2$ in $R^d$ is unsubstituted or substituted with one to two groups independently selected from the group consisting of: halogen, hydroxy, and $C_{1-4}$alkyl unsubstituted or substituted with one to five fluorines;

each $R^e$ is independently selected from the group consisting of: hydrogen, and $C_{1-6}$alkyl, wherein alkyl is unsubstituted or substituted with one to three substituents independently selected from the group consisting of: halogen, cyano, —$C_{1-4}$alkoxy, —$C_{1-4}$alkylthio, —$C_{1-4}$alkylsulfonyl, —$CO_2H$, and —$CO_2C_{1-4}$alkyl;

each $R^f$ is independently selected from the group consisting of: hydrogen, halogen, —$C_{1-6}$alkyl, —$OC_{1-6}$alkyl, $(CH_2)_nOR^e$, $(CH_2)_nN(R^e)_2$, $(CH_2)_nC≡N$, $(CH_2)_nCOR^e$, $(CH_2)_nS(O)_qR^e$, and aryl, wherein $CH_2$, alkyl and aryl are unsubstituted or substituted with one, two or three groups independently selected from halogen, hydroxy, and $C_{1-4}$alkyl unsubstituted or substituted with one to five fluorines;

each $R^g$ is independently selected from the group consisting of: hydrogen, and $C_{1-6}$alkyl;

m is an integer from 1 to 3;
n is an integer from 0 to 3;
p is an integer from 1 to 3;
q is an integer from 1 to 2;
r is an integer from 0 to 2;
s is an integer from 0 to 4;
t is an integer from 0 to 8;
d is an integer from 0 to 2; and
e is an integer from 0 to 2,
provided that d+e is 2.

Compounds of Formula (XXV) may be synthesized by methods known in the art, e.g., those described in International Patent Publication No. WO2011/011872. In some embodiments, the SCD inhibitor is a compound disclosed in International Patent Publication No. WO2011/011872, the compounds of which are herein incorporated by reference.

In some embodiments of any of the foregoing methods, the SCD inhibitor is a compound of Formula XXVI,

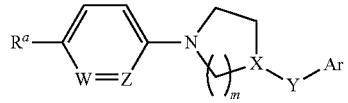

(XXVI)

or a pharmaceutically acceptable salt thereof, wherein
each n is independently 0, 1 or 2;
each p is independently 0, 1, or 2;
m is 1, 2, or 3;
W and Z are each independently CH or N, with the proviso that at least one of W and Z is N;
X—Y is N—C(O), N—S(O)$_2$, N—CR$^1$R$^2$, CH—O, CH—S(O)$_p$, CH—NR$^5$, or CH—CR$^1$R$^2$;
Ar is phenyl, benzyl, naphthyl, or heteroaryl each of which is optionally substituted with one to five R$^3$ substituents;
R$^a$ is phenyl, naphthyl, or a heteroaromatic ring selected from the group consisting of: oxazolyl, thiazolyl, imidazolyl, pyrrolyl, pyrazolyl, isoxazolyl,
isothiazolyl, 1,2,4-oxadiazol-5-yl, 1,2,4-oxadiazol-3-yl, 1,3,4-oxadiazolyl, 1,2,5-oxadiazolyl, 1,2,3-oxadiazolyl, 1,2,4-thiadiazol-5-yl, 1,2,4-thiadiazol-3-yl, 1,2,5-thiadiazolyl, 1,3,4-thiadiazolyl, 1,2,3-thiadiazolyl, 1,2,4-triazolyl, 1,2,3-triazolyl, tetrazolyl, indolyl, benzthiazolyl, benzoxazolyl, benzimidazolyl, benzisoxazolyl, benzisothiazolyl, and imidazo[1,2-a]pyridyl;
wherein phenyl, naphthyl, and the heteroaromatic ring are optionally substituted with one to three substituents independently selected from R$^6$;
R$^1$ and R$^2$ are each independently hydrogen or $C_{1-3}$alkyl, wherein alkyl is optionally substituted with one to three substituents independently selected from halogen and hydroxy;

each R$^6$ is independently selected from the group consisting of: $C_{1-6}$alkyl, $C_{2-4}$alkenyl, $(CH_2)_nOR^4$, $(CH_2)_n$-phenyl, $(CH_2)_n$-naphthyl, $(CH_2)_n$-heteroaryl, $(CH_2)_n$-heterocyclyl, $(CH_2)_nC_{3-7}$cycloalkyl, halogen, $(CH_2)_nN(R^4)_2$, $(CH_2)_nC≡N$, $(CH_2)_nCO_2R^4$, $(CH_2)_nOC(O)R^4$, $(CH_2)_nCOR^4$, $NO_2$, $(CH_2)_nNR^4SO_2R^4$, $(CH_2)_nSO_2N(R^4)_2$, $(CH_2)_nS(O)_pR^4$, $(CH_2)_nNR^4C(O)N(R^4)_2$, $(CH_2)_nC(O)N(R^4)_2$, $(CH_2)_nC(O)N(OR^4)R^4$, $(CH_2)_nC(O)N(NH_2)R^4$, $(CH_2)_nNR^4C(O)R^4$, $(CH_2)_nNR^4CO_2R^4$, $(CH_2)_nP(=O)(OR^4)_2$, $(CH_2)_nOP(=O)(OR^4)_2$, $(CH_2)_nO(CH_2)_nP(=O)(OR^4)_2$, $O(CH_2)_nC(O)N(R^4)_2$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkoxy, $C_{1-4}$alkylsulfonyl, $C_{3-6}$cycloalkyl, and $C_{1-4}$alkyl wherein alkyl is optionally substituted with hydroxy or one to three fluorines; and wherein any methylene ($CH_2$) carbon atom in R$^6$ is optionally substituted with one to two groups independently selected from fluorine, hydroxy, and $C_{1-4}$alkyl optionally substituted with one to five fluorines; or two substituents when on the same methylene ($CH_2$) group are taken together with the carbon atom to which they are attached to form a cyclopropyl group;

each R$^3$ is independently selected from the group consisting of: $C_{1-6}$alkyl, $(CH_2)_nOR^4$, $(CH_2)_n$-phenyl, $(CH_2)_n$-naphthyl, $(CH_2)_n$-heteroaryl, $(CH_2)_n$-heterocyclyl, $(CH_2)_nC_{3-7}$cycloalkyl, halogen, $(CH_2)_nN(R^4)_2$, $(CH_2)_nC≡N$, $(CH_2)_nCO_2R^4$, $(CH_2)_nCOR^4$, $NO_2$, $(CH_2)_nNR^4SO_2R^4$ $(CH_2)_nSO_2N(R^4)_2$, $(CH_2)_nS(O)_pR^4$, $(CH_2)_nNR^4C(O)N(R^4)_2$, $(CH_2)_nC(O)N(R^4)_2$, $(CH_2)_nC(O)N(OR^4)R^4$, $(CH_2)_nC(O)N(NH_2)R^4$, $(CH_2)_nNR^4C(O)R^4$, $(CH_2)_nNR^4CO_2R^4$, $O(CH_2)_nC(O)N(R^4)_2$, $(CH_2)_nP(=O)(OR^4)_2$, $(CH_2)_nOP(=O)(OR^4)_2$, $(CH_2)_nO(CH_2)_nP(=O)(OR^4)_2$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkoxy, $C_{3-6}$cycloalkyl, and $C_{1-4}$alkyl wherein alkyl is optionally substituted with hydroxy or one to three fluorines; and wherein any methylene ($CH_2$) carbon atom in R$^3$ is optionally substituted with one to two groups independently selected from fluorine, hydroxy, and $C_{1-4}$alkyl optionally substituted with one to five fluorines; or two substituents when on the same methylene ($CH_2$) group are taken together with the carbon atom to which they are attached to form a cyclopropyl group;

each R$^4$ is independently selected from the group consisting of: hydrogen, $C_{1-6}$alkyl, $(CH_2)_n$-phenyl, $(CH_2)_n$-heteroaryl, $(CH_2)_n$-naphthyl, and $(CH_2)_nC_{3-7}$cycloalkyl;

wherein alkyl, phenyl, heteroaryl, and cycloalkyl are optionally substituted with one to three groups independently selected from halogen, $C_{1-4}$ alkyl, and $C_{1-4}$alkoxy; or two R$^4$ groups together with the atom to which they are attached form a 4- to 8-membered mono- or bicyclic ring system optionally containing an additional heteroatom selected from O, S, and NC$_{1-4}$alkyl; and R$^5$ is hydrogen or $C_{1-6}$ alkyl optionally substituted with one to five fluorines.

Compounds of Formula (XXVI) may be synthesized by methods known in the art, e.g., those described in International Patent Publication No. WO2007/009236. In some embodiments, the SCD inhibitor is a compound disclosed in International Patent Publication No. WO2007/009236, the compounds of which are herein incorporated by reference.

In some embodiments of any of the foregoing methods, the SCD inhibitor is a compound of Formula XXVII, HetAr—W—X—Ar (XXVII)

or a pharmaceutically acceptable salt thereof; wherein
X is —O—, —S—, —S(O)—, —S(O)$_2$—, —NR$^9$—, or —CR$^{10}$R$^{11}$;
W is selected from the group consisting of:
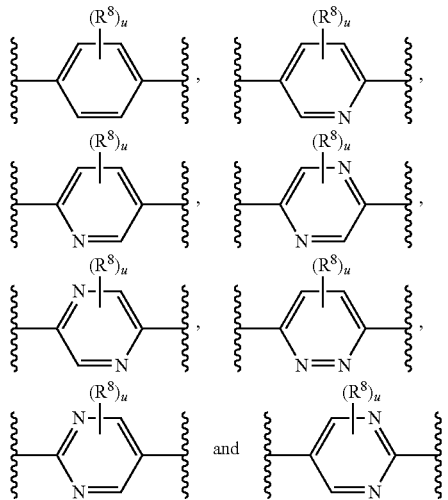
HetAr is heteroaryl selected from the group consisting of:
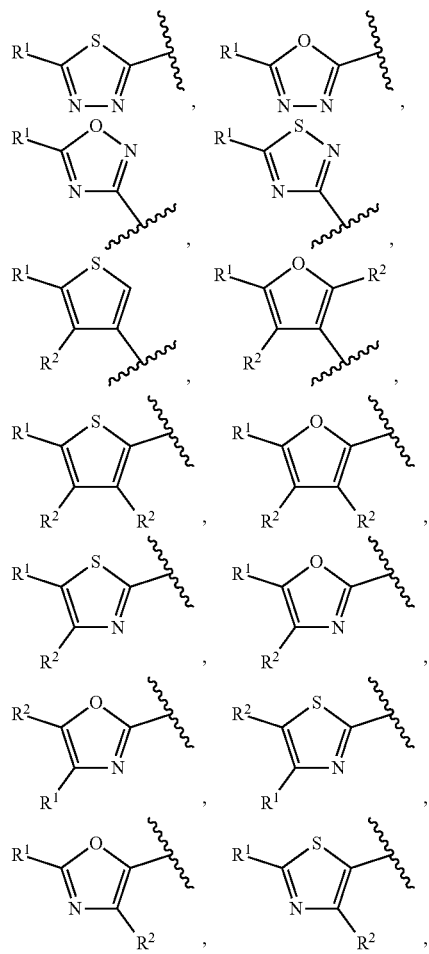
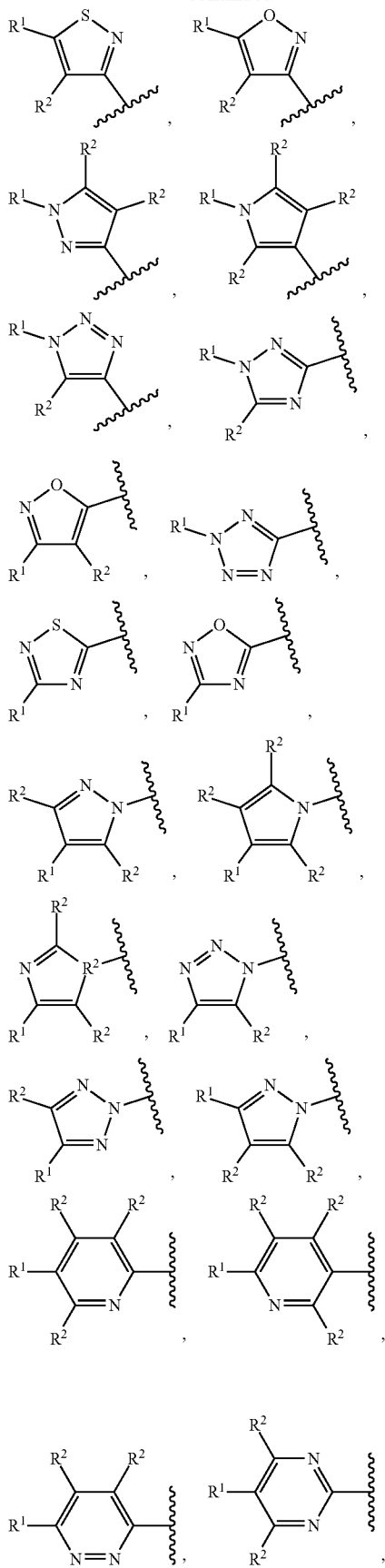

-continued

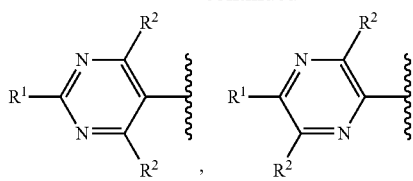

R¹ is heteroaryl selected from the group consisting of:

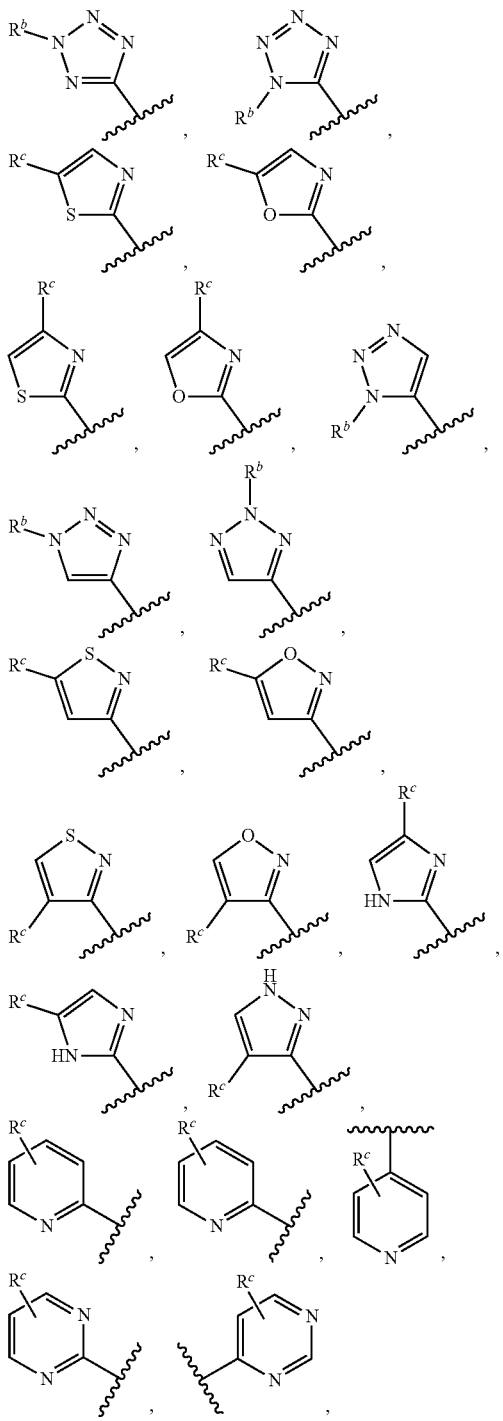

-continued

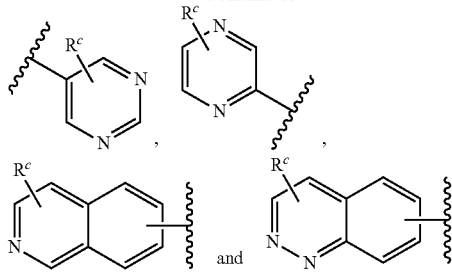

wherein
R$^b$ is —(CH$_2$)$_r$CO$_2$H, —(CH$_2$)$_r$CO$_2$C$_{1-3}$alkyl, —(CH$_2$)$_r$—Z—(CH$_2$)$_p$CO$_2$H, or —(CH$_2$)$_r$—Z—(CH$_2$)$_p$CO$_2$C$_{1-3}$alkyl;

R$^c$ is —(CH$_2$)$_m$CO$_2$H, —(CH$_2$)$_m$CO$_2$C$_{1-3}$alkyl, —(CH$_2$)$_m$—Z—(CH$_2$)$_p$CO$_2$H, or —(CH$_2$)$_m$—Z—(CH$_2$)$_p$CO$_2$C$_{1-3}$alkyl;

and wherein said R¹ heteroaryl ring is optionally substituted with a substituent selected from the group consisting of cyano, halogen, C$_{1-4}$alkyl, C$_{1-4}$alkoxy, C$_{1-4}$alkylthio, C$_{1-4}$alkylsulfonyl, and trifluoromethyl;

each R² is independently selected from the group consisting of:
hydrogen,
halogen,
hydroxy,
cyano,
amino,
nitro,
C$_{1-4}$alkyl, optionally substituted with one to five fluorines,
C$_{1-4}$alkoxy, optionally substituted with one to five fluorines,
C$_{1-4}$alkylthio, optionally substituted with one to five fluorines,
C$_{1-4}$alkylsulfonyl,
carboxy,
C$_{1-4}$alkyloxycarbonyl, and
C$_{1-4}$alkylcarbonyl;

Ar is phenyl or naphthyl optionally substituted with one to five R³ substituents; each R³ is independently selected from the group consisting of: C$_{1-6}$alkyl, C$_{2-6}$alkenyl, (CH$_2$)$_n$-phenyl, (CH$_2$)$_n$-naphthyl, (CH$_2$)$_n$-heteroaryl, (CH$_2$)$_n$-heterocyclyl, (CH$_2$)$_n$C$_{3-7}$cycloalkyl, halogen, nitro, (CH$_2$)$_n$OR$^4$, (CH$_2$)$_n$N(R$^4$)$_2$, (CH$_2$)$_n$C≡N, (CH$_2$)$_n$CO$_2$R$^4$, (CH$_2$)$_n$NR$^4$SO$_2$R$^4$(CH$_2$)$_n$SO$_2$N(R$^4$)$_2$, (CH$_2$)$_n$S(O)$_{0-2}$R$^4$, (CH$_2$)$_n$NR$^4$C(O)N(R$^4$)$_2$, (CH$_2$)$_n$C(O)N(R$^4$)$_2$, (CH$_2$)$_n$NR$^4$C(O)R$^4$, (CH$_2$)$_n$NR$^4$CO$_2$R$^4$, (CH$_2$)$_n$C(O)R$^4$, O(CH$_2$)$_n$C(O)N(R$^4$)$_2$, (CH$_2$)$_s$—Z—(CH$_2$)$_t$-phenyl, (CH$_2$)$_s$—Z—(CH$_2$)$_t$-naphthyl, (CH$_2$)$_s$—Z—(CH$_2$)$_t$-heteroaryl, (CH$_2$)$_s$—Z—(CH$_2$)$_t$-heterocyclyl, (CH$_2$)$_s$—Z—(CH$_2$)$_t$-C$_{3-7}$cycloalkyl, (CH$_2$)$_s$—Z—(CH$_2$)$_t$—OR$^4$, (CH$_2$)$_s$—Z—(CH$_2$)$_t$—N(R$^4$)$_2$, (CH$_2$)$_s$—Z—(CH$_2$)$_t$—NR$^4$SO$_2$R$^4$, (CH$_2$)$_s$—Z—(CH$_2$)$_t$—C≡N, (CH$_2$)$_s$—Z—(CH$_2$)$_t$—C$_2$R$^4$, (CH$_2$)$_s$—Z—(CH$_2$)$_t$—SO$_2$N(R$^4$)$_2$, (CH$_2$)$_s$—Z—(CH$_2$)$_t$—S(O)$_{0-2}$R$^4$, (CH$_2$)$_s$—Z—(CH$_2$)$_t$—NR$^4$C(O)N(R$^4$)$_2$, (CH$_2$)$_s$—Z—(CH$_2$)$_t$—C(O)N(R$^4$)$_2$, (CH$_2$)$_s$—Z—(CH$_2$)$_t$—NR$^4$C(O)R$^4$, (CH$_2$)$_s$—Z—(CH$_2$)$_t$—NR$^4$CO$_2$R$^4$, (CH$_2$)$_s$—Z—(CH$_2$)$_t$—C(O)R$^4$, CF$_3$, CH$_2$CF$_3$, OCF$_3$, and OCH$_2$CF$_3$;

in which phenyl, naphthyl, heteroaryl, cycloalkyl, and heterocyclyl are optionally substituted with one to three substituents independently selected from halogen, hydroxy, C$_{1-4}$alkyl, trifluoromethyl, and C$_{1-4}$alkoxy; and wherein any methylene (CH$_2$) carbon atom in R$^3$ is optionally substituted with one to two groups independently selected from fluorine, hydroxy, and C$_{1-4}$alkyl; or two substituents when on the same methylene (CH$_2$) group are taken together with the carbon atom to which they are attached to form a cyclopropyl group;

Z is O, S, or NR$^4$;

each R$^4$ is independently selected from the group consisting of: hydrogen, C$_{1-6}$alkyl, (CH$_2$)$_n$-phenyl, (CH$_2$)$_n$-heteroaryl, (CH$_2$)$_n$-naphthyl, and (CH$_2$)$_n$C$_{3-7}$cycloalkyl;

wherein alkyl, phenyl, heteroaryl, and cycloalkyl are optionally substituted with one to three groups independently selected from halogen, C$_{1-4}$alkyl, and C$_{1-4}$alkoxy; or two R$^4$ groups together with the atom to which they are attached form a 4- to 8-membered mono- or bicyclic ring system optionally containing an additional heteroatom selected from O, S, NH, and NC$_{1-4}$alkyl;

each R$^6$ and R$^7$ are independently hydrogen or C$_{1-3}$alkyl, wherein alkyl is optionally substituted with one to five fluorines;

each R$^8$ is independently selected from the group consisting of hydrogen, halogen, and C$_{1-4}$alkyl wherein alkyl is optionally substituted with one to five fluorines;

R$^9$, R$^{10}$, and R$^{11}$ are each independently hydrogen or C$_{1-3}$alkyl, wherein alkyl is optionally substituted with one to five fluorines;

u is an integer from 0 to 2;
r is an integer from 0 to 3;
m is an integer from 1 to 3;
each p is independently an integer from 1 to 3;
each n is independently an integer from 0 to 2;
each s is independently an integer from 1 to 3; and
each t is independently an integer from 1 to 3.

Compounds of Formula (XXVII) may be synthesized by methods known in the art, e.g., those described in International Patent Publication No. WO2009/073973. In some embodiments, the SCD inhibitor is a compound disclosed in International Patent Publication No. WO2009/073973, the compounds of which are herein incorporated by reference.

In some embodiments of any of the foregoing methods, the SCD inhibitor is a compound of Formula XXVIII, $$W—X—(CH_2)_u—Y—Ar \quad \quad (XXVIII)$$

or a pharmaceutically acceptable salt thereof; wherein any methylene (CH$_2$) carbon atom in (CH$_2$)$_u$ is optionally substituted with one to two R$^5$ substituents independently selected from fluorine, hydroxy, oxo, hydroxyrnethyl, and C$_{1-4}$alkyl; or two R$^5$ substituents, when on the same (CH$_2$) carbon atom, are taken together with the carbon atom to which they are attached to form a C$_{3-6}$cycloalkyl group; or any two methylene (CH$_2$) carbon atoms are taken together to form a saturated or monounsaturated five- or six-membered cycloalkyl group;

X and Y are each independently a bond, —O—, —S—, —S(O)—, —S(O)$_2$—, —NR$^6$—,

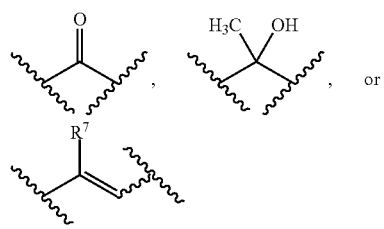

W is heteroaryl selected from the group consisting of:

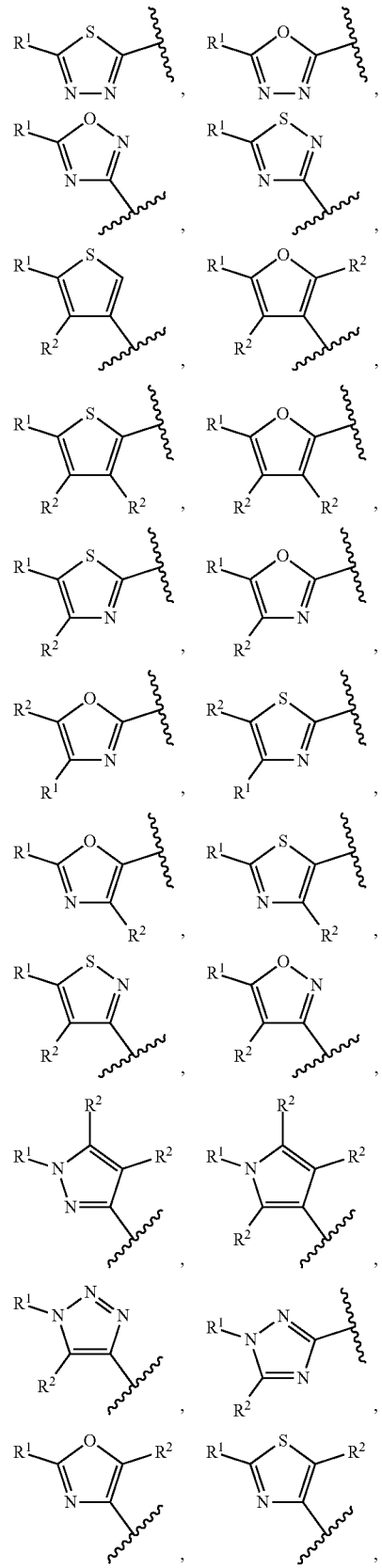

-continued
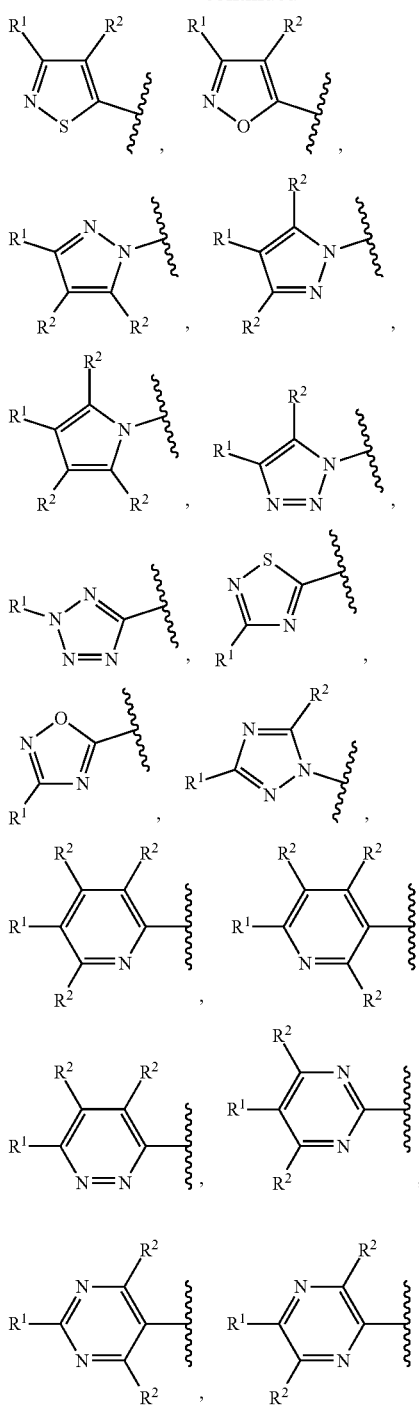
$R^1$ is heteroaryl selected from the group consisting of:
-continued
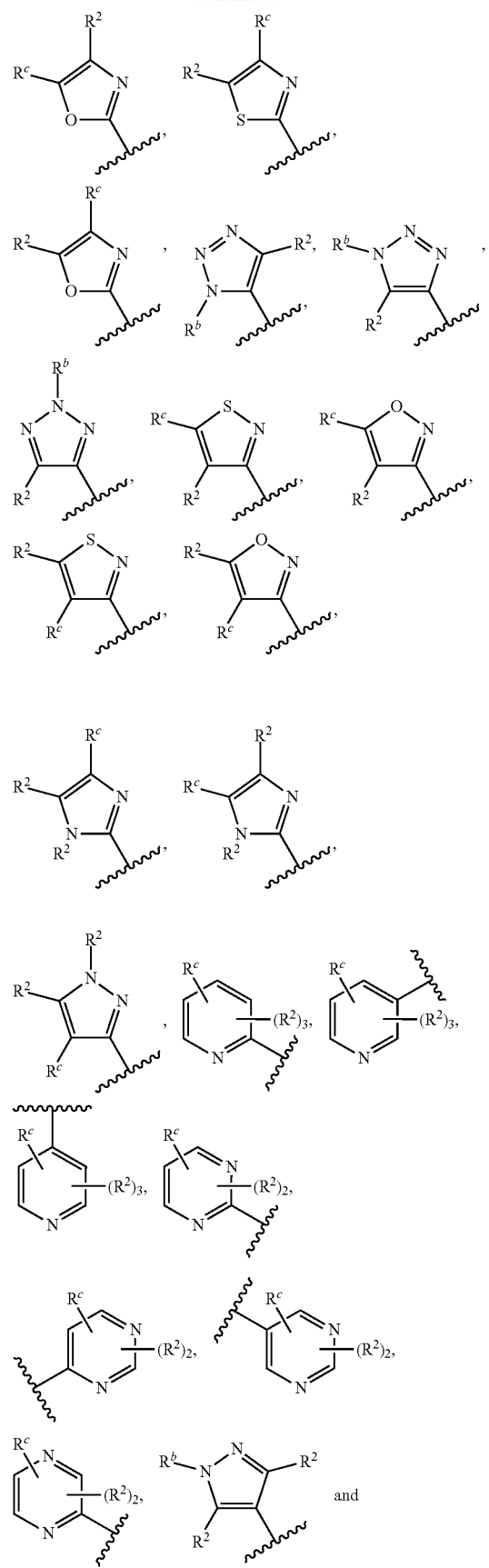
and

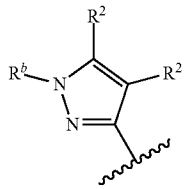

wherein $R^b$ is $-(CH_2)_rCO_2H$, $-(CH_2)_rCO_2C_{1-3}alkyl$, $-(CH_2)_r-Z-(CH_2)_pCO_2H$, or $-(CH_2)_r-Z-(CH_2)_pCO_2C_{1-3}alkyl$;

$R^c$ is $-(CH_2)_mCO_2H$, $-(CH_2)_mCO_2C_{1-3}alkyl$, $-(CH_2)_m-Z-(CH_2)_pCO_2H$, or $-(CH_2)_m-Z-(CH_2)_pCO_2C_{1-3}alkyl$;

and wherein said $R^1$ heteroaryl ring is optionally substituted with one substituent independently selected from the group consisting of cyano, halogen, $C_{1-4}alkyl$, $C_{1-4}alkoxy$, $C_{1-4}alkylthio$, $C_{1-4}alkylsulfonyl$, and trifluoromethyl;

each $R^2$ is independently selected from the group consisting of:
hydrogen,
halogen,
hydroxy,
cyano,
amino,
nitro,
$C_{1-4}alkyl$, optionally substituted with one to five fluorines,
$C_{1-4}alkoxy$, optionally substituted with one to five fluorines,
$C_{1-4}alkylthio$, optionally substituted with one to five fluorines,
$C_{1-4}alkylsulfonyl$,
carboxy,
$C_{1-4}alkyloxycarbonyl$, and
$C_{1-4}alkylcarbonyl$;

Ar is phenyl or naphthyl optionally substituted with one to five $R^3$ substituents; each $R^3$ is independently selected from the group consisting of: $C_{1-6}alkyl$, $C_{2-6}alkenyl$, $(CH_2)_n$-phenyl, $(CH_2)_n$-naphthyl, $(CH_2)_n$-heteroaryl, $(CH_2)_n$-heterocyclyl, $(CH_2)_nC_{3-7}cycloalkyl$, halogen, nitro, $(CH_2)_nOR^4$, $(CH_2)_nN(R^4)_2$, $(CH_2)_nC≡N$, $(CH_2)_nCO_2R^4$, $(CH_2)_nNR^4SO_2R^4(CH_2)_nSO_2N(R^4)_2$, $(CH_2)_nS(O)_{0-2}R^4$, $(CH_2)_nNR^4C(O)N(R^4)_2$, $(CH_2)_nC(O)N(R^4)_2$, $(CH_2)_nNR^4C(O)R^4$, $(CH_2)_nNR^4CO_2R^4$, $(CH_2)_nC(O)R^4$, $O(CH_2)_nC(O)N(R^4)_2$, $(CH_2)_s-Z-(CH_2)_t$-phenyl, $(CH_2)_s-Z-(CH_2)_t$-naphthyl, $(CH_2)_s-Z-(CH_2)_t$-heteroaryl, $(CH_2)_s-Z-(CH_2)_t$-heterocyclyl, $(CH_2)_s-Z-(CH_2)_t-C_{3-7}cycloalkyl$, $(CH_2)_s-Z-(CH_2)_t-OR^4$, $(CH_2)_s-Z-(CH_2)_t-N(R^4)_2$, $(CH_2)_s-Z-(CH_2)_t-NR^4SO_2R^4$, $(CH_2)_s-Z-(CH_2)_t-C≡N$, $(CH_2)_s-Z-(CH_2)_t-C_2R^4$, $(CH_2)_s-Z-(CH_2)_t-SO_2N(R^4)_2$, $(CH_2)_s-Z-(CH_2)_t-S(O)_{0-2}R^4$, $(CH_2)_s-Z-(CH_2)_t-NR^4C(O)N(R^4)_2$, $(CH_2)_s-Z-(CH_2)_t-C(O)N(R^4)_2$, $(CH_2)_s-Z-(CH_2)_t-NR^4C(O)R^4$, $(CH_2)_s-Z-(CH_2)_t-NR^4CO_2R^4$, $(CH_2)_s-Z-(CH_2)_t-C(O)R^4$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}alkyl$, trifluoromethyl, and $C_{1-4}$ alkoxy optionally substituted with one to five fluorines; and wherein any methylene ($CH_2$) carbon atom in $R^3$ is optionally substituted with one to two groups independently selected from fluorine, hydroxy, and $C_{1-4}alkyl$; or two substituents when on the same methylene ($CH_2$) group are taken together with the carbon atom to which they are attached to form a cyclopropyl group;

each $R^4$ is independently selected from the group consisting of: hydrogen, $C_{1-6}alkyl$, $(CH_2)_n$-phenyl, $(CH_2)_n$-heteroaryl, $(CH_2)_n$-naphthyl, and $(CH_2)_nC_{3-7}cycloalkyl$;

wherein alkyl, phenyl, heteroaryl, and cycloalkyl are optionally substituted with one to three groups independently selected from halogen, $C_{1-4}alkyl$, and $C_{1-4}alkoxy$; or two $R^4$ groups together with the atom to which they are attached form a 4- to 8-membered mono- or bicyclic ring system optionally containing an additional heteroatom selected from O, S, NH, and $NC_{1-4}$ alkyl;

each $R^6$ and $R^7$ are independently hydrogen or $C_{1-3}alkyl$, wherein alkyl is optionally substituted with one to five fluorines;

u is an integer from 1 to 4;
r is an integer from 1 to 3;
m is an integer from 0 to 3;
each p is independently an integer from 1 to 3;
each n is independently an integer from 0 to 2;
each s is independently an integer from 1 to 3; and
each t is independently an integer from 1 to 3.

Compounds of Formula (XXVIII) may be synthesized by methods known in the art, e.g., those described in International Patent Publication No. WO2008/128335. In some embodiments, the SCD inhibitor is a compound disclosed in International Patent Publication No. WO2008/128335, the compounds of which are herein incorporated by reference.

In some embodiments of any of the foregoing methods, the SCD inhibitor is a compound of Formula XXIX, W-Het-Ar　　　　(XXIX)

or a pharmaceutically acceptable salt thereof; wherein

Het is a heterobicyclic ring system selected from the group consisting of:

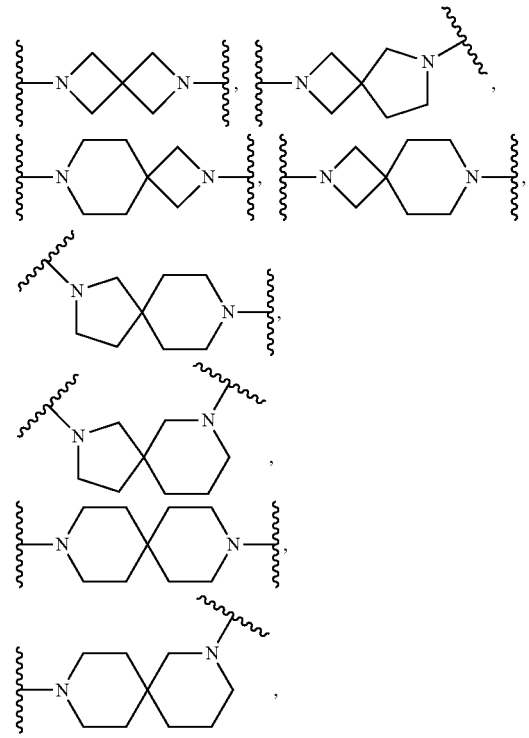

-continued
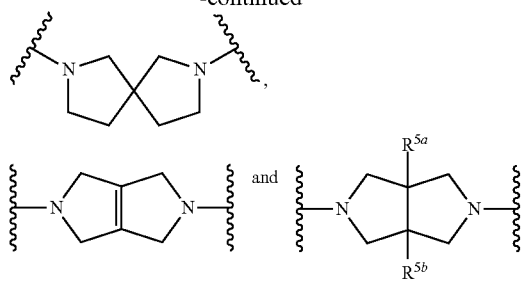
W is heteroaryl selected from the group consisting of:
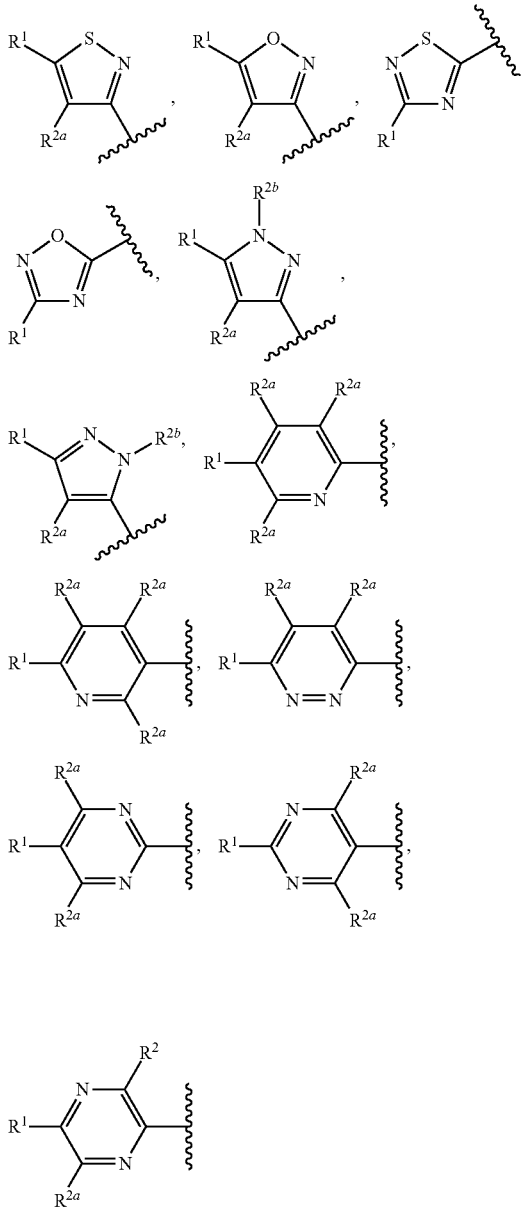
R[1] is heteroaryl selected from the group consisting of:
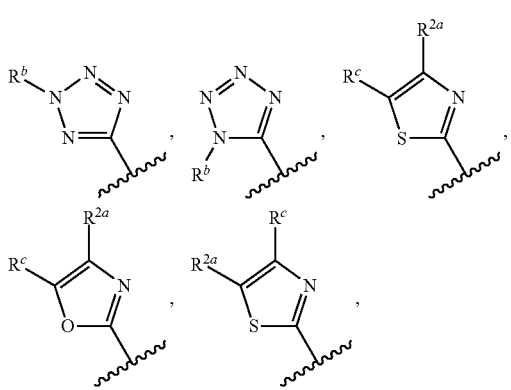

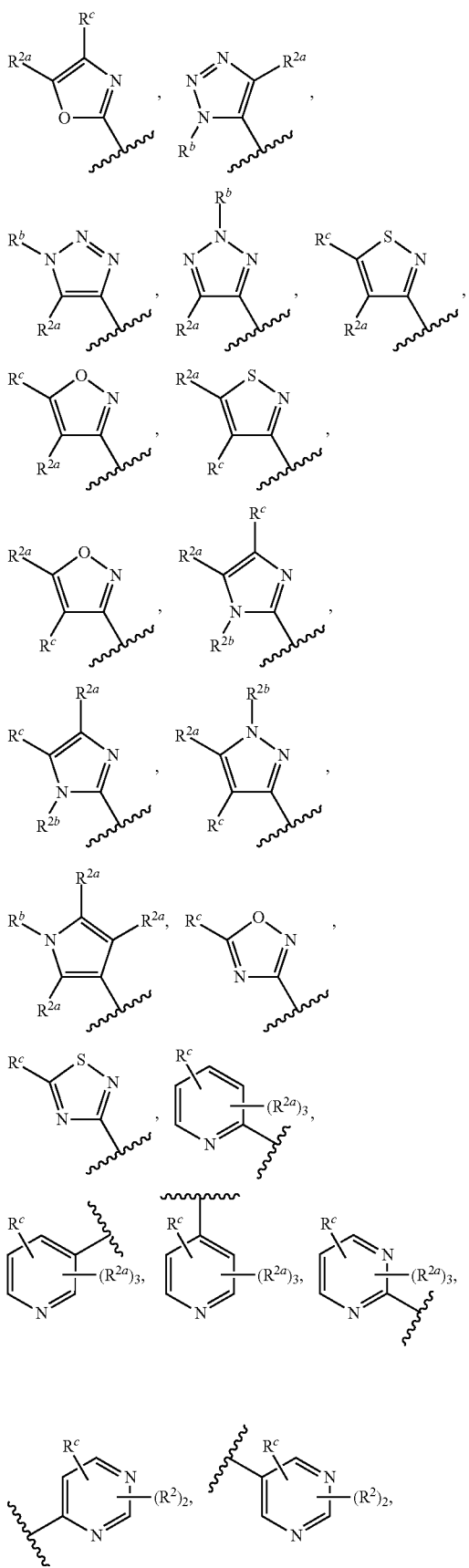
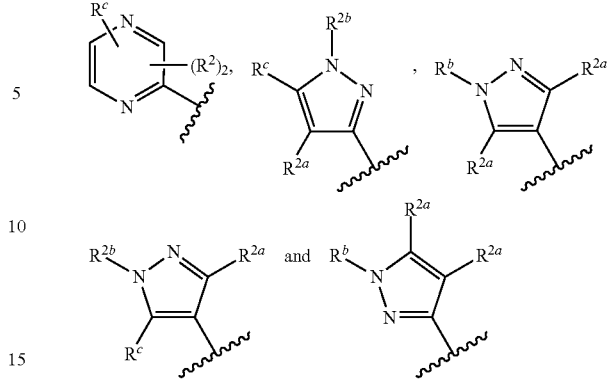

wherein $R^b$ is $(CH_2)_rCO_2H$, $-(CH_2)_rCO_2C_{1-3}alkyl$, $-(CH_2)_r-Z(CH_2)_pCO_2H$, or $(CH_2)_r-Z(CH_2)_pCO_2C_{1-3}alkyl$;

$R^c$ is $-(CH_2)_mCO_2H$, $-(CH_2)_mCO_2C_{1-3}alkyl$, $-(CH_2)_m-Z-(CH_2)_pCO_2H$, or $(CH_2)_m-Z-(CH_2)_pCO_2C_{1-3}alkyl$;

Z is O, $S(O)_q$, or $NR^4$;

each $R^{2a}$ is independently selected from the group consisting of:
hydrogen,
halogen,
hydroxy,
cyano,
$C_{1-4}$alkyl, optionally substituted with one to five fluorines,
$C_{1-4}$alkoxy, optionally substituted with one to five fluorines,
$C_{1-4}$alkylthio, optionally substituted with one to five fluorines,
$C_{1-4}$alkylsulfonyl, optionally substituted with one to five fluorines,
carboxy,
$C_{1-4}$alkyloxycarbonyl, and
$C_{1-4}$alkylcarbonyl;

each $R^{2b}$ is independently selected from the group consisting of:
hydrogen,
$C_{1-4}$alkyl, optionally substituted with one to five fluorines,
$C_{1-4}$alkylsulfonyl, optionally substituted with one to five fluorines,
$C_{1-4}$alkyloxycarbonyl, and
$C_{1-4}$alkylcarbonyl;

Ar is phenyl, naphthyl, thienyl, or pyridyl optionally substituted with one to five $R^3$ substituents;

each $R^3$ is independently selected from the group consisting of:
halogen,
cyano,
$C_{1-6}$alkyl, optionally substituted with one to five fluorines,
$C_{1-6}$alkoxy, optionally substituted with one to five fluorines,
$-OCH_2C_{3-6}$ cycloalkyl,
$C_{1-6}$alkylthio, optionally substituted with one to five fluorines,
$C_{1-6}$alkylsulfonyl, optionally substituted with one to five fluorines, and
phenyl, optionally substituted with one to three substituents independently selected from halogen, $C_{1-4}$alkyl, cyano, trifluoromethyl, and trifluoromethoxy;

each $R^4$ is independently selected from the group consisting of: hydrogen, $C_{1-6}$alkyl, $(CH_2)_n$-phenyl, $(CH_2)_n$-heteroaryl, $(CH_2)_n$-naphthyl, and $(CH_2)_nC_{3-7}$cycloalkyl;

wherein alkyl, phenyl, heteroaryl, naphthyl, and cycloalkyl are optionally substituted with one to three groups independently selected from halogen, $C_{1-4}$alkyl, and $C_{1-4}$alkoxy;

$R^{5a}$ and $R^{5b}$ are each independently selected from the group consisting of:
  hydrogen,
  fluorine,
  hydroxy,
  $C_{1-3}$alkyl, optionally substituted with one to five fluorines, and
  $C_{1-4}$alkylcarbonyloxy;
m is an integer from 0 to 3;
n is an integer from 0 to 2;
p is an integer from 1 to 3;
q is an integer from 0 to 2; and
r is an integer from 1 to 3.

Compounds of Formula (XXIX) may be synthesized by methods known in the art, e.g., those described in International Patent Publication No. WO2010/108268. In some embodiments, the SCD inhibitor is a compound disclosed in International Patent Publication No. WO2010/108268, the compounds of which are herein incorporated by reference.

In some embodiments of any of the foregoing methods, the SCD inhibitor is a compound of Formula XXX,

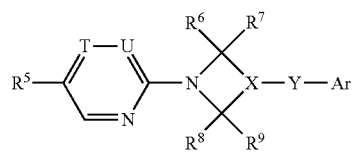

(XXX)

or a pharmaceutically acceptable salt thereof; wherein
X—Y is CH—O, CH—S or CH—$CR^1R^2$.
each of U and T is CH or N, with the proviso that at least one of U and T is N;
Ar is phenyl, benzyl, naphthyl, or pyridyl each of which is optionally substituted with one to five substituents independently selected from $R^3$;
$R^1$ and $R^2$ are each independently hydrogen or $C_{1-3}$alkyl, wherein alkyl is optionally substituted with one to three substituents independently selected from fluorine and hydroxy;
each $R^5$ is independently selected from the group consisting of: $(CH_2)_nCO_2R^4$, $(CH_2)_nOC(O)R^4$, $(CH_2)_nCOR^4$, $(CH_2)_nNR^4SO_2R^4$, $(CH_2)_nSO_2N(R^4)_2$, $(CH_2)_nS(O)_qR^4$, $(CH_2)_nNR^4C(O)N(R^4)_2$, $(CH_2)_nC(O)N(R^4)_2$, $(CH_2)_nC(O)N(OR^4)R^4$, $(CH_2)_nC(O)NR^4NC(O)R^4$, $(CH_2)_nNR^4C(O)R^4$, $(CH_2)_nNR^4CO_2R^4$, and $O(CH_2)_nC(O)N(R^4)_2$;

wherein any methylene ($CH_2$) carbon atom in $R^5$ is optionally substituted with one to two groups independently selected from fluorine, hydroxy, and $C_{1-4}$ alkyl optionally substituted with one to five fluorines; or two substituents when on the same methylene ($CH_2$) group are taken together with the carbon atom to which they are attached to form a cyclopropyl group;

each $R^3$ is independently selected from the group consisting of:
halogen,
$C_{1-6}$alkyl, optionally substituted with one to five fluorines,
$(CH_2)_nOR^4$,
$(CH_2)_nN(R^4)_2$,
$(CH_2)_nC\equiv N$,
$(CH_2)_nCOR^4$, and
$(CH_2)_nS(O)_qR^4$;

wherein alkyl is optionally substituted with hydroxy or one to three fluorines; and wherein any methylene ($CH_2$) carbon atom in $R^3$ is optionally substituted with one to two groups independently selected from fluorine, hydroxy, and $C_{1-4}$alkyl optionally substituted with one to five fluorines; or two substituents when on the same methylene ($CH_2$) group are taken together with the carbon atom to which they are attached to form a cyclopropyl group;

each $R^4$ is independently selected from the group consisting of: hydrogen, $C_{1-6}$alkyl, $(CH_2)_m$-phenyl, $(CH_2)_m$-heteroaryl, $(CH_2)_m$-naphthyl, and $(CH_2)_mC_{3-7}$cycloalkyl;

wherein alkyl is optionally substituted with one to three substituents independently selected from the group consisting of halogen, cyano, —$C_{1-4}$alkoxy, —$C_{1-4}$alkylthio, —$C_{1-4}$alkylsulfonyl, -carboxy, and —$CO_2C_{1-4}$alkyl; and wherein phenyl, naphthyl, and heteroaryl are optionally substituted with one to three groups independently selected from the group consisting of:
halogen,
$C_{1-4}$alkyl, optionally substituted with one to five fluorines,
$C_{1-4}$alkoxy, optionally substituted with one to five fluorines,
$C_{1-4}$alkylthio, optionally substituted with one to five fluorines,
$C_{1-4}$alkylsulfonyl, optionally substituted with one to five fluorines,
$C_{1-4}$alkylcarbonyl,
$C_{1-4}$alkyloxycarbonyl,
amino,
mono-($C_{1-4}$alkyl)amino,
di-($C_{1-4}$alkyl)amino,
—$O(CH_2)_pCO_2H$,
—$O(CH_2)_pCO_2C_{1-4}$alkyl,
—$S(O)_q(CH_2)_pCO_2H$,
—$S(O)_q(CH_2)_pCO_2C_{1-4}$alkyl,
—$NH(CH_2)_pCO_2H$,
—$NH(CH_2)_pCO_2C_{1-4}$alkyl,
—$(CH_2)_pCO_2H$,
—$(CH_2)_pCO_2C_{1-4}$alkyl,
—$N(R^{10})C(O)(R^{10})$,
phenyl, optionally substituted with one to two substituents selected from halogen, carboxy, and $C_{1-4}$alkyl, and heteroaryl, optionally substituted with one to two substituents selected from halogen, carboxy, and $C_{1-4}$alkyl;
or two $R^4$ groups together with the atom to which they are attached form a 4- to 8-membered mono- or bicyclic ring system optionally containing an additional heteroatom selected from O, S, and $NC_{1-4}$alkyl;
each n is independently an integer from 0 to 2;
each m is independently an integer from 0 to 2;
each p is independently an integer from 1 to 3;
each q is independently an integer from 0 to 2;
$R^6$, $R^7$, $R^8$, and $R^9$ are each independently hydrogen, fluorine, or $C_{1-3}$alkyl, wherein alkyl is optionally substituted with one to three substituents independently selected from fluorine and hydroxy; and each $R^{10}$ is independently hydrogen or $C_{1-4}$alkyl optionally substituted with one to five fluorines.

Compounds of Formula (XXX) may be synthesized by methods known in the art, e.g., those described in International Patent Publication No. WO2010/043052. In some embodiments, the SCD inhibitor is a compound disclosed in International Patent Publication No. WO2010/043052, the compounds of which are herein incorporated by reference.

In some embodiments of any of the foregoing methods, the SCD inhibitor is a compound of Formula XXXI,

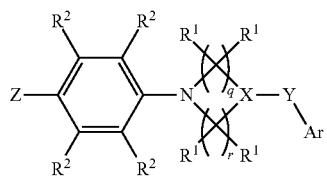

(XXXI)

or a pharmaceutically acceptable salt thereof; wherein
q is 1 or 2;
r is 1 or 2;
each n is independently 0, 1 or 2;
each m is independently 0, 1, or 2;
each p is independently 0, 1, or 2;
X—Y is N—C(O), N—S(O)$_2$, N—CR$^a$R$^b$, CH—O, CH—S(O)$_p$, CH—NR$^5$, or CH—CR$^a$R$^b$;
Ar is phenyl, naphthyl, or heteroaryl each of which is optionally substituted with one to five R$^6$ substituents;
Z is phenyl, naphthyl, or a heteroaromatic ring selected from the group consisting of: oxazolyl, thiazolyl, imidazolyl, pyrrolyl, pyrazolyl, isoxazolyl, isothiazolyl, 1,2,4-oxadiazol-5-yl, 1,2,4-oxadiazol-3-yl, 1,3,4-oxadiazolyl, 1,2,5-oxadiazolyl, 1,2,3-oxadiazolyl, 1,2,4-thiadiazol-5-yl, 1,2,4-thiadiazol-3-yl, 1,2,5-thiadiazolyl, 1,3,4-thiadiazolyl, 1,2,3-thiadiazolyl, 1,2,4-triazolyl, 1,2,3-triazolyl, tetrazolyl, indolyl, benzothiazolyl, benzoxazolyl, benzimidazolyl, benzisoxazolyl, benzisothiazolyl, and imidazo[1,2-a]pyridyl;
wherein phenyl, naphthyl, and the heteroaromatic ring are optionally substituted with one to three substituents independently selected from R$^3$;
R$^a$ and R$^b$ are each independently hydrogen or C$_{1-3}$alkyl, wherein alkyl is optionally substituted with one to three substituents independently selected from fluorine and hydroxy;
each R$^2$ is independently selected from the group consisting of:
  hydrogen,
  halogen,
  hydroxy,
  cyano,
  amino,
  nitro,
  C$_{1-4}$alkyl, optionally substituted with one to five fluorines,
  C$_{1-4}$alkoxy, optionally substituted with one to five fluorines,
  C$_{1-4}$alkylthio, optionally substituted with one to five fluorines,
  C$_{1-4}$alkylsulfonyl,
  carboxy,
  C$_{1-4}$alkyloxycarbonyl, and
  C$_{1-4}$alkylcarbonyl;
each R$^3$ is independently selected from the group consisting of: C$^{1-6}$alkyl, C$^{2-4}$alkenyl, (CH$_2$)$_n$OR$^4$, (CH$_2$)$_n$-phenyl, (CH$_2$)$_n$-naphthyl, (CH$_2$)$_n$-heteroaryl, (CH$_2$)$_n$-heterocyclyl, (CH$_2$)$_n$C$_{3-7}$cycloalkyl, halogen, (CH$_2$)$_n$N(R$^4$)$_2$, (CH$_2$)$_n$C≡N, (CH$_2$)$_n$CO$_2$R$^4$, (CH$_2$)$_n$OC(O)R$^4$, (CH$_2$)$_n$COR$^4$, NO$_2$, (CH$_2$)$_n$NR$^4$SO$_2$R$^4$, (CH$_2$)$_n$SO$_2$N(R$^4$)$_2$, (CH$_2$)$_n$S(O)$_p$R$^4$, (CH$_2$)$_n$NR$^4$C(O)(OR$^4$)R$^4$, (CH$_2$)$_n$C(O)N(NH$_2$)R$^4$, (CH$_2$)$_n$NR$^4$C(O)R$^4$, (CH$_2$)$_n$NR$^4$CO$_2$R$^4$, (CH$_2$)$_n$P(=O)(OR$^4$)$_2$, (CH$_2$)$_n$OP(=O)(OR$^4$)$_2$, (CH$_2$)$_n$OCH$_2$P(=O)(OR$^4$)$_2$, O(CH$_2$)$_n$C(O)N(R$^4$)$_2$, CF$_3$, CH$_2$CF$_3$, OCF$_3$, and OCH$_2$CF$_3$;

in which phenyl, naphthyl, heteroaryl, cycloalkyl, and heterocyclyl are optionally substituted with one to three substituents independently selected from halogen, hydroxy, C$_{1-4}$alkoxy, C$_{1-4}$alkylsulfonyl, C$_{3-6}$cycloalkyl, and C$_{1-4}$alkyl wherein alkyl is optionally substituted with hydroxy or one to three fluorines; and wherein any methylene (CH$_2$) carbon atom in R$^3$ is optionally substituted with one to two groups independently selected from fluorine, hydroxy, and C$_{1-4}$alkyl optionally substituted with one to five fluorines; or two substituents when on the same methylene (CH$_2$) group are taken together with the carbon atom to which they are attached to form a cyclopropyl group;
each R$^4$ is independently selected from the group consisting of: hydrogen, C$_{1-6}$alkyl, (CH$_2$)$_m$-phenyl, (CH$_2$)$_m$-heteroaryl, (CH$_2$)$_m$-naphthyl, and (CH$_2$)$_m$C$_{3-7}$cycloalkyl;
wherein alkyl, phenyl, heteroaryl, and cycloalkyl are optionally substituted with one to three groups independently selected from halogen, C$_{1-4}$alkyl, and C$_{1-4}$alkoxy, wherein alkyl and alkoxy are optionally substituted with one to five fluorines; or two R$^4$ groups together with the atom to which they are attached form a 4- to 8-membered mono- or bicyclic ring system optionally containing an additional heteroatom selected from O, S, and NC$_{1-4}$alkyl;
each R$^1$ is independently hydrogen, fluorine, or C$_{1-3}$alkyl, wherein alkyl is optionally substituted with one to three substituents independently selected from fluorine and hydroxy;
R$^5$ is hydrogen or C$_{1-6}$alkyl; and
each R$^6$ is independently selected from the group consisting of: C$_{1-6}$alkyl, (CH$_2$)$_n$OR$^4$, (CH$_2$)$_n$-phenyl, (CH$_2$)$_n$-naphthyl, (CH$_2$)$_n$-heteroaryl, (CH$_2$)$_n$-heterocyclyl, (CH$_2$)$_n$C$_{3-7}$cycloalkyl, halogen, (CH$_2$)$_n$N(R$^4$)$_2$, (CH$_2$)$_n$C≡N, (CH$_2$)$_n$CO$_2$R$^4$, (CH$_2$)$_n$COR$^4$, NO$_2$, (CH$_2$)$_n$NR$^4$SO$_2$R$^4$, (CH$_2$)$_n$SO$_2$N(R$^4$)$_2$, (CH$_2$)$_n$S(O)$_p$R$^4$, (CH$_2$)$_n$NR$^4$C(O)N(R$^4$)$_2$, (CH$_2$)$_n$C(O)N(R$^4$)$_2$, (CH$_2$)$_n$C(O)N(OR$^4$)R$^4$, (CH$_2$)$_n$C(O)N(NH$_2$)R$^4$, (CH$_2$)$_n$NR$^4$C(O)R$^4$, (CH$_2$)$_n$NR$^4$CO$_2$R$^4$, O(CH$_2$)$_n$C(O)N(R$^4$)$_2$, CF$_3$, CH$_2$CF$_3$, OCF$_3$, and OCH$_2$CF$_3$;

in which phenyl, naphthyl, heteroaryl, cycloalkyl, and heterocyclyl are optionally substituted with one to three substituents independently selected from halogen, hydroxy, C$_{1-4}$alkoxy, C$_{3-6}$ cycloalkyl, and C$_{1-4}$alkyl wherein alkyl is optionally substituted with hydroxy or one to three fluorines; and wherein any methylene (CH$_2$) carbon atom in R$^6$ is optionally substituted with one to two groups independently selected from fluorine, hydroxy, and C$_{1-4}$alkyl optionally substituted with one to five fluorines; or two substituents when on the same methylene (CH$_2$) group are taken together with the carbon atom to which they are attached to form a cyclopropyl group.

Compounds of Formula (XXXI) may be synthesized by methods known in the art, e.g., those described in International Patent Publication No. WO2007/134457. In some embodiments, the SCD inhibitor is a compound disclosed in International Patent Publication No. WO2007/134457, the compounds of which are herein incorporated by reference.

In some embodiments of any of the foregoing methods, the SCD inhibitor is a compound of Formula XXXIII,

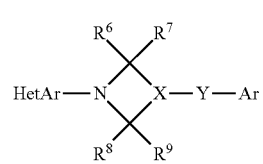

(XXXII)

or a pharmaceutically acceptable salt thereof; wherein
X—Y is N—C(O), N—CR$^1$R$^2$, CH—O, CH—S(O)$_p$, CH—NR$^{10}$, or CH—CR$^1$R$^2$;

Ar is phenyl, benzyl, naphthyl, or pyridyl each of which is optionally substituted with one to five substituents independently selected from R$^3$;

HetAr represents a heteroaromatic ring selected from the group consisting of: oxazolyl, thiazolyl, imidazolyl, pyrazolyl, isoxazolyl, isothiazolyl, pyridazinyl, pyridinyl, 1,2,4-oxadiazolyl, 1,3,4-oxadiazolyl, 1,2,5-oxadiazolyl, 1,2,3-oxadiazolyl, 1,2,4-thiadiazolyl, oxazolyl, thiazolyl, imidazolyl, pyrazolyl, isoxazolyl, isothiazolyl, pyridazinyl, pyridinyl, 1,2,4-oxadiazolyl, 1,3,4-oxadiazolyl, 1,2,5-oxadiazolyl, 1,2,3-oxadiazolyl, 1,2,4-thiadiazolyl, in which the heteroaromatic ring is optionally substituted with one to two substituents independently selected from R$^5$;

R$^1$ and R$^2$ are each independently hydrogen or C$_{1-3}$alkyl, wherein alkyl is optionally substituted with one to three substituents independently selected from fluorine and hydroxy;

each R$^5$ is independently selected from the group consisting of: C$_{1-6}$alkyl, C$_{2-4}$alkenyl, (CH$_2$)$_n$OR$^4$, (CH$_2$)$_n$-phenyl, (CH$_2$)$_n$-naphthyl, (CH$_2$)$_n$-heteroaryl, (CH$_2$)$_n$-heterocyclyl, (CH$_2$)$_n$C$_{3-7}$cycloalkyl, halogen, (CH$_2$)$_n$N(R$^4$)$_2$, (CH$_2$)$_n$O=N, (CH$_2$)$_n$CO$_2$R$^4$, (CH$_2$)$_n$OC(O)R$^4$, (CH$_2$)$_n$COR$^4$, NO$_2$, (CH$_2$)$_n$NR$^4$SO$_2$R$^4$ (CH$_2$)$_n$SO$_2$N(R$^4$)$_2$, (CH$_2$)$_n$S(O)$_p$R$^4$, (CH$_2$)$_n$NR$^4$C(O)N(R$^4$)$_2$, (CH$_2$)$_n$C(O)N(R$^4$)$_2$, (CH$_2$)$_n$C(O)N(OR$^4$)R$^4$, (CH$_2$)$_n$C(O)N(NH$_2$)R$^4$, (CH$_2$)$_n$C(O)NR$^4$NC(O)R$^4$; (CH$_2$)$_n$NR$^4$C(O)R$^4$, (CH$_2$)$_n$NR$^4$CO$_2$R$^4$, (CH$_2$)$_n$P(=O)(OR$^4$)$_2$, (CH$_2$)$_n$OP(=O)(OR$^4$)$_2$, (CH$_2$)$_n$O(CH$_2$)$_n$P(=O)(OR$^4$)$_2$, O(CH$_2$)$_n$C(O)N(R$^4$)$_2$, CF$_3$, CH$_2$CF$_3$, OCF$_3$, and OCH$_2$CF$_3$;

in which phenyl, naphthyl, heteroaryl, cycloalkyl, and heterocyclyl are optionally substituted with one to three substituents independently selected from halogen, hydroxy, C$_{1-4}$alkoxy, C$_{1-4}$alkylsulfonyl, C$_{3-6}$cycloalkyl, carboxy-C$_{1-3}$alkyl, C$_{1-3}$alkyloxycarbonyl-C$_{1-3}$alkyl, and C$_{1-4}$alkyl wherein alkyl is optionally substituted with hydroxy or one to three fluorines; and wherein any methylene (CH$_2$) carbon atom in R$^5$ is optionally substituted with one to two groups independently selected from fluorine, hydroxy, and C$_{1-4}$alkyl optionally substituted with one to five fluorines; or two substituents when on the same methylene (CH$_2$) group are taken together with the carbon atom to which they are attached to form a cyclopropyl group;

each R$^3$ is independently selected from the group consisting of: C$_{1-6}$alkyl, (CH$_2$)$_n$OR$^4$, (CH$_2$)$_n$-phenyl, (CH$_2$)$_n$-naphthyl, (CH$_2$)$_n$-heteroaryl, (CH$_2$)$_n$-heterocyclyl, (CH$_2$)$_n$C$_{3-7}$cycloalkyl, halogen, (CH$_2$)$_n$N(R$^4$)$_2$, (CH$_2$)$_n$C≡N, (CH$_2$)$_n$CO$_2$R$^4$, (CH$_2$)$_n$COR$^4$, NO$_2$, (CH$_2$)$_n$NR$^4$SO$_2$R$^4$ (CH$_2$)$_n$SO$_2$N(R$^4$)$_2$, (CH$_2$)$_n$S(O)$_p$R$^4$, (CH$_2$)$_n$NR$^4$C(O)N(R$^4$)$_2$, (CH$_2$)$_n$C(O)N(R$^4$)$_2$, (CH$_2$)$_n$C(O)N(OR$^4$)R$^4$, (CH$_2$)$_n$C(O)N(NH$_2$)R$^4$, (CH$_2$)$_n$NR$^4$C(O)R$^4$, (CH$_2$)$_n$NR$^4$CO$_2$R$^4$, O(CH$_2$)$_n$C(O)N(R$^4$)$_2$, (CH$_2$)$_n$P(=O)(OR$^4$)$_2$, (CH$_2$)$_n$OP(=O)(OR$^4$)$_2$, (CH$_2$)$_n$O(CH$_2$)$_n$P(=O)(OR$^4$)$_2$, CF$_3$, CH$_2$CF$_3$, OCF$_3$, and OCH$_2$CF$_3$;

in which phenyl, naphthyl, heteroaryl, cycloalkyl, and heterocyclyl are optionally substituted with one to three substituents independently selected from halogen, hydroxy, C$_{1-4}$alkoxy, C$_{3-6}$cycloalkyl, and C$_{1-4}$alkyl wherein alkyl is optionally substituted with hydroxy or one to three fluorines; and wherein any methylene (CH$_2$) carbon atom in R$^3$ is optionally substituted with one to two groups independently selected from fluorine, hydroxy, and C$_{1-4}$alkyl optionally substituted with one to five fluorines; or two substituents when on the same methylene (CH$_2$) group are taken together with the carbon atom to which they are attached to form a cyclopropyl group;

each R$^4$ is independently selected from the group consisting of: hydrogen, C$_{1-6}$alkyl, (CH$_2$)$_m$-phenyl, (CH$_2$)$_m$-heteroaryl, (CH$_2$)$_m$-naphthyl, and (CH$_2$)$_m$C$_{3-7}$cycloalkyl;

wherein alkyl, phenyl, heteroaryl, and cycloalkyl are optionally substituted with one to three groups independently selected from halogen, C$_{1-4}$alkyl, and C$_{1-4}$alkoxy; or two R$^4$ groups together with the atom to which they are attached form a 4- to 8-membered mono- or bicyclic ring system optionally containing an additional heteroatom selected from O, S, and NC$_{1-4}$alkyl;

each n is independently 0, 1 or 2;
each p is independently 0, 1, or 2;
each m is independently 0, 1 or 2;

R$^6$, R$^7$, R$^8$, and R$^9$ are each independently hydrogen, fluorine, or C$_{1-3}$alkyl, wherein alkyl is optionally substituted with one to three substituents independently selected from fluorine and hydroxy; and R$^{10}$ is hydrogen or C$_{1-6}$alkyl optionally substituted with one to five fluorines.

Compounds of Formula (XXXII) may be synthesized by methods known in the art, e.g., those described in International Patent Publication No. WO2007/143823. In some embodiments, the SCD inhibitor is a compound disclosed in International Patent Publication No. WO2007/143823, the compounds of which are herein incorporated by reference.

In some embodiments of any of the foregoing methods, the SCD inhibitor is a compound of Formula XXXIII,

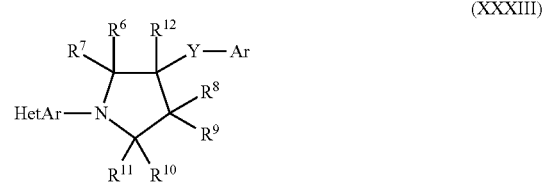

(XXXIII)

or a pharmaceutically acceptable salt thereof; wherein
Y is O, S(O)$_p$, or CR$^1$R$^2$;

Ar is phenyl, benzyl, naphthyl, or pyridyl each of which is optionally substituted with one to five substituents independently selected from R$^3$;

HetAr is a heteroaromatic ring selected from the group consisting of: oxazolyl, thiazolyl, imidazolyl, pyrazolyl, isoxazolyl, isothiazolyl, 1,2,4-oxadiazolyl, 1,3,4-oxadiazolyl, 1,2,5-oxadiazolyl, 1,2,3-oxadiazolyl, 1,2,4-thiadiazolyl, 1,2,5-thiadiazolyl, 1,3,4-thiadiazolyl, 1,2,3-thiadiazolyl, 1,2,4-triazolyl, 1,2,3-triazolyl, tetrazolyl, benzthiazolyl, benzoxazolyl, benzimidazolyl, benzisoxazolyl, and benzisothiazolyl;

in which the heteroaromatic ring is optionally substituted with one to two substituents independently selected from R$^5$;

R$^1$ and R$^2$ are each independently hydrogen or C$_{1-3}$alkyl, wherein alkyl is optionally substituted with one to three substituents independently selected from fluorine and hydroxy;

each R$^3$ is independently selected from the group consisting of: C$_{1-6}$alkyl, (CH$_2$)$_n$OR$^4$, (CH$_2$)$_n$-phenyl, (CH$_2$)$_n$-naphthyl, (CH$_2$)$_n$-heteroaryl, (CH$_2$)$_n$-heterocyclyl, (CH$_2$)$_n$C$_{3-7}$cycloalkyl, halogen, (CH$_2$)$_n$N(R$^4$)$_2$, (CH$_2$)$_n$C≡N, (CH$_2$)$_n$CO$_2$R$^4$, (CH$_2$)$_n$COR$^4$, NO$_2$, (CH$_2$)$_n$NR$^4$SO$_2$R$^4$, (CH$_2$)$_n$SO$_2$N(R$^4$)$_2$, (CH$_2$)$_n$S(O)$_p$R$^4$, (CH$_2$)$_n$NR$^4$C(O)N(R$^4$)$_2$, (CH$_2$)$_n$C(O)N(R$^4$)$_2$, (CH$_2$)$_n$C(O)N(OR$^4$)R$^4$, $(CH_2)_nC(O)N(NH_2)R^4$, $(CH_2)_nNR^4C(O)R^4$, $(CH_2)_n$ $NR^4CO_2R^4$, $O(CH_2)_nC(O)N(R^4)_2$, $(CH_2)_nP(=O)(OR^4)_2$, $(CH_2)_nOP(=O)(OR^4)_2$, $(CH_2)_nO(CH_2)_nP(=O)(OR^4)_2$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkoxy, $C_{3-6}$cycloalkyl, and $C_{1-4}$alkyl wherein alkyl is optionally substituted with hydroxy or one to three fluorines; and wherein any methylene ($CH_2$) carbon atom in $R^3$ is optionally substituted with one to two groups independently selected from fluorine, hydroxy, and $C_{1-4}$alkyl optionally substituted with one to five fluorines; or two substituents when on the same methylene ($CH_2$) group are taken together with the carbon atom to which they are attached to form a cyclopropyl group;

each $R^4$ is independently selected from the group consisting of: hydrogen, $C_{1-6}$alkyl, $(CH_2)_m$-phenyl, $(CH_2)_m$-heteroaryl, $(CH_2)_m$-naphthyl, and $(CH_2)_mC_{3-7}$cycloalkyl;

wherein alkyl, phenyl, heteroaryl, and cycloalkyl are optionally substituted with one to three groups independently selected from halogen, $C_{1-4}$alkyl, and $C_{1-4}$alkoxy, wherein alkyl and alkoxy are optionally substituted with one to five fluorines; or two $R^4$ groups together with the atom to which they are attached form a 4- to 8-membered mono- or bicyclic ring system optionally containing an additional heteroatom selected from O, S, and $NC_{1-4}$alkyl;

each $R^5$ is independently selected from the group consisting of: $C_{1-6}$alkyl, $C_{2-4}$alkenyl, $(CH_2)_nOR^4$, $(CH_2)_n$-phenyl, $(CH_2)_n$-naphthyl, $(CH_2)_n$-heteroaryl, $(CH_2)_n$-heterocyclyl, $(CH_2)_nC_{3-7}$cycloalkyl, halogen, $(CH_2)_nN(R^4)_2$, $(CH_2)_nC\equiv N$, $(CH_2)_nCO_2R^4$, $(CH_2)_nOC(O)R^4$, $(CH_2)_nCOR^4$, $NO_2$, $(CH_2)_nNR^4SO_2R^4$, $(CH_2)_nSO_2N(R^4)_2$, $(CH_2)_nS(O)_pR^4$, $(CH_2)_nNR^4C(O)N(R^4)_2$, $(CH_2)_nC(O)N(R^4)_2$, $(CH_2)_nC(O)N(OR^4)R^4$, $(CH_2)_nC(O)N(NH_2)R^4$, $(CH_2)_nC(O)NR^4NC(O)R^4$, $(CH_2)_nNR^4C(O)R^4$, $(CH_2)_nNR^4CO_2R^4$, $(CH_2)_nP(=O)(OR^4)_2$, $(CH_2)_nOP(=O)(OR^4)_2$, $(CH_2)_nO(CH_2)_nP(=O)(OR^4)_2$, $O(CH_2)_nC(O)N(R^4)_2$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkoxy, $C_{1-4}$alkylsulfonyl, $C_{3-6}$cycloalkyl, and $C_{1-4}$alkyl wherein alkyl is optionally substituted with carboxy, hydroxy, or one to three fluorines; and wherein any methylene ($CH_2$) carbon atom in $R^5$ is optionally substituted with one to two groups independently selected from fluorine, hydroxy, and $C_{1-4}$alkyl optionally substituted with one to five fluorines; or two substituents when on the same methylene ($CH_2$) group are taken together with the carbon atom to which they are attached to form a cyclopropyl group;

$R^6$, $R^7$, $R^8$, $R^9$, $R^{10}$, $R^{11}$, and $R^{12}$ are each independently hydrogen or $C_{1-3}$alkyl, wherein alkyl is optionally substituted with one to three substituents independently selected from fluorine and hydroxyl;

each n is independently 0, 1 or 2;
each m is independently 0, 1, or 2; and
p is 0, 1, or 2.

Compounds of Formula (XXXIII) may be synthesized by methods known in the art, e.g., those described in International Patent Publication No. WO2007/143824. In some embodiments, the SCD inhibitor is a compound disclosed in International Patent Publication No. WO2007/143824, the compounds of which are herein incorporated by reference.

In some embodiments of any of the foregoing methods, the SCD inhibitor is a compound of Formula XXXIV,

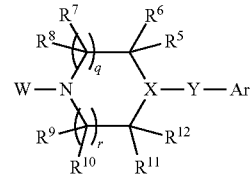
(XXXIV)

or a pharmaceutically acceptable salt thereof; wherein
q is 0 or 1;
r is 0 or 1;
Z is O, S, or $NR^4$;
X—Y is N—C(O), N—$CR^aR^b$, $CR^{14}$—O, $CR^{14}$—S$(O)_{0-2}$, or $CR_{13}$—$CR^aR^b$;
$R^a$ and $R^b$ are each independently hydrogen or $C_{1-3}$ alkyl, wherein alkyl is optionally substituted with one to three substituents independently selected from fluorine and hydroxy;
W is heteroaryl selected from the group consisting of:

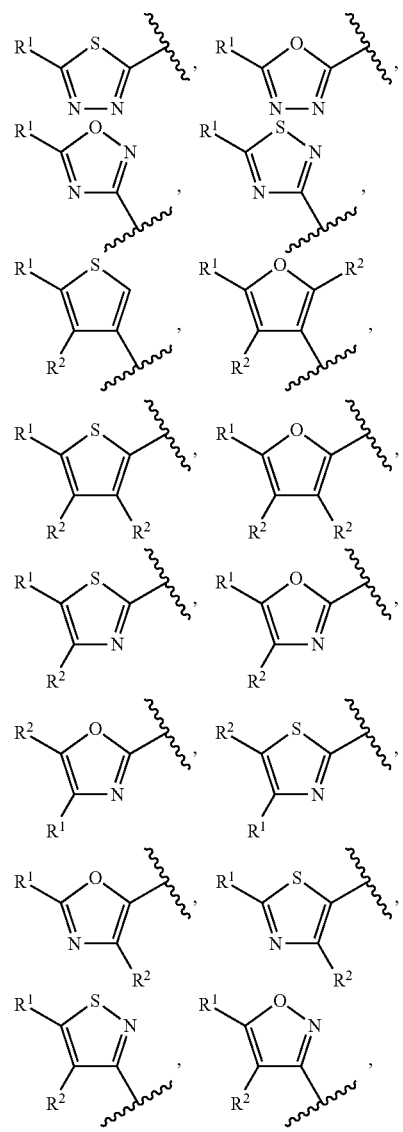

-continued

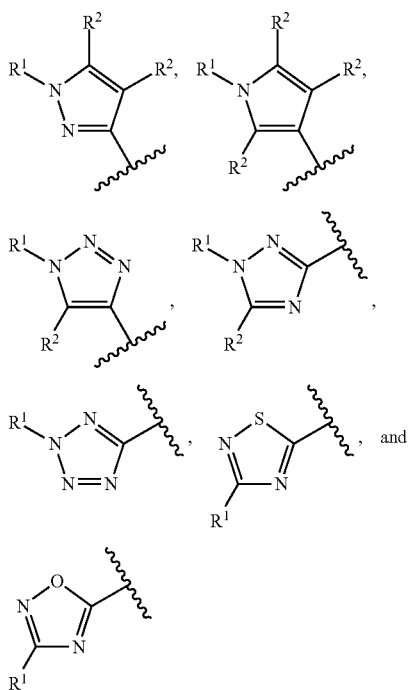

R¹ is heteroaryl selected from the group consisting of:

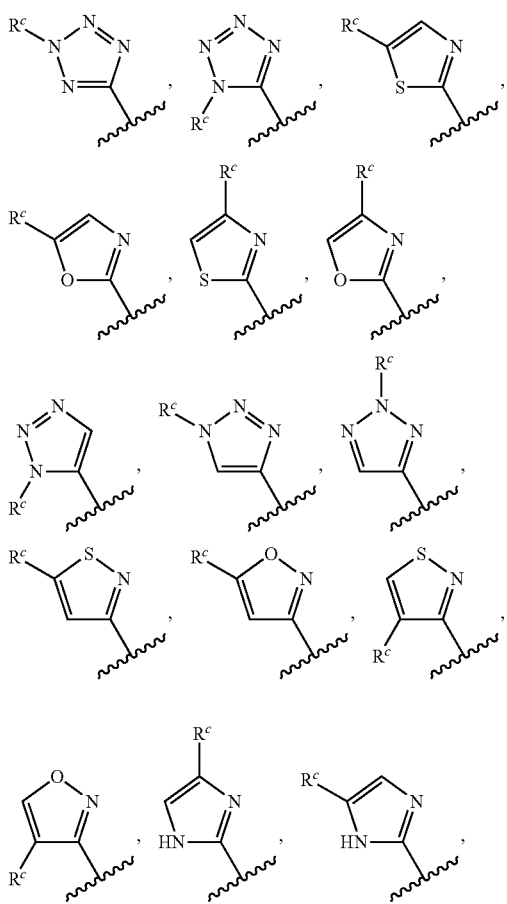

-continued

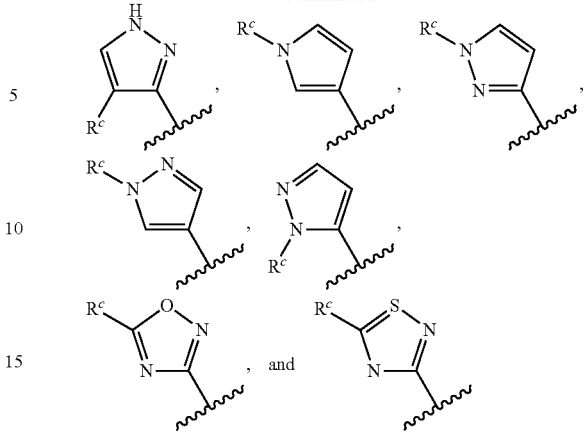

wherein $R^c$ is —$(CH_2)_mCO_2H$, —$(CH_2)_mCO_2C_{1-3}$alkyl, —$(CH_2)_m$—Z—$(CH_2)_pCO_2H$, or —$(CH_2)_m$—Z—$(CH_2)_p$ $CO_2C_{1-3}$alkyl; wherein any methylene ($CH_2$) carbon atom in $(CH_2)_m$ or $(CH_2)_p$ is optionally substituted with one hydroxy, one amino, or one to two fluorines; and wherein said $R^1$ heteroaryl ring is optionally substituted with one substituent independently selected from the group consisting of cyano, halogen, $C_{1-4}$alkyl, $C_{1-4}$alkoxy, $C_{1-4}$alkylthio, $C_{1-4}$alkylsulfonyl, and trifluoromethyl;

each $R^2$ is independently selected from the group consisting of:
hydrogen,
halogen,
hydroxy,
cyano,
amino,
nitro,
$C_{1-4}$alkyl, optionally substituted with one to five fluorines,
$C_{1-4}$alkoxy, optionally substituted with one to five fluorines,
$C_{1-4}$alkylthio, optionally substituted with one to five fluorines,
$C_{1-4}$alkylsulfonyl,
carboxy,
$C_{1-4}$alkyloxycarbonyl, and
$C_{1-4}$alkylcarbonyl;

Ar is phenyl, naphthyl, or heteroaryl optionally substituted with one to five $R^3$ substituents; each $R^3$ is independently selected from the group consisting of: $C_{1-6}$alkyl, $C_{2-6}$alkenyl, $(CH_2)_n$-phenyl, $(CH_2)_n$-naphthyl, $(CH_2)_n$-heteroaryl, $(CH_2)_n$-heterocyclyl, $(CH_2)_nC_{3-7}$cycloalkyl, halogen, nitro, $(CH_2)_nOR^4$, $(CH_2)_nN(R^4)_2$, $(CH_2)_nC\equiv N$, $(CH_2)_nCO_2R^4$, $(CH_2)_nNR^4SO_2R^4(CH_2)_nSO_2N(R^4)_2$, $(CH_2)_nS(O)_{0-2}R^4$, $(CH_2)_nNR^4C(O)N(R^4)_2$, $(CH_2)_nC(O)N(R^4)_2$, $(CH_2)_nNR^4C(O)R^4$, $(CH_2)_nNR^4CO_2R^4$, $(CH_2)_nC(O)R^4$, $O(CH_2)_nC(O)N(R^4)_2$, $(CH_2)_s$—Z—$(CH_2)_t$-phenyl, $(CH_2)_s$—Z—$(CH_2)_t$-naphthyl, $(CH_2)_s$—Z—$(CH_2)_t$-heteroaryl, $(CH_2)_s$—Z—$(CH_2)_t$-heterocyclyl, $(CH_2)_s$—Z—$(CH_2)_t$—$C_{3-7}$cycloalkyl, $(CH_2)_s$—Z—$(CH_2)_t$—$OR^4$, $(CH_2)_s$—Z—$(CH_2)_t$—$N(R^4)_2$, $(CH_2)_s$—Z—$(CH_2)_t$—$NR^4SO_2R^4$, $(CH_2)_s$—Z—$(CH_2)_t$—$C\equiv N$, $(CH_2)_s$—Z—$(CH_2)_t$—$C_2R^4$, $(CH_2)_s$—Z—$(CH_2)_t$—$SO_2N(R^4)_2$, $(CH_2)_s$—Z—$(CH_2)_t$—$S(O)_{0-2}R^4$, $(CH_2)_s$—Z—$(CH_2)_t$—$NR^4C(O)N(R^4)_2$, $(CH_2)_s$—Z—$(CH_2)_t$—$C(O)N(R^4)_2$, $(CH_2)_s$—Z—$(CH_2)_t$—$NR^4C(O)R^4$, $(CH_2)_s$—Z—$(CH_2)_t$—$NR^4CO_2R^4$, $(CH_2)_s$—Z—$(CH_2)_t$—$C(O)R^4$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkyl, trifluoromethyl, and $C_{1-4}$ alkoxy, optionally substituted with one to five fluorines; and wherein any methylene (CH$_2$) carbon atom in $R^3$ is optionally substituted with one to two groups independently selected from fluorine, hydroxy, and $C_{1-4}$alkyl; or two substituents when on the same methylene (CH$_2$) group are taken together with the carbon atom to which they are attached to form a cyclopropyl group;

each $R^4$ is independently selected from the group consisting of: hydrogen, $C_{1-6}$alkyl, (CH$_2$)$_n$-phenyl, (CH$_2$)$_n$-heteroaryl, (CH$_2$)$_n$-naphthyl, and (CH$_2$)$_n$C$_{3-7}$cycloalkyl;

wherein alkyl, phenyl, heteroaryl, and cycloalkyl are optionally substituted with one to three groups independently selected from halogen, $C_{1-4}$alkyl, and $C_{1-4}$alkoxy; or two $R^4$ groups together with the atom to which they are attached form a 4- to 8-membered mono- or bicyclic ring system optionally containing an additional heteroatom selected from O, S, NH, and NC$_{1-4}$alkyl;

$R^5$, $R^6$, $R^7$, $R^8$, $R^9$, $R^{10}$, $R^{11}$, and $R^{12}$ are each independently hydrogen, fluorine, or $C_{1-3}$alkyl, wherein alkyl is optionally substituted with one to three substituents independently selected from fluorine and hydroxy;

$R^{13}$ is hydrogen, $C_{1-3}$alkyl, fluorine, or hydroxy;

each $R^{14}$ is hydrogen or $C_{1-3}$alkyl;

each m is independently an integer from 0 to 4;

each p is independently an integer from 1 to 3;

each n is independently an integer from 0 to 2;

each s is independently an integer from 1 to 3; and each t is independently an integer from 1 to 3.

In some embodiments of the compound of Formula XXXIV, $R^2$ is hydrogen.

In some embodiments of the compound of Formula XXXIV, W is

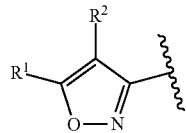

In some embodiments of the compound of Formula XXXIV, $R^1$ is heteroaryl selected from the group consisting of:

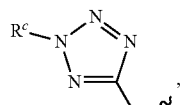 , 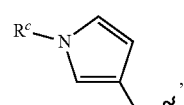 ,

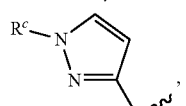 , 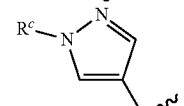 and

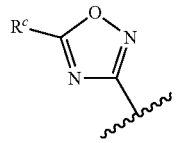

wherein $R^c$ is —CH$_2$CO$_2$H or —CH$_2$C$_2$C$_{1-3}$ alkyl.

In some embodiments of the compound of Formula XXXIV, $R^1$ is

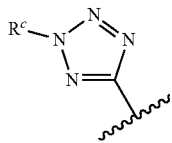

In some embodiments of the compound of Formula XXXIV, when q and r are both 1;

X—Y is CH—O;

W is heteroaryl selected from the group consisting of:

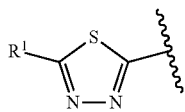 , 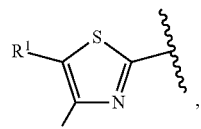 ,

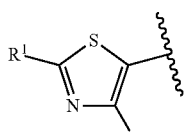 , 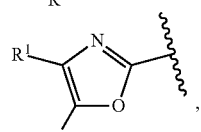 ,

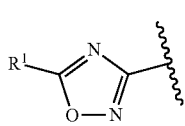 and 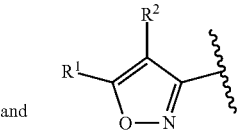

and $R^1$ is heteroaryl selected from the group consisting of:

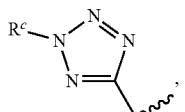 , 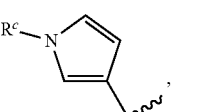 ,

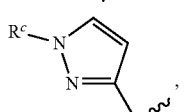 , 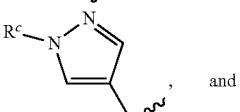 and

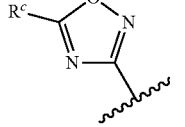

wherein $R^c$ is —CH$_2$CO$_2$H or —CH$_2$CO$_2$C$_{1-3}$alkyl.

In some embodiments of the compound of Formula XXXIV, W is

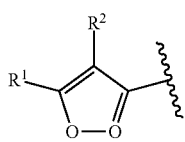

and R[1] is

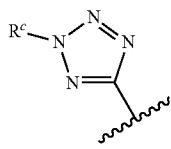

wherein $R^c$ is —CH$_2$CO$_2$H or —CH$_2$CO$_2$C$_{1-3}$alkyl.

In some embodiments of the compound of Formula XXXIV, $R^2$, $R^5$, $R^6$, $R^7$, $R^8$, $R^9$, $R^{10}$, $R^{11}$, and $R^{12}$ are each hydrogen.

In some embodiments, the compound of Formula XXXIV is selected from:

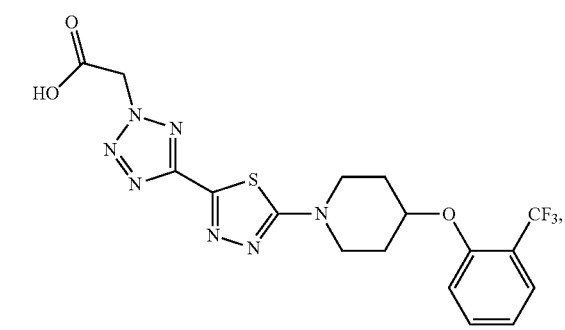

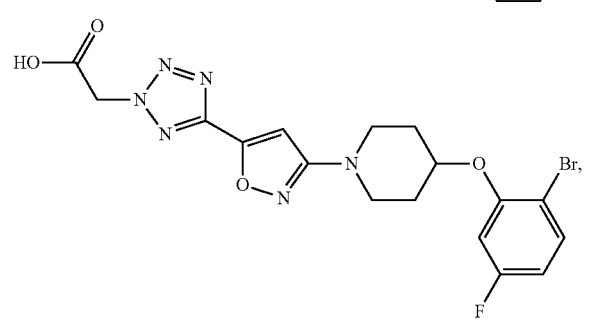

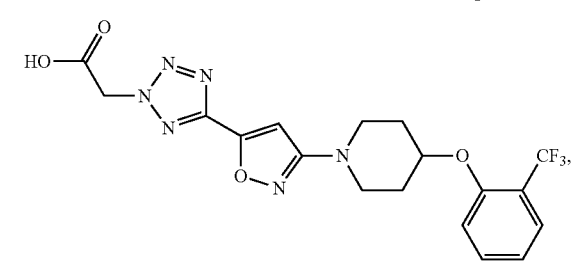

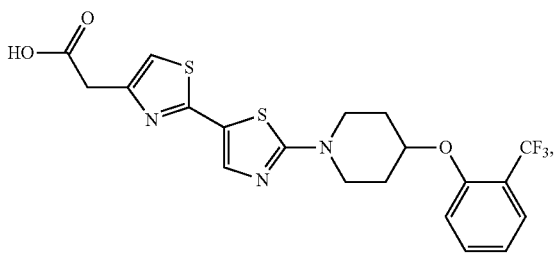

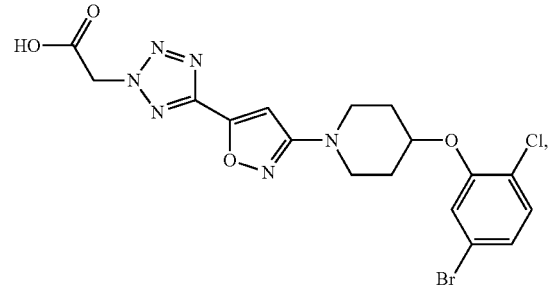

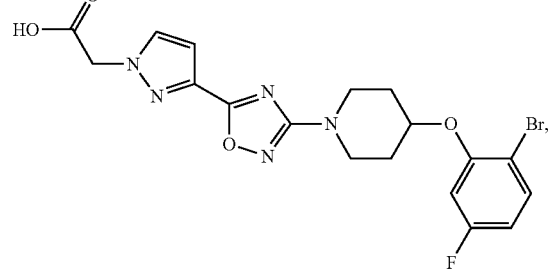

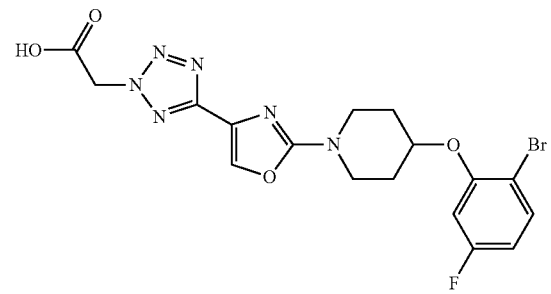

and

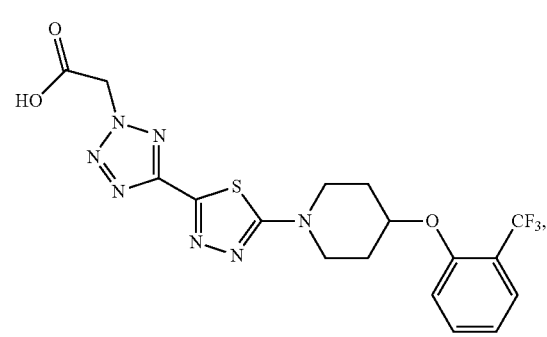

or a pharmaceutically acceptable salt thereof.

In other embodiments of any of the foregoing methods, the SCD inhibitor is

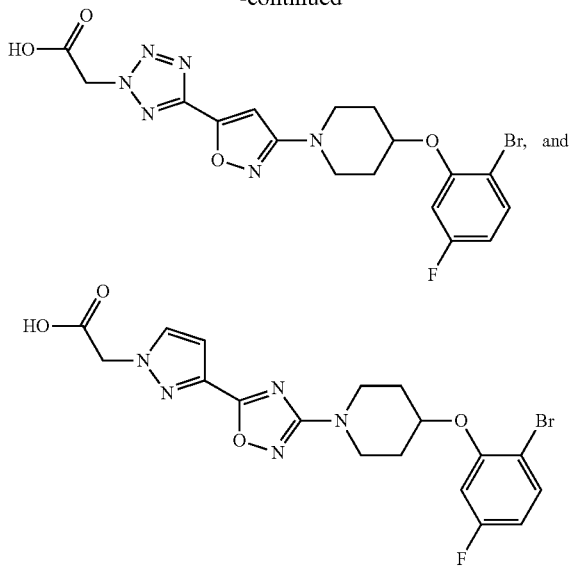

In some embodiments, the compound of Formula XXXIV is selected from:
[5-(5-{4-[2-(Trifluoromethyl)phenoxy]piperidin-1-yl}-1,3,4-thiadiazol-2-yl)-2H-tetrazol-2-yl]acetic acid
[5-(5-{4-[2-(Trifluoromethyl)phenoxy]piperidin-1-yl}-1,3,4-thiadiazol-2-yl)-1-H-tetrazol-1-yl]acetic acid
(5-{5-[4-(2-Bromo-5-fluorophenoxy)piperidin-1-yl]-1,3,4-thiadiazol-2-yl}-2H-tetrazol-2-yl)acetic acid
(5-{5-[4-(2-Bromo-5-fluorophenoxy)piperidin-1-yl]-1,3,4-thiadiazol-2-yl}-1H-tetrazol-1-yl)acetic acid
(2'-{4-[2-(Trifluoromethyl)phenoxy]piperidin-1-yl}-2,5'-bi-1,3-thiazol-4-yl)acetic acid
(5-{3-[4-(2-Bromo-5-fluorophenoxy)piperidin-1-yl]isoxazol-5-yl}-2H-tetrazol-2-yl)acetic acid
(3-{3-[4-(2-Bromo-5-fluorophenoxy)piperidin-1-yl]-1,2,4-oxadiazol-5-yl}-1H-pyrrol-1-yl)acetic acid
(3-{3-[4-(2-Bromo-5-fluorophenoxy)piperidin-1-yl]-1,2,4-oxadiazol-5-yl}-1-yl)acetic acid
(5-{3-[4-(2-Bromo-5-fluorophenoxy)piperidin-1-yl]-1,2,4-oxadiazol-5-yl}-1H-pyrazol-1-yl)acetic acid
(4-{3-[4-(2-Bromo-5-fluorophenoxy)piperidin-1-yl]-1,2,4-oxadiazol-5-yl}-1H-pyrazol-1-yl)acetic acid
Sodium(5-{3-[4-(2-bromo-5-fluorophenoxy)piperi-din-1-yl]-1,2,4-oxadiazol-5-yl}-2H-tetrazol-2-yl) acetate
3-(3-{5-[4-(2-Bromo-5-fluorophenoxy)piperidin-1-yl]-1,3,4-thiadiazol-2-yl}-1,2,4-oxadiazol-5-yl)propanoic acid
(5-{3-[4-(5-Bromo-2-chlorophenoxy)piperidin-1-yl]isoxazol-5-yl}-2H-tetrazol-2-yl)acetic acid
3-(3-{3-[4-(2-bromo-5-fluorophenoxy)piperidin-1-yl]-1,2,4-oxadiazol-5-yl}-1H-pyrazol-1-yl)propanoic acid
(2R)-3-(3-{5-[4-(2-Bromo-5-fluorophenoxy)piperi-din-1-yl]-1,3,4-thiadiazol-2-yl}-1,2,4-oxadiazol-5-yl)-2-hydroxypropanoic acid
(2S)-3-(3-{5-[4-(2-Bromo-5-fluorophenoxy)piperi-din-1-yl]-1,3,4-thiadiazol-2-yl}-1,2,4-oxadiazol-5-yl)-2-hydroxypropanoic acid
3-(3-{5-[4-(2-Bromo-5-fluorophenoxy)piperidin-1-yl]-1,3,4-thiadiazol-2-yl}-1,2,4-oxadiazol-5-yl)-L-alanine
{5-[3-(4-{[4-Chloro-4'-(trifluoromethoxy)biphenyl-3-yl]oxy}piperidin-1-yl)isoxazol-5-yl]-2H-tetrazol-2-yl}acetic acid
(5-{2-[4-(2-Bromo-5-fluorophenoxy)piperidin-1-yl]-1,3-oxazol-4-yl}-2H-tetrazol-2-yl)acetic acid
(5-{2-[4-(2-Bromo-5-fluorophenoxy)piperidin-1-yl]-1,3-oxazol-4-yl}-1H-tetrazol-1-yl)acetic acid Compounds of Formula (XXXIV) may be synthesized by methods known in the art, e.g., those described in U.S. Pat. No. 8,063,224 B2. In some embodiments, the SCD inhibitor is a compound disclosed in U.S. Pat. No. 8,063,224 B2, the compounds of which are herein incorporated by reference.

In some embodiments of any of the foregoing methods, the SCD inhibitor is a compound of Formula XXXV,

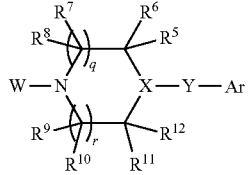

(XXXV)

or a pharmaceutically acceptable salt thereof; wherein
each m is independently an integer from 0 to 4;
each n is independently an integer from 0 to 2;
each s is independently an integer from 1 to 3;
each t is independently an integer from 1 to 3;
q is 0 or 1;
r is 0 or 1;
Z is O, S, or $NR^4$;
X—Y is N—$CR^aR^b$, $CR^{14}$—O, $CR^{14}$—$S(O)_{0-2}$, or $CR^{13}$—$CR^aR^b$;
W is heteroaryl selected from the group consisting of:

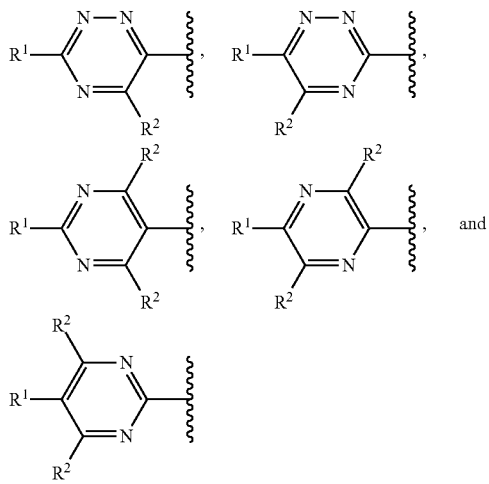

Ar is phenyl, naphthyl, or heteroaryl optionally substituted with one to five $R^3$ substituents;
$R^a$ and $R^b$ are each independently hydrogen or $C_{1-3}$alkyl, wherein alkyl is optionally substituted with one to three substituents independently selected from fluorine and hydroxy;
$R^1$ is heteroaryl selected from the group consisting of:

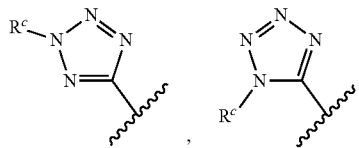

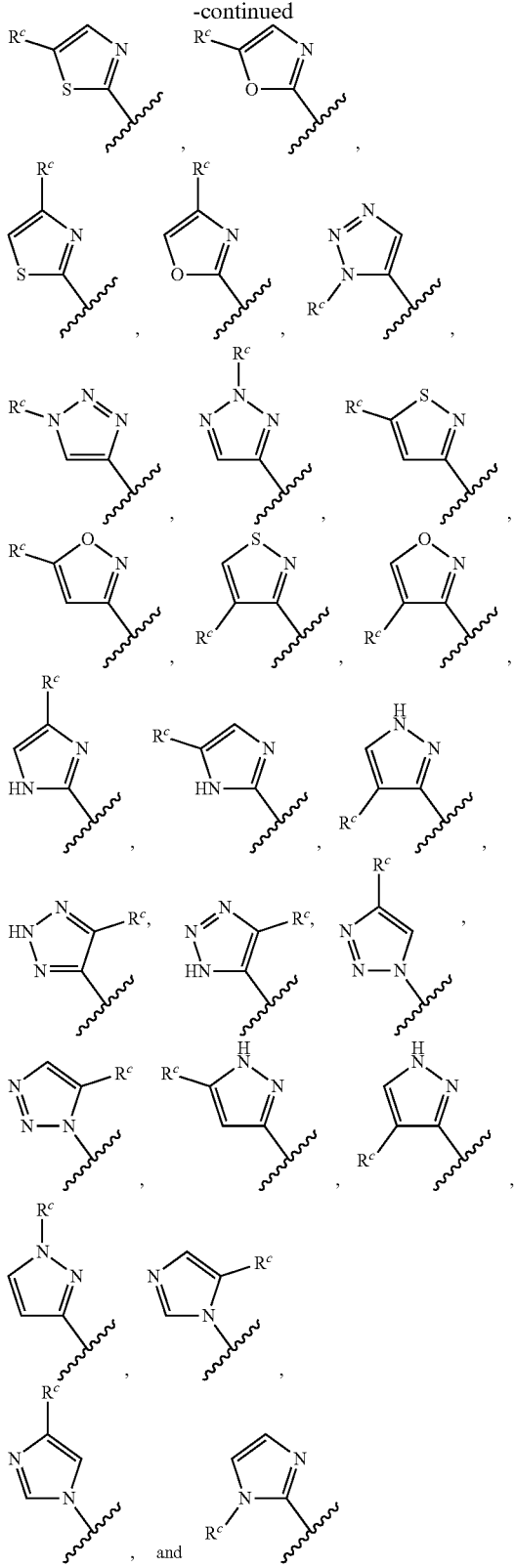

wherein $R^c$ is —$(CH_2)_m CO_2H$, —$(CH_2)_m CO_2C_{1-3}$alkyl, —$(CH_2)_m$—Z—$(CH_2)_p CO_2H$, or —$(CH_2)_m$—Z—$(CH_2)_p CO_2C_{1-3}$alkyl, wherein each $(CH_2)$ methylene group is optionally substituted with one or two substituents selected from the group consisting of $C_{1-4}$alkyl, fluorine, oxo, and hydroxy; and wherein said $R^1$ heteroaryl ring is optionally substituted with one substituent independently selected from the group consisting of cyano, halogen, $C_{1-4}$alkyl, $C_{1-4}$alkoxy, $C_{1-4}$alkylthio, $C_{1-4}$alkylsulfonyl, and trifluoromethyl;

each $R^2$ is independently selected from the group consisting of:
hydrogen,
halogen,
hydroxy,
cyano,
amino,
nitro,
$C_{1-4}$alkyl, optionally substituted with one to five fluorines,
$C_{1-4}$alkoxy, optionally substituted with one to five fluorines,
$C_{1-4}$alkylthio, optionally substituted with one to five fluorines,
$C_{1-4}$alkylsulfonyl,
carboxy,
$C_{1-4}$alkyloxycarbonyl, and
$C_{1-4}$alkylcarbonyl;

each $R^3$ is independently selected from the group consisting of: $C_{1-6}$alkyl, $C_{2-6}$alkenyl, $(CH_2)_n$-phenyl, $(CH_2)_n$-naphthyl, $(CH_2)_n$-heteroaryl, $(CH_2)_n$-heterocyclyl, $(CH_2)_n C_{3-7}$cycloalkyl, halogen, nitro, $(CH_2)_n OR^4$, $(CH_2)_n N(R^4)_2$, $(CH_2)_n C\equiv N$, $(CH_2)_n CO_2R^4$, $(CH_2)_n NR^4SO_2R^4$, $(CH_2)_n SO_2N(R^4)_2$, $(CH_2)_n S(O)_{0-2}R^4$, $(CH_2)_n NR^4C(O)N(R^4)_2$, $(CH_2)_n C(O)N(R^4)_2$, $(CH_2)_n NR^4C(O)R^4$, $(CH_2)_n NR^4CO_2R^4$, $(CH_2)_n C(O)R^4$, $O(CH_2)_n C(O)N(R^4)_2$, $(CH_2)_s$—Z—$(CH_2)_t$-phenyl, $(CH_2)_s$—Z—$(CH_2)_t$-naphthyl, $(CH_2)_s$—Z—$(CH_2)_t$-heteroaryl, $(CH_2)_s$—Z—$(CH_2)_t$-heterocyclyl, $(CH_2)_s$—Z—$(CH_2)_t$—$C_{3-7}$cycloalkyl, $(CH_2)_s$—Z—$(CH_2)_t$—$OR^4$, $(CH_2)_s$—Z—$(CH_2)_t$—$N(R^4)_2$, $(CH_2)_s$—Z—$(CH_2)_t$—$NR^4SO_2R^4$, $(CH_2)_s$—Z—$(CH_2)_t$—$C\equiv N$, $(CH_2)_s$—Z—$(CH_2)_t$—$CO_2R^4$, $(CH_2)_s$—Z—$(CH_2)_t$—$SO_2N(R^4)_2$, $(CH_2)_s$—Z—$(CH_2)_t$—$S(O)_{0-2}R^4$, $(CH_2)_s$—Z—$(CH_2)_t$—$NR^4C(O)N(R^4)_2$, $(CH_2)_s$—Z—$(CH_2)_t$—$C(O)N(R^4)_2$, $(CH_2)_s$—Z—$(CH_2)_t$—$NR^4C(O)R^4$ $(CH_2)_s$—Z—$(CH_2)_t$—$NR^4CO_2R^4$, $(CH_2)_s$—Z—$(CH_2)_t$—$C(O)R^4$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkyl, trifluoromethyl, and $C_{1-4}$alkoxy; and wherein any methylene $(CH_2)$ carbon atom in $R^3$ is optionally substituted with one to two groups independently selected from fluorine, hydroxy, and $C_{1-4}$alkyl; or two substituents when on the same methylene $(CH_2)$ group are taken together with the carbon atom to which they are attached to form a cyclopropyl group;

each $R^4$ is independently selected from the group consisting of: hydrogen, $C_{1-6}$alkyl, $(CH_2)_n$-phenyl, $(CH_2)_n$-heteroaryl, $(CH_2)_n$-naphthyl, and $(CH_2)_n C_{3-7}$cycloalkyl;

wherein alkyl, phenyl, heteroaryl, and cycloalkyl are optionally substituted with one to three groups independently selected from halogen, trifluoromethyl, $C_{1-4}$alkyl, and $C_{1-4}$ alkoxy; or two $R^4$ groups together with the atom to which they are attached form a 4- to 8-membered mono- or bicyclic ring system optionally containing an additional heteroatom selected from O, S, NH, and $NC_{1-4}$alkyl;

$R^5$, $R^6$, $R^7$, $R^8$, $R^9$, $R^{10}$, $R^{11}$, and $R^{12}$ are each independently hydrogen, fluorine, or $C_{1-3}$alkyl, wherein alkyl is optionally substituted with one to three substituents independently selected from fluorine and hydroxy;

$R^{13}$ is hydrogen, $C_{1-3}$alkyl, fluorine, or hydroxy; and each $R^{14}$ is hydrogen or $C_{1-3}$alkyl.

Compounds of Formula (XXXV) may be synthesized by methods known in the art, e.g., those described in International Patent Publication No. WO2008/089580. In some embodiments, the SCD inhibitor is a compound disclosed in International Patent Publication No. WO2008/089580, the compounds of which are herein incorporated by reference.

In some embodiments of any of the foregoing methods, the SCD inhibitor is a compound of Formula XXXVI:

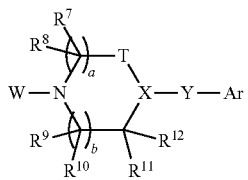

(XXXVI)

or a pharmaceutically acceptable salt thereof; wherein
a is an integer selected from 0, 1, and 2;
b is an integer selected from 0, 1, and 2;
with the proviso that a and b cannot both be 2;
X-T is N—CR$^5$R$^6$C=CR$^5$ or CR$^{13}$—CR$^5$R$^6$;
Y is a bond or C(=O);
W is heteroaryl selected from the group consisting of:

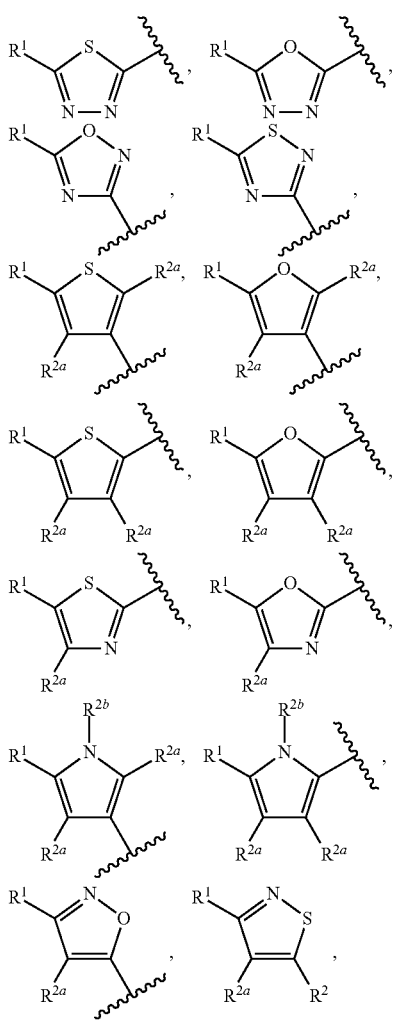

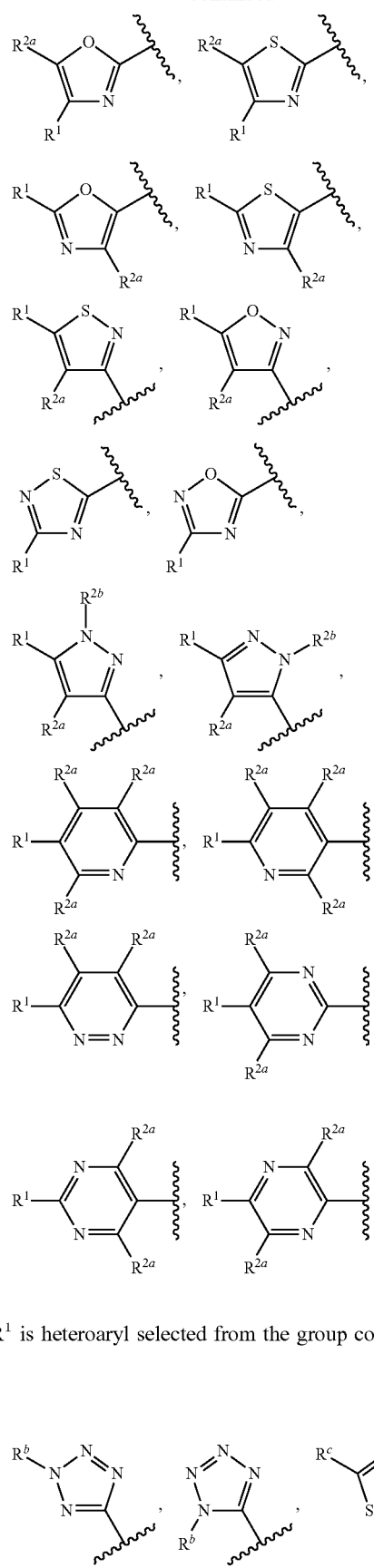

R$^1$ is heteroaryl selected from the group consisting of:

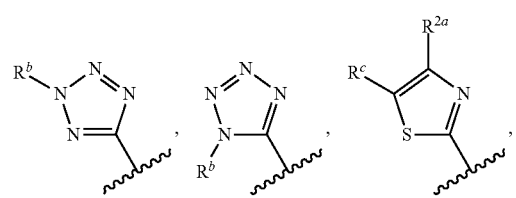

-continued

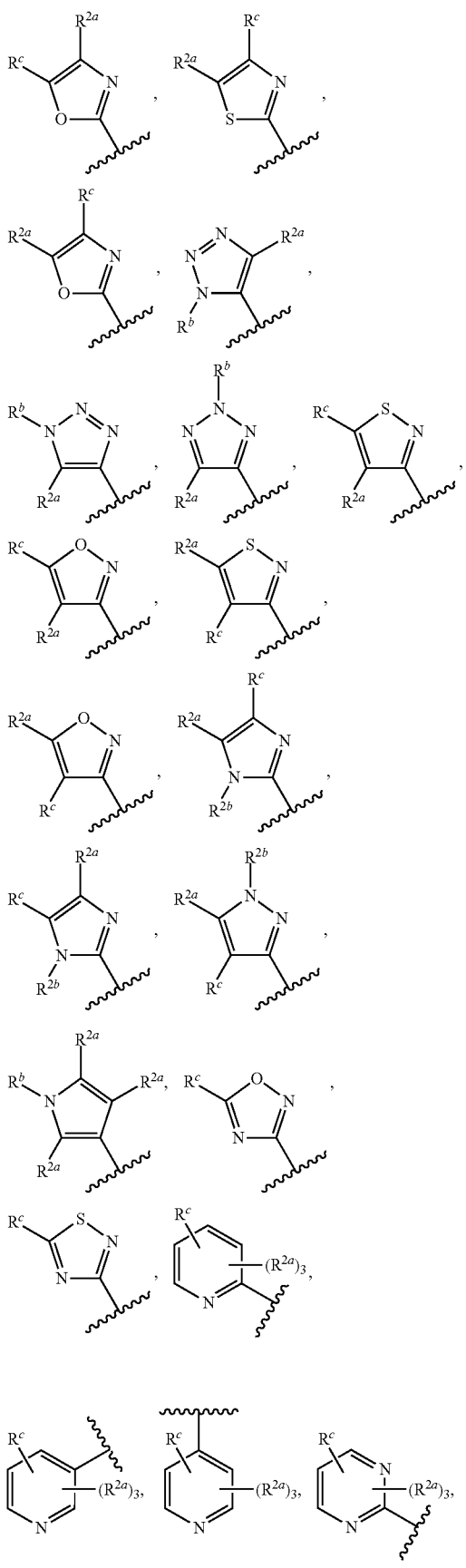

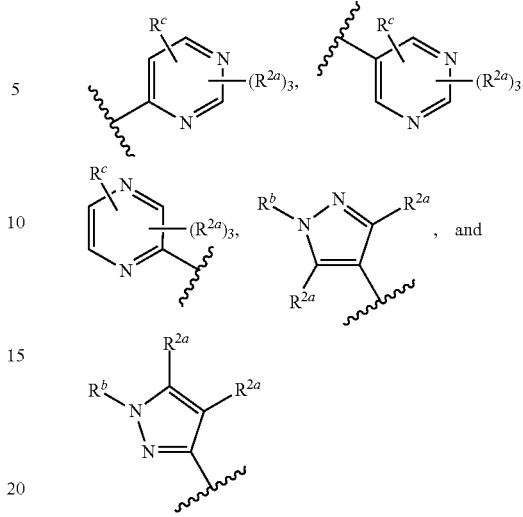

wherein
R$^b$ is —(CH$_2$)$_r$CO$_2$H, —(CH$_2$)$_r$CO$_2$C$_{1-3}$alkyl, —(CH$_2$)$_r$—Z(CH$_2$)$_p$CO$_2$H, or —(CH$_2$)$_r$—Z(CH$_2$)$_p$CO$_2$C$_{1-3}$alkyl;

R$^c$ is —(CH$_2$)$_m$CO$_2$H, —(CH$_2$)$_m$CO$_2$C$_{1-3}$alkyl, —(CH$_2$)$_m$—Z—(CH$_2$)$_p$CO$_2$H, or —(CH$_2$)$_m$—Z—(CH$_2$)$_p$CO$_2$C$_{1-3}$alkyl;

Z is O, S, or NR$^4$;

each R$^{2a}$ is independently selected from the group consisting of:
  hydrogen,
  halogen,
  hydroxy,
  cyano,
  amino,
  C$_{1-4}$alkyl, optionally substituted with one to five fluorines,
  C$_{1-4}$alkoxy, optionally substituted with one to five fluorines,
  C$_{1-4}$alkylthio, optionally substituted with one to five fluorines,
  C$_{1-4}$alkylsulfonyl, optionally substituted with one to five fluorines, carboxy,
  C$_{1-4}$alkyloxycarbonyl, and
  C$_{1-4}$alkylcarbonyl;

each R$^{2b}$ is independently selected from the group consisting of:
  hydrogen,
  C$_{1-4}$alkyl, optionally substituted with one to five fluorines,
  C$_{1-4}$alkylsulfonyl, optionally substituted with one to five fluorines,
  C$_{1-4}$alkyloxycarbonyl, and
  C$_{1-4}$ alkylcarbonyl;

Ar is phenyl, naphthyl, thienyl, or pyridyl optionally substituted with one to five R$^3$ substituents;

each R$^3$ is independently selected from the group consisting of:
  halogen,
  cyano,
  C$_{1-6}$alkyl, optionally substituted with one to five fluorines,
  C$_{3-5}$cycloalkyl,
  C$_{3-5}$cycloalkylmethyl, optionally substituted with C$_{1-3}$alkyl, C$_{1-6}$alkoxy, optionally substituted with one to five fluorines,
  C$_{1-6}$alkylthio, optionally substituted with one to five fluorines, and $C_{1-6}$alkylsulfonyl, optionally substituted with one to five fluorines;

each $R^4$ is independently selected from the group consisting of: hydrogen, $C_{1-6}$alkyl, $(CH_2)_n$-phenyl, $(CH_2)_n$-heteroaryl, $(CH_2)_n$-naphthyl, and $(CH_2)_nC_{3-7}$cycloalkyl;

wherein alkyl, phenyl, heteroaryl, naphthyl, and cycloalkyl are optionally substituted with one to three groups independently selected from halogen, $C_{1-4}$alkyl, and $C_{1-4}$alkoxy;

$R^5$, $R^6$, $R^7$, $R^8$, $R^9$, $R^{10}$, $R^{11}$, and $R^{12}$ are each independently hydrogen, fluorine, or $C_{1-3}$alkyl, wherein alkyl is optionally substituted with one to three substituents independently selected from fluorine and hydroxy;

or one of $R^5$, $R^6$, $R^7$, and $R^8$ together with one of $R^9$, $R^{10}$, $R^{11}$, and $R^{12}$ forms a direct bond or a $C_{1-2}$ alkylene bridge;

$R^{13}$ is hydrogen, $C_{1-3}$alkyl, fluorine, or hydroxy;

m is an integer from 0 to 3;

n is an integer from 0 to 2;

p is an integer from 1 to 3; and r is an integer from 1 to 3.

Compounds of Formula (XXXVI) may be synthesized by methods known in the art, e.g., those described in International Patent Publication No. WO2010/094126. In some embodiments, the SCD inhibitor is a compound disclosed in International Patent Publication No. WO2010/094126, the compounds of which are herein incorporated by reference.

In some embodiments of any of the foregoing methods, the SCD inhibitor is a compound of Formula XXXVII:

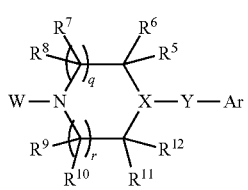

(XXXVII)

or a pharmaceutically acceptable salt thereof; wherein
each m is independently an integer from 0 to 4;
each n is independently an integer from 0 to 2;
each s is independently an integer from 1 to 3;
each t is independently an integer from 1 to 3;
q is 0 or 1;
r is 0 or 1;
Z is O, S, or $NR^4$;
X—Y is N—C(O), N—$CR^aR^b$, $CR^{14}$—O, $CR^{14}$—$S(O)_{0-2}$, or $CR^{13}$—$CR^aR^b$;
W is heteroaryl selected from the group consisting of:

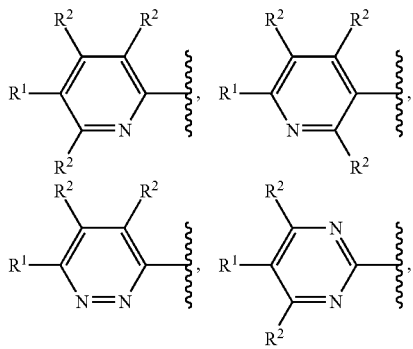

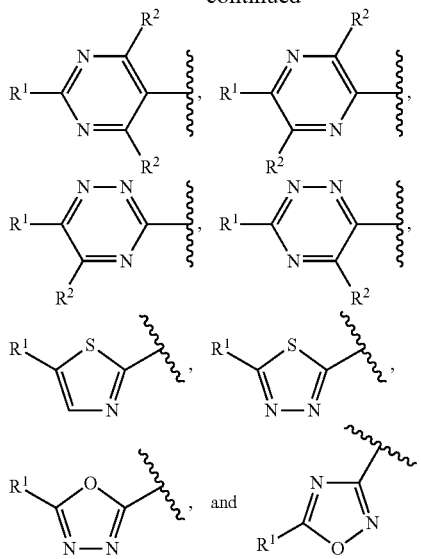

Ar is phenyl, naphthyl, or heteroaryl optionally substituted with one to five $R^3$ substituents;

$R^a$ and $R^b$ are each independently hydrogen or $C_{1-3}$alkyl, wherein alkyl is optionally substituted with one to three substituents independently selected from fluorine and hydroxy;

$R^1$ is heteroaryl selected from the group consisting of:

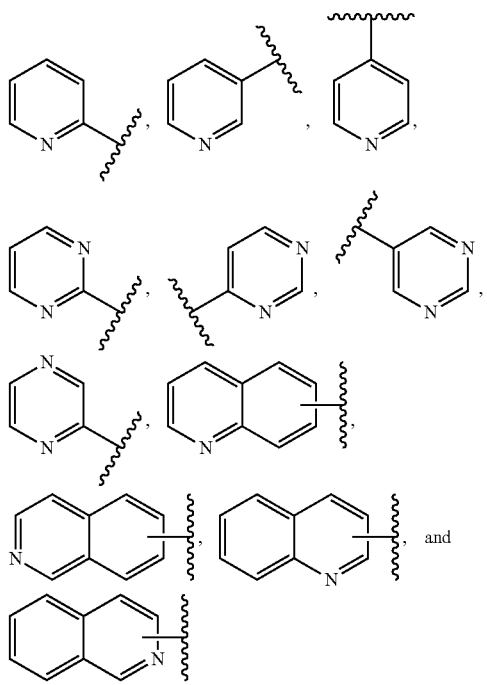

wherein heteroaryl is monosubstituted with —$(CH_2)_m$$CO_2H$ or —$(CH_2)_mCO_2C_{1-3}$alkyl and optionally substituted with one to three substituents independently selected from the group consisting of cyano, halogen, $C_{1-4}$alkyl, $C_{1-4}$alkoxy, $C_{1-4}$alkylthio, $C_{1-4}$alkylsulfonyl, and trifluoromethyl;

each $R^2$ is independently selected from the group consisting of:

hydrogen,
halogen,
hydroxy,
cyano,
amino,
nitro,
$C_{1-4}$alkyl, optionally substituted with one to five fluorines,
$C_{1-4}$alkoxy, optionally substituted with one to five fluorines,
$C_{1-4}$alkylthio, optionally substituted with one to five fluorines,
$C_{1-4}$alkylsulfonyl,
carboxy,
$C_{1-4}$alkyloxycarbonyl, and
$C_{1-4}$alkylcarbonyl;

each $R^3$ is independently selected from the group consisting of: $C_{1-6}$alkyl, $C_{2-6}$alkenyl, $(CH_2)_n$-phenyl, $(CH_2)_n$-naphthyl, $(CH_2)_n$-heteroaryl, $(CH_2)_n$-heterocyclyl, $(CH_2)_n$$C_{3-7}$cycloalkyl, halogen, nitro, $(CH_2)_nOR^4$, $(CH_2)_nN(R^4)_2$, $(CH_2)_nC\equiv N$, $(CH_2)_nCO_2R^4$, $(CH_2)_nNR_4SO_2R^4$ $(CH_2)_nSO_2N(R^4)_2$, $(CH_2)_nS(O)_{0-2}R^4$, $(CH_2)_nNR_4C(O)N(R^4)_2$, $(CH_2)_nC(O)N(R^4)_2$, $(CH_2)_nNR^4C(O)R^4$, $(CH_2)_nNR^4CO_2R^4$, $(CH_2)_nC(O)R^4$, $O(CH_2)_nC(O)N(R^4)_2$, $(CH_2)_s$—Z—$(CH_2)_t$-phenyl, $(CH_2)_s$—Z—$(CH_2)_t$-naphthyl, $(CH_2)_s$—Z—$(CH_2)_t$-heteroaryl, $(CH_2)_s$—Z—$(CH_2)_t$-heterocyclyl, $(CH_2)_s$—Z—$(CH_2)_t$—$C_{3-7}$cycloalkyl, $(CH_2)_s$—Z—$(CH_2)_t$—$OR^4$, $(CH_2)_s$—Z—$(CH_2)_t$—$N(R^4)_2$, $(CH_2)_s$—Z—$(CH_2)_t$—$NR^4SO_2R^4$, $(CH_2)_s$—Z—$(CH_2)_t$—$C\equiv N$, $(CH_2)_s$—Z—$(CH_2)_t$—$CO_2R^4$; $(CH_2)_s$—Z—$(CH_2)_t$—$SO_2N(R^4)_2$, $(CH_2)_s$—Z—$(CH_2)_t$—$S(O)_{0-2}R^4$, $(CH_2)_s$—Z—$(CH_2)_t$—$NR^4C(O)N(R^4)_2$, $(CH_2)_s$—Z—$(CH_2)_t$—$C(O)N(R^4)_2$, $(CH_2)_s$—Z—$(CH_2)_t$—$NR^4C(O)R^4$, $(CH_2)_s$—Z—$(CH_2)_t$—$NR^4CO_2R^4$, $(CH_2)_s$—Z—$(CH_2)_t$—$C(O)R^4$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkyl, trifluoromethyl, and $C_{1-4}$alkoxy; and wherein any methylene ($CH_2$) carbon atom in $R^3$ is optionally substituted with one to two groups independently selected from fluorine, hydroxy, and $C_{1-4}$alkyl; or two substituents when on the same methylene ($CH_2$) group are taken together with the carbon atom to which they are attached to form a cyclopropyl group;

each $R^4$ is independently selected from the group consisting of: hydrogen, $C_{1-6}$alkyl, $(CH_2)_n$-phenyl, $(CH_2)_n$-heteroaryl, $(CH_2)_n$-naphthyl, and $(CH_2)_nC_{3-7}$cycloalkyl;

wherein alkyl, phenyl, heteroaryl, and cycloalkyl are optionally substituted with one to three groups independently selected from halogen, $C_{1-4}$alkyl, and $C_{1-4}$alkoxy; or two $R^4$ groups together with the atom to which they are attached form a 4- to 8-membered mono- or bicyclic ring system optionally containing an additional heteroatom selected from O, S, NH, and N$C_{1-4}$alkyl;

$R^5$, $R^6$, $R^7$, $R^8$, $R^9$, $R^{10}$, $R^1$, and $R^{12}$ are each independently hydrogen, fluorine, or $C_{1-3}$alkyl, wherein alkyl is optionally substituted with one to three substituents independently selected from fluorine and hydroxy;

$R^{13}$ is hydrogen, $C_{1-3}$alkyl, fluorine, or hydroxy; and each $R^{14}$ is hydrogen or $C_{1-3}$ alkyl.

Compounds of Formula (XXXVII) may be synthesized by methods known in the art, e.g., those described in International Patent Publication No. WO2008/046226. In some embodiments, the SCD inhibitor is a compound disclosed in International Patent Publication No. WO2008/046226, the compounds of which are herein incorporated by reference.

In some embodiments of any of the foregoing methods, the SCD inhibitor is a compound of Formula XXXVIII:

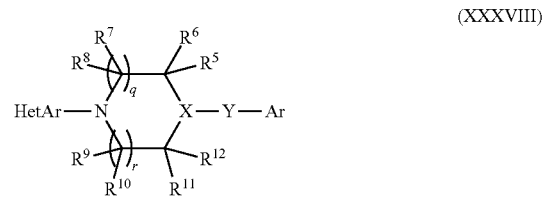

(XXXVIII)

or a pharmaceutically acceptable salt thereof; wherein
HetAr is a fused heteroaromatic ring selected from the group consisting of:

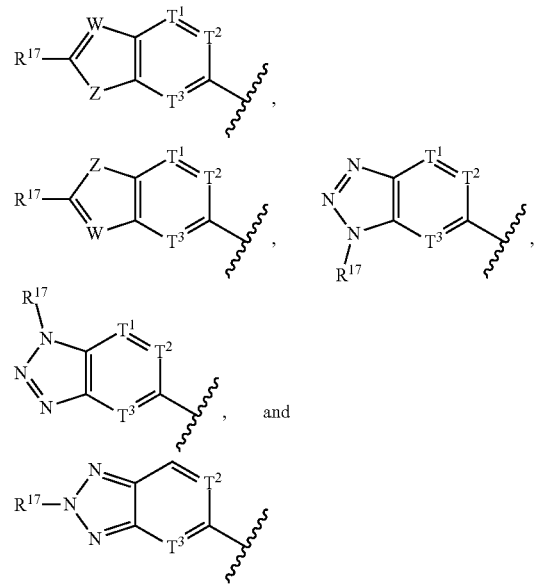

and wherein W is N or $CR^{16}$;
Z is O S or $NR^{15}$;
$T^1$, $T^2$, and $T^3$ are each independently N or $CR^{16}$, with the proviso that at least one of $T^1$, $T^2$, and $T^3$ is N;
q is 0 or 1;
r is 0 or 1;
X—Y is N—C(O), $CR^{14}$—O, $CR^{14}$—$S(O)_{0-2}$, or $CR^{13}$—$CR^1R^2$;
Ar is phenyl, benzyl, naphthyl, or heteroaryl each of which is optionally substituted with one to five $R^3$ substituents;
$R^1$ and $R^2$ are each independently hydrogen or $C_{1-3}$alkyl, wherein alkyl is optionally substituted with one to three substituents independently selected from fluorine and hydroxyl;
each $R^3$ is independently selected from the group consisting of: $C_{1-6}$alkyl, $C_{2-6}$alkenyl, $(CH_2)_n$-phenyl, $(CH_2)_n$-naphthyl, $(CH_2)_n$-heteroaryl, $(CH_2)_n$-heterocyclyl, $(CH_2)_n$$C_{3-7}$cycloalkyl, halogen, nitro, $(CH_2)_nOR^4$, $(CH_2)_nN(R^4)_2$, $(CH_2)_nC\equiv N$, $(CH_2)_nCO_2R^4$, $(CH_2)_nNR^4SO_2R^4$, $(CH_2)_nSO_2N(R^4)_2$, $(CH_2)_nS(O)_{0-2}R^4$, $(CH_2)_nNR^4C(O)N(R^4)_2$, $(CH_2)_nC(O)N(R^4)_2$, $(CH_2)_nNR^4C(O)R^4$, $(CH_2)_nNR^4CO_2R^4$, $(CH_2)_nC(O)R^4$, $O(CH_2)_nC(O)N(R^4)_2$, $(CH_2)_s$—Z—$(CH_2)_t$-phenyl, $(CH_2)_s$—Z—$(CH_2)_t$-naphthyl, $(CH_2)_s$—Z—$(CH_2)_t$-heteroaryl, $(CH_2)_s$—Z—$(CH_2)_t$-heterocyclyl, $(CH_2)_s$—Z—$(CH_2)_t$—$C_{3-7}$cycloalkyl, $(CH_2)_s$—Z—$(CH_2)_t$—$OR^4$, $(CH_2)_s$—Z—$(CH_2)_1$—$N(R^4)_2$, $(CH_2)_s$—Z—$(CH_2)_t$—$NR^4SO_2R^4$, $(CH_2)_s$—Z—$(CH_2)_t$—C≡N, $(CH_2)_s$—Z—$(CH_2)_t$—$CO_2R^4$, $(CH_2)_s$—Z—$(CH_2)_t$—$SO_2N(R^4)_2$, $(CH_2)_s$—Z—$(CH_2)_t$—$S(O)_{0-2}R^4$, $(CH_2)_s$—Z—$(CH_2)_t$—$NR^4C(O)N(R^4)_2$, $(CH_2)_s$—Z—$(CH_2)_t$—$C(O)N(R^4)_2$, $(CH_2)_s$—Z—$(CH_2)_t$—$NR^4C(O)R^4$, $(CH_2)_s$—Z—$(CH_2)_t$—$NR^4CO_2R^4$, $(CH_2)_s$—Z—$(CH_2)_t$—$C(O)R^4$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkyl, trifluoromethyl, and $C_{1-4}$alkoxy; and wherein any methylene ($CH_2$) carbon atom in $R^3$ is optionally substituted with one to two groups independently selected from fluorine, hydroxy, and $C_{1-4}$alkyl; or two substituents when on the same methylene ($CH_2$) group are taken together with the carbon atom to which they are attached to form a cyclopropyl group;

Z is O, S, or $NR^4$;

each $R^4$ is independently selected from the group consisting of: hydrogen, $C_{1-6}$alkyl, $(CH_2)_m$-phenyl, $(CH_2)_m$-heteroaryl, $(CH_2)_m$-naphthyl, and $(CH_2)_m C_{3-7}$cycloalkyl;

wherein alkyl, phenyl, heteroaryl, and cycloalkyl are optionally substituted with one to three groups independently selected from halogen, $C_{1-4}$alkyl, and $C_{1-4}$alkoxy; or two $R^4$ groups together with the atom to which they are attached form a 4- to 8-membered mono- or bicyclic ring system optionally containing an additional heteroatom selected from O, S, NH, and $NC_{1-4}$alkyl;

$R^5$, $R^6$, $R^7$, $R^8$, $R^9$, $R^{10}$, $R^{11}$, and $R^{12}$ are each independently hydrogen, fluorine, or $C_{1-3}$alkyl, wherein alkyl is optionally substituted with one to three substituents independently selected from fluorine and hydroxy;

$R^{13}$ is hydrogen, $C_{1-3}$alkyl, fluorine, or hydroxy;

each $R^{14}$ is hydrogen or $C_{1-3}$alkyl;

$R^{15}$ is selected from the group consisting of hydrogen, $C_{1-4}$alkyl, $C_{1-4}$alkylcarbonyl, aryl-$C_{1-2}$alkylcarbonyl, arylcarbonyl, $C_{1-4}$alkylaminocarbonyl, $C_{1-4}$alkylsulfonyl, arylsulfonyl, aryl-$C_{1-2}$alkylsulfonyl, $C_{1-4}$alkyloxycarbonyl, aryloxycarbonyl, and aryl-$C_{1-2}$alkyloxycarbonyl;

$R^{16}$ is hydrogen, amino, halogen, or $C_{1-3}$alkyl optionally substituted with one to five fluorines;

$R^{17}$ is selected from the group consisting of: —$(CH_2)_v C(O)R^a$, —$O(CH_2)_w C(O)R^a$, —$S(CH_2)_w C(O)R^a$, —$NH(CH_2)_w C(O)R^a$, —$NCH_3(CH_2)_w C(O)R^a$,

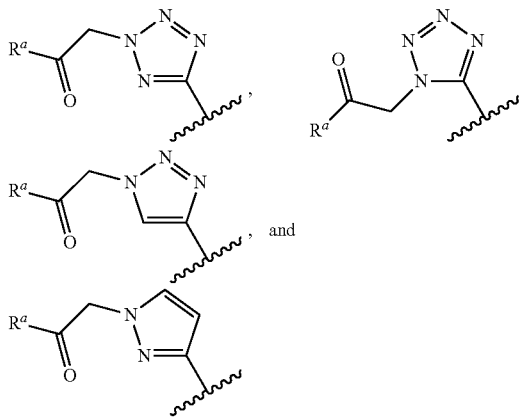

$R^a$ is -OH, —$OC_{1-4}$alkyl, —$NH_2$, —$NHSO_2C_{1-4}$alkyl, —$NHSO_2C_{3-6}$cycloalkyl, or —$NHSO_2CH_2C_{3-6}$cycloalkyl;

each m is independently an integer from 0 to 2;
each n is independently an integer from 0 to 2;
each s is independently an integer from 1 to 3;
each t is independently an integer from 1 to 3;
v is an integer from 1 to 3; and
each w is an integer from 1 to 2.

Compounds of Formula (XXXVIII) may be synthesized by methods known in the art, e.g., those described in International Patent Publication No. WO2009/012573. In some embodiments, the SCD inhibitor is a compound disclosed in International Patent Publication No. WO2009/012573, the compounds of which are herein incorporated by reference.

In some embodiments of any of the foregoing methods, the SCD inhibitor is a compound of Formula XXXIX:

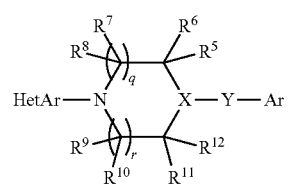

(XXXIX)

or a pharmaceutically acceptable salt thereof; wherein
HetAr is a fused heteroaromatic ring selected from the group consisting of:

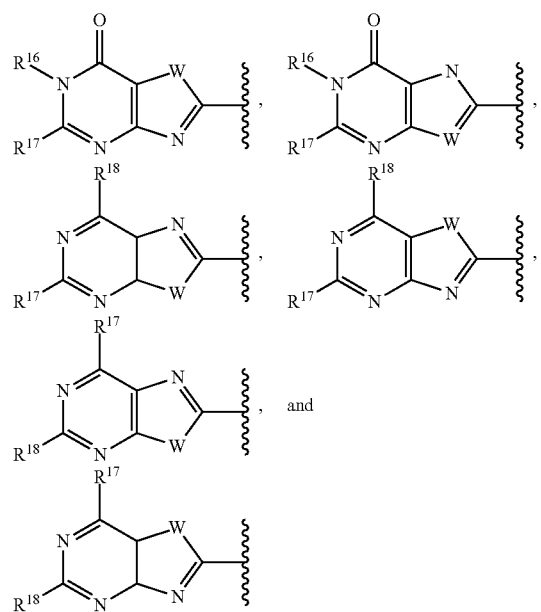

q is 0 or 1;
r is 0 or 1;
W is O, S, or $NR^{15}$;
X—Y is N—C(O), $CR^{14}$—O, $CR^{14}$—$S(O)_{0-2}$, or $CR_{13}$—$CR^1R^2$;
Ar is phenyl, naphthyl, or heteroaryl optionally substituted with one to five $R^3$ substituents;
$R^1$ and $R^2$ are each independently hydrogen or $C_{1-3}$alkyl, wherein alkyl is optionally substituted with one to three substituents independently selected from fluorine and hydroxy;

each $R^3$ is independently selected from the group consisting of: $C_{1-6}$alkyl, $C_{2-6}$alkenyl, $(CH_2)_n$-phenyl, $(CH_2)_n$-naphthyl, $(CH_2)_n$-heteroaryl, $(CH_2)_n$-heterocyclyl, $(CH_2)_n$$C_{3-7}$cycloalkyl, halogen, nitro, $(CH_2)_nOR^4$, $(CH_2)_nN(R^4)_2$, $(CH_2)_nC\equiv N$, $(CH_2)_nCO_2R^4$, $(CH_2)_nNR^4SO_2R^4$, $(CH_2)_nSO_2N(R^4)_2$, $(CH_2)_nS(O)_{0-2}R^4$, $(CH_2)_nNR^4C(O)N(R^4)_2$, $(CH_2)_nC(O)N(R^4)_2$, $(CH_2)_nNR^4C(O)R^4$, $(CH_2)_nNR^4CO_2R^4$, $(CH_2)_nC(O)R^4$, $O(CH_2)_nC(O)N(R^4)_2$, $(CH_2)_s$—Z—$(CH_2)_t$-phenyl, $(CH_2)_s$—Z—$(CH_2)_t$-naphthyl, $(CH_2)_s$—Z—$(CH_2)_t$-heteroaryl, $(CH_2)_s$—Z—$(CH_2)_t$-heterocyclyl, $(CH_2)_s$—Z—$(CH_2)_t$—$C_{3-7}$cycloalkyl, $(CH_2)_s$—Z—$(CH_2)_t$—$OR^4$, $(CH_2)_s$—Z—$(CH_2)_t$—$N(R^4)_2$, $(CH_2)_s$—Z—$(CH_2)_t$—$NR^4SO_2R^4$, $(CH_2)_s$—Z—$(CH_2)_t$—$C\equiv N$, $(CH_2)_s$—Z—$(CH_2)_t$—$CO_2R^4$, $(CH_2)_s$—Z—$(CH_2)_t$—$SO_2N(R^4)_2$, $(CH_2)_s$—Z—$(CH_2)_t$—$S(O)_{0-2}R^4$, $(CH_2)_s$—Z—$(CH_2)_t$—$NR^4C(O)N(R^4)_2$, $(CH_2)_s$—Z—$(CH_2)_t$—$C(O)N(R^4)_2$, $(CH_2)_s$—Z—$(CH_2)_t$—$NR^4C(O)R^4$, $(CH_2)_s$—Z—$(CH_2)_t$—$NR^4CO_2R^4$, $(CH_2)_s$—Z—$(CH_2)_t$—$C(O)R^4$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkyl, trifluoromethyl, and $C_{1-4}$alkoxy; and wherein any methylene ($CH_2$) carbon atom in $R_3$ is optionally substituted with one to two groups independently selected from fluorine, hydroxy, and $C_{1-4}$alkyl; or two substituents when on the same methylene ($CH_2$) group are taken together with the carbon atom to which they are attached to form a cyclopropyl group;

Z is O, S, or $NR^4$;

each $R^4$ is independently selected from the group consisting of: hydrogen, $C_{1-6}$alkyl, $(CH_2)_m$-phenyl, $(CH_2)_m$-heteroaryl, $(CH_2)_m$-naphthyl, and $(CH_2)_mC_{3-7}$cycloalkyl;

wherein alkyl, phenyl, heteroaryl, and cycloalkyl are optionally substituted with one to three groups independently selected from halogen, $C_{1-4}$alkyl, and $C_{1-4}$alkoxy; or two $R^4$ groups together with the atom to which they are attached form a 4- to 8-membered mono- or bicyclic ring system optionally containing an additional heteroatom selected from O, S, NH, and $NC_{1-4}$alkyl;

$R^5$, $R^6$, $R^7$, $R^8$, $R^9$, $R^{10}$, $R^{11}$ and $R^{12}$ are each independently hydrogen, fluorine, or $C_{1-3}$alkyl, wherein alkyl is optionally substituted with one to three substituents independently selected from fluorine and hydroxy;

$R^{13}$ is hydrogen, $C_{1-3}$alkyl, fluorine, or hydroxy; each $R^{14}$ is independently hydrogen or $C_{1-3}$alkyl;

$R^{15}$ is selected from the group consisting of hydrogen, $C_{1-4}$alkyl, $C_{1-4}$alkylcarbonyl, aryl-$C_{1-2}$alkylcarbonyl, arylcarbonyl, $C_{1-4}$alkylaminocarbonyl, $C_{1-4}$alkylsulfonyl, arylsulfonyl, aryl-$C_{1-2}$alkylsulfonyl, $C_{1-4}$alkyloxycarbonyl, aryloxycarbonyl, and aryl-$C_{1-2}$alkyloxycarbonyl;

$R^{16}$ is hydrogen or $C_{1-3}$alkyl optionally substituted with one to five fluorines;

$R^{17}$ is selected from the group consisting of: —$(CH_2)_vC(O)R^a$, —$(CH_2)_y$-T-$(CH_2)_zC(O)R^a$, —$(CH_2)_y$-T-$(CH_2)_z$$SO_3H$, —$(CH_2)_y$-T-$(CH_2)_w$-phenyl, —$(CH_2)_y$-T-$(CH_2)_w$-heteroaryl,

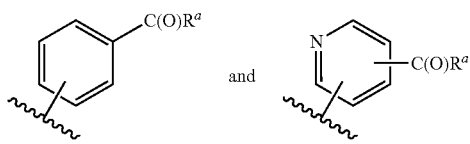

wherein phenyl and heteroaryl are optionally substituted with one to two substituents independently selected from halogen, $C_{1-4}$alkyl, —$(CH_2)_xC(O)R^a$, and —$CH=CHC(O)R^a$;

wherein any methylene ($CH_2$) carbon atom in $R^{17}$ is optionally substituted with one to two groups independently selected from amino, carboxy, fluorine, hydroxy, and $C_{1-4}$alkyl; or two substituents when on the same methylene ($CH_2$) group are taken together with the carbon atom to which they are attached to form a cyclopropyl group;

T is OS or $NR^{14}$;

$R^a$ is -OH, —$OC_{1-4}$alkyl, —$NH_2$, —$NHSO_2C_{1-4}$alkyl, —$NHSO_2C_{3-6}$cycloalkyl, or —$NHSO_2CH_2C_{3-6}$cycloalkyl;

$R^{18}$ is selected from the group consisting of: amino, halogen, $C_{1-4}$alkoxy, optionally substituted with hydroxy or carboxy, $C_{1-4}$alkylthio, optionally substituted with hydroxy or carboxy, $C_{1-4}$alkylamino, di-($C_{1-4}$alkyl)amino, arylamino, aryl-$C_{1-2}$alkylamino, $C_{1-4}$alkylcarbonylamino, aryl-$C_{1-2}$alkylcarbonylamino, arylcarbonylamino, $C_{1-4}$alkylaminocarbonylamino, $C_{1-4}$alkylsulfonylamino, arylsulfonylamino, aryl-$C_{1-2}$alkylsulfonylamino, $C_{1-4}$alkyloxycarbonylamino, aryloxycarbonylamino, and aryl-$C_{1-2}$alkyloxycarbonylamino;

each m is independently an integer from 0 to 2;

each n is independently an integer from 0 to 2;

each s is independently an integer from 1 to 3;

each t is independently an integer from 1 to 3;

v is an integer from 0 to 4;

w is an integer from 0 to 2;

z is 1 or 2;

each x is an integer from 0 to 2; and each y is 0 or 1.

Compounds of Formula (XXXIX) may be synthesized by methods known in the art, e.g., those described in International Patent Publication No. WO2008/141455. In some embodiments, the SCD inhibitor is a compound disclosed in International Patent Publication No. WO2008/141455, the compounds of which are herein incorporated by reference.

In some embodiments of any of the foregoing methods, the SCD inhibitor is a compound of Formula XL:

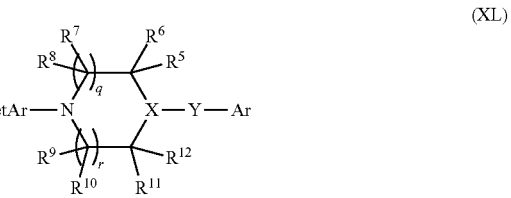

or a pharmaceutically acceptable salt thereof; wherein each n is independently 0, 1 or 2;

q is 0 or 1;

r is 0 or 1;

p is 0, 1, or 2;

X—Y is N—C(O), N—S(O)$_2$, N—CR$^1$R$^2$, CH—O, CH—S(O)$_p$, CH—NR$^{13}$, or CR$^{17}$—CR$^1$R$^2$;

Ar is phenyl, naphthyl, or heteroaryl optionally substituted with one to five $R^3$ substituents;

HetAr is a fused heteroaromatic ring selected from the group consisting of:

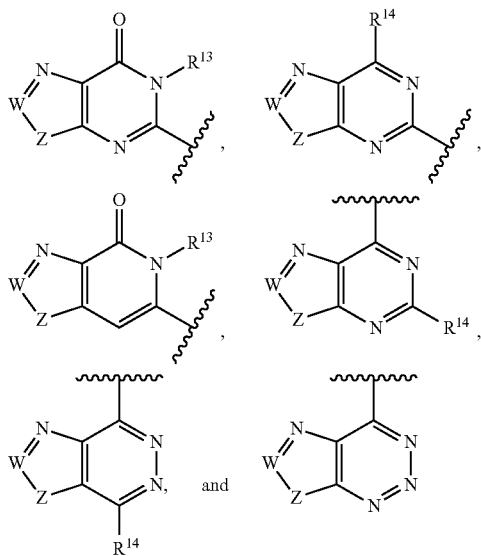

wherein Z is O, S, or N—$R^{18}$;

W is N or C—$R^{15}$;

$R^1$ and $R^2$ are each independently hydrogen, halogen, or $C_{1-3}$alkyl, wherein alkyl is optionally substituted with one to three substituents independently selected from fluorine and hydroxy; or $R^1$ and $R^2$ together with the carbon atom to which they are attached can form a spirocyclopropyl ring system;

each $R^3$ is independently selected from the group consisting of: $C_{1-6}$alkyl, $(CH_2)_n$-phenyl, $(CH_2)_n$-naphthyl, $(CH_2)_n$-heteroaryl, $(CH_2)_n$-heterocyclyl, $(CH_2)_nC_{3-7}$cycloalkyl, halogen, $OR^4(CH_2)_nN(R^4)_2$, $(CH_2)_nC\equiv N$, $(CH_2)_nCO_2R^4$, $NO_2$, $(CH_2)_nNR^4SO_2R^4(CH_2)_nSO_2N(R^4)_2$, $(CH_2)_nS(O)_pR^4$, $(CH_2)_nNR^4C(O)N(R^4)_2$, $(CH_2)_nC(O)N(R^4)_2$, $(CH_2)_nNR^4C(O)R^4$, $(CH_2)_nNR^4CO_2R^4$, $O(CH_2)_nC(O)N(R^4)_2$, $CF_3$, $CH_2CF_3$, $OCF_3$, and $OCH_2CF_3$;

in which phenyl, naphthyl, heteroaryl, cycloalkyl, and heterocyclyl are optionally substituted with one to three substituents independently selected from halogen, hydroxy, $C_{1-4}$alkyl, trifluoromethyl, and $C_{1-4}$alkoxy; and wherein any methylene ($CH_2$) carbon atom in $R^3$ is optionally substituted with one to two groups independently selected from fluorine, hydroxy, and $C_{1-4}$alkyl; or two substituents when on the same methylene ($CH_2$) group are taken together with the carbon atom to which they are attached to form a cyclopropyl group;

each $R^4$ is independently selected from the group consisting of: hydrogen, $C_{1-6}$alkyl, $(CH_2)_n$-phenyl, $(CH_2)_n$-heteroaryl, $(CH_2)_n$-naphthyl, and $(CH_2)_nC_{3-7}$cycloalkyl;

wherein alkyl, phenyl, heteroaryl, and cycloalkyl are optionally substituted with one to three groups independently selected from halogen, $C_{1-4}$alkyl, and $C_{1-4}$alkoxy; or two $R^4$ groups together with the atom to which they are attached form a 4- to 8-membered mono- or bicyclic ring system optionally containing an additional heteroatom selected from O, S, NH, and $NC_{1-4}$alkyl;

$R^5$, $R^6$, $R^7$, $R^8$, $R^9$, $R^{10}$, $R^{11}$, and $R^{12}$ are each independently hydrogen, fluorine, or $C_{1-3}$alkyl, wherein alkyl is optionally substituted with one to three substituents independently selected from fluorine and hydroxy;

each $R^{13}$ is independently hydrogen or $C_{1-6}$alkyl;

$R^{14}$ is independently selected from the group consisting of amino, hydroxy, mercapto, $C_{1-4}$alkoxy, $C_{1-4}$alkylthio, $C_{1-4}$alkylamino, di-($C_{1-4}$alkyl)amino, arylamino, aryl-$C_{1-2}$alkylamino, $C_{1-4}$alkylcarbonylamino, aryl-$C_{1-2}$alkylcarbonylamino, arylcarbonylamino, $C_{1-4}$alkylaminocarbonylamino, $C_{1-4}$alkylsulfonylamino, arylsulfonylamino, aryl-$C_{1-2}$alkylsulfonylamino, $C_{1-4}$alkyloxycarbonylamino, aryloxycarbonylamino, and aryl-$C_{1-2}$alkyloxycarbonylamino;

$R^{15}$ and $R^{16}$ are each independently hydrogen or $C_{1-4}$alkyl optionally substituted with amino, hydroxy, $C_{1-4}$alkoxy, $C_{1-4}$alkylthio, $C_{1-4}$alkylsulfonyl, $C_{1-4}$alkylcarbonyloxy, phenyl, heteroaryl, or one to five halogens;

$R^{17}$ is hydrogen, $C_{1-3}$alkyl, fluorine, or hydroxy; and $R^{18}$ is selected from the group consisting of hydrogen, $C_{1-4}$alkyl, $C_{1-4}$alkylcarbonyl, aryl-$C_{1-2}$alkylcarbonyl, arylcarbonyl, $C_{1-4}$alkylaminocarbonyl, $C_{1-4}$alkylsulfonyl, arylsulfonyl, aryl-$C_{1-2}$alkylsulfonyl, $C_{1-4}$alkyloxycarbonyl, aryloxycarbonyl, aryl-$C_{1-2}$alkyloxycarbonyl, β-D-ribofuranosyl, α-D-ribofuranosyl, β-D-glucopyranosyl, and α-D-glucopyranosyl.

Compounds of Formula (XL) may be synthesized by methods known in the art, e.g., those described in International Patent Publication No. WO2008/017161. In some embodiments, the SCD inhibitor is a compound disclosed in International Patent Publication No. WO2008/017161, the compounds of which are herein incorporated by reference.

In some embodiments of any of the foregoing methods, the SCD inhibitor is a compound of Formula XLI:

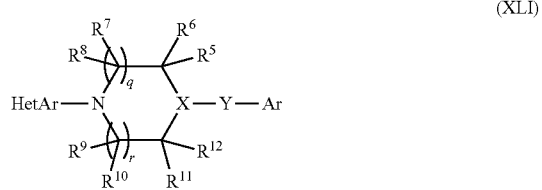

(XLI)

or a pharmaceutically acceptable salt thereof; wherein each n is independently 0, 1 or 2;

p is 0, 1, or 2;

X—Y is N—C(O), N—S(O)$_2$, N—$CR^1R^2$, CH—O, CH—S(O)$_p$, CH—$NR^{13}$, $CR^{17}$—$CR^1R^2$, or CH—C(O);

Ar is phenyl, naphthyl, or heteroaryl optionally substituted with one to five $R^3$ substituents;

HetAr is a fused heteroaromatic ring selected from the group consisting of:

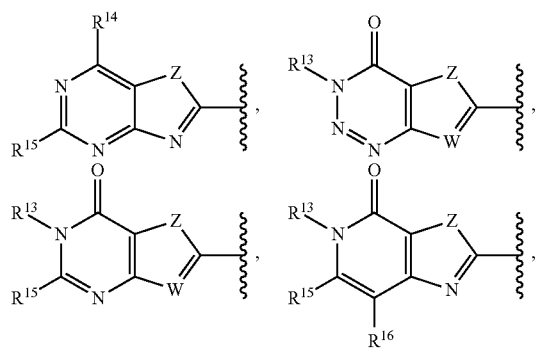

-continued

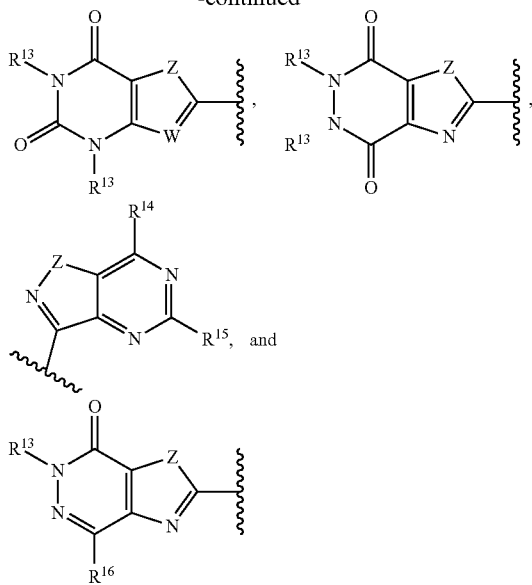

wherein Z is O, S, or N—R$^{18}$;

R$^1$ and R$^2$ are each independently hydrogen, halogen, or C$_{1-3}$alkyl, wherein alkyl is optionally substituted with one to three substituents independently selected from fluorine and hydroxy; or R$^1$ and R$^2$ together with the carbon atom to which they are attached can form a spirocyclopropyl ring system; each R$^3$ is independently selected from the group consisting of: C$_{1-6}$ alkyl, (CH$_2$)$_n$-phenyl, (CH$_2$)$_n$-naphthyl, (CH$_2$)$_n$-heteroaryl, (CH$_2$)$_n$-heterocyclyl, (CH$_2$)$_n$C$_{3-7}$cycloalkyl, halogen, OR$^4$, (CH$_2$)$_n$N(R$^4$)$_2$, (CH$_2$)$_n$C≡N, (CH$_2$)$_n$CO$_2$R$^4$, NO$_2$, (CH$_2$)$_n$NR$^4$SO$_2$R$^4$(CH$_2$)$_n$SO$_2$N(R$^4$)$_2$, (CH$_2$)$_n$S(O)$_p$R$^4$, (CH$_2$)$_n$NR$^4$C(O)N(R$^4$)$_2$, (CH$_2$)$_n$C(O)N(R$^4$)$_2$, (CH$_2$)$_n$NR$^4$C(O)R$^4$, (CH$_2$)$_n$NR$^4$CO$_2$R$^4$, O(CH$_2$)$_n$C(O)N(R$^4$)$_2$, CF$_3$, CH$_2$CF$_3$, OCF$_3$, and OCH$_2$CF$_3$;

in which phenyl, naphthyl, heteroaryl, cycloalkyl, and heterocyclyl are optionally substituted with one to three substituents independently selected from halogen, hydroxy, C$_{1-4}$alkyl, trifluoromethyl, and C$_{1-4}$alkoxy; and wherein any methylene (CH$_2$) carbon atom in R$^3$ is optionally substituted with one to two groups independently selected from fluorine, hydroxy, and C$_{1-4}$alkyl; or two substituents when on the same methylene (CH$_2$) group are taken together with the carbon atom to which they are attached to form a cyclopropyl group;

each R$^4$ is independently selected from the group consisting of: hydrogen, C$_{1-6}$alkyl, (CH$_2$)$_n$-phenyl, (CH$_2$)$_n$-heteroaryl, (CH$_2$)$_n$-naphthyl, and (CH$_2$)$_n$C$_{3-7}$cycloalkyl;

wherein alkyl, phenyl, heteroaryl, and cycloalkyl are optionally substituted with one to three groups independently selected from halogen, C$_{1-4}$alkyl, and C$_{1-4}$alkoxy; or two R$^4$ groups together with the atom to which they are attached form a 4- to 8-membered mono- or bicyclic ring system optionally containing an additional heteroatom selected from O, S, NH, and NC$_{1-4}$alkyl;

R$^5$, R$^6$, R$^7$, R$^8$, R$^9$, R$^{10}$, R$^{11}$, and R$^{12}$ are each independently hydrogen, fluorine, or C$_{1-3}$alkyl, wherein alkyl is optionally substituted with one to three substituents independently selected from fluorine and hydroxy;

each R$^{13}$ is independently hydrogen or C$_{1-6}$alkyl;

R$^{14}$ is independently selected from the group consisting of amino, hydroxy, mercapto, C$_{1-4}$alkoxy, C$_{1-4}$alkylthio, C$_{1-4}$alkylamino, di-(C$_{1-4}$alkyl)amino, arylamino, aryl-C$_{1-2}$alkylamino, C$_{1-4}$alkylcarbonylamino, aryl-C$_{1-2}$alkylcarbonylamino, arylcarbonylamino, C$_{1-4}$alkylaminocarbonylamino, C$_{1-4}$alkylsulfonylamino, arylsulfonylamino, aryl-C$_{1-2}$alkylsulfonylamino, C$_{1-4}$alkyloxycarbonylamino, aryloxycarbonylamino, and aryl-C$_{1-2}$alkyloxycarbonylamino;

R$^{15}$ and R$^{16}$ are each independently hydrogen or C$_{1-4}$alkyl optionally substituted with amino, hydroxy, C$_{1-4}$alkoxy, C$_{1-4}$alkylthio, C$_{1-4}$alkylsulfonyl, C$_{1-4}$alkylcarbonyloxy, phenyl, heteroaryl, or one to five halogens;

R$^{17}$ is hydrogen, C$_{1-3}$alkyl, fluorine, or hydroxy; and

R$^{18}$ is selected from the group consisting of hydrogen, C$_{1-4}$alkyl, C$_{1-4}$alkylcarbonyl, aryl-C$_{1-2}$alkylcarbonyl, arylcarbonyl, C$_{1-4}$alkylaminocarbonyl, C$_{1-4}$alkylsulfonyl, arylsulfonyl, aryl-C$_{1-2}$alkylsulfonyl, C$_{1-4}$alkyloxycarbonyl, aryloxycarbonyl, and aryl-C$_{1-2}$alkyloxycarbonyl.

Compounds of Formula (XLI) may be synthesized by methods known in the art, e.g., those described in International Patent Publication No. WO2007/056846. In some embodiments, the SCD inhibitor is a compound disclosed in International Patent Publication No. WO2007/056846, the compounds of which are herein incorporated by reference.

In some embodiments of any of the foregoing methods, the SCD inhibitor is a compound of Formula XLII:

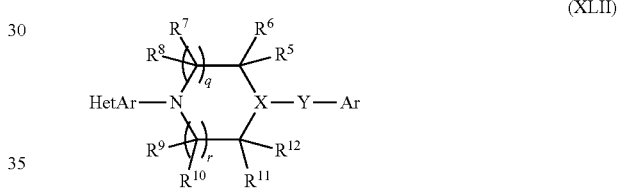

(XLII)

or a pharmaceutically acceptable salt thereof; wherein
each n is independently 0, 1 or 2;
each m is independently 0, 1, or 2;
each p is independently 0, 1, or 2;
X—Y is N—C(O), N—S(O)$_2$, N—CR$^1$R$^2$, CH—O, CH—S(O)$_p$, CH—NR$^{13}$, CH—CR$^1$R$^2$, or CH—C(O);

Ar is phenyl, naphthyl, or heteroaryl each of which is optionally substituted with one to five R$^{3a}$ substituents;

HetAr is an optionally fused five-membered heteroaromatic ring selected from the group consisting of: oxazolyl, thiazolyl, imidazolyl, pyrazolyl, isoxazolyl, isothiazolyl, 1,2,4-oxadiazolyl, 1,3,4-oxadiazolyl, 1,2,5-oxadiazolyl, 1,2,3-oxadiazolyl, 1,2,4-thiadiazolyl, 1,2,5-thiadiazolyl, 1,3,4-thiadiazolyl, 1,2,3-thiadiazolyl, 1,2,4-triazolyl, 1,2,3-triazolyl, tetrazolyl, benzthiazolyl, benzoxazolyl, benzimidazolyl, benzisoxazolyl, and benzisothiazolyl;

in which the heteroaromatic ring is optionally substituted with one to two substituents independently selected from R$^{3b}$;

R$^1$ and R$^2$ are each independently hydrogen or C$_{1-3}$alkyl, wherein alkyl is optionally substituted with one to three substituents independently selected from fluorine and hydroxy;

each R$^{3a}$ and each R$^{3b}$ is independently selected from the group consisting of: C$_{1-6}$alkyl, (CH$_2$)$_n$OR$_4$, (CH$_2$)$_n$-phenyl, (CH$_2$)$_n$-naphthyl, (CH$_2$)$_n$-heteroaryl, (CH$_2$)$_n$-heterocyclyl, (CH$_2$)$_n$C$_{3-7}$cycloalkyl, halogen, (CH$_2$)$_n$N(R$^4$)$_2$, (CH$_2$)$_n$C≡N, (CH$_2$)$_n$CO$_2$R$^4$, (CH$_2$)$_n$COR$^4$, NO$_2$, (CH$_2$)$_n$NR$^4$SO$_2$R$^4$, (CH$_2$)$_n$SO$_2$N(R$^4$)$_2$, (CH$_2$)$_n$S(O)$_p$R$^4$, (CH$_2$)$_n$NR$^4$C(O)N(R$^4$)$_2$, (CH$_2$)$_n$C(O)N(R$^4$)$_2$, (CH$_2$)$_n$C(O)N(OR$^4$)R$^4$, (CH$_2$)$_n$C (O)N(NH$_2$)R$^4$, (CH$_2$)$_n$NR$^4$C(O)R$^4$, (CH$_2$)$_n$NR$^4$CO$_2$R$^4$, O(CH$_2$)$_n$C(O)N(R$^4$)$_2$, CF$_3$, CH$_2$CF$_3$, OCF$_3$, and OCH$_2$CF$_3$;

in which phenyl, naphthyl, heteroaryl, cycloalkyl, and heterocyclyl are optionally substituted with one to three substituents independently selected from halogen, hydroxy, C$_{1-4}$alkoxy, C$_{3-6}$cycloalkyl, and C$_{1-4}$alkyl wherein alkyl is optionally substituted with hydroxy or one to three fluorines; and wherein any methylene (CH$_2$) carbon atom in R$^{3a}$ or R$^{3b}$ is optionally substituted with one to two groups independently selected from fluorine, hydroxy, and C$_{1-4}$alkyl optionally substituted with one to five fluorines; or two substituents when on the same methylene (CH$_2$) group are taken together with the carbon atom to which they are attached to form a cyclopropyl group;

each R$^4$ is independently selected from the group consisting of: hydrogen, C$_{1-6}$alkyl, (CH$_2$)$_m$-phenyl, (CH$_2$)$_m$-heteroaryl, (CH$_2$)$_m$-naphthyl, and (CH$_2$)$_m$C$_{3-7}$cycloalkyl;

wherein alkyl, phenyl, heteroaryl, and cycloalkyl are optionally substituted with one to three groups independently selected from halogen, C$_{1-4}$alkyl, and C$_{1-4}$alkoxy, wherein alkyl and alkoxy are optionally substituted with one to five fluorines; or two R$^4$ groups together with the atom to which they are attached form a 4- to 8-membered mono- or bicyclic ring system optionally containing an additional heteroatom selected from O, S, and NC$_{1-4}$alkyl;

R$^5$, R$^6$, R$^7$, R$^8$, R$^9$, R$^{10}$, R$^{11}$, and R$^{12}$ are each independently hydrogen, fluorine, or C$_{1-3}$alkyl, wherein alkyl is optionally substituted with one to three substituents independently selected from fluorine and hydroxy; and R$^{13}$ is hydrogen or C$_{1-6}$alkyl.

Compounds of Formula (XLII) may be synthesized by methods known in the art, e.g., those described in International Patent Publication No. WO2006/130986. In some embodiments, the SCD inhibitor is a compound disclosed in International Patent Publication No. WO2006/130986, the compounds of which are herein incorporated by reference.

In some embodiments of any of the foregoing methods, the SCD inhibitor is a compound of Formula XLIII,

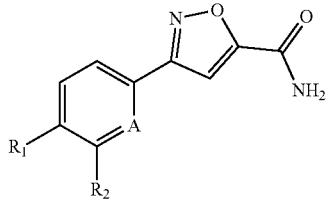

(XLIII)

wherein:
A is —CH— or nitrogen;
R$^1$ is —O—CH$_2$—R$^3$, —CH$_2$—O—R$^3$ or —CH$_2$—R$^4$;
R$^2$ is hydrogen or halogen;
R$^3$ is -phenyl, optionally mono- or bi-substituted independently with lower alkyl, alkoxy, halogen, —CN, —CF$_3$, —OCF$_3$, —SCF$_3$, —S(=O)CF$_3$ or —SO$_2$CH$_3$, or -pyridinyl, optionally substituted with lower alkyl or halogen; and
R$^4$ is indolyl, dihydroindolyl, isoindolyl, dihydroisoindolyl, benzotriazolyl, benzoimidazolyl, indazolyl, tetrahydroquinolinyl, methyldihydroindolyl or methylindolyl;
or a pharmaceutically acceptable salt thereof.

In some embodiments of the compound of Formula XLIII, A is —CH—;
In some embodiments of the compound of Formula XLIII, R$^1$ is —O—CH$_2$—R$^3$;
In some embodiments of the compound of Formula XLIII, R$^1$ is —CH$_2$—O—R$^3$;
In some embodiments of the compound of Formula XLIII, R$^1$ is —CH$_2$—R$^4$;
In some embodiments of the compound of Formula XLIII, R$^2$ is hydrogen or chlorine;
In some embodiments of the compound of Formula XLIII, R$^3$ is phenyl, mono- or bi-substituted independently with lower alkyl, alkoxy, halogen, —CN, —CF$_3$, —OCF$_3$, —SCF$_3$, —S(=O)CF$_3$ or —SO$_2$CH$_3$;
In some embodiments of the compound of Formula XLIII, R$^3$ is pyridinyl substituted with lower alkyl or halogen;
In some embodiments of the compound of Formula XLIII, R$^4$ is indolyl, dihydroindolyl, isoindolyl, dihydroisoindolyl;
In some embodiments of the compound of Formula XLIII, R$^4$ is benzotriazolyl, benzoimidazolyl, indazolyl, tetrahydroquinolinyl, methyldihydroindolyl or methylindolyl;
In some embodiments, the compound of Formula XLIII is selected from:
3-[4-(2-Trifluoromethylsulfanyl-benzyloxy)-phenyl]-isoxazole-5-carboxylic acid amide;
3-[4-(2-Trifluoromethanesulfinyl-benzyloxy)-phenyl]-isoxazole-5-carboxylic acid amide;
3-[4-(2-Methoxy-benzyloxy)-phenyl]-isoxazole-5-carboxylic acid amide;
3-[4-(3,4-Dimethyl-benzyloxy)-phenyl]-isoxazole-5-carboxylic acid amide;
3-[4-(2-Cyano-benzyloxy)-phenyl]-isoxazole-5-carboxylic acid amide;
3-[4-(2,6-Dichloro-benzyloxy)-phenyl]-isoxazole-5-carboxylic acid amide;
3-[4-(3,4-Difluoro-benzyloxy)-phenyl]-isoxazole-5-carboxylic acid amide;
3-[4-(2-Fluoro-benzyloxy)-phenyl]-isoxazole-5-carboxylic acid amide;
3-[4-(2-Methyl-benzyloxy)-phenyl]-isoxazole-5-carboxylic acid amide;
3-[4-(2-Trifluoromethoxy-benzyloxy)-phenyl]-isoxazole-5-carboxylic acid amide;
3-[4-(2-Iodo-benzyloxy)-phenyl]-isoxazole-5-carboxylic acid amide;
3-[4-(2-Chloro-6-fluoro-benzyloxy)-phenyl]-isoxazole-5-carboxylic acid amide;
3-[4-(2-Chloro-5-fluoro-benzyloxy)-phenyl]-isoxazole-5-carboxylic acid amide;
3-[5-(2-Chloro-benzyloxy)-pyridin-2-yl]-isoxazole-5-carboxylic acid amide;
3-[4-(2-Chloro-pyridin-3-ylmethoxy)-phenyl]-isoxazole-5-carboxylic acid amide;
3-[4-(3-Fluoro-benzyloxy)-phenyl]-isoxazole-5-carboxylic acid amide;
3-[4-(3-Trifluoromethyl-benzyloxy)-phenyl]-isoxazole-5-carboxylic acid amide;
3-[4-(3-Chloro-benzyloxy)-phenyl]-isoxazole-5-carboxylic acid amide;
3-[4-(2-Chloro-benzyloxy)-phenyl]-isoxazole-5-carboxylic acid amide;
3-[4-(2-Bromo-benzyloxy)-phenyl]-isoxazole-5-carboxylic acid amide;
3-[4-(2-Trifluoromethyl-benzyloxy)-phenyl]-isoxazole-5-carboxylic acid amide;
3-[4-(2-Methanesulfonyl-benzyloxy)-phenyl]-isoxazole-5-carboxylic acid amide;

3-(4-o-Tolyloxymethyl-phenyl)-isoxazole-5-carboxylic acid amide;
3-(4-m-Tolyloxymethyl-phenyl)-isoxazole-5-carboxylic acid amide;
3-[4-(2-Methoxy-phenoxymethyl)-phenyl]-isoxazole-5-carboxylic acid amide;
3-[4-(3-Methoxy-phenoxymethyl)-phenyl]-isoxazole-5-carboxylic acid amide;
3-[4-(4-Methoxy-phenoxymethyl)-phenyl]-isoxazole-5-carboxylic acid amide;
3-[4-(2,6-Dimethyl-phenoxymethyl)-phenyl]-isoxazole-5-carboxylic acid amide;
3-[4-(2-Isopropyl-phenoxymethyl)-phenyl]-isoxazole-5-carboxylic acid amide;
3-[4-(2-Trifluoromethoxy-phenoxymethyl)-phenyl]-isoxazole-5-carboxylic acid amide;
3-[4-(2-Ethyl-phenoxymethyl)-phenyl]-isoxazole-5-carboxylic acid amide;
3-[4-(2-tert-Butyl-phenoxymethyl)-phenyl]-isoxazole-5-carboxylic acid amide;
3-[4-(2-Trifluoromethyl-phenoxymethyl)-phenyl]-isoxazole-5-carboxylic acid amide;
3-[4-(2-Cyano-phenoxymethyl)-phenyl]-isoxazole-5-carboxylic acid amide;
3-[4-(3-Methyl-pyridin-2-yloxymethyl)-phenyl]-isoxazole-5-carboxylic acid amide;
3-[4-(2-Fluoro-phenoxymethyl)-phenyl]-isoxazole-5-carboxylic acid amide;
3-[4-(5-Chloro-2-methyl-phenoxymethyl)-phenyl]-isoxazole-5-carboxylic acid amide;
3-[4-(3-Chloro-2-methy 1-phenoxymethyl)-phenyl]-isoxazole-5-carboxylic acid amide;
3-[4-(4-Fluoro-2-methyl-phenoxymethyl)-phenyl]-isoxazole-5-carboxylic acid amide;
3-[4-(5-Fluoro-2-methyl-phenoxymethyl)-phenyl]-isoxazole-5-carboxylic acid amide;
3-[4-(2-Methyl-pyridin-3-yloxymethyl)-phenyl]-isoxazole-5-carboxylic acid amide;
3-[4-(2,3-Dihydro-indol-1-ylmethyl)-phenyl]-isoxazole-5-carboxylic acid amide;
3-[4-(1,3-Dihydro-isoindol-2-ylmethyl)-phenyl]-isoxazole-5-carboxylic acid amide;
3-(4-Indol-1-ylmethyl-phenyl)-isoxazole-5-carboxylic acid amide;
3-(4-Benzotriazol-1-ylmethyl-phenyl)-isoxazole-5-carboxylic acid amide;
3-(4-Benzoimidazol-1-ylmethyl-phenyl)-isoxazole-5-carboxylic acid amide;
3-(4-Indazol-1-ylmethyl-phenyl)-isoxazole-5-carboxlic acid amide;
3-(4-Indazol-2-ylmethyl-phenyl)-isoxazole-5-carboxylic acid amide;
3-[4-(3,4-Dihydro-2H-quinolin-1-ylmethyl)-phenyl]-isoxazole-5-carboxylic acid amide;
3-[4-(2-Methyl-2,3-dihydro-indol-1-ylmethyl)-phenyl]-isoxazole-5-carboxylic acid amide;
3-[4-(4-Methyl-indol-1-ylmethyl)-phenyl]-isoxazole-5-carboxylic acid amide; or
3-[3-Chloro-4-(2-trifluoromethyl-benzyloxy)-phenyl]-isoxazole-5-carboxylic acid amide.

Compounds of Formula (XLIII) may be synthesized by methods known in the art, e.g., those described in U.S. Pat. No. 9,296,711 B2. In some embodiments, the SCD inhibitor is a compound disclosed in U.S. Pat. No. 9,296,711 B2, the compounds of which are herein incorporated by reference.

In some embodiments of any of the foregoing methods, the SCD inhibitor is a compound of Formula XLIV,

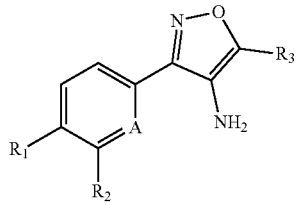

(XLIV)

wherein:
A is —CH— or nitrogen;
$R^1$ is —O(CH$_2$)$_n$R$^4$, —CH$_2$NHR$^4$, —CH$_2$CH$_2$R$^4$, —OCH$_2$C(O)R$^4$ or —CH$_2$OR$^4$;
$R^2$ is hydrogen or halogen;
$R^3$ is hydrogen or lower alkyl;
$R^4$ is phenyl, pyridinyl, 1,1-dioxo-2,3-dihydro-1H-1 lambda*6*-benzo[b]thiophenyl or 1,1-dioxo-1H-1 lambda*6*-benzo[b]thiophenyl, said phenyl optionally mono- or bi-substituted independently with halogen, lower alkyl, alkoxy, —C(O)OCH$_3$, —S(O)$_2$CH$_3$, —NO$_2$, —CN, —CF$_3$, —OCF$_3$, —SCH$_3$, —SO$_2$-phenyl, —SCF$_3$ or —SO$_2$CH$_2$CH$_3$; and
n is 1, 2 or 3;
or a pharmaceutically acceptable salt thereof.

In some embodiments of the compound of Formula XLIV, A is —CH—;
In some embodiments of the compound of Formula XLIV, $R^1$ is —O(CH$_2$)$_n$R$^4$ or —CH$_2$NHR$^4$;
In some embodiments of the compound of Formula XLIV, $R^1$ is —O(CH$_2$)$_n$R$^4$;
In some embodiments of the compound of Formula XLIV, $R^1$ is —OCH$_2$R$^4$;
In some embodiments of the compound of Formula XLIV, $R^2$ is hydrogen;
In some embodiments of the compound of Formula XLIV, $R^3$ is hydrogen or methyl;
In some embodiments of the compound of Formula XLIV, $R^4$ is unsubstituted phenyl, pyridinyl, 1,1-dioxo-2,3-dihydro-1H-1 lambda*6*-benzo[b]thiophenyl or 1,1-dioxo-1H-1 lambda*6*-benzo[b]thiophenyl;
In some embodiments of the compound of Formula XLIV, $R^4$ is unsubstituted phenyl;
In some embodiments of the compound of Formula XLIV, $R^4$ is phenyl mono-substituted with Cl, F, I, methyl, isopropyl, —OCH$_3$, —C(O)OCH$_3$, S(O)$_2$CH$_3$, —NO$_2$, —CN, CF$_3$, —OCF$_3$, —SCH$_3$, —SO$_2$-phenyl, —SCF$_3$ or —SO$_2$CH$_2$CH$_3$;
In some embodiments of the compound of Formula XLIV, $R^4$ is phenyl bi-substituted independently with methyl or halogen;
In some embodiments, the compound of Formula XLIII is selected from:
3-[4-(4-Fluoro-benzyloxy)-phenyl]-isoxazol-4-ylamine;
3-(4-Benzyloxy-phenyl)-isoxazol-4-ylamine;
3-[4-(4-Methoxy-benzyloxy)-phenyl]-isoxazol-4-ylamine;
4-[4-(4-Amino-isoxazol-3-yl)-phenoxymethyl]-benzoic acid methyl ester hydrochloride;
3-[4-(4-Methanesulfonyl-benzyloxy)-phenyl]-isoxazol-4-ylamine;
3-{4-[(4-methanesulfonyl-phenylamino)-methyl]-phenyl}-isoxazol-4-ylamine hydrochloride;
3-[4-(2-Chloro-4-methanesulfonyl-benzyloxy)-phenyl]-isoxazol-4-ylamine;
3-{4-[2-(4-Methanesulfonyl-phenyl)-ethyl]-phenyl}-isoxazol-4-ylamine;

3-(5-Phenethyloxy-pyridin-2-yl)-isoxazol-4-ylamine;
3-[4-(3-Phenyl-propoxy)-phenyl]-isoxazol-4-ylamine;
3-[5-(4-Methanesulfonyl-benzyloxy)-pyridin-2-yl]-isoxazol-4-ylamine;
3-[4-(4-Methanesulfonyl-benzyloxy)-phenyl]-5-methyl-isoxazol-4-ylamine;
3-[4-(Pyridin-3-ylmethoxy)-phenyl]-isoxazol-4-ylamine;
2-[4-(4-Amino-isoxazol-3-yl)-phenoxy]-1-phenyl-ethanone hydrochloride;
3-[4-(4-Nitro-benzyloxy)-phenyl]-isoxazol-4-ylamine hydrochloride;
4-[4-(4-Amino-isoxazol-3-yl)-phenoxymethyl]-benzonitrile hydrochloride;
3-[4-(4-Amino-isoxazol-3-yl)-phenoxymethyl]-benzonitrile hydrochloride;
3-[4-(4-Trifluoromethyl-benzyloxy)-phenyl]-isoxazol-4-ylamine hydrochloride;
3-[4-(4-Trifluoromethoxy-benzyloxy)-phenyl]-isoxazol-4-ylamine hydrochloride;
3-[4-(3,5-Difluoro-benzyloxy)-phenyl]-isoxazol-4-ylamine hydrochloride;
3-[4-(2-Chloro-benzyloxy)-phenyl]-isoxazol-4-ylamine hydrochloride;
3-[4-(3,4-Dimethyl-benzyloxy)-phenyl]-isoxazol-4-ylamine hydrochloride;
3-[4-(3-Trifluoromethoxy-benzyloxy)-phenyl]-isoxazol-4-ylamine hydrochloride;
3-[4-(4-Chloro-benzyloxy)-phenyl]-isoxazol-4-ylamine;
3-[4-(3,4-Dichloro-benzyloxy)-phenyl]-isoxazol-4-ylamine hydrochloride;
3-[4-(4-Methyl-benzyloxy)-phenyl]-isoxazol-4-ylamine hydrochloride;
3-[4-(4-Iodo-benzyloxy)-phenyl]-isoxazol-4-ylamine;
3-[4-(4-Isopropyl-benzyloxy)-phenyl]-isoxazol-4-ylamine;
3-[4-(4-Methanesulfonyl-benzyloxy)-phenyl]-isoxazol-4-ylamine hydrochloride;
3-[4-(4-Ethanesulfonyl-benzyloxy)-phenyl]-isoxazol-4-ylamine;
3-[4-(1,1-Dioxo-2,3-dihydro-1H-1 lambda*6*-benzo[b]thiophen-5-ylmethoxy)-phenyl]-isoxazol-4-ylamine;
3-[4-(1,1-Dioxo-1H-1 lambda*6*-benzo[b]thiophen-5-ylmethoxy)-phenyl]-isoxazol-4-ylamine;
3-[4-(4-Benzenesulfonyl-benzyloxy)-phenyl]-isoxazol-4-ylamine;
3-[4-(4-Methylsulfanyl-benzyloxy)-phenyl]-isoxazol-4-ylamine; and
3-[4-(4-Trifluoromethylsulfanyl-benzyloxy)-phenyl]-isoxazol-4-ylamine.

Compounds of Formula (XLIV) may be synthesized by methods known in the art, e.g., those described in U.S. Pat. No. 9,290,465 B2. In some embodiments, the SCD inhibitor is a compound disclosed in U.S. Pat. No. 9,290,465 B2, the compounds of which are herein incorporated by reference.

In some embodiments of any of the foregoing methods, the SCD inhibitor is a compound of Formula XLV,

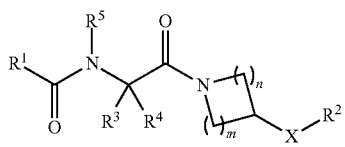
(XLV)

wherein
R$^1$ is aryl or heteroaryl;
R$^2$ is aryl or heteroaryl;
R$^3$ and R$^4$ are each independently hydrogen, halogen or alkyl; or
R$^3$ and R$^4$, together with the carbon atom to which they are attached, form a cycloalkyl group;
R$^5$ is hydrogen or alkyl;
m and n are, independently, 1 or 2;
X is —O—, —NR$^6$—, —S—, —S(O)— or —S(O)$_2$—
where R$^6$ is hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkythio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
or pharmaceutically acceptable salts, solvates, hydrates, solvates of pharmaceutically acceptable salts thereof, or enantiomer or diasteromer thereof;
with the proviso that said compound is not
4-[[(2R)-2,3-dihydro-2-methyl-6-nitroimidazo[2,1-b]oxazol-2-yl]methoxy]-N-[2-oxo-2-[4-[4-(trifluoromethoxy)phenoxy]-1-piperidinyl]ethyl]-benzamide,
N-[2-[4-[[4-amino-5-(2,6-difluorobenzoyl)-2-thiazolyl]amino]-1-piperidinyl]-2-oxoethyl]-M-methyl-benzamide,
4-amino-N-[2-[4-[[4-amino-5-(2,6-difluorobenzoyl)-2-thiazolyl]amino]-1-piperidinyl]-2-oxoethyl]-benzamide,
or a pharmaceutically acceptable salt thereof.

In some embodiments of the compound of Formula XLV,
R$^1$ is aryl or heteroaryl;
R$^2$ is aryl or heteroaryl;
R$^3$ and R$^4$ are each independently hydrogen, halogen or alkyl; or
R$^3$ and R$^4$, together with the carbon atom to which they are attached, form a cycloalkyl group;
R$^5$ is hydrogen or alkyl;
m and n are, independently, 1 or 2;
X is —O—, —NR$^6$—, —S—, —S(O)— or —S(O)$_2$—
where R$^6$ is hydrogen or alkyl;
wherein, when present, an aryl or heteroaryl group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
or pharmaceutically acceptable salts, or enantiomer or diastereomer thereof;
with the proviso that said compound is not
4-[[(2R)-2,3-dihydro-2-methyl-6-nitroimidazo[2,1-b]oxazol-2-yl]methoxy]-N-[2-oxo-2-[4-[4-(trifluoromethoxy)phenoxy]-1-piperidinyl]ethyl]-benzamide,
N-[2-[4-[[4-amino-5-(2,6-difluorobenzoyl)-2-thiazolyl]amino]-1-piperidinyl]-2-oxoethyl]-M-methyl-benzamide,
4-amino-N-[2-[4-[[4-amino-5-(2,6-difluorobenzoyl)-2-thiazolyl]amino]-1-piperidinyl]-2-oxoethyl]-benzamide, or a pharmaceutically acceptable salt thereof.

In some embodiments of the compound of Formula XLV, $R^1$ is aryl that is substituted by one or more aryl groups.

In some embodiments of the compound of Formula XLV, $R^1$ is heteroaryl and is substituted by one or more aryl or heteroaryl groups.

In some embodiments of the compound of Formula XLV, $R^1$ is pyrazole, triazole, or isoxazole.

In some embodiments of the compound of Formula XLV, $R^2$ is aryl.

In some embodiments, the compound of Formula XLV is selected from:

1-Cyclopentyl-1H-[1,2,3]triazole-4-carboxylic acid {2-[4-(5-chloro-pyridin-3-yloxy)-piperidin-1-yl]-2-oxo-ethyl}-amide;

1-Pyridin-3-yl-1H-[1,2,3]triazole-4-carboxylic acid {2-[4-(5-cyano-2-methyl-phenoxy)-piperidin-1-yl]-2-oxo-ethyl}-amide;

1-Morpholin-4-yl-1H-[1,2,3]triazole-4-carboxylic acid {2-oxo-2-[4-(3-trifluoromethyl-phenoxy)-piperidin-1-yl]-ethyl}-amide;

1-Morpholin-4-yl-1H-[1,2,3]triazole-4-carboxylic acid {2-[4-(2-chloro-5-fluoro-phenoxy)-piperidin-1-yl]-2-oxo-ethyl}-amide;

1-Pyridin-3-yl-1H-[1,2,3]triazole-4-carboxylic acid {2-[3-(2,5-difluoro-phenoxy)-pyrrolidin-1-yl]-2-oxo-ethyl}-amide;

1-Phenyl-1H-imidazole-4-carboxylic acid {2-[4-(2,5-difluoro-phenoxy)-piperidin-1-yl]-2-oxo-ethyl}-amide; and 1-Phenyl-1H-imidazole-4-carboxylic acid {2-[4-(2-chloro-phenoxy)-piperidin-1-yl]-2-oxo-ethyl}-amide,
or pharmaceutically acceptable salts thereof.

In some embodiments, the compound of Formula XLV is selected from:

Biphenyl-4-carboxylic acid {2-oxo-2-[4-(2-trifluoromethyl-phenoxy)-piperidin-1-yl]-ethyl}-amide, Biphenyl-4-carboxylic acid {2-[4-(2-bromo-phenoxy)-piperidin-1-yl]-2-oxo-ethyl}-amide, Biphenyl-4-carboxylic acid {2-[4-(2-bromo-phenylamino)-piperidin-1-yl]-2-oxo-ethyl}-amide, Biphenyl-4-carboxylic acid {2-[4-(2-chloro-phenylamino)-piperidin-1-yl]-2-oxo-ethyl}-amide, Biphenyl-4-carboxylic acid {2-oxo-2-[4-(2-trifluoromethyl-phenylamino)-piperidin-1-yl]-ethyl}-amide, Biphenyl-4-carboxylic acid (2-{4-[methyl-(2-trifluoromethyl-phenyl)-amino]-piperidin-1-yl}-2-oxo-ethyl)-amide, Biphenyl-4-carboxylic acid (2-{4-[(2-chloro-phenyl)-methyl-amino]-piperidin-1-yl}-2-oxo-ethyl)-amide, Biphenyl-4-carboxylic acid (2-{4-[(2-bromo-phenyl)-methyl-amino]-piperidin-1-yl}-2-oxo-ethyl)-amide, 5-Phenyl-isoxazole-3-carboxylic acid {2-[4-(2-bromo-phenoxy)-piperidin-1-yl]-2-oxo-ethyl}-amide, 5-Phenyl-isoxazole-3-carboxylic acid {2-[4-(2-bromo-phenylamino)-piperidin-1-yl]-2-oxo-ethyl}-amide, 5-Phenyl-isoxazole-3-carboxylic acid {2-[4-(2-chloro-phenylamino)-piperidin-1-yl]-2-oxo-ethyl}-amide, 5-Phenyl-isoxazole-3-carboxylic acid (2-{4-[(2-bromo-phenyl)-methyl-amino]-piperidin-1-yl}-2-oxo-ethyl)-amide, 5-Phenyl-isoxazole-3-carboxylic acid {2-oxo-2-[4-(2-trifluoromethyl-phenylamino)-piperidin-1-yl]-ethyl}-amide, 5-Phenyl-isoxazole-3-carboxylic acid (2-{-4-[methyl-(2-trifluoromethyl-phenyl)-amino]-piperidin-1-yl}-2-oxo-ethyl)-amide, N-{2-oxo-2-[4-(2-trifluoromethyl-phenylamino)-piperidin-1-yl]-ethyl}-4-phenylamino-benzamide, N-{2-[4-(2-Chloro-phenylamino)-piperidin-1-yl]-2-oxo-ethyl}-4-phenylamino-benzamide N-{2-[4-(2-Bromo-phenylamino)-piperidin-1-yl]-2-oxo-ethyl}-4-phenylamino-benzamide N-(2-{4-[Methyl-(2-trifluoromethyl-phenyl)-amino]-piperidin-1-yl}-2-oxo-ethyl)-4-phenylamino-benzamide, N-{2-[4-(2-Bromo-phenoxy)-piperidin-1-yl]-2-oxo-ethyl}-4-phenylamino-benzamide 5-Phenyl-1H-pyrazole-3-carboxylic acid {2-[4-(2-bromo-phenylamino)-piperidin-1-yl]-2-oxo-ethyl}

5-Phenyl-1H-pyrazole-3-carboxylic acid {2-[4-(2-chloro-phenylamino)-piperidin-1-yl]-2-oxo-ethyl}

5-Phenyl-1H-pyrazole-3-carboxylic acid {2-[4-(2-bromo-phenoxy)-piperidin-1-yl]-2-oxo-ethyl}

5-Phenyl-1H-pyrazole-3-carboxylic acid {2-[4-(2-chloro-phenoxy)-piperidin-1-yl]-2-oxo-ethyl}

5-Phenyl-1H-pyrazole-3-carboxylic acid {2-[4-(2-chloro-5-fluoro-phenoxy)-piperidin-1-yl]-2-oxo-ethyl}

5-Phenyl-1H-pyrazole-3-carboxylic acid {2-oxo-2-[4-(2-trifluoromethyl-phenylsulfanyl)-piperidin-1-yl]-ethyl}-amide, 5-Phenyl-1H-pyrazole-3-carboxylic acid {2-[4-(2-chloro-phenylsulfanyl)-piperidin-1-yl]-2-oxo-ethyl}-amide, 5-Phenyl-1H-pyrazole-3-carboxylic acid {2-[4-(2-nitro-phenoxy)-piperidin-1-yl]-2-oxo-ethyl}

5-Phenyl-1H-pyrazole-3-carboxylic acid {2-[4-(2-amino-phenoxy)-piperidin-1-yl]-2-oxo-ethyl}-amide, 5-Phenyl-1H-pyrazole-3-carboxylic acid {2-[4-(2,3-dimethyl-phenylamino)-piperidin-1-yl]-2-oxo-ethyl}-amide, and 5-Phenyl-1H-pyrazole-3-carboxylic acid {2-[4-(2,4-dimethyl-phenylamino)-piperidin-1-yl]-2-oxo-ethyl}-amide,
or pharmaceutically acceptable salts thereof.

In some embodiments, the compound of Formula XLV is selected from:

5-Phenyl-1H-pyrazole-3-carboxylic acid {2-[4-(2,5-dimethyl-phenylamino)-piperidin-1-yl]-2-oxo-ethyl}

5-Phenyl-1H-pyrazole-3-carboxylic acid {2-[4-(2-tert-butyl-phenylamino)-piperidin-1-yl]-2-oxo-ethyl}

5-Phenyl-1H-pyrazole-3-carboxylic acid {2-[4-(2,5-difluoro-phenoxy)-piperidin-1-yl]-2-oxo-ethyl}

5-Phenyl-1H-pyrazole-3-carboxylic acid {2-[4-(2-bromo-phenylsulfanyl)-piperidin-1-yl]-2-oxo-ethyl}

5-Phenyl-1H-pyrazole-3-carboxylic acid [2-oxo-2-(4-o-tolylamino-piperidin-1-yl)-ethyl]-amide, 5-(3-Hydroxy-phenyl)-1H-pyrazole-3-carboxylic acid {2-[4-(2-chloro-phenylamino)-piperidin-1-yl]-2-oxo-ethyl}-amide, 5-Phenyl-pyridine-2-carboxylic acid {2-oxo-2-[4-(2-chloro-phenoxy)-piperidin-1-yl]-ethyl}-amide, 5-Phenyl-pyridine-2-carboxylic acid {2-[4-(2-chloro-5-fluoro-phenoxy)-piperidin-1-yl]-2-oxo-ethyl}-amide, 5-(4-Hydroxy-phenyl)-1H-pyrazole-3-carboxylic acid {2-[4-(2-chloro-phenylamino)-piperidin-1-yl]-2-oxo-ethyl}-amide, 5-(2-Hydroxy-phenyl)-1-methyl-1H-pyrazole-3-carboxylic acid {2-[4-(2-chloro-phenylamino)-piperidin-1-yl]-2-oxo-ethyl}-amide, Synthesis of 5-(2-Hydroxy-phenyl)-isoxazole-3-carboxylic acid {2-[4-(2-chloro-phenoxy)-piperidin-1-yl]-2-oxo-ethyl}-amide, 5-(2-Hydroxy-phenyl)-isoxazole-3-carboxylic acid {2-[4-(2-chloro-phenylamino)-piperidin-1-yl]-2-oxo-ethyl}-amide, 5-(2-Hydroxy-phenyl)-1H-pyrazole-3-carboxylic acid {2-[4-(2-chloro-phenylamino)-piperidin-1-yl]-2-oxo-ethyl}-amide, 5-(2-Hydroxy-phenyl)-1H-pyrazole-3-carboxylic acid {2-[4-(2-chloro-phenoxy)-piperidin-1-yl]-2-oxo-ethyl}-amide, N-{2-[4-(2-Chloro-phenoxy)-piperidin-1-yl]-2-oxo-ethyl}-6-phenylamino-nicotinamide, N-{2-[4-(2-Chloro-phenylamino)-piperidin-1-yl]-2-oxo-ethyl}-6-phenylamino-nicotinamide, 5-Phenylamino-pyridine-2-carboxylic acid {2-[4-(2-chloro-phenylamino)-piperidin-1-yl]-2-oxo-ethyl}-amide, 5-Phenylamino-pyridine-2-carboxylic acid {2-[4-(2-chloro-phenylamino)-piperidin-1-yl]-2-oxo-ethyl}-amide, 5-Phenyl-1H-pyrazole-3-carboxylic acid {2-[4-(5-bromo-2-methoxy-phenylamino)-piperidin-1-yl]-2-oxo-ethyl}-amide, 5-Phenyl-1H-pyrazole-3-carboxylic acid {2-oxo-2-[4-(3-trifluoromethyl-phenoxy)-piperidin-1-yl]-ethyl}-amide, 5-Phenyl-1H-pyrazole-3-carboxylic acid {2-[4-(2-cyano-phenoxy)-piperidin-1-yl]-2-oxo-ethyl}-amide, 5-(2-Fluoro-phenyl)-1H-pyrazole-3-carboxylic acid {2-[4-(2-chloro-phenylamino)-piperidin-1-yl]-2-oxo-ethyl}-amide, 5-Phenyl-1H-pyrazole-3-carboxylic acid {2-[4-(2,4-difluoro-phenylamino)-piperidin-1-yl]-2-oxo-ethyl}-amide, 5-Phenyl-1H-pyrazole-3-carboxylic acid {2-[4-(5-fluoro-2-trifluoromethyl-phenylamino)-piperidin-1-yl]-2-oxo-ethyl}-amide, 5-Phenyl-1H-pyrazole-3-carboxylic acid {2-[4-(4-fluoro-2-trifluoromethyl-phenylamino)-piperidin-1-yl]-2-oxo-ethyl}-amide, 5-Phenyl-1H-pyrazole-3-carboxylic acid {2-[4-(2-acetyl-phenoxy)-piperidin-1-yl]-2-oxo-ethyl}-amide, 5-Phenyl-1H-pyrazole-3-carboxylic acid {2-[4-(5-cyano-2-methyl-phenylamino)-piperidin-1-yl]-2-oxo-ethyl}-amide, 5-Phenyl-1H-pyrazole-3-carboxylic acid {2-oxo-2-[4-(2-trifluoromethyl-benzenesulfinyl)-piperidin-1-yl]-ethyl}-amide, 5-Phenyl-1H-pyrazole-3-carboxylic acid {2-oxo-2-[4-(pyridin-4-yloxy)-piperidin-1-yl]-ethyl}-amide, and 5-Phenyl-1H-pyrazole-3-carboxylic acid {2-[4-(5-chloro-pyridin-3-yloxy)-piperidin-1-yl]-2-oxo-ethyl}-amide, or pharmaceutically acceptable salts thereof.

In some embodiments, the compound of Formula XLV is selected from:

5-Phenyl-1H-pyrazole-3-carboxylic acid {2-[4-(2-hydroxy-phenoxy)-piperidin-1-yl]-2-oxo-ethyl}-amide, 5-Phenyl-1H-pyrazole-3-carboxylic acid {2-oxo-2-[4-(2-trifluoromethyl-benzenesulfonyl)-piperidin-1-yl]-ethyl}-amide, 5-Phenyl-1H-pyrazole-3-carboxylic acid {2-[4-(6-chloro-pyridin-2-yloxy)-piperidin-1-yl]-2-oxo-ethyl}-amide, 4-Methyl-3-(1-{2-[(5-phenyl-1H-pyrazole-3-carbonyl)-amino]-acetyl}-piperidin-4-yloxy)-benzoic acid methyl ester, 5-Phenyl-1H-pyrazole-3-carboxylic acid {2-[4-(2-fluoro-5-trifluoromethyl-phenoxy)-piperidin-1-yl]-2-oxo-ethyl}-amide, 5-(2-Fluoro-phenyl)-1H-pyrazole-3-carboxylic acid {2-[4-(2-chloro-phenoxy)-piperidin-1-yl]-2-oxo-ethyl}-amide, 5-(2-Fluoro-phenyl)-1H-pyrazole-3-carboxylic acid {2-oxo-2-[4-(3-trifluoromethyl-phenoxy)-piperidin-1-yl]-ethyl}-amide, 5-(4-Trifluoromethyl-phenyl)-1H-pyrazole-3-carboxylic acid {2-[4-(2-chloro-phenoxy)-piperidin-1-yl]-2-oxo-ethyl}-amide, 5-(3-Fluoro-phenyl)-1H-pyrazole-3-carboxylic acid {2-oxo-2-[4-(3-trifluoromethyl-phenoxy)-piperidin-1-yl]-ethyl}-amide, 5-(3-Fluoro-phenyl)-1H-pyrazole-3-carboxylic acid {2-[4-(2-chloro-phenylamino)-piperidin-1-yl]-2-oxo-ethyl}-amide, 5-(2-Trifluoromethyl-phenyl)-1H-pyrazole-3-carboxylic acid {2-oxo-2-[4-(3-trifluoromethyl-phenoxy)-piperidin-1-yl]-ethyl}-amide, 5-(4-Hydroxy-phenyl)-1H-pyrazole-3-carboxylic acid {2-oxo-2-[4-(3-trifluoromethyl-phenoxy)-piperidin-1-yl]-ethyl}-amide, 5-(3-Hydroxy-phenyl)-1H-pyrazole-3-carboxylic acid {2-oxo-2-[4-(3-trifluoromethyl-phenoxy)-piperidin-1-yl]-ethyl}-amide, 5-(4-Fluoro-phenyl)-1H-pyrazole-3-carboxylic acid {2-oxo-2-[4-(3-trifluoromethyl-phenoxy)-piperidin-1-yl]-ethyl}-amide, 5-(4-Fluoro-phenyl)-1H-pyrazole-3-carboxylic acid {2-[4-(2-chloro-pyridin-3-yloxy)-piperidin-1-yl]-2-oxo-ethyl}-amide, 5-(4-Fluoro-phenyl)-1H-pyrazole-3-carboxylic acid {2-[4-(5-chloro-pyridin-3-yloxy)-piperidin-1-yl]-2-oxo-ethyl}-amide, 5-Phenyl-1H-pyrazole-3-carboxylic acid {2-[4-(3-chloro-phenoxy)-piperidin-1-yl]-2-oxo-ethyl}-amide, 3-(1-{2-[(5-Phenyl-1H-pyrazole-3-carbonyl)-amino]-acetyl}-piperidin-4-yloxy)-benzoic acid, 5-(3-Fluoro-phenyl)-1H-pyrazole-3-carboxylic acid {2-[4-(5-chloro-pyridin-3-yloxy)-piperidin-1-yl]-2-oxo-ethyl}-amide, 5-Phenyl-1H-pyrazole-3-carboxylic acid [2-oxo-2-(4-m-tolyloxy-piperidin-1-yl)-ethyl]-amide, 5-Phenyl-1H-pyrazole-3-carboxylic acid {2-[4-(2-methyl-pyridin-3-yloxy)-piperidin-1-yl]-2-oxo-ethyl}-amide, 5-Pyridin-2-yl-1H-pyrazole-3-carboxylic acid {2-[4-(2-chloro-phenoxy)-piperidin-1-yl]-2-oxo-ethyl}-amide, 3-(5-{2-oxo-2-[4-(3-trifluoromethyl-phenoxy)-piperidin-1-yl]-ethylcarbamoyl}-1H-pyrazol-3-yl)-benzoic acid, 5-Pyridin-3-yl-1H-pyrazole-3-carboxylic acid {2-oxo-2-[4-(3-trifluoromethyl-phenoxy)-piperidin-1-yl]-ethyl}-amide, 5-Pyridin-3-yl-1H-pyrazole-3-carboxylic acid {2-[4-(2-chloro-phenoxy)-piperidin-1-yl]-2-oxo-ethyl}-amide, 5-Phenyl-1H-pyrazole-3-carboxylic acid {2-[4-(4-methyl-pyridin-3-yloxy)-piperidin-1-yl]-2-oxo-ethyl}-amide, 5-Phenyl-1H-pyrazole-3-carboxylic acid {2-oxo-2-[4-(5-trifluoromethyl-pyridin-3-yloxy)-piperidin-1-yl]-ethyl}-amide, 5-(5-Chloro-thiophen-2-yl)-1H-pyrazole-3-carboxylic acid {2-oxo-2-[4-(3-trifluoromethyl-phenoxy)-piperidin-1-yl]-ethyl}-amide, 5-(5-Chloro-thiophen-2-yl)-1H-pyrazole-3-carboxylic acid {2-[4-(2,5-difluoro-phenoxy)-piperidin-1-yl]-2-oxo-ethyl}-amide, and 5-(2-Hydroxy-phenyl)-1H-pyrazole-3-carboxylic acid {2-oxo-2-[4-(3-trifluoromethyl-phenoxy)-piperidin-1-yl]-ethyl}-amide, or pharmaceutically acceptable salts thereof.

In some embodiments, the compound of Formula XLV is selected from:

5-Phenyl-1H-pyrazole-3-carboxylic acid {2-[4-(2-methanesulfonyl-phenoxy)-piperidin-1-yl]-2-oxo-ethyl}-amide, 5-(2-Fluoro-phenyl)-isoxazole-3-carboxylic acid {2-[4-(2-chloro-phenylamino)-piperidin-1-yl]-2-oxo-ethyl}-amide, 5-Phenyl-isoxazole-3-carboxylic acid {2-oxo-2-[4-(3-trifluoromethyl-phenoxy)-piperidin-1-yl]-ethyl}-amide,
5-(2-Fluoro-phenyl)-isoxazole-3-carboxylic acid {2-oxo-2-[4-(3-trifluoromethyl-phenoxy)-piperidin-1-yl]-ethyl}-amide,
5-(2-Hydroxy-phenyl)-isoxazole-3-carboxylic acid {2-oxo-2-[4-(3-trifluoromethyl-phenoxy)-piperidin-1-yl]-ethyl}-amide,
5-(3-Hydroxy-phenyl)-isoxazole-3-carboxylic acid {2-oxo-2-[4-(3-trifluoromethyl-phenoxy)-piperidin-1-yl]-ethyl}-amide,
5-(4-Hydroxy-phenyl)-isoxazole-3-carboxylic acid {2-oxo-2-[4-(3-trifluoromethyl-phenoxy)-piperidin-1-yl]-ethyl}-amide,
5-(3-Fluoro-phenyl)-isoxazole-3-carboxylic acid {2-oxo-2-[4-(3-trifluoromethyl-phenoxy)-piperidin-1-yl]-ethyl}-amide,
5-(4-Fluoro-phenyl)-isoxazole-3-carboxylic acid {2-oxo-2-[4-(3-trifluoromethyl-phenoxy)-piperidin-1-yl]-ethyl}-amide,
5-(4-Fluoro-phenyl)-isoxazole-3-carboxylic acid {2-[4-(5-chloro-pyridin-3-yloxy)-piperidin-1-yl]-2-oxo-ethyl}-amide,
5-(4-Fluoro-phenyl)-isoxazole-3-carboxylic acid {2-[4-(2-chloro-pyridin-3-yloxy)-piperidin-1-yl]-2-oxo-ethyl}-amide,
5-(3-Fluoro-phenyl)-isoxazole-3-carboxylic acid {2-[4-(5-chloro-pyridin-3-yloxy)-piperidin-1-yl]-2-oxo-ethyl}-amide,
1-Phenyl-1H-pyrazole-4-carboxylic acid {2-[4-(2-chloro-phenoxy)-piperidin-1-yl]-2-oxo-ethyl}-amide,
2-[(Biphenyl-4-ylmethyl)-amino]-1-[4-(2-chloro-phenoxy)-piperidin-1-yl]-ethanone,
N-{2-[4-(2-Chloro-phenoxy)-piperidin-1-yl]-2-oxo-ethyl}-4-[1,3,4]oxadiazol-2-yl-benzamide,
4-Phenyl-pyrazole-1-carboxylic acid {2-[4-(2-chloro-phenoxy)-piperidin-1-yl]-2-oxo-ethyl}-amide,
1-Phenyl-1H-[1,2,3]triazole-4-carboxylic acid {2-[4-(2-chloro-phenoxy)-piperidin-1-yl]-2-oxo-ethyl}-amide,
1-Phenyl-1H-[1,2,3]triazole-4-carboxylic acid {2-[4-(2-chloro-phenoxy)-piperidin-1-yl]-2-oxo-ethyl}-amide,
1-(3-Fluoro-phenyl)-1H-[1,2,3]triazole-4-carboxylic acid {2-oxo-2-[4-(3-trifluoromethyl-phenoxy)-piperidin-1-yl]-ethyl}-amide,
1-(3-Fluoro-phenyl)-1H-[1,2,3]triazole-4-carboxylic acid {2-[4-(2-chloro-5-fluoro-phenoxy)-piperidin-1-yl]-2-oxo-ethyl}-amide
1-m-Tolyl-1H-[1,2,3]triazole-4-carboxylic acid {2-oxo-2-[4-(3-trifluoromethyl-phenoxy)-piperidin-1-yl]-ethyl}-amide,
1-m-Tolyl-1H-[1,2,3]triazole-4-carboxylic acid {2-[4-(2-chloro-5-fluoro-phenoxy)-piperidin-1-yl]-2-oxo-ethyl}-amide,
1-(2-Cyano-phenyl)-1H-[1,2,3]triazole-4-carboxylic acid {2-oxo-2-[4-(3-trifluoromethyl-phenoxy)-piperidin-1-yl]-ethyl}-amide,
1-(2-Cyano-phenyl)-1H-[1,2,3]triazole-4-carboxylic acid {2-oxo-2-[4-(3-trifluoromethyl-phenoxy)-piperidin-1-yl]-ethyl}-amide,
1-o-Tolyl-1H-[1,2,3]triazole-4-carboxylic acid {2-oxo-2-[4-(3-trifluoromethyl-phenoxy)-piperidin-1-yl]-ethyl}-amide,
1-Pyridin-3-yl-1H-[1,2,3]triazole-4-carboxylic acid {2-[4-(2-chloro-phenoxy)-piperidin-1-yl]-2-oxo-ethyl}-amide,
1-Cyclopentyl-1H-[1,2,3]triazole-4-carboxylic acid {2-[4-(5-chloro-pyridin-3-yloxy)-piperidin-1-yl]-2-oxo-ethyl}-amide,
1-(5-Fluoro-pyridin-3-yl)-1H-[1,2,3]triazole-4-carboxylic acid {2-[4-(2-chloro-phenoxy)-piperidin-1-yl]-2-oxo-ethyl}-amide,
N-{2-[4-(2-Chloro-phenoxy)-piperidin-1-yl]-2-oxo-ethyl}-4-(5-methyl-[1,3,4]oxadiazol-2-yl)-benzamide, and
3'-Dimethylamino-biphenyl-4-carboxylic acid {2-[4-(2-chloro-phenoxy)-piperidin-1-yl]-2-oxo-ethyl}-amide,
or pharmaceutically acceptable salts thereof.

In some embodiments, the compound of Formula XLV is selected from:
N-{2-Oxo-2-[4-(3-trifluoromethyl-phenoxy)-piperidin-1-yl]-ethyl}-4-(pyrrolidine-1-carbonyl)-benzamide,
9H-Carbazole-3-carboxylic acid {2-oxo-2-[4-(3-trifluoromethyl-phenoxy)-piperidin-1-yl]-ethyl}-amide,
1-Phenyl-1H-imidazole-4-carboxylic acid {2-oxo-2-[4-(3-trifluoromethyl-phenoxy)-piperidin-1-yl]-ethyl}-amide,
1-Phenyl-1H-imidazole-4-carboxylic acid {2-[4-(2-chloro-5-fluoro-phenoxy)-piperidin-1-yl]-2-oxo-ethyl}-amide,
5-Phenyl-1H-pyrazole-3-carboxylic acid {2-[4-(2-formyl-phenoxy)-piperidin-1-yl]-2-oxo-ethyl}-amide,
2-(1-{2-[(5-Phenyl-1H-pyrazole-3-carbonyl)-amino]-acetyl}-piperidin-4-yloxy)-benzoic acid,
5-Phenyl-1H-pyrazole-3-carboxylic acid {2-[4-(2-hydroxymethyl-phenoxy)-piperidin-1-yl]-2-oxo-ethyl}-amide,
5-Phenyl-1H-pyrazole-3-carboxylic acid {2-oxo-2-[4-(3,4,5-trifluoro-phenoxy)-piperidin-1-yl]-ethyl}-amide,
5-Phenyl-1H-pyrazole-3-carboxylic acid (2-{4-[2-(hydroxyimino-methyl)-phenoxy]-piperidin-1-yl}-2-oxo-ethyl)-amide,
5-Phenyl-1H-pyrazole-3-carboxylic acid {2-oxo-2-[4-(2-trifluoromethyl-phenoxy)-piperidin-1-yl]-ethyl}-amide,
5-Phenyl-1H-pyrazole-3-carboxylic acid {2-[4-(3-cyano-phenoxy)-piperidin-1-yl]-2-oxo-ethyl}-amide,
5-Phenyl-1H-pyrazole-3-carboxylic acid (2-{4-[2-(methoxyimino-methyl)-phenoxy]-piperidin-1-yl}-2-oxo-ethyl)-amide,
5-Phenyl-1H-pyrazole-3-carboxylic acid {2-[4-(2-methylcarbamoyl-phenoxy)-piperidin-1-yl]-2-oxo-ethyl}-amide,
5-Phenyl-1H-pyrazole-3-carboxylic acid {2-[4-(2-carbamoyl-phenoxy)-piperidin-1-yl]-2-oxo-ethyl}-amide,
5-(2-Trifluoromethyl-phenyl)-1H-pyrazole-3-carboxylic acid {2-[4-(2-chloro-phenylamino)-piperidin-1-yl]-2-oxo-ethyl}-amide,
5-Phenyl-1H-pyrazole-3-carboxylic acid {2-[4-(3-cyano-phenylamino)-piperidin-1-yl]-2-oxo-ethyl}-amide,
5-Phenyl-1H-pyrazole-3-carboxylic acid {2-[4-(adamantan-2-ylamino)-piperidin-1-yl]-2-oxo-ethyl}-amide,
5-(2-Methoxy-phenyl)-1H-pyrazole-3-carboxylic acid {2-[4-(2-chloro-phenylamino)-piperidin-1-yl]-2-oxo-ethyl}-amide,
1-Pyrrolidin-3-yl-1H-[1,2,3]triazole-4-carboxylic acid {2-oxo-2-[4-(3-trifluoromethyl-phenoxy)-piperidin-1-yl]-ethyl}-amide,
1-(1-Methyl-pyrrolidin-3-yl)-1H-[1,2,3]triazole-4-carboxylic acid {2-oxo-2-[4-(3-trifluoromethyl-phenoxy)-piperidin-1-yl]-ethyl}-amide,
1-(3,5-Difluoro-phenyl)-1H-[1,2,3]triazole-4-carboxylic acid {2-[4-(2-chloro-phenoxy)-piperidin-1-yl]-2-oxo-ethyl}-amide,
1-(3,5-Difluoro-phenyl)-1H-[1,2,3]triazole-4-carboxylic acid {2-[4-(5-chloro-pyridin-3-yloxy)-piperidin-1-yl]-2-oxo-ethyl}-amide,
1-Piperidin-4-yl-1H-[1,2,3]triazole-4-carboxylic acid {2-oxo-2-[4-(3-trifluoromethyl-phenoxy)-piperidin-1-yl]-ethyl}-amide hydrochloride, 1-(1-Methyl-piperidin-4-yl)-1H-[1,2,3]triazole-4-carboxylic acid {2-oxo-2-[4-(3-trifluoromethyl-phenoxy)-piperidin-1-yl]-ethyl}-amide, 1-Pyridin-3-yl-1H-[1,2,3]triazole-4-carboxylic acid {2-[4-(2,5-difluoro-phenoxy)-piperidin-1-yl]-2-oxo-ethyl}-amide, 1-Pyridin-3-yl-1H-[1,2,3]triazole-4-carboxylic acid {2-[4-(5-cyano-2-methyl-phenoxy)-piperidin-1-yl]-2-oxo-ethyl}-amide, 5-Phenyl-1H-pyrazole-3-carboxylic acid {2-oxo-2-[3-(3-trifluoromethyl-phenoxy)-pyrrolidin-1-yl]-ethyl}-amide, 4-(2-Oxo-pyrrolidin-1-yl)-N-{2-oxo-2-[4-(3-trifluoromethyl-phenoxy)-piperidin-1-yl]-ethyl}-benzamide, 1-Cyclopropyl-1H-[1,2,3]triazole-4-carboxylic acid {2-oxo-2-[4-(3-trifluoromethyl-phenoxy)-piperidin-1-yl]-ethyl}-amide, and 1-Morpholin-4-yl-1H-[1,2,3]triazole-4-carboxylic acid {2-oxo-2-[4-(3-trifluoromethyl-phenoxy)-piperidin-1-yl]-ethyl}-amide, or pharmaceutically acceptable salts thereof.

In some embodiments, the compound of Formula XLV is selected from:

1-Phenyl-1H-[1,2,3]triazole-4-carboxylic acid {2-[4-(3-cyano-phenoxy)-piperidin-1-yl]-2-oxo-ethyl}-amide, 1-Pyridin-3-yl-1H-[1,2,3]triazole-4-carboxylic acid {2-[3-(2,5-difluoro-phenoxy)-pyrrolidin-1-yl]-2-oxo-ethyl}-amide, 5-Phenyl-1H-pyrazole-3-carboxylic acid {2-oxo-2-[3-(3-trifluoromethyl-phenoxy)-azetidin-1-yl]-ethyl}-amide, 5-Pyridin-3-yl-1H-pyrazole-3-carboxylic acid {2-oxo-2-[3-(3-trifluoromethyl-phenoxy)-azetidin-1-yl]-ethyl}-amide, 5-Phenyl-1H-pyrazole-3-carboxylic acid {2-[3-(2,5-difluoro-phenoxy)-pyrrolidin-1-yl]-2-oxo-ethyl}-amide, 1-Phenyl-1H-imidazole-4-carboxylic acid {2-[4-(2,5-difluoro-phenoxy)-piperidin-1-yl]-2-oxo-ethyl}-amide, 1-Phenyl-1H-imidazole-4-carboxylic acid {2-[4-(2-chloro-phenoxy)-piperidin-1-yl]-2-oxo-ethyl}-amide, 1-Phenyl-1H-imidazole-4-carboxylic acid {2-[4-(5-cyano-2-methyl-phenoxy)-piperidin-1-yl]-2-oxo-ethyl}-amide, 1-Phenyl-1H-imidazole-4-carboxylic acid {2-[3-(3-fluoro-5-trifluoromethyl-phenoxy)-azetidin-1-yl]-2-oxo-ethyl}-amide, 1-Phenyl-1H-imidazole-4-carboxylic acid {2-[4-(3-fluoro-5-trifluoromethyl-phenoxy)-piperidin-1-yl]-2-oxo-ethyl}-amide, 1-Phenyl-1H-imidazole-4-carboxylic acid {2-[4-(4-fluoro-3-trifluoromethyl-phenoxy)-piperidin-1-yl]-2-oxo-ethyl}-amide, 1-Phenyl-1H-imidazole-4-carboxylic acid {2-[3-(2-chloro-phenoxy)-azetidin-1-yl]-2-oxo-ethyl}-amide, 1-Phenyl-1H-imidazole-4-carboxylic acid {2-[3-(5-cyano-2-methyl-phenoxy)-azetidin-1-yl]-2-oxo-ethyl}-amide, 1-Phenyl-1H-imidazole-4-carboxylic acid {2-[3-(2-chloro-phenoxy)-pyrrolidin-1-yl]-2-oxo-ethyl}-amide, 5-Phenyl-isoxazole-3-carboxylic acid {2-[3-(2,5-difluoro-phenoxy)-pyrrolidin-1-yl]-2-oxo-ethyl}-amide, 2-Phenyl-4H-thieno[3,2-b]pyrrole-5-carboxylic acid {2-[4-(2-chloro-5-fluoro-phenoxy)-piperidin-1-yl]-2-oxo-ethyl}-amide, 6-Pyrazol-1-yl-imidazo[1,2-a]pyridine-2-carboxylic acid {2-[4-(2-chloro-phenoxy)-piperidin-1-yl]-2-oxo-ethyl}-amide, 1-Pyridin-3-yl-1H-[1,2,3]triazole-4-carboxylic acid {2-[4-(3-cyano-phenoxy)-piperidin-1-yl]-2-oxo-ethyl}-amide, 1-Pyridin-3-yl-1H-[1,2,3]triazole-4-carboxylic acid {2-[3-(3-fluoro-5-trifluoromethyl-phenoxy)-azetidin-1-yl]-2-oxo-ethyl}-amide, 1-Pyridin-3-yl-1H-[1,2,3]triazole-4-carboxylic acid {2-[4-(3-fluoro-5-trifluoromethyl-phenoxy)-piperidin-1-yl]-2-oxo-ethyl}-amide, 1-Pyridin-3-yl-1H-[1,2,3]triazole-4-carboxylic acid {2-[3-(2-chloro-phenoxy)-pyrrolidin-1-yl]-2-oxo-ethyl}-amide, 1-Pyridin-3-yl-1H-[1,2,3]triazole-4-carboxylic acid {2-[4-(4-fluoro-3-trifluoromethyl-phenoxy)-piperidin-1-yl]-2-oxo-ethyl}-amide, 1-Pyridin-3-yl-1H-[1,2,3]triazole-4-carboxylic acid {2-[3-(2-chloro-phenoxy)-azetidin-1-yl]-2-oxo-ethyl}-amide, 1-Pyridin-3-yl-1H-[1,2,3]triazole-4-carboxylic acid {2-[3-(5-cyano-2-methyl-phenoxy)-azetidin-1-yl]-2-oxo-ethyl}-amide, 1-Pyridin-3-yl-1H-[1,2,3]triazole-4-carboxylic acid {2-oxo-2-[4-(2-trifluoromethyl-phenoxy)-piperidin-1-yl]-ethyl}-amide, 5-Phenyl-1H-pyrazole-3-carboxylic acid {2-[3-(3-fluoro-5-trifluoromethyl-phenoxy)-azetidin-1-yl]-2-oxo-ethyl}-amide, 5-Phenyl-1H-pyrazole-3-carboxylic acid {2-[4-(3-fluoro-5-trifluoromethyl-phenoxy)-piperidin-1-yl]-2-oxo-ethyl}-amide, 5-Phenyl-1H-pyrazole-3-carboxylic acid {2-[4-(4-fluoro-3-trifluoromethyl-phenoxy)-piperidin-1-yl]-2-oxo-ethyl}-amide, 5-Phenyl-1H-pyrazole-3-carboxylic acid {2-[3-(2-chloro-phenoxy)-azetidin-1-yl]-2-oxo-ethyl}-amide, and 5-Phenyl-1H-pyrazole-3-carboxylic acid {2-[3-(5-cyano-2-methyl-phenoxy)-azetidin-1-yl]-2-oxo-ethyl}-amide, or pharmaceutically acceptable salts thereof.

In some embodiments, the compound of Formula XLV has the structure:

wherein $R^1$ is heteroaryl;

$R^2$ is aryl or heteroaryl;

$R^3$ and $R^4$ are each independently hydrogen, halogen or alkyl; or $R^3$ and $R^4$, together with the carbon atom to which they are attached, form a cycloalkyl group;

$R^5$ is hydrogen or alkyl;

m and n are, independently, 1 or 2;

X is —O—, —$NR^6$—, —S—, —S(O)— or —S(O)$_2$— where $R^6$ is hydrogen or alkyl;

wherein, when present, an aryl or heteroaryl group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;

or pharmaceutically acceptable salts or enantiomer or diastereomer thereof.

In some embodiments, the compound of Formula XLV has the structure:

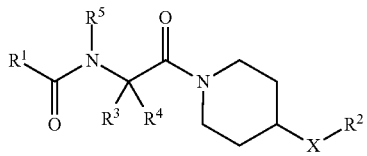

wherein
R¹ is aryl or heteroaryl;
R² is aryl or heteroaryl;
R³ and R⁴ are each independently hydrogen, halogen or alkyl; or
R³ and R⁴, together with the carbon atom to which they are attached, form a cycloalkyl group;
R⁵ is hydrogen or alkyl;
X is —O—, —NR⁶—, —S—, —S(O)— or —S(O)₂— where R⁶ is hydrogen or alkyl;
wherein, when present, an aryl or heteroaryl group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts thereof;
with the proviso that said compound is not
4-[[(2R)-2,3-dihydro-2-methyl-6-nitroimidazo[2,1-b]oxazol-2-yl]methoxy]-N-[2-oxo-2-[4-[4-(trifluoromethoxy)phenoxy]-1-piperidinyl]ethyl]-benzamide,
N-[2-[4-[[4-amino-5-(2,6-difluorobenzoyl)-2-thiazolyl]amino]-1-piperidinyl]-2-oxoethyl]-M-methyl-benzamide,
4-amino-N-[2-[4-[[4-amino-5-(2,6-difluorobenzoyl)-2-thiazolyl]amino]-1-piperidinyl]-2-oxoethyl]-benzamide,
or a pharmaceutically acceptable salt thereof.

In some embodiments, the compound of Formula XLV has the structure:

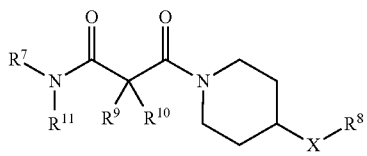

wherein
R⁷ is aryl or heteroaryl;
R⁸ is aryl or heteroaryl;
R⁹ and R¹⁰ are each independently hydrogen, halogen or alkyl; or
R⁹ and R¹⁰, together with the carbon atom to which they are attached, form a cycloalkyl group;
R¹¹ is hydrogen or alkyl;
X is —O—, —NR¹²—, —S—, —S(O)— or —S(O)₂— where R¹² is hydrogen or alkyl;
wherein, when present, an aryl or heteroaryl group may optionally be substituted by one or more halogen, hydroxy, cyano, nitro, amino, alkylamino, dialkylamino, arylamino, diarylamino, amido, alkylamido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof.

In some embodiments, of the compound of Formula XLV is selected from:
N-Biphenyl-4-yl-3-[4-(2-bromo-phenoxy)-piperidin-1-yl]-3-oxo-propionamide,
N-Biphenyl-4-yl-3-[4-(2-chloro-5-fluoro-phenoxy)-piperidin-1-yl]-3-oxo-propionamide,
N-Biphenyl-4-yl-3-[4-(2-bromo-phenylamino)-piperidin-1-yl]-3-oxo-propionamide,
N-Biphenyl-4-yl-3-[4-(2-bromo-phenylsulfanyl)-piperidin-1-yl]-3-oxo-propionamide,
N-Biphenyl-4-yl-3-oxo-3-(4-o-tolylamino-piperidin-1-yl)-propionamide,
N-Biphenyl-4-yl-3-[4-(2-nitro-phenoxy)-piperidin-1-yl]-3-oxo-propionamide,
3-[4-(2-Amino-phenoxy)-piperidin-1-yl]-N-biphenyl-4-yl-3-oxo-propionamide,
N-Biphenyl-4-yl-3-[4-(2,3-dimethyl-phenylamino)-piperidin-1-yl]-3-oxo-propionamide,
N-Biphenyl-4-yl-3-[4-(2,4-dimethyl-phenylamino)-piperidin-1-yl]-3-oxo-propionamide,
N-Biphenyl-4-yl-3-[4-(2,5-dimethyl-phenylamino)-piperidin-1-yl]-3-oxo-propionamide,
N-Biphenyl-4-yl-3-[4-(2-tert-butyl-phenylamino)-piperidin-1-yl]-3-oxo-propionamide,
N-Biphenyl-4-yl-3-[4-(2,5-difluoro-phenoxy)-piperidin-1-yl]-3-oxo-propionamide,
3-[4-(2-Chloro-5-fluoro-phenoxy)-piperidin-1-yl]-3-oxo-N-(6-phenyl-pyridin-3-yl)-propionamide,
3-[4-(2-Chloro-5-fluoro-phenoxy)-piperidin-1-yl]-3-oxo-N-(5-phenyl-pyridin-2-yl)-propionamide,
3-[4-(2-Chloro-phenoxy)-piperidin-1-yl]-3-oxo-N-(6-phenyl-pyridin-3-yl)-propionamide,
3-[4-(2-Chloro-phenylamino)-piperidin-1-yl]-3-oxo-N-(6-phenyl-pyridin-3-yl)-propionamide,
3-[4-(2-Bromo-phenylamino)-piperidin-1-yl]-3-oxo-N-(6-phenyl-pyridin-3-yl)-propionamide,
3-Oxo-N-(6-phenyl-pyridin-3-yl)-3-[4-(2-trifluoromethyl-phenylamino)-piperidin-1-yl]-propionamide,
3-[4-(2-Chloro-phenylsulfanyl)-piperidin-1-yl]-3-oxo-N-(6-phenyl-pyridin-3-yl)-propionamide,
3-[4-(2-Bromo-phenylsulfanyl)-piperidin-1-yl]-3-oxo-N-(6-phenyl-pyridin-3-yl)-propionamide,
3-Oxo-N-(6-phenyl-pyridin-3-yl)-3-[4-(2-trifluoromethyl-phenylsulfanyl)-piperidin-1-yl]-propionamide,
3-Oxo-N-(6-phenyl-pyridin-3-yl)-3-[4-(2-trifluoromethyl-phenoxy)-piperidin-1-yl]-propionamide,
3-Oxo-N-(6-phenyl-pyridin-3-yl)-3-(4-o-tolylamino-piperidin-1-yl)-propionamide,
3-[4-(2-Chloro-phenoxy)-piperidin-1-yl]-3-oxo-N-(3-phenyl-[1,2,4]thiadiazol-5-yl)-propionamide,
3-[4-(2-Chloro-phenoxy)-piperidin-1-yl]-N-(4-[1,2,4]oxadiazol-3-yl-phenyl)-3-oxo-propionamide,
3-[4-(2-Chloro-phenoxy)-piperidin-1-yl]-3-oxo-N-(5-phenyl-thiazol-2-yl)-propionamide,
3-[4-(2-Chloro-phenylamino)-piperidin-1-yl]-3-oxo-N-(5-phenyl-thiazol-2-yl)-propionamide, 1-[4-(2-Chloro-phenoxy)-piperidine-1-carbonyl]-cyclopropane carboxylic acid biphenyl-4-ylamide,
N-Biphenyl-4-yl-3-oxo-3-[4-(3,4,5-trifluoro-phenoxy)-piperidin-1-yl]-propionamide, and
N-Biphenyl-4-yl-3-[4-(3-cyano-phenoxy)-piperidin-1-yl]-3-oxo-propionamide, and pharmaceutically acceptable salts thereof.

In some embodiments of the compound of Formula XLV, the compound is:
Biphenyl-4-carboxylic acid (2-{4-[methyl-(2-trifluoromethyl-phenyl)-amino]-piperidin-1-yl}-2-oxo-ethyl)-amide or a pharmaceutically acceptable salt thereof.

In some embodiments of the compound of Formula XLV, the compound is:
5-Phenyl-isoxazole-3-carboxylic acid {2-[4-(2-chloro-phenylamino)-piperidin-1-yl]-2-oxo-ethyl}-amide or a pharmaceutically acceptable salt thereof.

In some embodiments of the compound of Formula XLV, the compound is:
5-Phenyl-1H-pyrazole-3-carboxylic acid {2-oxo-2-[4-(3-trifluoromethyl-phenoxy)-piperidin-1-yl]-ethyl}-amide or a pharmaceutically acceptable salt thereof.

In some embodiments of the compound of Formula XLV, the compound is:
1-Pyridin-3-yl-1H-[1,2,3]triazole-4-carboxylic acid {2-[4-(5-cyano-2-methyl-phenoxy)-piperidin-1-yl]-2-oxo-ethyl} or a pharmaceutically acceptable salt thereof.

In some embodiments of the compound of Formula XLV, the compound is:
1-Phenyl-1H-imidazole-4-carboxylic acid {2-[4-(2,5-difluoro-phenoxy)-piperidin-1-yl]-2-oxo-ethyl}-amide or a pharmaceutically acceptable salt thereof.

Compounds of Formula (XLV) may be synthesized by methods known in the art, e.g., those described in U.S. Pat. No. 8,129,376 B2. In some embodiments, the SCD inhibitor is a compound disclosed in U.S. Pat. No. 8,129,376 B2, the compounds of which are herein incorporated by reference.

In some embodiments of any of the foregoing methods, the SCD inhibitor is a compound of Formula XLVI,

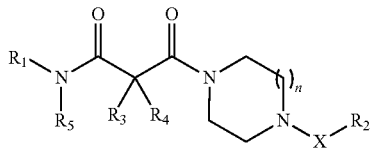

wherein
n is 1 or 2;
$R^1$ is aryl, heterocycloalkane, heteroaryl or heterocycle;
$R^2$ is aryl, heteroaryl or heterocycle;
$R^3$ and $R^4$ are each independently hydrogen, halogen or alkyl; or
$R^3$ and $R^4$, together with the carbon atom to which they are attached, form a cycloalkyl group;
$R^5$ is hydrogen or alkyl;
wherein when n is 1, then X is —C(O)—, —S(O)$_2$—, or —S(O)—, and when n is 2, then X is —C(O)—, —S(O)$_2$—, —S(O)— or —CR$^6$R$^7$— where $R^6$ and $R^7$ are each independently hydrogen or alkyl;
wherein, when present, an aryl, heteroaryl or heterocycle group may optionally be substituted by one or more halogen, hydroxy, cyano, nitro, amino, alkylamino, dialkylamino, arylamino, diarylamino, amido, alkylamido, —O—C(O)—NH—, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkythio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;
and pharmaceutically acceptable salts, solvates, hydrates, or solvates of pharmaceutically acceptable salts thereof.

Compounds of Formula (XLVI) may be synthesized by methods known in the art, e.g., those described in International Patent Publication No. WO2009/117659. In some embodiments, the SCD inhibitor is a compound disclosed in International Patent Publication No. WO2009/117659, the compounds of which are herein incorporated by reference.

In some embodiments of any of the foregoing methods, the SCD inhibitor is a compound of Formula XLVII,

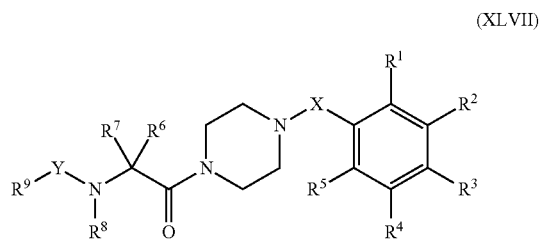

(XLVII)

wherein
$R^1$ is halogenated alkyl (e.g., CF$_3$);
$R^2$, $R^3$, $R^4$ and $R^5$ are each independently hydrogen, halogen, hydroxy, cyano, nitro, amino, alkylamino, dialkylamino, carboxyl, alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, cycloalkyloxy, cycloalkylalkyloxy, arylalkyloxy, heteroarylalkyloxy, alkythio, arylthio, alkylsulfinyl, alkylsulfonyl, alkoxycarbonyl, aryloxycarbonyl or heteroaryloxycarbonyl;
$R^6$ and $R^7$ are each independently hydrogen, hydroxyl, cyano, alkyl, alkenyl, alkynyl, aryl, arylalkyl, heteroaryl, heteroarylalkyl, heterocycle or heterocyclealkyl;
$R^8$ is hydrogen, alkyl, alkenyl, alkynyl, aryl, arylalkyl, heteroaryl, heteroarylalkyl, heterocycle or heterocyclealkyl;
$R^9$ is hydrogen, alkyl, alkenyl, alkynyl, aryl, arylalkyl, heteroaryl, heteroarylalkyl, heterocycle or heterocyclealkyl;
X is —C(O)—, —C(O)—O—, —S(O)$_2$—, —S(O)—, or —C(O)NR$^{10}$—, where R$^{10}$ is hydrogen, alkyl, alkenyl, alkynyl, cycloalkyl, cycloalkylalkyl, aryl, arylalkyl, heteroaryl, heteroarylalkyl, heterocycle or heterocyclealkyl;
Y is —C(O)—, —S(O)$_2$—, or —S(O)—;
wherein, when present, any aryl, heteroaryl, or heterocycle group may optionally be substituted by halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkythio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl, arylalkyl-C(O)—, —C(O)O-alkyl, benzodioxol, benzo[d]oxazol-2(3H)-one, cycloalkyl-NH—C(O)—, and combinations thereof;

or pharmaceutically acceptable salts or solvates (e.g., hydrates) or N-oxides thereof, or solvates of pharmaceutically acceptable salts thereof, or pharmaceutically acceptable salts or solvates of N-oxides thereof; or prodrugs thereof;

with the proviso that said compound is not 4-chloro-N-[2-oxo-2-[4-[[2-(trifluoromethyl)phenyl]sulfonyl]-1-piperazinyl]ethyl]benzamide or a pharmaceutically acceptable salt thereof.

Compounds of Formula (XLVII) may be synthesized by methods known in the art, e.g., those described in International Patent Publication No. WO2008/157844. In some embodiments, the SCD inhibitor is a compound disclosed in International Patent Publication No. WO2008/157844, the compounds of which are herein incorporated by reference.

In some embodiments of any of the foregoing methods, the SCD inhibitor is a compound of Formula XLVIII,

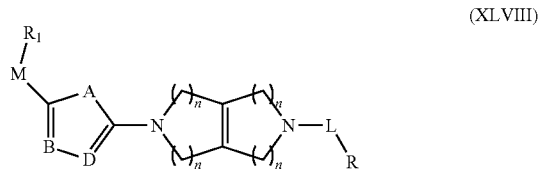

(XLVIII)

R is hydrogen, $(C_1-C_{16})$-alkyl, $(C_1-C_5)$-alkyloxy, $(C_1-C_5)$-alkylthio, $(C_1-C_5)$-alkylamino, di-$(C_2-C_8)$-alkylamino, $(C_0-C_4)$-alkylene-$(C_6-C_{10})$-aryl, $(C_0-C_4)$-alkylene-$(C_5-C_{12})$-heteroaryl, $(C_0-C_4)$-alkylene-$(C_3-C_{12})$-heterocyclyl, $(C_0-C_4)$-alkylene-$(C_3-C_{12})$-cycloalkyl, a bicyclic-$(C_8-C_{14})$ ring system, where aryl, heteroaryl, heterocyclyl, cycloalkyl or the bicyclic-$(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;

$R^1$ is hydrogen, $(C_1-C_{10})$-alkyl, $-(C_6-C_{10})$-aryl, $-(C_5-C_{12})$-heteroaryl, $-(C_3-C_{12})$-heterocyclyl, or $-(C_3-C_{12})$-cycloalkyl; where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, $-(C_6-C_{10})$-aryl, $-(C_5-C_{12})$-heteroaryl, $-(C_3-C_{12})$-heterocyclyl or $-(C_3-C_{12})$-cycloalkyl, where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, $(C_1-C_6)$-alkyl-mercapto, amino, $(C_1-C_6)$-alkylamino, or di-$(C_2-C_{12})$-alkylamino;

$R^2$ is hydrogen, $(C_1-C_{16})$-alkyl or $(C_0-C_4)$-alkylene-$(C_6-C_{10})$-aryl;

$R^3$ is hydrogen, $(C_1-C_6)$-alkyl, $(C_1-C_3)$-alkyloxy, hydroxyl, $(C_1-C_6)$-alkyl-mercapto, amino, $(C_1-C_6)$-alkylamino, di-$(C_2-C_{12})$-alkylamino, cyano, $(C_1-C_6)$-alkylcarbonyl, halogen, trifluoromethyl, trifluoromethyloxy, $(C_1-C_6)$-alkylsulfonyl, or aminosulfonyl;

A is O, S, N($R^2$), C($R^3$) or C($R^3$)=C($R^3$);

B is C($R^3$) or N;

D is C($R^3$) or N; where at least one of the members A, B or D must be nitrogen;

n is in each case independently 1 or 2;

L is a bond, —C(=O)—, —C(=S)—, —C(=O)—N($R^2$)—, —C(=O)—O—, —S(O)$_{0-2}$—, —S(O)$_{0-2}$—N($R^2$)—, a mono- or bicyclic ring system in which one or more ring members may be N($R^3$), O, S or —C(=O)—;

M is —O— or —O—CH$_2$—;

and physiologically compatible salts thereof.

In some embodiments, the compound of Formula XLVIII has the structure:

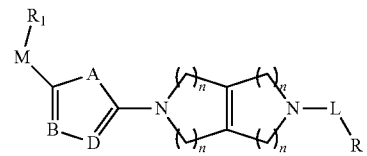

in which

R is hydrogen, $(C_1-C_{16})$-alkyl, $(C_1-C_5)$-alkyloxy, $(C_1-C_5)$-alkylthio, $(C_1-C_5)$-alkylamino, di-$(C_2-C_8)$-alkylamino, $(C_0-C_4)$-alkylene-$(C_6-C_{10})$-aryl, $(C_0-C_4)$-alkylene-$(C_1-C_{12})$-heteroaryl, $(C_0-C_4)$-alkylene-$(C_3-C_{12})$-heterocyclyl, $(C_0-C_4)$-alkylene-$(C_3-C_{12})$-cycloalkyl, a bicyclic-$(C_8-C_{14})$ ring system, where aryl, heteroaryl, heterocyclyl, cycloalkyl or the bicyclic-$(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;

$R^1$ is hydrogen, $(C_1-C_{10})$-alkyl, $-(C_6-C_{10})$-aryl, $-(C_5-C_{12})$-heteroaryl, $-(C_3-C_{12})$-heterocyclyl, or $-(C_3-C_{12})$-cycloalkyl;

where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, $-(C_6-C_{10})$-aryl, $-(C_5-C_{12})$-heteroaryl, $-(C_3-C_{12})$-heterocyclyl or $-(C_3-C_{12})$-cycloalkyl, where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, or di-$(C_2-C_{12})$-alkylamino;

$R^2$ is hydrogen, $(C_1-C_{16})$-alkyl, or $(C_0-C_4)$-alkylene-$(C_6-C_{10})$-aryl;

$R^3$ is hydrogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, cyano, $(C_1-C_6)$-alkylcarbonyl, halogen, trifluoromethyl, trifluoromethyloxy, $(C_1-C_6)$-alkylsulfonyl, or aminosulfonyl;

A is O, S, N($R^2$), C($R^3$), or C($R^3$)=C($R^3$);

B is C($R^3$) or N;

D is C($R^3$) or N;

where at least one of the members A, B or D must be nitrogen;

n is in each case independently 1 or 2;

L is a bond, —C(=O)—, —C(=S)—, —C(=O)—N($R^2$)—, —S(O)$_{0-2}$—, —S(O)$_{0-2}$—N($R^2$)—, a mono- or bicyclic ring system in which one or more ring members may be N($R^3$), O, S or —C(=O)—;

M is —O— or —O—CH$_2$—;

and physiologically compatible salts thereof.

In some embodiments, the compound of Formula XLVIII has the structure:

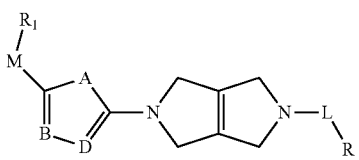

wherein

R is hydrogen, $(C_1-C_{16})$-alkyl, $(C_1-C_5)$-alkyloxy, $(C_1-C_5)$-alkylthio, $(C_1-C_5)$-alkylamino, di-$(C_2-C_8)$-alkylamino, $(C_0-C_4)$-alkylene-$(C_6-C_{10})$-aryl, $(C_0-C_4)$-alkylene-$(C_1-C_{12})$-heteroaryl, $(C_0-C_4)$-alkylene-$(C_3-C_{12})$-heterocyclyl, $(C_0-C_4)$-alkylene-$(C_3-C_{12})$-cycloalkyl, a bicyclic-$(C_8-C_{14})$ ring system, where aryl, heteroaryl, heterocyclyl, cycloalkyl or the bicyclic-$(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;

$R^1$ is $(C_1-C_{10})$-alkyl, —$(C_6-C_{10})$-aryl; —$(C_5-C_{12})$-heteroaryl, —$(C_3-C_{12})$-heterocyclyl, —$(C_3-C_{12})$-cycloalkyl, where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, —$(C_6-C_{10})$-aryl, —$(C_5-C_{12})$-heteroaryl, —$(C_3-C_{12})$-heterocyclyl or —$(C_3-C_{12})$-cycloalkyl, where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, or di-$(C_2-C_{12})$-alkylamino;

$R^2$ is hydrogen, $(C_1-C_{16})$-alkyl, or $(C_0-C_4)$-alkylene-$(C_6-C_{10})$-aryl;

$R^3$ is hydrogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, cyano, $(C_1-C_6)$-alkylcarbonyl, halogen, trifluoromethyl, trifluoromethyloxy, $(C_1-C_6)$-alkylsulfonyl, or aminosulfonyl;

A is O, S, N($R^2$), C($R^3$), or C($R^3$)=C($R^3$);

B is C($R^3$), or N;

D is C($R^3$), or N;

where at least one of the members A, B or D must be nitrogen;

L is a bond, —C(=O)—, —C(=S)—, —C(=O)—N($R^2$)—, —C(=O)—O—, —S(O)$_{0-2}$—, —S(O)$_{0-2}$—N($R^2$)—, a mono- or bicyclic ring system in which one or more ring members may be N($R^3$), O, S or —C(=O)—;

M is —O—, or —O—CH$_2$—;

and physiologically compatible salts thereof.

In some embodiments of the compound of Formula XLVIII, R is hydrogen, $(C_1-C_{16})$-alkyl, $(C_1-C_5)$-alkyloxy, $(C_1-C_5)$-alkylthio, $(C_1-C_5)$-alkylamino, di-$(C_2-C_8)$-alkylamino, $(C_0-C_4)$-alkylene-$(C_6-C_{10})$-aryl, $(C_0-C_4)$-alkylene-$(C_5-C_{12})$-heteroaryl, $(C_0-C_4)$-alkylene-$(C_3-C_{12})$-heterocyclyl, $(C_0-C_4)$-alkylene-$(C_3-C_{12})$-cycloalkyl, a bicyclic-$(C_8-C_{14})$ ring system, where aryl, heteroaryl, heterocyclyl, cycloalkyl or the bicyclic-$(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;

$R^1$ is $(C_1-C_{10})$-alkyl, —$(C_6-C_{10})$-aryl, —$(C_5-C_{12})$-heteroaryl, —$(C_3-C_{12})$-heterocyclyl, —$(C_3-C_{12})$-cycloalkyl, where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, —$(C_6-C_{10})$-aryl, —$(C_5-C_{12})$-heteroaryl, —$(C_3-C_{12})$-heterocyclyl or —$(C_3-C_{12})$-cycloalkyl, where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, or di-$(C_2-C_{12})$-alkylamino;

$R^2$ is hydrogen, $(C_1-C_{16})$-alkyl, or $(C_0-C_4)$-alkylene-$(C_6-C_{10})$-aryl;

$R^3$ is hydrogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, cyano, $(C_1-C_6)$-alkylcarbonyl, halogen, trifluoromethyl, trifluoromethyloxy, $(C_1-C_6)$-alkylsulfonyl, or aminosulfonyl;

A is S, or C($R^3$)=C($R^3$);

B is C($R^3$), or N;

D is N;

L is a bond, —C(=O)—, —C(=S)—, —C(=O)—N($R^2$)—, —C(=O)—O—, —S(O)$_{0-2}$—, —S(O)$_{0-2}$—N($R^2$)—, a mono- or bicyclic ring system in which one or more ring members may be N($R^3$), O, S or —C(=O)—;

M is —O—, or —O—CH$_2$—;

and physiologically compatible salts thereof.

In some embodiments of the compound of Formula XLVIII, R is $(C_1-C_{16})$-alkyl, $(C_1-C_5)$-alkyloxy, $(C_0-C_4)$-alkylene-$(C_6-C_{10})$-aryl, a bicyclic-$(C_8-C_{14})$ ring system, where aryl or the bicyclic-$(C_8-C_{14})$ ring system may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl or aminosulfonyl;

$R^1$ is $(C_1-C_{10})$-alkyl, —$(C_6-C_{10})$-aryl, —$(C_5-C_{12})$-heteroaryl, —$(C_3-C_{12})$-heterocyclyl, —$(C_3-C_{12})$-cycloalkyl, where alkyl may be substituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, —$(C_6-C_{10})$-aryl, —$(C_5-C_{12})$-heteroaryl, —$(C_3-C_{12})$-heterocyclyl or —$(C_3-C_{12})$-cycloalkyl, where aryl, heteroaryl, heterocyclyl or cycloalkyl may optionally be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, or di-$(C_2-C_{12})$-alkylamino;

$R^2$ is hydrogen, $(C_1-C_6)$-alkyl, or $(C_0-C_4)$-alkylene-$(C_6-C_{10})$-aryl;

$R^3$ is hydrogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, cyano, $(C_1-C_6)$-alkylcarbonyl, halogen, trifluoromethyl, trifluoromethyloxy, $(C_1-C_6)$-alkylsulfonyl, or aminosulfonyl;

A is S, or C($R^3$)=C($R^3$);

B is C($R^3$), or N;

D is N;

L is a bond, or —C(=O)—;

M is —O—;

and physiologically compatible salts thereof.

In some embodiments of the compound of Formula XLVIII, R is $(C_0-C_4)$-alkylene-$(C_6-C_{10})$-aryl, where aryl may be mono- or polysubstituted by halogen, $(C_1-C_6)$-alkyl, $(C_1-C_3)$-alkyloxy, hydroxyl, $(C_1-C_6)$-alkylmercapto, amino, $(C_1-C_6)$-alkylamino, di-$(C_2-C_{12})$-alkylamino, mono-$(C_1$-

$C_6$)-alkylaminocarbonyl, di-($C_2$-$C_8$)-alkylaminocarbonyl, ($C_1$-$C_6$)-alkoxycarbonyl, ($C_1$-$C_6$)-alkylcarbonyl, cyano, trifluoromethyl, trifluoromethyloxy, ($C_1$-$C_6$)-alkylsulfonyl or aminosulfonyl;

$R^1$ is ($C_0$-$C_4$)-alkylene-($C_6$-$C_{10}$)-aryl, ($C_0$-$C_4$)-alkylene-($C_5$-$C_{12}$)-heteroaryl, where aryl or heteroaryl may optionally be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, or di-($C_2$-$C_{12}$)-alkylamino;

$R^3$ is hydrogen;

A is $C(R^3)=C(R^3)$;

B is $C(R^3)$, N;

D is N;

L is —C(=O)—;

M is —O—;

and physiologically compatible salts thereof.

In some embodiments, the compound of Formula XLVIII has the structure:

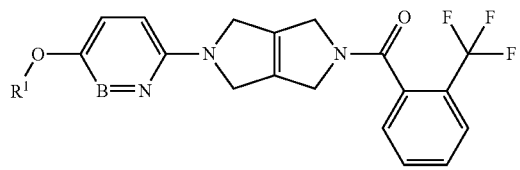

in which $R^1$ is ($C_0$-$C_4$)-alkylene-($C_6$-$C_{10}$O-aryl, ($C_0$-$C_4$)-alkylene-($C_5$-$C_{12}$)-heteroaryl, where aryl or heteroaryl may optionally be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, or di-($C_2$-$C_{12}$)-alkylamino;

B is CH, or N;

or physiologically compatible salts thereof.

In some embodiments of the compound of Formula XLVIII, $R^1$ is ($C_1$-$C_4$)-alkylenephenyl, ($C_1$-$C_4$)-alkylene-($C_5$-$C_6$)-heteroaryl, where heteroaryl is a monocyclic aromatic ring with one or two ring heteroatoms selected from N, O or S and where phenyl or heteroaryl may optionally be mono- or polysubstituted by halogen, ($C_1$-$C_6$)-alkyl, ($C_1$-$C_3$)-alkyloxy, hydroxyl, ($C_1$-$C_6$)-alkylmercapto, amino, ($C_1$-$C_6$)-alkylamino, or di-($C_2$-$C_{12}$)-alkylamino;

B is CH, or N;

or physiologically compatible salts thereof.

Compounds of Formula (XLVIII) may be synthesized by methods known in the art, e.g., those described in U.S. Pat. No. 8,673,917 B2. In some embodiments, the SCD inhibitor is a compound disclosed in U.S. Pat. No. 8,673,917 B2, the compounds of which are herein incorporated by reference.

In some embodiments of any of the foregoing methods, the SCD inhibitor is a fatty acid-bile acid conjugate, e.g., a bile acid such as cholic acid conjugated with a fatty acid through an amide bond at position 3, or a pharmaceutically acceptable salt thereof. For example, in some embodiments, the SCD inhibitor has the structure of Formula XLIX:

Formula XLIX

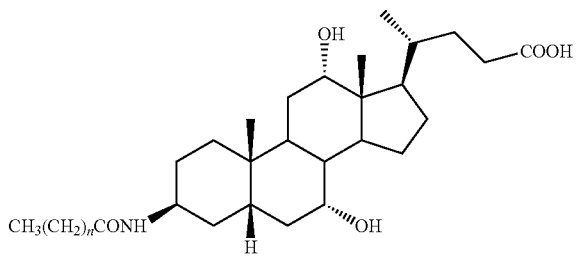

wherein n is an integer from 1 to 20, or a pharmaceutically acceptable salt thereof.

In some embodiments, the SCD inhibitor is 3β-arachidylamido-7α,12α-dihydroxy-5β-cholan-24-oic acid, also known as Aramchol, or a pharmaceutically acceptable salt thereof.

In some embodiments of any of the foregoing methods, the SCD inhibitor is a 10, 12 linoleic acid isomer or a pharmaceutically acceptable salt thereof. In some embodiments of any of the foregoing methods, the SCD inhibitor is an oxadiazole pyyridazine or a pharmaceutically acceptable salt thereof. In some embodiments of any of the foregoing methods, the SCD inhibitor is a 1-(4-phenoxypiperidin-1-yl)-2-arylaminoethanone compound or a pharmaceutically acceptable salt thereof. In some embodiments of any of the foregoing methods, the SCD inhibitor is a cyclpropenoid fatty acid or a pharmaceutically acceptable salt thereof. In some embodiments of any of the foregoing methods, the SCD inhibitor is a thia-fatty acid or a pharmaceutically acceptable salt thereof. In some embodiments of any of the foregoing methods, the SCD inhibitor is pioglitazone, rosiglitazone, ciglitazone, englitazone, troglitazone, leptin, or a pharmaceutically acceptable salts thereof.

In some embodiments of any of the foregoing methods, the SCD inhibitor is a compound of Formula L:

Formula L

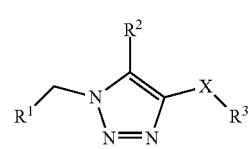

wherein X represents —CONH—, —NHCO— or —CH$_2$NH—;

$R^1$ represents —$C_{6-10}$aryl (such as phenyl) optionally substituted by one, two or three groups independently selected from:

(a) —$C_{1-6}$alkyl (such as —CH$_3$, or —CH(CH$_3$)$_2$), —OCH$_3$, —$C_{1-6}$haloalkyl (such as —CF$_3$), —OC$_{1-5}$haloalkyl (such as —OCF$_3$), —$C_{3-5}$cycloalkyl, —OC$_{3-5}$cycloalkyl or halogen (such as chloro, bromo or fluoro);

(b) phenyl optionally substituted by one, two or three groups independently selected from: halogen (such as chloro, bromo or fluoro);

$R^2$ represents hydrogen or —$C_{1-6}$alkyl (such as —CH$_3$);

$R^3$ represents —$C_{6-10}$aryl (such as phenyl) optionally substituted by one, two or three groups independently selected from:

(a) —$C_{1-5}$alkyl (such as —CH$_3$), —$C_{1-5}$alkenyl, —$C_{1-5}$alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$CO$_2$R$^5$, —(CH$_2$)$_n$OC(=O)R$^5$, —C$_{0\text{-}6}$alkylOH (such as —CH$_2$OH, —C(CH$_3$)$_2$OH or —CH(CH$_3$)OH), —C(=O)NHR$^6$, —(CH$_2$)$_p$NHC(=O)R$^7$, —O(CH$_2$)$_q$NR$^8$R$^9$, —OC$_{1\text{-}5}$alkylOH, —C$_{1\text{-}5}$haloalkyl (such as —CF$_3$), —OC$_{1\text{-}5}$haloalkyl (such as —OCF$_3$), —C$_{3\text{-}5}$cycloalkyl, —OC$_{3\text{-}5}$cycloalkyl or halogen (such as chloro, bromo or fluoro);

(b) —C$_5$heteroaryl (such as oxazole);

R$^4$ represents —C$_{6\text{-}10}$aryl (such as phenyl);

R$^5$ represents —H or —C$_{1\text{-}6}$alkyl (such as —CH$_3$);

R$^6$ represents —H or —C$_{1\text{-}3}$alkyl (such as —CH$_3$) or —C$_{1\text{-}3}$alkylOH;

R$^7$ represents —H or —C$_{1\text{-}3}$alkyl (such as —CH$_3$);

R$^8$ represents —H or —C$_{1\text{-}3}$alkyl (such as —CH$_3$);

R$^9$ represents —H or —C$_{1\text{-}3}$alkyl (such as —CH$_3$);

m represents 1-3;

n represents 0-3;

p represents 0-3; and q represents 1-3;

or a pharmaceutically acceptable salt thereof.

In some embodiments, X represents —CONH—. In some embodiments, X represents —NHCO—. In some embodiments, X represents —CH$_2$NH—. In some embodiments, X represents —CONH— or —CH$_2$NH—.

In some embodiments, R$^1$ represents phenyl substituted by one, two or three groups independently selected from:

(a) —C$_{1\text{-}5}$alkyl (such as —CH$_3$ or —CH(CH$_3$)$_2$), —OCH$_3$, —C$_{1\text{-}5}$haloalkyl (such as —CF$_3$), —OC$_{1\text{-}5}$haloalkyl (such as —OCF$_3$), —C$_{3\text{-}5}$cycloalkyl, —OC$_{3\text{-}5}$cycloalkyl or halogen (such as chloro, bromo or fluoro).

(b) phenyl optionally substituted by one, two or three groups selected from: halogen (such as chloro, bromo or fluoro).

In some embodiments, R$^1$ represents phenyl optionally substituted by one, two or three groups independently selected from:

(a) —C$_{1\text{-}6}$alkyl (such as —CH$_3$ or —CH(CH$_3$)$_2$), —OCH$_3$, —C$_{1\text{-}6}$haloalkyl (such as —CF$_3$), —OC$_{1\text{-}5}$haloalkyl (such as —OCF$_3$), —C$_{3\text{-}5}$cycloalkyl, —OC$_{3\text{-}5}$cycloalkyl or halogen (such as chloro, bromo or fluoro), (b) phenyl optionally substituted by one, two or three groups selected from: halogen (such as chloro, bromo or fluoro).

In some embodiments, R$^1$ represents phenyl optionally substituted by one or two groups independently selected from: —C$_{1\text{-}5}$alkyl (such as —CH$_3$ or CH(CH$_3$)$_2$), —OCH$_3$, —C$_{1\text{-}5}$haloalkyl (such as —CF$_3$), —OC$_{1\text{-}5}$haloalkyl (such as —OCF$_3$), —C$_{3\text{-}5}$cycloalkyl, —OC$_{3\text{-}6}$cycloalkyl or halogen (such as chloro, bromo or fluoro), or phenyl optionally substituted by one or two groups selected from: halogen (such as chloro, bromo or fluoro). In some embodiments, R$^1$ represents phenyl optionally substituted by one, two or three groups independently selected from: —C$_{1\text{-}3}$alkyl (such as —CH$_3$ or —CH(CH$_3$)$_2$), —OCH$_3$, —C$_{1\text{-}3}$haloalkyl (such as —CF$_3$), —OC$_{1\text{-}3}$haloalkyl (such as —OCF$_3$), —C$_{3\text{-}5}$cycloalkyl, —OC$_{3\text{-}6}$cycloalkyl or halogen (such as chloro, bromo or fluoro), or phenyl optionally substituted by one or two groups selected from: halogen (such as chloro, bromo or fluoro). In some embodiments, R$^1$ represents phenyl optionally substituted by one, two or three groups independently selected from: —C$_{1\text{-}6}$alkyl (such as —CH$_3$ or —CH(CH$_3$)$_2$) or halogen (such as chloro, bromo or fluoro) or phenyl optionally substituted by one, two or three groups selected from: halogen (such as chloro, bromo or fluoro). In some embodiments, R$^1$ represents phenyl optionally substituted by one or two groups independently selected from: —C$_{1\text{-}6}$alkyl (such as —CH$_3$ or —CH(CH$_3$)$_2$) or halogen (such as chloro, bromo or fluoro) or phenyl optionally substituted by one or two groups selected from: halogen (such as chloro, bromo or fluoro). In some embodiments, R$^1$ represents phenyl optionally substituted by one, two or three groups independently selected from: —C$_{1\text{-}3}$alkyl (such as —CH$_3$ or —CH(CH$_3$)$_2$) or halogen (such as chloro, bromo or fluoro) or phenyl optionally substituted by one, two or three groups selected from: halogen (such as chloro, bromo or fluoro). In some embodiments, R$^1$ represents phenyl optionally substituted by one or two groups independently selected from: —C$_{1\text{-}3}$alkyl (such as —CH$_3$ or —CH(CH$_3$)$_2$) or halogen (such as chloro, bromo or fluoro) or phenyl optionally substituted by one or two groups selected from: halogen (such as chloro, bromo or fluoro). In some embodiments, R$^1$ represents phenyl optionally substituted by one, two or three groups independently selected from: —CH$_3$, —CH(CH$_3$)$_2$ or halogen (such as chloro, bromo or fluoro) or phenyl optionally substituted by one, two or three groups selected from: halogen (such as chloro, bromo or fluoro). In some embodiments, R$^1$ represents phenyl optionally substituted by one or two groups independently selected from: —CH$_3$, —CH(CH$_3$)$_2$ or halogen (such as chloro, bromo or fluoro) or phenyl optionally substituted by one or two groups selected from: halogen (such as chloro, bromo or fluoro). In some embodiments, R$^1$ represents phenyl substituted by two groups independently selected from halogen (such as chloro, bromo or fluoro). In some embodiments, R$^1$ represents phenyl substituted by a group independently selected from halogen (such as chloro, bromo or fluoro). In some embodiments, R$^1$ represents phenyl substituted by phenyl optionally substituted by halogen (such as chloro, bromo or fluoro). In some embodiments, R$^1$ represents phenyl substituted by phenyl. In some embodiments, R$^1$ represents phenyl substituted by two chloro groups. In some embodiments, R$^1$ is phenyl substituted in the meta position, that is in the 3 position, and the para position, that is in the 4 position, by halogen e.g chloro. In some embodiments, R$^1$ is phenyl substituted in the meta position, that is in the 3 position and 5 position, by halogen e.g chloro. In some embodiments, R$^1$ is phenyl.

In some embodiments, R$^2$ represents hydrogen. In some embodiments, R$^2$ represents —C$_{1\text{-}6}$alkyl. In some embodiments, R$^2$ represents —C$_{1\text{-}3}$alkyl. In some embodiments, R$^2$ represents —CH$_3$ (methyl). In some embodiments, R$^2$ represents hydrogen or —C$_{1\text{-}3}$alkyl.

In some embodiments, R$^3$ represents phenyl optionally substituted by one, two or three groups independently selected from: (a) —C$_{1\text{-}6}$alkyl (such as —CH$_3$), —C$_{1\text{-}6}$alkenyl, —C$_{1\text{-}6}$alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$CO$_2$R$^5$, —(CH$_2$)$_n$OC(=O)R$^5$, —C$_{0\text{-}6}$alkylOH (such as —CH$_2$OH, —C(CH$_3$)$_2$OH or —CH(CH$_3$)OH), —C(=O)NHR$^6$, —(CH$_2$)$_p$NHC(=O)R$^7$, —O(CH$_2$)$_q$NR$^8$R$^9$, —OC$_{1\text{-}5}$ alkylOH, —C$_{1\text{-}5}$haloalkyl (such as —CF$_3$), —OC$_{1\text{-}5}$ haloalkyl (such as —OCF$_3$), —C$_{3\text{-}5}$cycloalkyl, —OC$_{3\text{-}5}$cycloalkyl or halogen (such as chloro, bromo or fluoro), (b) —C$_5$heteroaryl (such as oxazole). In some embodiments, R$^3$ represents phenyl optionally substituted by one or two groups independently selected from: (a) —C$_{1\text{-}5}$alkyl (such as —CH$_3$), —C$_{1\text{-}5}$alkenyl, —C$_{1\text{-}5}$alkoxy (such as —OCH$_3$ or OC$_2$H$_4$CH(CH$_3$)$_2$), —O(CH$_2$)$_m$R$^4$, —(CH$_2$)$_m$OC(=O)R$^4$, —(CH$_2$)$_n$CO$_2$R$^5$, —(CH$_2$)$_n$OC(=O)R$^5$, —C$_{0-6}$alkylOH (such as —CH$_2$OH, —C(CH$_3$)$_2$OH or —CH(CH$_3$)OH), —C(=O)NHR$^6$, —(CH$_2$)$_p$NHC(=O)R$^7$, —O(CH$_2$)$_q$NR$^8$R$^9$, —OC$_{1-5}$alkylOH, —C$_{1-5}$haloalkyl (such as —CF$_3$), —OC$_{1-5}$haloalkyl (such as —OCF$_3$), —C$_{3-5}$cycloalkyl, —OC$_{3-5}$cycloalkyl or halogen (such as chloro, bromo or fluoro), (b) —C$_5$heteroaryl (such as oxazole). In some embodiments, R$^3$ represents phenyl optionally substituted by: (i) one group independently selected from —(CH$_2$)$_n$CO$_2$R$^5$ or —C(=O)NHR$^6$ and/or, (ii) one, two or three groups independently selected from: (a) —C$_{1-6}$alkyl (such as —CH$_3$), —C$_{1-6}$alkenyl, —C$_{1-6}$alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$OC(=O)R$^5$, —C$_{1-5}$alkylOH (such as —CH$_2$OH, —C(CH$_3$)$_2$OH or —CH(CH$_3$)OH), —(CH$_2$)$_p$NHC(=O)R$^7$, —O(CH$_2$)$_q$NR$^8$R$^9$, —OC$_{1-5}$alkylOH, —C$_{1-5}$haloalkyl (such as —CF$_3$), —OC$_{1-5}$haloalkyl (such as —OCF$_3$), —C$_{3-5}$cycloalkyl, —OC$_{3-5}$cycloalkyl or halogen (such as chloro, bromo or fluoro), (b) —C$_5$heteroaryl (such as oxazole). In some embodiments, R$^3$ represents phenyl optionally substituted by: (i) one group independently selected from —(CH$_2$)$_n$CO$_2$R$^5$ or —C(=O)NHR$^6$ and/or, (ii) one or two groups independently selected from: (a) —C$_{1-5}$alkyl (such as —CH$_3$), —C$_{1-5}$alkenyl, —C$_{1-5}$ alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$OC(=O)R$^5$, —C$_{0-5}$alkylOH (such as —CH$_2$OH, —C(CH$_3$)$_2$OH or —CH(CH$_3$)OH), —(CH$_2$)$_p$NHC(=O)R$^7$, —O(CH$_2$)$_q$NR$^8$R$^9$, —OC$_{1-5}$alkylOH, —C$_{1-5}$haloalkyl (such as —CF$_3$), —OC$_{1-5}$haloalkyl (such as —OCF$_3$), —C$_{3-6}$cycloalkyl, —OC$_{3-6}$cycloalkyl or halogen (such as chloro, bromo or fluoro), (b) —C$_5$heteroaryl (such as oxazole). In some embodiments, R$^3$ represents phenyl optionally substituted by: (i) one group independently selected from —(CH$_2$)$_n$CO$_2$R$^5$ or —C(=O)NHR$^6$ and/or, (ii) one, two or three groups independently selected from: (a) —C$_{1-3}$alkyl (such as —CH$_3$), —C$_{1-3}$alkenyl, —C$_{1-6}$alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$OC(=O)R$^5$, —C$_{0-3}$alkylOH (such as —CH$_2$OH, —C(CH$_3$)$_2$OH or —CH(CH$_3$)OH), —(CH$_2$)$_p$NHC(=O)R$^7$, —O(CH$_2$)$_q$NR$^8$R$^9$, —OC$_{1-5}$alkylOH, —C$_{1-3}$haloalkyl (such as —CF$_3$), —OC$_{1-3}$haloalkyl (such as —OCF$_3$), —C$_{3-5}$cycloalkyl, —OC$_{3-5}$cycloalkyl or halogen (such as chloro, bromo or fluoro), (b) —C$_5$heteroaryl (such as oxazole). In some embodiments, R$^3$ represents phenyl optionally substituted by: (i) one group independently selected from —(CH$_2$)$_n$CO$_2$R$^5$ or —C(=O)NHR$^6$ and/or, (ii) one or two groups independently selected from: (a) —C$_{1-3}$alkyl (such as —CH$_3$), —C$_{1-3}$alkenyl, —C$_{1-5}$alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$OC(=O)R$^5$, —C$_{0-3}$alkylOH (such as —CH$_2$OH, —C(CH$_3$)$_2$OH or —CH(CH$_3$)OH), —(CH$_2$)$_p$NHC(=O)R$^7$, —O(CH$_2$)$_q$NR$^8$R$^9$, —OC$_{1-5}$alkylOH, —C$_{1-3}$haloalkyl (such as —CF$^3$), —OC$_{1-3}$haloalkyl (such as —OCF$_3$), —C$_{3-6}$cycloalkyl, —OC$_{3-6}$cycloalkyl or halogen (such as chloro, bromo or fluoro), (b) —C$_5$heteroaryl (such as oxazole). In some embodiments, R$^3$ represents phenyl optionally substituted by: (i) one group independently selected from —(CH$_2$)$_n$CO$_2$R$^5$ or —C(=O)NHR$^6$ and/or, (ii) one, two or three groups independently selected from: (a) —C$_{1-3}$alkyl (such as —CH$_3$), —C$_{1-3}$alkenyl, —C$_{1-5}$alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$OC(=O)R$^5$, —C$_{0-3}$alkylOH (such as —CH$_2$OH, —C —CH(CH$_3$)$_2$OH or —CH(CH$_3$)OH) —(CH$_2$)$_p$NHC(=O)R$^7$, —O(CH$_2$)$_q$NR$^8$R$^9$, —OC$_{1-6}$alkylOH or halogen (such as chloro, bromo or fluoro), (b) —C$_5$heteroaryl (such as oxazole). In some embodiments, R$^3$ represents phenyl optionally substituted by: (i) one group independently selected from —(CH$_2$)$_n$CO$_2$R$^5$ or —C(=O)NHR$^6$ and/or, (ii) one or two groups independently selected from: (a) —C$_{1-3}$alkyl (such as —CH$_3$), —C$_{1-3}$alkenyl, —C$_{1-5}$alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$OC(=O)R$^5$, —C$_{0-3}$alkylOH (such as —CH$_2$OH, —C(CH$_3$)$_2$OH or —CH(CH$_3$)OH), —(CH$_2$)$_p$NHC(=O)R$^7$, —O(CH$_2$)$_q$NR$^8$R$^9$, —OC$_{1-6}$alkylOH or halogen (such as chloro, bromo or fluoro), (b) —C$_5$heteroaryl (such as oxazole). In some embodiments, R$^3$ represents phenyl optionally substituted by: (i) one group independently selected from —(CH$_2$)$_n$CO$_2$R$^5$ or —C(=O)NHR$^6$ and/or, (ii) one, two or three groups independently selected from: (a) —C$_{1-3}$alkyl (such as —CH$_3$), —C$_{1-3}$alkenyl, —C$_{1-5}$ alkoxy (such as —OCH$_3$ or —OC$_2$H$_4$CH(CH$_3$)$_2$), —O(CH$_2$)$_m$R$^4$, —(CH$_2$)$_m$OC(=O)R$^4$, —(CH$_2$)$_n$OC(=O)R$^5$, —C$_{0-3}$alkylOH (such as —CH$_2$OH, —C(CH$_3$)$_2$OH or —CH(CH$_3$)OH), —(CH$_2$)$_p$NHC(=O)R$^7$, —O(CH$_2$)$_q$NR$^8$R$^9$, —OC$_{1-6}$alkylOH or halogen (such as chloro, bromo or fluoro), (b) oxazole. In some embodiments, R$^3$ represents phenyl optionally substituted by: (i) one group independently selected from —CO$_2$H, —CO$_2$CH$_3$, —C$_2$C$_2$H$_5$, —CH$_2$CO$_2$CH$_3$, —CH$_2$CO$_2$C$_2$H$_5$, —C(=O)NH$_2$, —C(=O)NHCH$_3$, —C(=O)NHC$_2$H$_5$ or —C(=O)NHC$_2$H$_4$OH and/or, (ii) one, two or three groups independently selected from: (a) —CH$_3$, —C(=CH$_2$)CH$_3$, —OCH$_3$, —OC$_2$H$_4$CH(CH$_3$)$_2$, —OCH$_2$R$^4$, —CH$_2$OC(=O)R$^4$, —CH$_2$OC(=O)CH$_3$, —CH$_2$OH, —C$_2$H$_4$OH, —CH(CH$_3$)OH, —C(CH$_3$)$_2$OH, —OH, —CH$_2$NHC(=O)CH$_3$, —NHC(=O)CH$_3$, —OC$_2$H$_4$N(CH$_3$)$_2$, —OC$_2$H$_4$OH or halogen (such as chloro, bromo or fluoro), (b) oxazole. In some embodiments, R$^3$ represents phenyl optionally substituted by: (i) one group independently selected from —CO$_2$H, —CO$_2$CH$_3$, —CO$_2$O$_2$H$_5$, —CH$_2$CO$_2$CH$_3$, —CH$_2$CO$_2$C$_2$H$_5$, —C(=O)NH$_2$, —C(=O)NHCH$_3$, —C(=O)NHC$_2$H$_5$ or —C(=O)NHC$_2$H$_4$OH and/or, (ii) one or two groups independently selected from: (a) —CH$_3$, —C(=CH$_2$)CH$_3$, —OCH$_3$, —OC$_2$H$_4$CH(CH$_3$)$_2$, —OCH$_2$R$^4$, —CH$_2$OC(=O)R$^4$, —CH$_2$OC(=O)CH$_3$, —CH$_2$OH, —C$_2$H$_4$OH, —CH(CH$_3$)OH, —C(CH$_3$)$_2$OH, —OH, —CH$_2$NHC(=O)CH$_3$, NHC(=O)CH$_3$ —OC$_2$H$_4$N(CH$_3$)$_2$, —OC$_2$H$_4$OH or halogen (such as chloro, bromo or fluoro), (b) oxazole. In some embodiments, R$^3$ represents phenyl optionally substituted by one or two —CH$_2$OH groups. In some embodiments, R$^3$ represents phenyl substituted by one or two —CH$_2$OH groups. In some embodiments, R$^3$ represents phenyl substituted in the meta position, that is in the 3 and 5 position, by —CH$_2$OH. In some embodiments, R$^3$ represents phenyl substituted in the meta position, that is in the 3 position and the para position, that is in the 4 position, by —CH$_2$OH. In some embodiments, R$^3$ represents phenyl substituted by —CH$_2$OH.

In some embodiments, R$^4$ represents phenyl.

In some embodiments, R$^5$ represents hydrogen. In some embodiments, R$^5$ represents —C$_{1-6}$alkyl. In some embodiments, R$^5$ represents —C$_{1-3}$alkyl. In some embodiments, R$^5$ represents ethyl. In some embodiments, R$^5$ represents methyl.

In some embodiments, R$^6$ represents hydrogen. In some embodiments, R$^6$ represents —C$_{1-3}$alkyl. In some embodiments, R$^6$ represents ethyl. In some embodiments, R$^6$ represents methyl. In some embodiments, R$^6$ represents —C$_{1-3}$alkylOH. In some embodiments, R$^6$ represents —C$_2$H$_{40}$H.

In some embodiments, $R^7$ represents hydrogen. In some embodiments, $R^7$ represents —$C_{1-3}$alkyl. In some embodiments, $R^7$ represents methyl.

In some embodiments, $R^8$ represents hydrogen. In some embodiments, $R^8$ represents —$C_{1-3}$alkyl. In some embodiments, $R^8$ represents methyl.

In some embodiments, $R^9$ represents hydrogen. In some embodiments, $R^9$ represents —$C_{1-3}$alkyl. In some embodiments, $R^9$ represents methyl.

In some embodiments, m represents 1 or 2. In some embodiments, m represents 2. In some embodiments, m represents 1.

In some embodiments, n represents 0, 1 or 2. In some embodiments, n represents 3. In some embodiments, n represents 2. In some embodiments, n represents 1. In some embodiments, n represents 0.

In some embodiments, p represents 0, 1 or 2. In some embodiments, p represents 2. In some embodiments, p represents 1. In some embodiments, p represents 0.

In some embodiments, q represents 1 or 2. In some embodiments, q represents 2. In some embodiments, q represents 1.

In some embodiments, the SCD inhibitors is N-[3,4-bis(methyloxy)phenyl]-1-[(4-fluorophenyl)methyl]-5-methyl-1H-1,2,3-triazole-4-carboxamide, N-[3,4-bis(methyloxy)phenyl]-1-[(4-bromophenyl)methyl]-5-methyl-1H-1,2,3-triazole-4-carboxamide, 1-[(4-Bromophenyl)methyl]-5-methyl-N-{4-[(phenylmethyl)oxy]phenyl}-1H-1,2,3-triazole-4-carboxamide, 1-[(4-Fluorophenyl)methyl]-5-methyl-N-{4-[(phenylmethyl)oxy]phenyl}-1H-1,2,3-triazole-4-carboxamide, 1-[(4-Fluorophenyl)methyl]-5-methyl-N-{4-[(3-methylbutyl)oxy]phenyl}-1H-1,2,3-triazole-4-carboxamide, 1-[(4-Bromophenyl)methyl]-5-methyl-N-{4-[(3-methylbutyl)oxy]phenyl}-1H-1,2,3-triazole-4-carboxamide, 5-Methyl-1-(phenylmethyl)-N-{4-[(phenylmethyl)oxy]phenyl}-1H-1,2,3-triazole-4-carboxamide, 5-Methyl-N-{4-[(3-methylbutyl)oxy]phenyl}-1-(phenylmethyl)-1H-1,2,3-triazole-4-carboxamide, 1-[(2'-Chloro-4-biphenylyl)methyl]-5-methyl-N-{4-[(3-methylbutyl)oxy]phenyl}-1H-1,2,3-triazole-4-carboxamide, 5-Methyl-N-{4-[(3-methylbutyl)oxy]phenyl}-1-[(4-methylphenyl)methyl]-1H-1,2,3-triazole-4-carboxamide, 5-Methyl-N-{4-[(3-methylbutyl)oxy]phenyl}-1-{[4-(1-methylethyl)phenyl]methyl}-1H-1,2,3-triazole-4-carboxamide, N-[3,4-Bis(methyloxy)phenyl]-5-methyl-1-[(4-methylphenyl)methyl]-1H-1,2,3-triazole-4-carboxamide, 1-(2-Biphenylylmethyl)-N-[3,4-bis(methyloxy)phenyl]-5-methyl-1H-1,2,3-triazole-4-carboxamide, N-[3,4-Bis(methyloxy)phenyl]-1-[(4-fluorophenyl)methyl]-1H-1,2,3-triazole-4-carboxamide, 1-[(3,4-Dichlorophenyl)methyl]-5-methyl-N-[4-(1,3-oxazol-2-yl)phenyl]-1H-1,2,3-triazole-4-carboxamide, 1-[(3,4-Dichlorophenyl)methyl]-N-[4-(hydroxymethyl)phenyl]-5-methyl-1H-1,2,3-triazole-4-carboxamide, Methyl-4-[({1-[(3,4-dichlorophenyl)methyl]-5-methyl-1H-1,2,3-triazol-4-yl}carbonyl)amino]-3-(methyloxy)benzoate, 1-[(3,4-Dichlorophenyl)methyl]-5-methyl-N-{3-[(methylamino)carbonyl]phenyl}-1H-1,2,3-triazole-4-carboxamide, 1-[(3,4-Dichlorophenyl)methyl]-5-methyl-N-{4-[(methyl amino)carbonyl]phenyl}-1H-1,2,3-triazole-4-carboxamide, Ethyl-3-[({1-[(3,4-dichlorophenyl)methyl]-5-methyl-1H-1,2,3-triazol-4-yl}carbonyl)amino]benzoate, N-[3-(acetylamino)phenyl]-1-[(3,4-dichlorophenyl)methyl]-5-methyl-1H-1,2,3-triazole-4-carboxamide, N-[4-(acetylamino)phenyl]-1-[(3,4-dichlorophenyl)methyl]-5-methyl-1H-1,2,3-triazole-4-carboxamide, 1-[(3,4-Dichlorophenyl)methyl]-N-[3-(hydroxymethyl)-2-methylphenyl]-5-methyl-1H-1,2,3-triazole-4-carboxamide, 1-[(3,4-Dichlorophenyl)methyl]-N-[3-(hydroxymethyl)phenyl]-5-methyl-1H-1,2,3-triazole-4-carboxamide, Methyl-3-[({1-[(3,4-dichlorophenyl)methyl]-5-methyl-1H-1,2,3-triazol-4-yl}carbonyl)amino]-4-(methyloxy)benzoate, 1-[(3,4-Dichlorophenyl)methyl]-N-[4-hydroxy-3-(hydroxymethyl)phenyl]-5-methyl-1H-1,2,3-triazole-4-carboxamide, Ethyl-{4-[({1-[(3,4-dichlorophenyl)methyl]-5-methyl-1H-1,2,3-triazol-4-yl}carbonyl)amino]phenyl}acetate, Methyl-4-[({1-[(3,4-dichlorophenyl)methyl]-5-methyl-1H-1,2,3-triazol-4-yl}carbonyl)amino]-2-(methyloxy)benzoate, Methyl-5-[({1-[(3,4-dichlorophenyl)methyl]-5-methyl-1H-1,2,3-triazol-4-yl}carbonyl)amino]-2-hydroxybenzoate, Methyl {3-[({1-[(3,4-dichlorophenyl)methyl]-5-methyl-1H-1,2,3-triazol-4-yl}carbonyl)amino]phenyl}acetate, 1-[(3,4-Dichlorophenyl)methyl]-N-(3-hydroxyphenyl)-5-methyl-1H-1,2,3-triazole-4-carboxamide, Methyl-5-[({1-[(3,4-dichlorophenyl)methyl]-5-methyl-1H-1,2,3-triazol-4-yl}carbonyl)amino]-2-fluorobenzoate, N-[5-(Aminocarbonyl)-2-(methyloxy)phenyl]-1-[(3,4-dichlorophenyl)methyl]-5-methyl-1H-1,2,3-triazole-4-carboxamide, Methyl 4-chloro-3-[({1-[(3,4-dichlorophenyl)methyl]-5-methyl-1H-1,2,3-triazol-4-yl}carbonyl)amino]benzoate, Methyl 3-[({1-[(3,4-dichlorophenyl)methyl]-5-methyl-1H-1,2,3-triazol-4-yl}carbonyl)amino]-4-(methyloxy)phenyl]acetate, Methyl 3-[({1-[(3,4-dichlorophenyl)methyl]-5-methyl-1H-1,2,3-triazol-4-yl}carbonyl)amino]-4-fluorobenzoate, N-[3-(hydroxymethyl)phenyl]-5-methyl-1-(phenylmethyl)-1H-1,2,3-triazole-4-carboxamide, N-[4-(hydroxymethyl)phenyl]-5-methyl-1-(phenylmethyl)-1H-1,2,3-triazole-4-carboxamide, N-[3-(hydroxymethyl)-2-methylphenyl]-5-methyl-1-(phenylmethyl)-1H-1,2,3-triazole-4-carboxamide, 1-[(3,5-Dichlorophenyl)methyl]-N-[3-(hydroxymethyl)phenyl]-5-methyl-1H-1,2,3-triazole-4-carboxamide, Methyl 3-[({1-[(3,5-dichlorophenyl)methyl]-5-methyl-1H-1,2,3-triazol-4-yl}carbonyl)amino]-4-(methyloxy)benzoate, 1-[(3,5-Dichlorophenyl)methyl]-N-[3-(hydroxymethyl)-2-methylphenyl]-5-methyl-1H-1,2,3-triazole-4-carboxamide, N-{3-[(Acetylamino)methyl]phenyl}-1-[(3,4-dichlorophenyl)methyl]-5-methyl-1H-1,2,3-triazole-4-carboxamide, 1-[(3,4-Dichlorophenyl)methyl]-N-[3-(1-hydroxyethyl)phenyl]-5-methyl-1H-1,2,3-triazole-4-carboxamide, N-[4-chloro-3-(hydroxymethyl)phenyl]-1-[(3,4-dichlorophenyl)methyl]-5-methyl-1H-1,2,3-triazole-4-carboxamide, Dimethyl 4-[({1-[(3,4-dichlorophenyl)methyl]-5-methyl-1H-1,2,3-triazol-4-yl}carbonyl)amino]-1,2-benzenedicarboxylate, Methyl 5-[({1-[(3,5-dichlorophenyl)methyl]-5-methyl-1H-1,2,3-triazol-4-yl}carbonyl)amino]-2-fluorobenzoate, Ethyl 4-[({1-[(3,4-dichlorophenyl)methyl]-5-methyl-1H-1,2,3-triazol-4-yl}carbonyl)amino]benzoate, 1-[(3,4-Dichlorophenyl)methyl]-N-[4-(hydroxymethyl)-2-(methyloxy)phenyl]-5-methyl-1H-1,2,3-triazole-4-carboxamide, 1-[(3,4-Dichlorophenyl)methyl]-N-[4-(2-hydroxyethyl)phenyl]-5-methyl-1H-1,2,3-triazole-4-carboxamide, 1-[(3,4-Dichlorophenyl)methyl]-N-[5-(hydroxymethyl)-2-(methyloxy)phenyl]-5-methyl-1H-1,2,3-triazole-4-carboxamide, N-[3,5-Bis(hydroxymethyl)phenyl]-1-[(3,4-dichlorophenyl)methyl]-5-methyl-1H-1,2,3-triazole-4-carboxamide, 1-[(3,4-Dichlorophenyl)methyl]-N-[4-fluoro-3-(hydroxymethyl)phenyl]-5-methyl-1H-1,2,3-triazole-4-carboxamide, 1-[(3,4-Dichlorophenyl)methyl]-N-[5-(2-hydroxyethyl)-2-(methyloxy)phenyl]-5-methyl-1H-1,2,3-triazole-4-carboxamide, 1-[(3,4-Dichlorophenyl)methyl]-N-[2-fluoro-5-(hydroxymethyl)phenyl]-5-methyl-1H-1,2,3-triazole-4-carboxamide, N-[2-chloro-5-(hydroxymethyl)phenyl]-1-[(3,4-dichlorophenyl)methyl]-5-methyl-1H-1,2, 3-triazole-4-carboxamide, 1-[(3,5-Dichlorophenyl)methyl]-N-[5-(hydroxymethyl)-2-(methyloxy)phenyl]-5-methyl-1H-1,2,3-triazole-4-carboxamide, N-[3,4-Bis(hydroxymethyl)phenyl]-1-[(3,4-dichlorophenyl)methyl]-5-methyl-1H-1,2,3-triazole-4-carboxamide, 1-[(3,5-Dichlorophenyl)methyl]-N-[4-fluoro-3-(hydroxymethyl)phenyl]-5-methyl-1H-1,2,3-triazole-4-carboxamide, N-[3,5-bis(hydroxymethyl)phenyl]-5-methyl-1-(phenylmethyl)-1H-1,2,3-triazole-4-carboxamide, N-[3,5-bis(hydroxymethyl)phenyl]-1-[(3-chlorophenyl)methyl]-5-methyl-1H-1,2,3-triazole-4-carboxamide, 1-[(3,4-Dichlorophenyl)methyl]-N-[3-(2-hydroxyethyl)phenyl]-5-methyl-1H-1,2,3-triazole-4-carboxamide, 3-[({1-[(3,4-Dichlorophenyl)methyl]-5-methyl-1H-1,2,3-triazol-4-yl}carbonyl)amino]benzoic acid, 3-[({1-[(3,4-Dichlorophenyl)methyl]-5-methyl-1H-1,2,3-triazol-4-yl}carbonyl)amino]-4-(methyloxy)benzoic acid, 5-({[5-Methyl-1-(phenylmethyl)-1H-1,2,3-triazol-4-yl]carbonyl}amino)-1,3-benzenedicarboxylic acid, 4-[({1-[(3,4-Dichlorophenyl)methyl]-5-methyl-1H-1,2,3-triazol-4-yl}carbonyl)amino]benzoic acid, 1-[(3,4-Dichlorophenyl)methyl]-N-{3-[(ethylamino)carbonyl]phenyl}-5-methyl-1H-1,2,3-triazole-4-carboxamide, 1-[(3,4-Dichlorophenyl)methyl]-N-(3-{[(2-hydroxyethyl)amino]carbonyl}phenyl)-5-methyl-1H-1,2,3-triazole-4-carboxamide, 1-[(3,4-Dichlorophenyl)methyl]-5-methyl-N-[5-[(methylamino)carbonyl]-2-(methyloxy)phenyl]-1H-1,2,3-triazole-4-carboxamide, {3-[({1-[(3,4-Dichlorophenyl)methyl]-5-methyl-1H-1,2,3-triazol-4-yl}carbonyl)amino]phenyl}methylacetate, {3-[({1-[(3,5-Dichlorophenyl)methyl]-5-methyl-1H-1,2,3-triazol-4-yl}carbonyl)amino]phenyl}methylacetate, {3-[({1-[(3,4-Dichlorophenyl)methyl]-5-methyl-1H-1,2,3-triazol-4-yl}carbonyl)amino]phenyl}methylbenzoate, {3-[({1-[(3,5-Dichlorophenyl)methyl]-5-methyl-1H-1,2,3-triazol-4-yl}carbonyl)amino]phenyl}methylbenzoate, 1-[(3,4-Dichlorophenyl)methyl]-N-{4-[(2-hydroxyethyl)oxy]phenyl}-5-methyl-1H-1,2,3-triazole-4-carboxamide, 1-[(3,4-Dichlorophenyl)methyl]-5-methyl-N-[4-(1-methylethenyl)-2-(methyloxy)phenyl]-1H-1,2,3-triazole-4-carboxamide, 1-[(3,4-Dichlorophenyl)methyl]-N-[3-(1-hydroxy-1-methylethyl)phenyl]-5-methyl-1H-1,2,3-triazole-4-carboxamide, 1-[(3,4-Dichlorophenyl)methyl]-N-[4-{[2-(dimethylamino)ethyl]oxy}-3-(hydroxymethyl)phenyl]-5-methy-1H-1,2,3-triazole-4-carboxamide, 1-[(3,4-Dichlorophenyl)methyl]-N-{3-[(2-hydroxyethyl)oxy]phenyl}-5-methyl-1H-1,2,3-triazole-4-carboxamide, or {5-[({1-[(3,4-Dichlorophenyl)methyl]-5-methyl-1H-1,2,3-triazol-4-yl}methyl)amino]benzene-1,3-diyl}dimethanol, or a pharmaceutically acceptable salt thereof.

In some embodiments, the SCD inhibitor is N-[3,4-bis(hydroxymethyl)phenyl]-5-methyl-1-(phenylmethyl)-1H-1,2,3-triazole-4-carboxamide, N-[3,5-bis(hydroxymethyl)phenyl]-1-[(4-fluorophenyl)methyl]-5-methyl-1H-1,2,3-triazole-4-carboxamide, N-[3,4-bis(hydroxymethyl)phenyl]-1-[(3-chlorophenyl)methyl]-5-methyl-1H-1,2,3-triazole-4-carboxamide, N-[3,4-bis(hydroxymethyl)phenyl]-1-[(4-fluorophenyl)methyl]-5-methyl-1H-1,2,3-triazole-4-carboxamide, N-[3,5-bis(hydroxymethyl)phenyl]-1-[(3-fluorophenyl)methyl]-5-methyl-1H-1,2,3-triazole-4-carboxamide, N-[3,4-bis(hydroxymethyl)phenyl]-1-[(3-fluorophenyl)methyl]-5-methyl-1H-1,2,3-triazole-4-carboxamide, 1-[(3-chlorophenyl)methyl]-N-[3-(hydroxymethyl)phenyl]-5-methyl-1H-1,2,3-triazole-4-carboxamide, 1-[(4-fluorophenyl)methyl]-N-[3-(hydroxymethyl)phenyl]-5-methyl-1H-1,2,3-triazole-4-carboxamide, 1-[(3-chlorophenyl)methyl]-N-[4-(hydroxymethyl)phenyl]-5-methyl-1H-1,2,3-triazole-4-carboxamide, 1-[(3-fluorophenyl)methyl]-N-[3-(hydroxymethyl)phenyl]-5-methyl-1H-1,2,3-triazole-4-carboxamide, 1-[(4-fluorophenyl)methyl]-N-[4-(hydroxymethyl)phenyl]-5-methyl-1H-1,2,3-triazole-4-carboxamide, 1-[(3-fluorophenyl)methyl]-N-[4-(hydroxymethyl)phenyl]-5-methyl-1H-1,2,3-triazole-4-carboxamide, 1-[(3,4-dichlorophenyl)methyl]-N-{3-(hydroxymethyl)-5-[(methylamino)carbonyl]phenyl}-5-methyl-1H-1,2,3-triazole-4-carboxamide, or N-{1-[(3,4-dichlorophenyl)methyl]-5-methyl-1H-1,2,3-triazol-4-yl}-4-(hydroxymethyl)benzamide, or a pharmaceutically acceptable salt thereof.

In some embodiments, the SCD inhibitor is N-{1-[(3,4-dichlorophenyl)methyl]-5-methyl-1H-1,2,3-triazol-4-yl}-4-(hydroxymethyl)benzamide, or a pharmaceutically acceptable salt thereof.

Compounds of Formula L may be synthesized by methods known in the art, e.g., those described in International Patent Publication No. WO2009/060053.

In some embodiments of any of the foregoing methods, the SCD inhibitor is a compound of Formula LI:

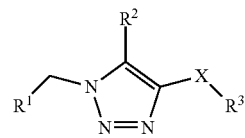

Formula LI wherein X represents —CONH—, —NHCO— or —CH$_2$NH—;

R$^1$ represents: —C$_{6-10}$aryl (such as phenyl) optionally substituted by one, two or three groups independently selected from: —C$_{1-3}$alkyl (such as —CH$_3$), —C$_{1-5}$alkoxy (such as —OCH$_3$), —C$_{1-5}$haloalkyl (such as —CF$_3$), —OC$_{1-5}$haloalkyl (such as —OCF$_3$), —OC$_{3-5}$cycloalkyl or halogen (such as chloro, bromo or fluoro);

R$^2$ represents hydrogen, —C$_{1-6}$alkyl (such as —CH$_3$) or —C$_{1-3}$alkylOC$_{1-3}$alkyl (such as —CH$_2$OCH$_3$);

R$^3$ represents: —C$_{5-9}$heteroaryl optionally substituted by one, two or three groups independently selected from: —C$_{1-3}$alkyl (such as —CH$_3$), —C$_{1-6}$alkoxy (such as —OCH$_3$), —CO$_2$R$^4$, —C(=O)NR$^5$R$^6$, —C(=O)NHC$_{1-3}$alkylNR$^7$R$^8$, —C(=O)NHC$_{1-3}$alkylOC$_{1-3}$alkyl, —C(=O)NHC$_{1-3}$alkylOH, —C(=O)R$^9$, —C$_{1-6}$alkylOH (such as —CH$_2$OH or —C$_2$H$_{40}$H), —C=O, —CHO, —C$_{1-3}$alkylCO$_2$C$_{1-3}$alkyl, —C$_{1-3}$alkylOC$_{1-3}$alkyl, —C$_{1-5}$haloalkyl (such as —CF$_3$), —OC$_{1-5}$haloalkyl (such as —OCF$_3$), —OC$_{3-6}$cycloalkyl, —C$_{3-6}$cycloalkyl, or halogen (such as chloro, bromo or fluoro);

R$^4$ represents —H or —C$_{1-3}$alkyl (such as —CH$_3$ or —C$_2$H$_5$);

R$^5$ represents —H or —C$_{1-3}$alkyl (such as —CH$_3$);
R$^6$ represents —H or —C$_{1-3}$alkyl (such as —CH$_3$);
R$^7$ represents —H or —C$_{1-3}$alkyl (such as —CH$_3$);
R$^8$ represents —H or —C$_{1-3}$alkyl (such as —CH$_3$);
R$^9$ represents —C$_6$heterocycle (such as morpholine or piperazine) which is optionally substituted by a group independently selected from: —C$_{1-6}$alkyl (such as —CH$_3$);

or a pharmaceutically acceptable salt thereof.

Compounds of Formula LI may be synthesized by methods known in the art, e.g., those described in International Patent Publication No. WO2009/060054. In some embodiments, the SCD inhibitor is a compound disclosed in International Patent Publication No. WO2009/060054, the compounds of which are herein incorporated by reference.

In some embodiments, the SCD inhibitor is a compound of Formula LII:

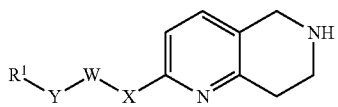

Formula LII wherein X represents —CONH— or —NHCO—;

R$^1$ represents: (i) a substituent selected from: H, —C$_{1-5}$ alkyl, —C$_{3-5}$cycloalkyl or —C$_{3-5}$cycloalkenyl; (ii) —C$_{6-10}$ aryl (such as phenyl or napthyl) optionally substituted by one, two or three groups independently selected from (a) —C$_{1-5}$alkyl (such as —CH$_3$), —C$_{1-5}$alkoxy (such as —OCH$_3$ or —OC$_4$H$_9$), —C$_{1-5}$haloalkyl (such as CF$_3$), —C$_{3-6}$cycloalkyl, —OC$_{1-6}$haloalkyl (such as —OCF$_3$), —CN, or halogen (such as chloro, bromo or fluoro); (b) —C$_{5-10}$aryl (such as phenyl), —C$_{5-10}$heteroaryl or —C$_{5-10}$ heterocyclyl, wherein the —C$_{5-10}$aryl (such as phenyl), —C$_{5-10}$heteroaryl or —C$_{5-10}$heterocyclyl ring is optionally substituted by one, two or three groups independently selected from: —C$_{1-5}$alkyl (such as —CH$_3$), —C$_{1-5}$alkoxy (such as —OCH$_3$), —C$_{1-5}$haloalkyl (such as —CF$_3$) or halogen (such as chloro, bromo or fluoro);

Y represents —CH$_2$— or —OCH$_2$—; and

W represents a —C$_{5-10}$heteroaryl optionally substituted by one, two or three —C$_{1-6}$alkyl (such as —CH$_3$) groups; or a pharmaceutically acceptable salt thereof.

Compounds of Formula LII may be synthesized by methods known in the art, e.g., those described in International Patent Publication No. WO2009/056556. In some embodiments, the SCD inhibitor is a compound disclosed in International Patent Publication No. WO2009/056556, the compounds of which are herein incorporated by reference.

In some embodiments, the SCD inhibitor is a compound of Formula LIII:

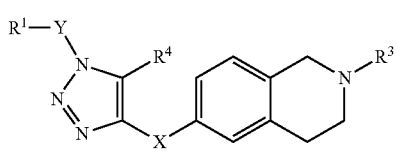

Formula LIII wherein X represents —CONH— or —NHCO—;

R$^1$ represents (i) a substituent selected from: —H or —C$_{1-6}$alkyl, (ii) —C$_{6-10}$aryl (such as phenyl or naphthyl) optionally substituted by one, two or three groups independently selected from: (a) —C$_{1-2}$alkyl (such as methyl), —C$_{1-6}$haloalkyl (such as —CF$_3$) or halogen (such as chloro, bromo or fluoro), (b) —C$_{6-10}$aryl (such as phenyl), —C$_{5-10}$ heteroaryl or —C$_{5-10}$heterocyclyl, wherein the —C$_{6-10}$aryl, —C$_{5-10}$heteroaryl or —C$_{5-10}$heterocyclyl ring is optionally substituted by one, two or three groups independently selected from: —C$_{1-3}$alkyl, —C$_{1-5}$alkoxy, or —C$_{1-6}$haloalkyl (such as —CF$_3$), (iii) benzothiophene or thiophene wherein the benzothiophene or thiophene is optionally substituted by one, two or three groups independently selected from: —C$_{1-6}$alkyl, —C$_{1-6}$haloalkyl (such as —CF$_3$), or halogen (such as chloro, bromo or fluoro), Y represents —CH$_2$— or —OCH$_2$—, R$^2$ represents H, R$^3$ represents —H or —C$_{1-2}$alkyl (such as methyl), or a pharmaceutically acceptable salt thereof.

Compounds of Formula LIII may be synthesized by methods known in the art, e.g., those described in International Patent Publication No. WO2009/016216. In some embodiments, the SCD inhibitor is a compound disclosed in International Patent Publication No. WO2009/016216, the compounds of which are herein incorporated by reference.

In some embodiments, the SCD inhibitor is a compound of Formula LIV:

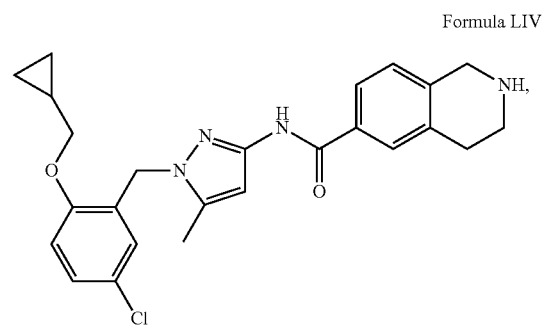 [SMILES: Cc1cc(NC(=O)c2ccc3c(c2)CCNC3)nn1Cc1cc(Cl)ccc1OCC1CC1]

Formula LIV or a pharmaceutically acceptable salt thereof.

Compounds of Formula LIV may be synthesized by methods known in the art, e.g., those described in International Patent Publication No. WO2009/010560. In some embodiments, the SCD inhibitor is a compound disclosed in International Patent Publication No. WO2009/010560, the compounds of which are herein incorporated by reference.

In some embodiments, the SCD inhibitor is a compound of Formula LV:

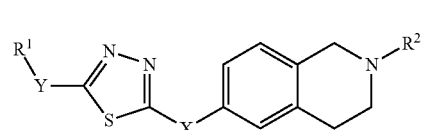

Formula LV wherein X represents —CONH—, —NHCO— or —N(CH$_3$)CO—,

R$^1$ represents (i) a substituent selected from: H, —C$_{1-6}$ alkyl or —C$_{3-6}$cycloalkyl, (ii) —C$_{6-10}$aryl (such as phenyl or naphthyl) optionally substituted by one, two or three groups independently selected from: (a) —C$_{1-6}$alkyl (such as —CH$_3$), —C$_{1-6}$haloalkyl (such as —CF$_3$), —C$_{3-6}$cycloalkyl, —C$_{1-5}$alkoxy (such as —OCH$_3$), —OR$^3$, —CN or halogen (such as chloro, bromo or fluoro), (b) —C$_{6-10}$aryl (such as phenyl), —C$_{5-10}$heteroaryl or —C$_{5-10}$heterocyclyl, wherein the —C$_{5-10}$aryl, —C$_{5-10}$heteroaryl or —C$_{5-10}$heterocyclyl ring is optionally substituted by one, two or three groups independently selected from: —C$_{1-6}$alkyl (such as —CH$_3$), —C$_{1-6}$haloalkyl (such as —CF$_3$), —C$_{1-6}$alkoxy (such as —OCH$_3$), —OR$^3$, —CN or halogen (such as chloro, bromo or fluoro), (iii) —C$_{5-10}$heteroaryl or —C$_{5-10}$ heterocyclyl wherein the —C$_{5-10}$heteroaryl or —C$_{5-10}$heterocyclyl is optionally substituted by one, two or three groups independently selected from: (a) —C$_{1-5}$alkyl (such as —CH$_3$), —C$_{1-5}$haloalkyl (such as —CF$_3$), —C$_{3-5}$cycloalkyl, —C$_{1-5}$alkoxy (such as —OCH$_3$), —OR$^3$, —CN or halogen (such as chloro, bromo or fluoro), (b) —C$_{5-10}$aryl (such as phenyl), —C$_{5-10}$heteroaryl or —C$_{5-10}$heterocyclyl wherein the —C$_{5-10}$aryl, —C$_{5-10}$heteroaryl or —C$_{5-10}$heterocyclyl ring is optionally substituted by one, two or three groups independently selected from: —C$_{1-6}$alkyl (such as —CH$_3$), —C$_{1-5}$haloalkyl (such as —CF$_3$), —C$_{1-5}$alkoxy (such as —OCH$_3$), —OR$^3$, —CN or halogen (such as chloro, bromo or fluoro), Y represents —(CH$_2$)$_m$—, —O(CH$_2$)$_m$— or —NR$^7$(CH$_2$)$_m$—, R$^2$ represents H, —C$_{1-5}$ alkyl, —C(=O)C$_{1-6}$alkyl, —C(=O)C$_{3-5}$cycloalkyl, —C(=O)C$_{6-10}$aryl, —C(=O)C$_{1-5}$alkylOH, —COC$_{1-3}$alkylNR$^4$R$^5$ or —C$_5$heteroarylR$^6$, R$^3$ represents —C$_{1-6}$haloalkyl (such as —CF$_3$) or —C$_{3-6}$ cycloalkyl, R$^4$ represents H or —C$_{1-3}$alkyl (such as —CH$_3$), R$^5$ represents H or —C$_{1-3}$alkyl (such as —CH$_3$), R$^6$ represents —C$_{1-3}$alkylOH, R$^7$ represents H or —C$_{1-3}$alkyl (such as —CH$_3$), and m represents integers from 1 to 4, or a pharmaceutically acceptable salt thereof.

Compounds of Formula LV may be synthesized by methods known in the art, e.g., those described in International Patent Publication No. WO2008/104524. In some embodiments, the SCD inhibitor is a compound disclosed in International Patent Publication No. WO2008/104524, the compounds of which are herein incorporated by reference.

In some embodiments, the SCD inhibitor is a compound of Formula LVI:

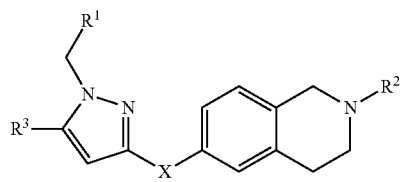

Formula LVI wherein X represents —CONH— or —NHCO—;

R$^1$ represents —C$_{5-10}$aryl (such as phenyl) substituted by —C$_{1-5}$alkoxy or —OC$_{1-5}$haloalkyl (such as —OCF$_3$), and is further optionally substituted by one or two groups independently selected from: (a) —C$_{1-5}$alkyl, —C$_{1-5}$alkoxy, —C$_{1-5}$haloalkyl (such as —CF$_3$), —OC$_{1-5}$haloalkyl (such as —OCF$_3$), —C$_{3-6}$cycloalkyl or halogen (such as chloro, bromo or fluoro), (b) —C$_{5-10}$aryl (such as phenyl), —C$_{5-10}$heteroaryl or —C$_{5-10}$heterocyclyl, wherein the —C$_{5-10}$aryl, —C$_{5-10}$heteroaryl or —C$_{5-10}$heterocyclyl ring is optionally substituted by one, two or three groups independently selected from: —C$_{1-6}$alkyl, —OR$^5$, —C$_{1-6}$haloalkyl (such as CF$_3$) or halogen (such as chloro, bromo or fluoro);

R$^2$ represents H or —C$_{2-6}$alkyl; and

R$^3$ represents —C$_{2-5}$alkyl or —C$_{3-5}$cycloalkyl;

or a pharmaceutically acceptable salt thereof.

Compounds of Formula LVI may be synthesized by methods known in the art, e.g., those described in International Patent Publication No. WO2008/074834. In some embodiments, the SCD inhibitor is a compound disclosed in International Patent Publication No. WO2008/074834, the compounds of which are herein incorporated by reference.

In some embodiments, the SCD inhibitor is a compound of Formula LVII:

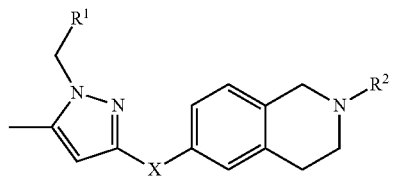

Formula LVII wherein X represents —CONH— or —NHCO—;

R$^1$ represents phenyl substituted by —OCH$_3$ or —OCF$_3$ and is further optionally substituted by one or two or three groups independently selected from: —C$_{1-6}$alkyl, —C$_{1-6}$alkoxy, —C$_{1-6}$haloalkyl (such as —CF$_3$), —OC$_{1-6}$haloalkyl (such as —OCF$_3$), —C$_{3-6}$cycloalkyl or halogen (such as chloro, bromo or fluoro); and R$^2$ represents H or —C$_{2-6}$alkyl;

or a pharmaceutically acceptable salt thereof.

Compounds of Formula LVII may be synthesized by methods known in the art, e.g., those described in International Patent Publication No. WO2008/074833. In some embodiments, the SCD inhibitor is a compound disclosed in International Patent Publication No. WO2008/074833, the compounds of which are herein incorporated by reference.

In some embodiments, the SCD inhibitor is a compound of Formula LVIII:

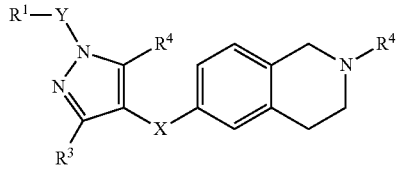

Formula LVIII wherein X represents —CONH—, —NHCO— or —NHCONH—,

R$^1$ represents (i) a substituent selected from: H, —C$_{1-5}$alkyl or —C$_{3-5}$cycloalkyl, (ii) —C$_{6-10}$aryl (such as phenyl or naphthyl) optionally substituted by one, two or three groups independently selected from: (a) —C$_{1-5}$alkyl (such as —CH$_3$), —C$_{1-5}$haloalkyl (such as —CF$_3$), —C$_{3-5}$cycloalkyl, —C$_{1-6}$alkoxy (such as —OCH$_3$), —OR$^5$, —CN or halogen (such as chloro, bromo or fluoro), (b) —C$_{5-10}$aryl (such as phenyl), —C$_{5-10}$heteroaryl or —C$_{5-10}$heterocyclyl, wherein the —C$_{6-10}$aryl, —C$_{5-10}$heteroaryl or —C$_{5-10}$heterocyclyl ring is optionally substituted by one, two or three groups independently selected from: —C$_{1-6}$alkyl (such as —CH$_3$), —OR$^5$, —C$_{1-6}$alkoxy (such as —OCH$_3$), —C$_{1-6}$haloalkyl (such as —CF$_3$), —CN or halogen (such as chloro, bromo or fluoro), (iii) —C$_{5-10}$heteroaryl or —C$_{5-10}$heterocyclyl wherein the —C$_{5-10}$heteroaryl or —C$_{5-10}$heterocyclyl is optionally substituted by one, two or three groups independently selected from: (a) —C$_{1-5}$alkyl (such as —CH$_3$), —C$_{1-5}$haloalkyl (such as —CF$_3$), —C$_{3-5}$cycloalkyl, —C$_{1-5}$alkoxy (such as —OCH$_3$), —OR$^5$, —CN or halogen (such as chloro, bromo or fluoro), (b) —C$_{6-10}$aryl (such as phenyl), —C$_{5-10}$heteroaryl or —C$_{5-10}$heterocyclyl wherein the —C$_{5-10}$ aryl, —C$_{5-10}$heteroaryl or —C$_{5-10}$heterocyclyl ring is optionally substituted by one, two or three groups independently selected from: —C$_{1-6}$alkyl (such as —CH$_3$), —OR$^5$, —C$_{1-6}$alkoxy (such as —OCH$_3$), —C$_{1-6}$haloalkyl (such as —CF$_3$), —CN or halogen (such as chloro, bromo or fluoro), Y represents —(CH$_2$)$_m$— or —O(CH$_2$)$_m$—, one of R$^2$ or R$^3$ represents hydrogen and the other represents H, —C$_{1-6}$alkyl (such as —CH$_3$) or —C$_{3-5}$cycloalkyl, R$^4$ represents H, —C$_{1-6}$alkyl, —C(=O)C$_{1-5}$alkyl, —C(=O)C$_{3-6}$cycloalkyl, or —C$_2$C$_{1-6}$alkyl, R$^5$ represents —C$_{1-6}$haloalkyl (such as —CF$_3$) or —C$_{3-6}$cycloalkyl, and m represents integers from 1 to 3, or a pharmaceutically acceptable salt thereof.

Compounds of Formula LVIII may be synthesized by methods known in the art, e.g., those described in International Patent Publication No. WO2008/074824. In some embodiments, the SCD inhibitor is a compound disclosed in International Patent Publication No. WO2008/074824, the compounds of which are herein incorporated by reference.

In some embodiments, the SCD inhibitor is a compound of Formula LIX:

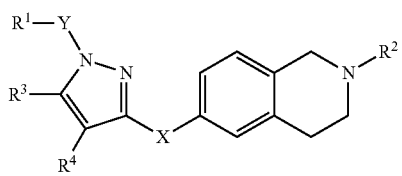

Formula LIX wherein X represents —CONH— or —NHCO—;

R$^1$ represents (i) a substituent selected from: —C$_{1-6}$alkyl or —C$_{3-6}$cycloalkyl, (ii) —C$_{5-10}$aryl (such as phenyl) optionally substituted by one, two or three groups independently selected from: (a) —C$_{1-6}$alkyl (such as —CH$_3$), —C$_{1-6}$haloalkyl (such as —CF$_3$), —C$_{3-6}$cycloalkyl or halogen (such as chloro, bromo or fluoro), (b) —C$_{5-10}$aryl (such as phenyl), —C$_{5-10}$heteroaryl or —C$_{5-10}$heterocyclyl, wherein the —C$_{5-10}$aryl, —C$_{5-10}$heteroaryl or —C$_{5-10}$heterocyclyl ring is optionally substituted by one, two or three groups independently selected from: —C$_{1-6}$alkyl, —OR$^5$, —C$_{1-6}$haloalkyl (such as —CF$_3$) or halogen (such as chloro, bromo or fluoro), (iii) —C$_{5-10}$heteroaryl or —C$_{5-10}$heterocyclyl wherein the —C$_{5-10}$heteroaryl or —C$_{5-10}$heterocyclyl is optionally substituted by one, two or three groups independently selected from: (a) —C$_{1-5}$alkyl, —C$_{1-5}$haloalkyl (such as —CF$_3$), —C$_{3-5}$cycloalkyl, —C$_{1-5}$alkoxy, —OC$_{1-6}$haloalkyl, —O(CH$_2$)$_n$C$_{3-6}$cycloalkyl, —OR$^5$ or halogen (such as chloro, bromo or fluoro), (b) —C$_{5-10}$aryl (such as phenyl), —C$_{5-10}$heteroaryl or —C$_{5-10}$heterocyclyl wherein the —C$_{5-10}$aryl, —C$_{5-10}$heteroaryl or —C$_{5-10}$heterocyclyl ring is optionally substituted by one, two or three groups independently selected from: —C$_{1-6}$alkyl, —OR$^5$, —C$_{1-6}$haloalkyl (such as —CF$_3$) or halogen (such as chloro, bromo or fluoro), R$^2$ represents H or —C$_{2-6}$alkyl;

R$^3$ and R$^4$ independently represent hydrogen, —C$_{1-6}$alkyl (such as methyl) or —C$_{3-6}$cycloalkyl with the proviso that R$^3$ and R$^4$ do not both represent hydrogen;

R$^5$ represents —C$_{1-6}$haloalkyl (such as —CF$_3$) or —C$_{3-6}$cycloalkyl; and n represents integers from 0 to 6;

or a pharmaceutically acceptable salt thereof.

Compounds of Formula LIX may be synthesized by methods known in the art, e.g., those described in International Patent Publication No. WO2008/074832. In some embodiments, the SCD inhibitor is a compound disclosed in International Patent Publication No. WO2008/074832, the compounds of which are herein incorporated by reference.

In some embodiments, the SCD inhibitor is a compound of Formula LX:

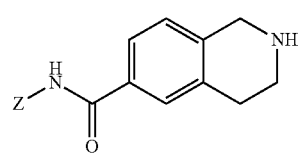

Formula LX wherein Z represents:

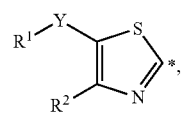

(A)

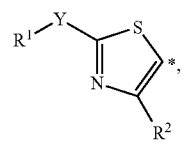

(B)

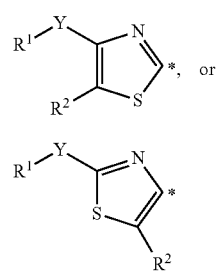

(C)

(D)

where * represents the point of attachment, when Z represents (A) or (B) then R$^1$ represents (i) H or —C$_{1-6}$alkyl, (ii) —C$_{6-10}$aryl (such as phenyl or napthyl) optionally substituted by one, two or three groups independently selected from: (a) —C$_{1-6}$alkyl (such as —CH$_3$), —C$_{1-6}$haloalkyl (such as —CF$_3$), —C$_{3-6}$cycloalkyl, —C$_{1-6}$alkoxy (such as —OCH$_3$ or —OCH$_2$CH(CH$_3$)$_2$), —OR$^3$, —CN, —NO$_2$ or halogen (such as chloro, bromo or fluoro), (b) —C$_{6-10}$aryl (such as phenyl), —C$_{5-10}$heteroaryl or —C$_{5-10}$heterocyclyl, wherein the —C$_{5-10}$aryl, —C$_{5-10}$heteroaryl or —C$_{5-10}$heterocyclyl ring is optionally substituted by one, two or three groups independently selected from: —C$_{1-5}$alkyl (such as —CH$_3$), —C$_{1-5}$haloalkyl (such as —CF$_3$), —C$_{3-5}$cycloalkyl, —C$_{1-5}$alkoxy (such as —OCH$_3$), —OR$^3$, —CN, —NO$_2$ or halogen (such as chloro, bromo or fluoro), (iii) —C$_{5-10}$heteroaryl or —C$_{5-10}$heterocyclyl wherein the —C$_{5-10}$heteroaryl or —C$_{5-10}$heterocyclyl is optionally substituted by one, two or three groups independently selected from: (a) —C$_{1-5}$alkyl (such as —CH$_3$), —C$_{1-5}$haloalkyl (such as —CF$_3$), —C$_{3-5}$cycloalkyl, —C$_{1-6}$alkoxy (such as —OCH$_3$), —OR$^3$, —CN, —NO$_2$ or halogen (such as chloro, bromo or fluoro), (b) —C$_{6-10}$aryl (such as phenyl), —C$_{5-10}$heteroaryl or —C$_{5-10}$heterocyclyl wherein the —C$_{5-10}$aryl, —C$_{5-10}$heteroaryl or —C$_{5-10}$heterocyclyl ring is optionally substituted by one, two or three groups independently selected from: —C$_{1-5}$alkyl (such as —CH$_3$), —C$_{1-5}$haloalkyl (such as —CF$_3$), —C$_{3-5}$cycloalkyl, —C$_{1-5}$alkoxy (such as —OCH$_3$), —OR$^3$, —CN, —NO$_2$ or halogen (such as chloro, bromo or fluoro), Y represents —(CH$_2$)$_m$— or —CONHCH$_2$—, R$^2$ represents H, —C$_{1-5}$alkyl (such as —CH$_3$, —C$_2$H$_4$ or —C$_3$H$_7$) or —C$_{3-5}$cycloalkyl, R$^3$ represents —C$_{1-6}$haloalkyl (such as —CF$_3$) or —C$_{3-6}$cycloalkyl, and m represents 1 or 2, when Z represents (C) or (D) than R$^1$ represents: (i) —C$_{6-10}$aryl (such as phenyl or napthyl) optionally substituted by one, two or three groups independently selected from: (a) —C$_{1-5}$alkyl (such as —CH$_3$), —C$_{1-5}$haloalkyl (such as —CF$_3$), —C$_{3-5}$cycloalkyl, —OR$^3$, —CN, —NO$_2$ or halogen (such as chloro, bromo or fluoro), (b) —C$_{6-10}$aryl (such as phenyl), —C$_{5-10}$heteroaryl or —C$_{5-10}$ heterocyclyl, wherein the —C$_{5-10}$aryl, —C$_{5-10}$heteroaryl or —C$_{5-10}$heterocyclyl ring is optionally substituted by one, two or three groups independently selected from: —C$_{1-5}$alkyl (such as —CH$_3$), —C$_{1-5}$haloalkyl (such as —CF$_3$), —C$_{3-5}$cycloalkyl, —C$_{1-5}$alkoxy (such as —OCH$_3$), —OR$_3$, —CN, —NO$_2$ or halogen (such as chloro, bromo or fluoro), (ii) —C$_{5-10}$heteroaryl or —C$_{5-10}$heterocyclyl wherein the —C$_{5-10}$heteroaryl or —C$_{5-10}$heterocyclyl is optionally substituted by one, two or three groups independently selected from: (a) —C$_{1-5}$alkyl (such as —CH$_3$), —C$_{1-5}$haloalkyl (such as —CF$_3$), —C$_{3-5}$cycloalkyl, —C$_{1-6}$alkoxy (such as —OCH$_3$), —OR$^3$, —CN, —NO$_2$ or halogen (such as chloro, bromo or fluoro), (b) —C$_{6-10}$aryl (such as phenyl), —C$_{5-10}$heteroaryl or —C$_{5-10}$heterocyclyl wherein the —C$_{5-10}$aryl, —C$_{5-10}$heteroaryl or —C$_{5-10}$heterocyclyl ring is optionally substituted by one, two or three groups independently selected from: —C$_{1-5}$alkyl (such as —CH$_3$), C$_{1-5}$haloalkyl (such as —CF$_3$), —C$_{3-5}$cycloalkyl, —C$_{1-5}$alkoxy (such as —OCH$_3$), —OR$^3$, —CN, —NO$_2$ or halogen (such as chloro, bromo or fluoro), Y represents —(CH$_2$)$_m$—, R$^2$ represents H, —C$_{1-5}$alkyl (such as —CH$_3$ or —C$_2$H$_4$) or —C$_{3-5}$cycloalkyl, R$^3$ represents, —C$_{1-6}$haloalkyl (such as —CF$_3$) or —C$_{3-6}$cycloalkyl, and m represents 0, 1, or 2, or a pharmaceutically acceptable salt thereof.

Compounds of Formula LX may be synthesized by methods known in the art, e.g., those described in International Patent Publication No. WO2009/150196. In some embodiments, the SCD inhibitor is a compound disclosed in International Patent Publication No. WO2009/150196, the compounds of which are herein incorporated by reference.

In some embodiments, the SCD inhibitor is a compound of Formula LXI:

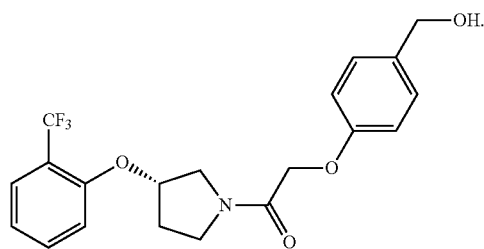

Formula LXI

Compounds of Formula LXI may be synthesized by methods known in the art, e.g., those described in International Patent Publication No. WO2009/019566. In some embodiments, the SCD inhibitor is a compound disclosed in International Patent Publication No. WO2009/019566, the compounds of which are herein incorporated by reference.

In some embodiments, the SCD inhibitor is a compound disclosed in any one of International Patent Publication Nos. WO2015/137385, WO2015/132610, WO2014/116386, WO2013/160811, WO2012/046681, WO2011/131593, WO2011/030312, WO2011/015629, WO2010/045374, WO2010/045371, WO2010/035052, WO2010/006962, WO2010/007482, WO2009/124259, WO2013/134546, WO2013/085954, WO2013/085957, WO2011/011508, WO2011/011506, WO2010/056230, WO2009/070533, WO2009/037542, WO2008/139845, WO2008/120744, WO2008/120759, WO2008/123469, WO2008/116898, WO2008/096746, WO2008/062276, WO2008/056687, WO2008/044767, WO2008/043087, WO2008/029266, WO2008/003753, WO2006/057902, WO2006/015621, WO2005/011657, nd WO1999/063979, U.S. Patent Publication Nos. US2012/252850, US2010/160323, US2009/253738, US2009/170822, US2009/253693, US2009/149466, US2008/249100, US2008/255130, US2008/255161, US2007/087363, and US2005/119242, Japanese Patent Publication Nos. JP2010/043052, JP2009/019013, and JP2005/213233, and Korean Patent Publication Nos. KR2015/014719 and KR2015/015305, the compounds of each of which are herein incorporated by reference.

In some embodiments, the SCD inhibitor is a nucleic acid molecule capable of mediating RNA interference against SCD genes. For example, in some embodiments, the SCD inhibitor is a small nucleic acid molecule such as a short interfering nucleic acid (siNA), a short interfering RNA (siRNA), a double-stranded RNA (dsRNA), a micro-RNA (miRNA), or short hairpin RNA (shRNA) capable of mediating RNA interference against SCD genes. Nucleic acid molecules capable of mediating RNA interference against SCD genes may be synthesized by methods known in the art, e.g., those described in International Patent Publication Nos. WO2003/070885 and WO2005/014607 and U.S. Patent Publication No. US2005/256068. In some embodiments, the SCD inhibitor is a nucleic acid molecule disclosed in International Patent Publication Nos. WO2003/070885 or WO2005/014607, or U.S. Patent Publication No. US2005/0256068, the nucleic acid molecules of each of which are herein incorporated by reference.

Chemical Terms

It is to be understood that the terminology employed herein is for the purpose of describing particular embodiments and is not intended to be limiting.

The term "acyl," as used herein, represents a hydrogen or an alkyl group, as defined herein, that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). An alkylene is a divalent alkyl group.

The term "alkenyl," as used herein, alone or in combination with other groups, refers to a straight-chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight-chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents —N($R^{N1}$)$_2$, wherein each $R^{N1}$ is, independently, H, OH, NO$_2$, N($R^{N2}$)$_2$, SO$_{2}$$R^{N2}$, SO$_2$$R^{N2}$, SOR$^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., —NH$_2$) or a substituted amino (i.e., —N($R^{N1}$)$_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_{1-6}$alkyl $C_{6-10}$aryl, $C_{1-10}$alkyl $C_{6-10}$aryl, or $C_{1-20}$alkyl $C_{6-10}$aryl), such as, benzyl and phenethyl. In some embodiments, the alkyl and the aryl each can be further substituted with 1, 2, 3, or 4 substituent groups as defined herein for the respective groups.

The term "azido," as used herein, represents a —N$_3$ group.

The term "cyano," as used herein, represents a —CN group.

The terms "carbocyclyl," as used herein, refer to a non-aromatic $C_{3-12}$monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, and adamantyl.

The term "halogen," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_{1-6}$alkyl $C_{2-9}$heteroaryl, $C_{1-10}$alkyl $C_{2-9}$heteroaryl, or $C_{1-20}$alkyl $C_{2-9}$heteroaryl). In some embodiments, the alkyl and the heteroaryl each can be further substituted with 1, 2, 3, or 4 substituent groups as defined herein for the respective groups.

The term "heterocyclyl," as used herein, denotes a mono- or polycyclic radical having 3 to 12 atoms having at least one ring containing one, two, three, or four ring heteroatoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_{1-6}$ alkyl $C_{2-9}$ heterocyclyl, $C_{1-10}$ alkyl $C_{2-9}$ heterocyclyl, or $C_{1-20}$ alkyl $C_{2-9}$ heterocyclyl). In some embodiments, the alkyl and the heterocyclyl each can be further substituted with 1, 2, 3, or 4 substituent groups as defined herein for the respective groups.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., NH$_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more Definitions The term "alpha-synuclein" refers to proteins whose amino acid sequence comprises or consists of an amino acid sequence of a naturally occurring wild-type alpha-synuclein protein as well as proteins whose amino acid sequence comprises or consists of an amino acid sequence of a naturally occurring mutant alpha-synuclein protein. Alpha-synuclein is also referred to as synuclein alpha (SNCA). Human alpha-synuclein has NCBI Gene ID NO 6622. Alpha-synuclein is considered an intrinsically disordered protein. Naturally occurring mutant alpha-synuclein proteins include A53T, A30P, E46K, H50Q, and G51 D.

As used herein, "alpha-synuclein-induced toxicity" and "alpha-synuclein-mediated toxicity" are used interchangeably to refer to a reduction, impairment, or other abnormality in one or more cellular functions or structures, a reduction in growth or viability, or a combination thereof, occurring as a result of or associated with expression of an alpha-synuclein protein. In the context of a yeast cell, alpha-synuclein-mediated toxicity may be manifested as a reduction in growth or viability, e.g., reduced viability or non-viability, or a reduction, impairment, or other abnormality in one or more cellular functions or structures, e.g., reduction, impairment, or other abnormality in endocytosis or vesicle trafficking. In the context of a neuron or glial cell, e.g., a mammalian neuron or glial cell, alpha-synuclein-mediated toxicity may be manifested as a reduction in growth or viability, e.g., reduced viability or non-viability, or a reduction, impairment, or other abnormality in one or more cellular functions or structures. Cellular functions include any of the biological processes and pathways performed in a cell or by a cell, either itself or together with one or more other cells, in vitro or in vivo (e.g., in the context of a tissue or organ in vivo). In some embodiments, a cellular function is endocytosis, vesicle trafficking, axonal transport, mitochondrial function (e.g., ATP production), neurite outgrowth, neurotransmission, neurogenesis, or maintaining homeostasis. Alpha-synuclein-mediated toxicity toxicity in vivo may be manifested to a variety of extents and in a variety of ways ranging from cellular dysfunction to death. In some embodiments alpha-synuclein-mediated toxicity may be evidenced in a subject by development of a synucleinopathy or by an increased propensity to develop a synucleinopathy. In some embodiments alpha-synuclein-mediated toxicity may be manifested as a decrease or defect in cognition, behavior, or memory, as compared with a normal control. In some embodiments, contacting mammalian cells or treating a mammalian subject with an agent as described herein alleviates one or more manifestations of alpha-synuclein-mediated toxicity.

The term "apolipoprotein E (ApoE)" refers to proteins whose amino acid sequence comprises or consists of an amino acid sequence of a naturally occurring wild type ApoE protein as well as proteins whose amino acid sequence comprises or consists of an amino acid sequence of a naturally occurring allelic variant ApoE protein. Human APOE has NCBI Gene ID NO 348. APOE has three common alleles in humans: APOE ε2 (frequency 8%), APOE ε3 (frequency 80%), and APOE ε4 (frequency 14%). The proteins encoded by the three common APOE alleles differ at two amino acids, located at positions 112 and 158 in the mature protein. ApoE2 has cysteine at residues 112 and 158; ApoE3 has cysteine at residue 112 and arginine at residue 158; and ApoE4 has arginine at residues 112 and 158. Human ApoE protein is naturally synthesized as a precursor polypeptide of 317 amino acids, including an 18 amino acid signal sequence, which is cleaved to produce the mature 299 amino acid polypeptide. The sequence of human ApoE3 precursor polypeptide is found under NCBI RefSeq Acc. No. NP_000032.1. Naturally occurring ApoE mutations include ApoE4(L28P), which confers on carriers an increased risk for late-onset AD that remains significant even after adjusting for the effect of ApoE4 itself (Kamboh et al. *Neurosci Lett.* 263(2-3):129-32, 1999). Other variants include E13K, R136C, G196S, Q248E, R251G, and G278W (Tindale et al., *Neurobiology of Aging* 35, 727e1-727e3, 2014).

As used herein, "ApoE-induced toxicity" and "ApoE-mediated toxicity" are used interchangeably to refer to a reduction, impairment, or other abnormality in one or more cellular functions or structures, a reduction in growth or viability, or a combination thereof, occurring as a result of or associated with expression of an ApoE protein. In the context of a yeast cell, ApoE-mediated toxicity may be manifested as a reduction in growth or viability, e.g., reduced viability or non-viability, or a reduction, impairment, or other abnormality in one or more cellular functions or structures, e.g., reduction, impairment, or other abnormality in endocytosis or vesicle trafficking. In the context of a neuron or glial cell, e.g., a mammalian neuron or glial cell, ApoE-mediated toxicity may be manifested as a reduction in growth or viability, e.g., reduced viability or non-viability, or a reduction, impairment, or other abnormality in one or more cellular functions or structures. Cellular functions include any of the biological processes and pathways performed in a cell or by a cell, either itself or together with one or more other cells, in vitro or in vivo (e.g., in the context of a tissue or organ in vivo). In some embodiments, a cellular function is endocytosis, vesicle trafficking, axonal transport, mitochondrial function (e.g., ATP production), neurite outgrowth, neurotransmission, neurogenesis, or maintaining homeostasis. ApoE-mediated toxicity in vivo may be manifested to a variety of extents and in a variety of ways ranging from cellular dysfunction to death. In some embodiments ApoE-mediated toxicity may be evidenced in a subject by development of an ApoE-mediated disease (or one or more symptoms or signs of an ApoE-mediated disease) or by an increased propensity to develop an ApoE-mediated disease in subjects who express a particular ApoE isoform. In some embodiments ApoE-mediated toxicity may be manifested at least in part as an increase in the formation, deposition, accumulation, or persistence of amyloid beta aggregates or an increase in amyloid beta-mediated toxicity as compared with a normal control. In some embodiments ApoE-mediated toxicity may be manifested as a decrease or defect in cognition, behavior, or memory, as compared with a normal control. In some embodiments, contacting mammalian cells or treating a mammalian subject with an agent as described herein alleviates one or more manifestations of ApoE-mediated toxicity.

By "determining the level of a protein" is meant the detection of a protein or mRNA by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

In the practice of the methods of the present invention, an "effective amount" of any one of the compounds of the invention or a combination of any of the compounds of the invention or a pharmaceutically acceptable salt thereof, is administered via any of the usual and acceptable methods known in the art, either singly or in combination.

By "level" is meant a level of a protein or mRNA, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, µg/mL, ng/mL) or percentage relative to total protein or mRNA in a sample.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "neurodegenerative disorder" refers to a disorder characterized by progressive loss of the number (e.g., by cell death), structure, and/or function of neurons. In some instances, a neurodegenerative disease may be associated with protein misfolding, defects in protein degradation, genetic defects, programmed cell death, membrane damage, or other processes. Exemplary, non-limiting neurodegenerative disorders include AD, PD, ApoE-associated neurodegenerative disorders, Alpers' disease, ataxia telangectsia, Canavan disease, Cockayne syndrome, corticobasal degeneration, Kennedy's disease, Krabbe disease, Pelizaeus-Merzbacher disease, primary lateral sclerosis, Refsum's disease, Sandhoff disease, Schilder's disease, Steele-Richardson-Olszewski disease, tabes dorsalis, vascular dementia, and Guillain-Barre Syndrome.

An "ApoE-associated neurodegenerative disorder" refers to a neurodegenerative disorder that is associated with and/or mediated at least in part by an ApoE protein (e.g., ApoE4). Exemplary ApoE-associated neurodegenerative disorders include, e.g., Alzheimer's disease (AD), dementia with Lewy bodies (DLB; also referred to as "Lewy body dementia"), mild cognitive impairment (MCI), frontotemporal dementia (FTD), cerebral amyloid angiopathy (CAA), CAA-associated intracerebral hemorrhage, vascular cognitive impairment, Parkinson's disease (PD), multiple sclerosis (MS), traumatic brain injury (TBI), or Fragile X-associated tremor/ataxia syndrome.

A "neurological disorder," as used herein, refers to a disorder of the nervous system, for example, the central nervous system (CNS). Examples of neurological disorders include, without limitation, proteopathies (e.g., synucleinopathies, tauopathies, prion diseases, and amyloidosis (e.g., Aβ-amyloidosis) and/or neurodegenerative disorders (e.g., ApoE-associated neurodegenerative disorders).

It is to be understood that the above lists are not all-inclusive, and that a disorder or disease may fall within various categories. For example, Alzheimer's disease can be considered a neurodegenerative disease, a proteopathy, and, in some instances, may also be considered a synucleinopathy. Likewise, Parkinson's disease can be considered a neurodegenerative disease and a proteopathy.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of formula (I). For example pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in Pharmaceutical Salts: Properties, Selection, and Use, (Eds. P. H. Stahl and C. G.

Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

A "proteopathy" is a disorder that is characterized by structural abnormalities of proteins (e.g., protein misfolding and/or protein aggregation) that disrupt the function of cells, tissues, and/or organs of a subject. In some cases, misfolding can lead to loss of a protein's usual function. In other cases, a misfolded protein can gain toxic functions. In some cases, proteins can be induced to have structural abnormalities by exposure to the same (or a similar) protein that has folded into a disease-causing conformation (e.g., amyloid beta, tau, alpha-synuclein, superoxide dismutase-1 (SOD-1), polyglutamine, prion, and TAR DNA-binding protein-43 (TDP-43)). Exemplary, non-limiting proteopathies include AD, Parkinson's disease, Alexander disease, amyotrophic lateral sclerosis (ALS), a prion disease (e.g., Creutzfeldt-Jakob disease), Huntington's disease, Machado-Joseph disease, Pick's disease, or frontotemporal dementia.

By a "reference" is meant any useful reference used to compare protein or mRNA levels related to neurological disorders. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having neurological disorders; a sample from a subject that is diagnosed with cardiac artery aneurysms or stenosis; a sample from a subject that has been treated for neurological disorders; or a sample of a purified protein (e.g., any described herein) at a known normal concentration. By "reference standard or level" is meant a value or number derived from a reference sample. A "normal control value" is a predetermined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a neurological disorder. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

A "synucleinopathy" is a disorder characterized by misfolding and/or abnormal accumulation of aggregates of alpha-synuclein in the central nervous system (e.g., in neurons or glial cells). Exemplary, non-limiting synucleinopathies include Parkinson's disease (PD), dementia with Lewy bodies, pure autonomic failure, multiple system atrophy, incidental Lewy body disease, pantothenate kinase-associated neurodegeneration, Alzheimer's disease, Down's Syndrome, Gaucher disease, or the Parkinsonism-dementia complex of Guam.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

BRIEF DESCRIPTION OF THE DRAWINGS

The application file contains at least one drawing executed in color. Copies of this patent or patent application with color drawings will be provided by the Office upon request and payment of the necessary fee.

(FIG. 1A) Compound 1, a representative 1,2,4-oxadiazole, was profiled in ApoE4 (top) and control (bottom) non-inducing conditions at 12-point dose (x-axis). The Y-axis shows raw $OD_{600}$. Compound 1 exhibited a bell-shaped dose-response curve (DRC) in the ApoE4 model. Rescue decreased at concentrations just above the maximal efficacy (Emax). In the control condition (bottom panel), growth decreased at this same concentration. (FIG. 1B) The relationship between Emax (rescue in ApoE4) and growth inhibition (in the control condition) correlated across 34 tested 1,2,4-oxadiazoles. The maximal rescue dose (EC100) is shown on the y-axis for ApoE4 and minimal inhibitory dose (IC100) in the control condition is shown on the x-axis. This correlation indicates that growth inhibition is caused by the same on-target activity that rescues ApoE4 toxicity.

(FIG. 2A) Growth inhibition (24 h) of strain GM yap1 flr1 by Ole1/SCD-targeting 1,2,4-oxadiazoles is reversed by exogenous 0.5 mM oleic/palmitoleic acid, which did not affect growth inhibition by other compounds (black dots indicate other scaffolds tested). Maximal growth inhibition across a dose range from 33 nM to 33 μM is plotted. (FIG. 2B) Rescue (40 h) of the yeast alpha-synuclein ("aSyn") model by 1,2,4-oxadiazoles was reversed by exogenous 0.5 mM oleic/palmitoleic acid, which did not affect rescue by other scaffolds. Maximal model rescue across a dose range from 33 nM to 33 μM is plotted.

(FIG. 3A) Yeast cells deleted for the chromosomal copy of OLE1 and expressing OLE1 (wild-type), ole1P123T, or ole1E188Q mutants from a pRS316-based plasmid were grown in complete synthetic medium (CSM)-glucose media at the indicated doses of 1,2,4-oxadiazole Compound 2 for 24 h. Growth was normalized to samples treated with the solvent control dimethyl sulfoxide (DMSO), set as "1". (FIG. 3B) Yeast cells deleted for the chromosomal copy of OLE1 and expressing OLE1 (Wild-type), ole1P123T, or ole1E188Q mutants from a pRS316-based plasmid were grown in CSM-galactose media (inducing expression of alpha-Synuclein) at the indicated doses of the 1,2,4-oxadiazole Compound 2 for 40 h. Growth was normalized to samples treated with the solvent control DMSO, where rescue is set as "1".

FIGS. 8A-8D are graphs showing that treatment of yeast cells with the 1,2,4-oxadiazole Compound 2 inhibits lipid desaturation. Exponentially-growing wild-type yeast cells were treated with the indicated doses of the 1,2,4-oxadiazole Compound 2 for the indicated times before cellular lysis, lipid extraction, and analysis by global LC-MS/MS profiling. The relative abundance (fraction of total cellular lipid signal) after 1.5 h and 8 h of the most abundant saturated lipid, phosphatidylcholine 26:0, is depicted in FIGS. 8A and 8B, respectively. The relative abundance after 1.5 h and 8 h drug treatment of the most abundant lipid with 2 or more degrees of unsaturation, phosphatidylcholine 16:1; 18:1, is depicted in FIGS. 8C and 8D, respectively. The data indicate a >300-fold increase in the abundance of the saturated lipid phosphatidylcholine 26:0 after 8 h treatment with Compound 2, and a >12-fold decrease in the abundance of the unsaturated lipid phosphatidylcholine 16:1, 18:1, indicating that Compound 2 blocks cellular fatty acid desaturase activity (Ole1 is the only fatty acid desaturase in yeast).

(FIG. 11A) Total RNA was extracted from differentiated human neurons derived from iPSC cells obtained from a patient with alpha-synuclein gene triplication (S3), U2OS cells and rat PC-12 cells. Quantitative reverse transcription-polymerase chain reaction (RT-PCR) was performed to quantify mRNA levels of human SCD1 (hSCD1) and human SCD5 (hSCD5). All samples were normalized to hSCD1 level in U2OS cells, which was set to 1.0. Bars depict mean values of triplicate determinations; error bars indicate standard deviation. (FIG. 11B) Analysis of SCD1 protein levels in S3 neurons and U2OS cells. Protein extracts from S3 and U2OS cells were analyzed by immunoblotting with an antibody specific for human SCD1. Duplicate immunoblots were probed with an antibody against R-tubulin as a loading control.

(FIG. 12A) Cellular heath was assessed 48 h after transfection by evaluating ATP levels. Cell toxicity in the alpha-synuclein plus SCR siRNA was set as the floor of the assay, and then all samples were normalized to pcDNA with SCD5 siRNA (set to 100%) to calculate the normalized percent rescue. Bars depict mean values of triplicate determinations; error bars indicate standard deviation. A two-tailed t-test was used to compare control conditions with SCR or SCD5 siRNA (*p 0.05). Cells transfected with alpha-synuclein were analyzed together by ANOVA with Dunnett's post-test to correct for multiple comparisons (p 0.01, **p 0.0001). Significance is shown for the comparison of each alpha-synuclein plus SCD5 siRNA concentration compared against the alpha-synuclein plus SCR control. (FIG. 12B) Quantitative RT-PCR was utilized to confirm the levels of SCD5 mRNA. Values shown are the fold change in SCD5 mRNA levels relative to the SCR controls at 24 hours.

FIGS. 18E and 18F show evaluation of brain samples for the relative levels of linoleic acid (18:2n6) (FIG. 18E) and gamma-linoleic acid (18:3n6) (FIG. 18F). Both species are essential omega-6 fatty acids, and both significantly increased with administration of SCD5-selective or non-selective compounds. n=8 for each group. Individual points plotted, mean indicated by black bars. Error bars represent standard deviation. Data was analyzed by one-way ANOVA with Tukey's post-hoc test to account for multiple comparisons. $p<0.01$, *$p<0.005$, ****$p<0.0001$. Upper black bars across graph and corresponding black significance marks indicate comparison to vehicle controls. Lower bars across graph and corresponding significance marks indicate comparison between the compound-treated groups. Non-significant changes/comparisons are indicated (n.s.).

DETAILED DESCRIPTION OF THE INVENTION

Figures 1A, 1B:
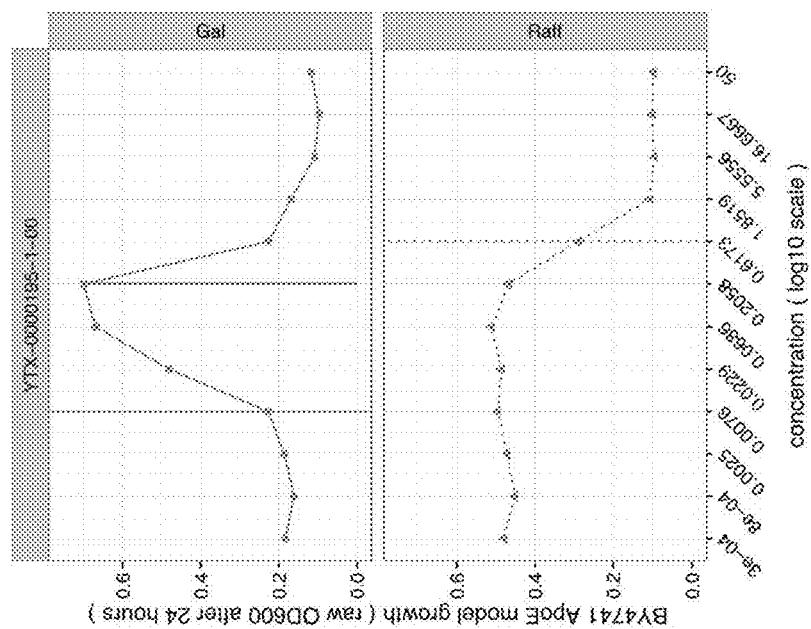
FIGS. 1A and 1B are graphs showing that growth inhibition of by 1,2,4-oxadiazoles occurs through same mechanism as the rescue of toxicity in the apolipoprotein E4 (ApoE4) Alzheimer's disease yeast model.

The present disclosure provides methods for the treatment of neurological disorders, e.g., by suppressing toxicity in cells related to protein misfolding and/or aggregation.

SCD Inhibitors

SCD inhibitors include any compound described herein such as a compound of any one of Formula I-LXI, or pharmaceutically acceptable salts thereof.

A number of approaches are known in the art for determining whether a compound modulates expression or activity of SCD, for example, to determine whether a compound is an SCD inhibitor (e.g., an SCD1 inhibitor and/or an SCD5 inhibitor), and any suitable approach can be used in the context of the invention. The SCD activity assay may be cell-based, cell-extract-based (e.g., a microsomal assay), a cell-free assay (e.g., a transcriptional assay), or make use of substantially purified proteins. For example, identification of compounds as SCD inhibitors can be performed using an SCD liver microsomal assay, for example, as described by Shanklin et al. *Proc. Natl. Acad. Sci. USA* 88:2510-2514, 1991 or Miyazaki et al. *J. Biol. Chem.* 275:30132-30138, 2000. In some instances, liquid-chromatography/mass spectrometry (LC/MS)-based approaches can be used to measure SCD activity, for example, as described by Dillon et al. *Anal. Chim. Acta.* 627(1):99-104, 2008. A high-throughput assay can be used, for example, as described by Soulard et al. *Anal. Chim. Acta.* 627(1):105-111, 2008. Still further approaches to measure SCD activity are described in U.S. Pat. No. 7,790,408.

Any suitable method can be used to determine whether a compound binds to SCD (e.g., SCD1 and/or SCD5), for instance, mass spectrometry, surface plasmon resonance (SPR), or immunoassays (e.g., immunoprecipitation or enzyme-linked immunosorbent assay).

Any suitable method can be used to determine whether a compound modulates expression of SCD (e.g., SCD1 and/or SCD5), for instance, Northern blotting, Western blotting, RT-PCR, mass spectrometry, or RNA sequencing.

Pharmaceutical Uses

The compounds described herein are useful in the methods of the invention and, while not bound by theory, are believed to exert their desirable effects through their ability to inhibit toxicity caused by protein misfolding and/or aggregation, e.g., α-synuclein misfolding and/or aggregation, in a cell.

Another aspect of the present invention relates to methods of treating and/or preventing a neurological disorders such as neurodegenerative diseases in a subject in need thereof. The pathology of neurodegenerative disease, may be characterized by the presence of inclusion bodies in brain tissue of affected patients.

In certain embodiments, neurological disorders that may be treated and/or prevented by the inventive methods include, but are not limited to, Alexander disease, Alpers' disease, AD, amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, PD, Pelizaeus-Merzbacher disease, Pick's disease, primary lateral sclerosis, Ref sum's disease, Sandhoff disease, Schilder's disease, Steele-Richardson-Olszewski disease, tabes dorsalis, and Guillain-Barre Syndrome.

Combination Formulations and Uses Thereof

The compounds of the invention can be combined with one or more therapeutic agents. In particular, the therapeutic agent can be one that treats or prophylactically treats any neurological disorder described herein.

Combination Therapies

A compound of the invention can be used alone or in combination with other agents that treat neurological disorders or symptoms associated therewith, or in combination with other types of treatment to treat, prevent, and/or reduce the risk of any neurological disorders. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65:S3-S6, 2005). In this case, dosages of the compounds when combined should provide a therapeutic effect.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20$^{th}$ ed.) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered. Preferred dose ranges include, for example, between 0.05-15 mg/kg or between 0.5-15 mg/kg.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

EXAMPLES

Example 1: Stearoyl-CoA Desaturase (SCD) is the Target of 1,2,4-Oxadiazoles, and SCD Inhibition Rescues Alpha-Synuclein and ApoE4-Dependent Toxicity in Yeast Disease Models A. Materials and Methods Strain Construction and OLE1 Replacement with SCD1 or SCD5

Strain GMYF was constructed from the ABC16/Green monster strain described in Suzuki et al. *Nat. Methods* 8(2):159-164, 2011. In this strain, YAP1 was deleted using a HIS3-MX6 cassette, and FLR1 was deleted using a NAT-MX6 cassette using standard methods. The knockout cassettes were PCR-amplified from plasmid templates (see, e.g., Bahler et al. *Yeast* 14(10):943-951, 1998; Longtine et al. *Yeast* 14(10):953-961, 1998) and transformed into yeast using lithium acetate-based transformation (Gietz et al. *Methods Mol. Biol.* 1205:1-12, 2014). The yap1::his3 deletion strain was selected on media lacking histidine and flr1::NAT on plates containing 100 µg/mL nourseothricin. All strains were confirmed by diagnostic PCR. Strain W303 pdr1Δ pdr3Δ was constructed from W303-1A (American Type Culture Collection (ATCC) 208352) by deleting PDR1 and PDR3 with kan-MX6 cassettes separately in MATa and MATa W303a isolates, mating, sporulating, and identifying the double deletion haploids by tetrad dissection and identification of non-parental ditype tetrads. Strain W-erg3 was derived from W303 pdr1 Δ pdr3Δ by deleting SNQ2 with NAT-MX6, YAP1 with HIS3-MX6, and ERG3 with BleMX.

Strain ApoE-mga2Δ was generated by amplifying 1000 base pairs (bp) upstream and downstream of the MGA2 ORF in a strain in which MGA2 was deleted using a G418 (GENETICIN®) resistance cassette (kanMX) (Piotrowski et al. *Proc. Natl. Acad. Sci. USA* 112(12):E1490-1497, 2015) and transforming the resulting deletion cassette into the ApoE4 strain in the BY4741 (ATCC 201388) genetic background. The ApoE strain is described, for example, in International Patent Application Publication No. WO 2016/040794, which is incorporated herein by reference in its entirety.

The alpha-synuclein expression strain was made in the same manner as described in Su et al. *Dis. Model Mech.* 3(3-4):194-208, 2010, except that the alpha-synuclein construct lacked the green fluorescent protein (GFP) tag.

Strain ole1Δ (yeast ole1 deletion mutant) was constructed by deleting OLE1 with NAT-MX6 in BY4741, amplifying the deletion cassette from the genomic DNA of the resulting strain with primers flanking the ORF by 1000 bp upstream and downstream, transforming the resulting deletion cassette into W303 pdr1Δ pdr3Δ, and plating transformants on YPD media containing G418 (200 µg/mL) and nourseothricin (100 µg/mL) with 0.01% TWEEN®-20 and 0.5 mM oleic and palmitoleic acids.

To generate yeast strains expressing SCD1 or SCD5 as the sole desaturase, the human SCD1 and SCD5 genes were cloned from cDNAs (Harvard PlasmID database Clone ID HsCD00340237 for SCD1 and HsCD00342695 for SCD5) into yeast plasmid pRS316 (ATCC 77145) between the yeast TDH3 promoter and the CYC1 terminator. The coding sequence of yeast OLE1 was also cloned into this plasmid). These clones were then transformed into the ole1d strain and plated on CSM-Ura media (CSM lacking uracil) with 2% glucose (w/v) and independent colonies were isolated and amplified.

Compound Profiling Methods

All compound profiling experiments were performed using the same basic protocol. Different genetic backgrounds (e.g., gene deletions) or conditions (e.g., addition of oleic and palmitoleic acid) were replaced as indicated below.

Yeast were cultured using standard techniques in complete synthetic media (CSM) and yeast nitrogen base supplemented with 2% (w/v) carbon source (glucose, raffinose, or galactose) to regulate the expression of the toxic disease protein. An initial starter culture was inoculated in 3 mL CSM-Glucose media and incubated overnight in a 30° C. shaker incubator (225 rpm). Saturated morning cultures were then diluted 1:20 in fresh CSM-Raffinose media and grown for 6 h to an $OD_{600}$ (optical density) of 0.4-0.8 at 30° C. with shaking.

Compound stocks (10 mM in 100% DMSO) were arrayed into 384 round well, v-bottom polypropylene plates and diluted according to indicated dilution factors. Compound administration was performed in two separate steps. First, 15 µL of CSM-Galactose (induces expression of toxic protein) was dispensed into clear 384 well assay plates using a MULTIDROP™ Combi reagent dispenser. The diluted compound stock plates were then applied to the assay plates using an automated workstation (Perkin Elmer JANUS™) outfitted with a 384 pin tool containing slotted pins that deliver 100 nL of compound. The cultures described above were then diluted to a 2× concentration (0.03 and 0.08 for alpha-synuclein and ApoE, final $OD_{600}$ of 0.015 and 0.04) in CSM-Galactose. For wild-type and Ole1/SCD1/SCD5 plasmid-containing strains, the 2× cell density was 0.02. In all experiments, 15 µL culture was then dispensed into the pinned assay plate to achieve 30 µL of the 1×$OD_{600}$ culture and a top drug concentration of 33.3 M. For 96-well assays (FIGS. 1A and 1B), compound dilutions in DMSO were generated in 96 well plates and 1 µL was manually pipetted into 96 well clear bottom assay plates.

For experiments with oleic and palmitoleic acid supplementation (FIGS. 2A, 2B, 4, and 5), TWEEN®-20 was first added to culture media at a concentration of 0.01%. Oleic and palmitoleic acid were both then added at the indicated concentrations (0.08 to 0.5 mM) and mixed thoroughly prior to compound pinning or the addition of yeast.

For experiments using a plasmid-borne copy of Ole1, SCD1, or SCD5 (FIGS. 3B, 6, and 7), media lacking uracil (SX-Ura, where X is glucose, raffinose, or galactose), was used for all steps of the compound profiling protocol to ensure its maintenance throughout the assay.

After yeast delivery, assay plates were incubated under humidified conditions at 30° C. for 24 to 40 h. ApoE4 rescue experiments were stopped at 24 h, aSyn experiments at 40 h, Ole1 at 24 h, and SCD1/SCD5 at 40 h. The growth of yeast was monitored by reading the $OD_{600}$ of each well using a microplate reader (Perkin Elmer EnVision™). Data were analyzed as follows. For model rescue experiments, raw data were processed by background subtracting and calculating a fold-change relative to DMSO control [(EXP-0.035)/(DMSO-0.035)—where 0.035 is the $OD_{600}$ contributed by an empty well containing 30 µL of media alone]. For growth inhibition of wild-type cells, raw data were processed by background subtracting and converting values to a percent of the nontreated condition for that strain [(EXP-0.035)/(DMSO-0.035)×100%].

Compound Sources

Compounds were sourced as follows: cycloheximide (Sigma Aldrich), A939572 (Abcam), CAY10566 (Abcam), MF-438 (Calbiochem), MK-8245 (Selleckchem), oleic acid (Sigma Aldrich), palmitoleic acid (Acros organics), mycophenolic acid (Sigma Aldrich), and tunicamycin (Cayman Chemical).

Compound 1 has the structure:

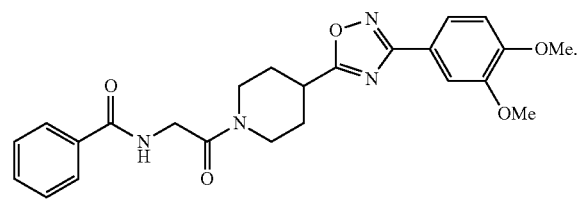 [SMILES: COc1ccc(-c2noc(C3CCN(C(=O)CNC(=O)c4ccccc4)CC3)n2)cc1OC]

Compound 1 may be synthesized by methods known in the art. For example, as shown in the scheme below:

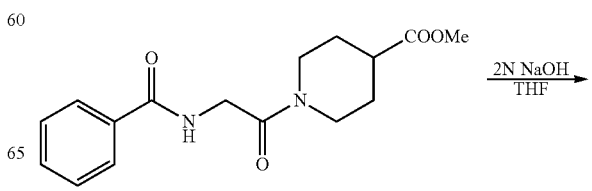

Step 1: Preparation of
1-(2-benzamidoacetyl)piperidine-4-carboxylic acid

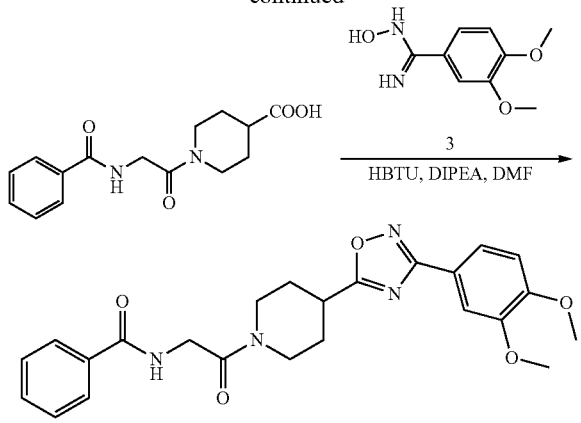

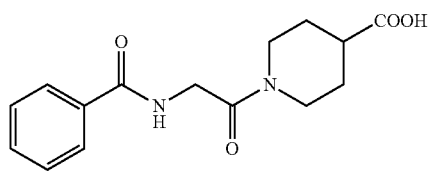 [SMILES: O=C(NCC(=O)N1CCC(C(=O)O)CC1)c1ccccc1]

To a stirred solution of methyl 1-(2-benzamidoacetyl) piperidine-4-carboxylate (5.0 g, 16.4 mmol) in tetrahydrofuran (50 mL) was added aqueous sodium hydroxide (2 M, 16.4 mL). The mixture was stirred at 20° C. for 2 h and then acidified by the addition of concentrated hydrochloric acid until pH 1. The mixture was extracted with dichloromethane (80 mL×3). The combined organic phases were washed with saturated aqueous sodium chloride solution (30 mL), dried over anhydrous sodium sulfate, filtered, and concentrated to give crude product 1-(2-benzamidoacetyl)piperidine-4-carboxylic acid (3.25 g, 11.2 mmol, 68%) as a yellow solid. $^1$H NMR (400 MHz, Methanol-d4) δ 7.87 (d, J=7.5 Hz, 2H), 7.59-7.42 (m, 3H), 4.39-4.20 (m, 3H), 3.92 (d, J=14.1 Hz, 1H), 3.24 (t, J=11.5 Hz, 1H), 2.98-2.88 (m, 1H), 2.62 (s, 1H), 2.08-1.89 (m, 2H), 1.81-1.53 (m, 2H).

Step 2: Preparation of N-(2-(4-(3-(3,4-dimethoxyphenyl)-1,2,4-oxadiazol-5-yl)piperidin-1-yl)-2-oxoethyl)benzamide

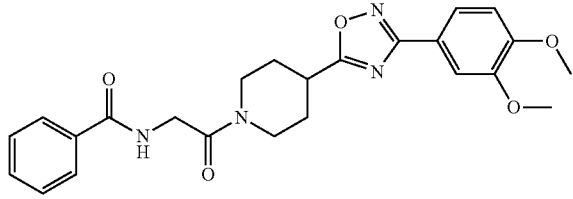 [SMILES: COc1ccc(-c2noc(C3CCN(C(=O)CNC(=O)c4ccccc4)CC3)n2)cc1OC]

To a stirred solution of 1-(2-benzamidoacetyl)piperidine-4-carboxylic acid (2.0 g, 6.89 mmol) in N,N-dimethylformamide (30 mL) was added N-hydroxy-3,4-dimethoxybenzimidamide (1.62 g, 8.27 mmol), N-ethyl-N-(propan-2-yl)propan-2-amine (2.67 g, 20.67 mmol, 3.61 mL) and 1-[bis(dimethylamino)methylene]-1H-1,2,3-triazolo[4,5-b]pyridinium 3-oxide hexafluorophosphate (2.62 g, 6.89 mmol). The mixture was stirred at 20° C. for 2 h and then warmed at 120° C. for 2 h. The reaction mixture was quenched by addition of water (40 mL), then the mixture was extracted with ethyl acetate (80 mL×3). The combined organic phases were washed with saturated aqueous sodium chloride solution (30 mL), dried over anhydrous sodium sulfate, filtered, and concentrated to give crude product that was purified by chromatography (silica, petroleum ether: ethyl acetate=20:1 to 1:2) to give a yellow solid. The yellow solid was washed with ethyl acetate (30 mL), then the mixture was filtered, and the filter cake was dried in vacuo to give N-(2-(4-(3-(3,4-dimethoxyphenyl)-1,2,4-oxadiazol-5-yl)piperidin-1-yl)-2-oxoethyl)benzamide (1.29 g, 2.86 mmol, 42%) as a white solid. $^1$H NMR (400 MHz, CDCl$_3$) δ 7.92-7.84 (m, 2H), 7.80 (s, 1H), 7.58-7.44 (m, 3H), 7.41-7.35 (m, 1H), 7.28-7.26 (m, 2H), 6.92 (d, J=8.9 Hz, 1H), 4.58-4.47 (m, 1H), 4.32 (d, J=3.9 Hz, 2H), 3.99-3.88 (m, 7H), 3.37-3.06 (m, 3H), 2.28-2.13 (m, 2H), 2.07-1.89 (m, 2H); LCMS (ESI) [M+H]$^+$=451.3.

Compound 2 has the Structure:

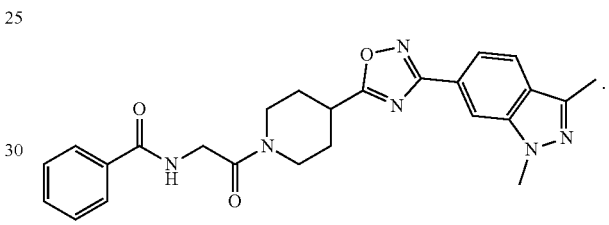

Compound 2 may be synthesized by methods known in the art. For example, Compound 2 may be synthesized as shown in the scheme below:

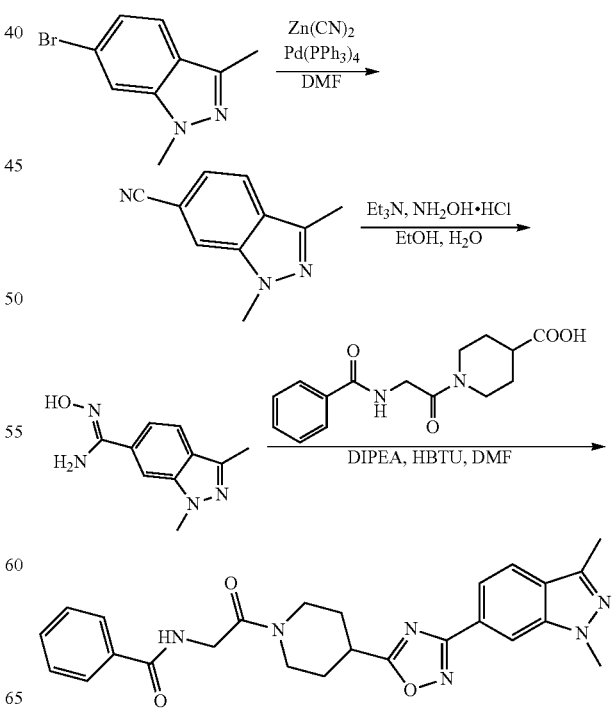

Step 1: Preparation of 1,3-dimethyl-1H-indazole-6-carbonitrile

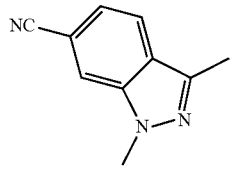

To a stirred solution of 6-bromo-1,3-dimethyl-1H-indazole (400 mg, 1.78 mmol) in N,N-dimethylformamide (5 mL) was added zinc cyanide (209 mg, 1.78 mmol, 112 μL) and tetrakis(triphenylphosphine)palladium(O) (205 mg, 178 μmol, 0.10 eq) under nitrogen. The mixture was heated at 100° C. for 16 h, then cooled to 20° C., water (10 mL) added, and the resulting mixture was extracted with ethyl acetate (40 mL×3). The combined organic phases were washed with saturated aqueous sodium chloride solution (15 mL) and dried over anhydrous sodium sulfate. The organic phase was filtered and concentrated in vacuo to give crude product. Petroleum ether (40 mL) was added to the crude product, then the mixture was filtered, and the filter cake dried in vacuo to give 1,3-dimethyl-1H-indazole-6-carbonitrile (250 mg, 1.46 mmol, 82%) as a white solid. $^1$H NMR (400 MHz, CDCl$_3$) δ 7.78-7.71 (m, 2H), 7.34 (dd, J=1.3, 8.3 Hz, 1H), 4.07 (s, 3H), 2.61 (s, 3H).

Step 2: Preparation of (Z)—N'-hydroxy-1,3-dimethyl-1H-indazole-6-carboximidamide

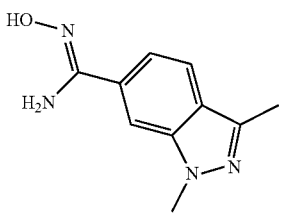

To a stirred solution of 1,3-dimethyl-1H-indazole-6-carbonitrile (100 mg, 584 μmol) in ethanol (2 mL) was added hydroxylamine hydrochloride (81 mg, 1.17 mmol), triethylamine (118 mg, 1.17 mmol, 161 L) and water (200 μL). The mixture was heated at 75° C. for 2 h. After cooling to 20° C., water (5 mL) was added to the solution. The mixture was extracted with dichloromethane (30 mL×3). The combined organic phases were washed with saturated aqueous sodium chloride solution (5 mL) and dried over anhydrous sodium sulfate, then filtered and concentrated in vacuo to give (Z)—N'-hydroxy-1,3-dimethyl-1H-indazole-6-carboximidamide (140 mg) as a white solid. LCMS (ESI) m/z: [M+H]$^+$=205.1.

Step 3: Preparation of N-(2-(4-(3-(1,3-dimethyl-1H-indazol-6-yl)-1,2,4-oxadiazol-5-yl)piperidin-1-yl)-2-oxoethyl)benzamide

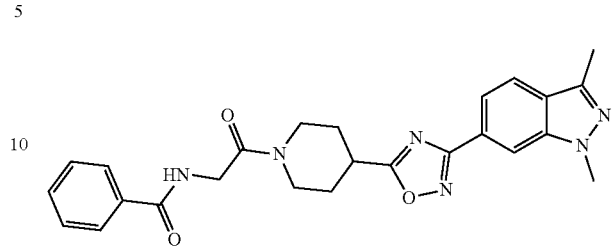

To a stirred solution of 1-(2-benzamidoacetyl)piperidine-4-carboxylic acid (120 mg, 413 μmol) in N,N-dimethylformamide (2 mL) was added (Z)—N'-hydroxy-1,3-dimethyl-1H-indazole-6-carboximidamide (101 mg, 496 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (160 mg, 1.24 mmol, 216 μL). The mixture was stirred at 20° C. for 2 h, then heated at 120° C. for 2 h. The reaction mixture cooled then purified directly by prep-HPLC (column: Waters Xbridge 150×2.5 mm 5 μm; mobile phase: [water (10 mM ammonium carbonate)-acetonitrile]; B %: 30%-65%, 12 min) to give N-(2-(4-(3-(1,3-dimethyl-1H-indazol-6-yl)-1,2,4-oxadiazol-5-yl)piperidin-1-yl)-2-oxoethyl)benzamide (46 mg, 101 μmol, 25%) as a yellow solid. $^1$H NMR (400 MHz, CDCl$_3$) δ 8.02 (s, 1H), 7.81-7.73 (m, 3H), 7.66 (dd, J=0.6, 8.4 Hz, 1H), 7.48-7.42 (m, 1H), 7.42-7.35 (m, 2H), 7.26 (br. s., 1H), 4.46 (d, J=14.1 Hz, 1H), 4.24 (d, J=3.9 Hz, 2H), 4.01 (s, 3H), 3.86 (d, J=13.7 Hz, 1H), 3.29 (ddd, J=3.6, 10.5, 14.2 Hz, 2H), 3.13-3.04 (m, 1H), 2.53 (s, 3H), 2.26-2.15 (m, 2H), 2.04-1.89 (m, 2H); LCMS (ESI) m/z: [M+H]$^+$=459.3.

Compound 3 has the structure:

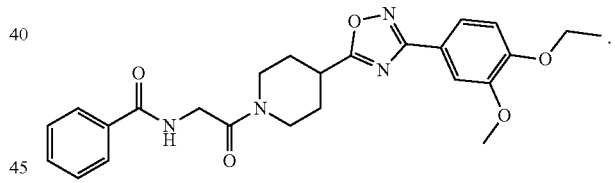

Compound 3 may be synthesized by methods known in the art. For example, Compound 3 may be synthesized as shown in the scheme below:

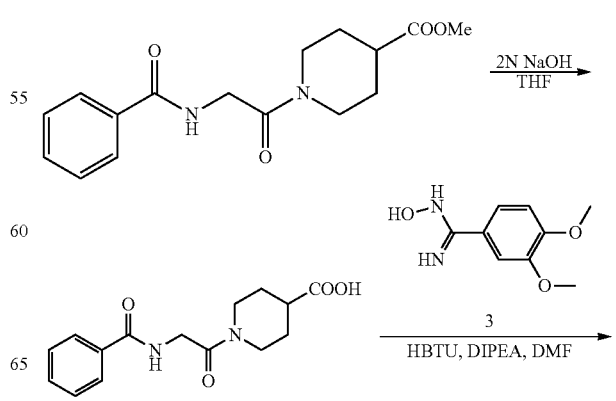

-continued

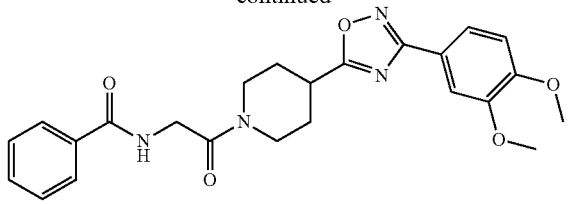

Step 1: Preparation of
1-(2-benzamidoacetyl)piperidine-4-carboxylic acid

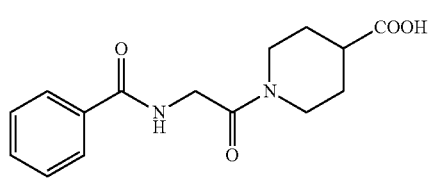 [SMILES: O=C(NCC(=O)N1CCC(C(=O)O)CC1)c1ccccc1]

To a stirred solution of methyl 1-(2-benzamidoacetyl) piperidine-4-carboxylate (5.0 g, 16.4 mmol) in tetrahydrofuran (50 mL) was added aqueous sodium hydroxide (2 M, 16.4 mL). The mixture was stirred at 20° C. for 2 h and then acidified by the addition of concentrated hydrochloric acid until pH 1. The mixture was extracted with dichloromethane (80 mL×3). The combined organic phases were washed with saturated aqueous sodium chloride solution (30 mL), dried over anhydrous sodium sulfate, filtered, and concentrated to give crude product 1-(2-benzamidoacetyl)piperidine-4-carboxylic acid (3.25 g, 11.2 mmol, 68%) as a yellow solid. $^1$H NMR (400 MHz, Methanol-d4) δ 7.87 (d, J=7.5 Hz, 2H), 7.59-7.42 (m, 3H), 4.39-4.20 (m, 3H), 3.92 (d, J=14.1 Hz, 1H), 3.24 (t, J=11.5 Hz, 1H), 2.98-2.88 (m, 1H), 2.62 (s, 1H), 2.08-1.89 (m, 2H), 1.81-1.53 (m, 2H).

Step 2: Preparation of N-(2-(4-(3-(3,4-dimethoxyphenyl)-1,2,4-oxadiazol-5-yl)piperidin-1-yl)-2-oxoethyl)benzamide

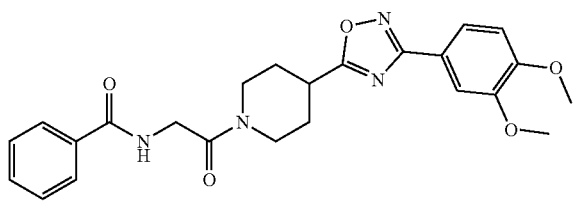 [SMILES: COc1ccc(-c2noc(C3CCN(C(=O)CNC(=O)c4ccccc4)CC3)n2)cc1OC]

To a stirred solution of 1-(2-benzamidoacetyl)piperidine-4-carboxylic acid (2.0 g, 6.89 mmol) in N,N-dimethylformamide (30 mL) was added N-hydroxy-3,4-dimethoxybenzimidamide (1.62 g, 8.27 mmol), N-ethyl-N-(propan-2-yl) propan-2-amine (2.67 g, 20.67 mmol, 3.61 mL) and 1-[bis (dimethylamino)methylene]-1H-1,2,3-triazolo[4,5-b] pyridinium 3-oxide hexafluorophosphate (2.62 g, 6.89 mmol). The mixture was stirred at 20° C. for 2 h and then warmed at 120° C. for 2 h. The reaction mixture was quenched by addition of water (40 mL), then the mixture was extracted with ethyl acetate (80 mL×3). The combined organic phases were washed with saturated aqueous sodium chloride solution (30 mL), dried over anhydrous sodium sulfate, filtered, and concentrated to give crude product that was purified by chromatography (silica, petroleum ether: ethyl acetate=20:1 to 1:2) to give a yellow solid. The yellow solid was washed with ethyl acetate (30 mL), then the mixture was filtered, and the filter cake was dried in vacuo to give N-(2-(4-(3-(3,4-dimethoxyphenyl)-1,2,4-oxadiazol-5-yl)piperidin-1-yl)-2-oxoethyl)benzamide (1.29 g, 2.86 mmol, 42%) as a white solid. $^1$H NMR (400 MHz, CDCl$_3$) δ 7.92-7.84 (m, 2H), 7.80 (s, 1H), 7.58-7.44 (m, 3H), 7.41-7.35 (m, 1H), 7.28-7.26 (m, 2H), 6.92 (d, J=8.9 Hz, 1H), 4.58-4.47 (m, 1H), 4.32 (d, J=3.9 Hz, 2H), 3.99-3.88 (m, 7H), 3.37-3.06 (m, 3H), 2.28-2.13 (m, 2H), 2.07-1.89 (m, 2H); LCMS (ESI) [M+H]$^+$=451.3.

Compound 4 has the structure:

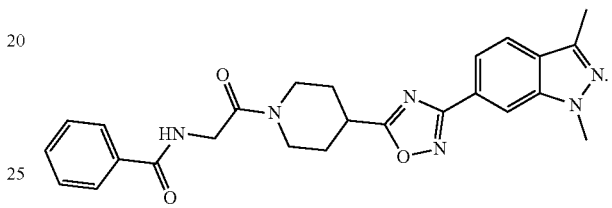

Compound 4 may be synthesized by methods known in the art. For example, Compound 4 may be synthesized as shown in the scheme below:

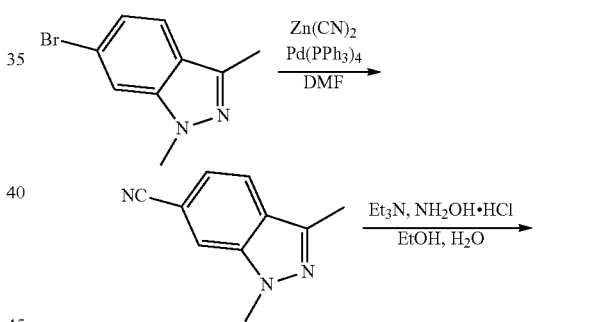

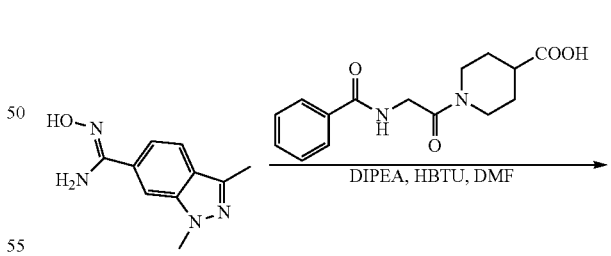

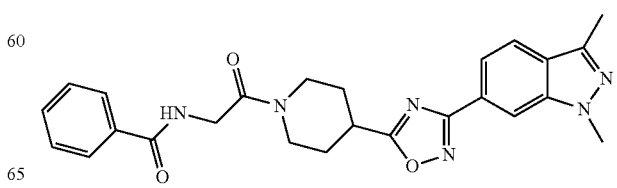

Step 1: Preparation of 1,3-dimethyl-1H-indazole-6-carbonitrile

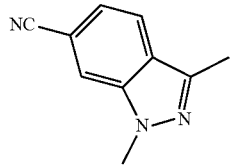

To a stirred solution of 6-bromo-1,3-dimethyl-1H-indazole (400 mg, 1.78 mmol) in N,N-dimethylformamide (5 mL) was added zinc cyanide (209 mg, 1.78 mmol, 112 μL) and tetrakis(triphenylphosphine)palladium(O) (205 mg, 178 μmol, 0.10 eq) under nitrogen. The mixture was heated at 100° C. for 16 h, then cooled to 20° C., water (10 mL) added, and the resulting mixture was extracted with ethyl acetate (40 mL×3). The combined organic phases were washed with saturated aqueous sodium chloride solution (15 mL) and dried over anhydrous sodium sulfate. The organic phase was filtered and concentrated in vacuo to give crude product. Petroleum ether (40 mL) was added to the crude product, then the mixture was filtered, and the filter cake dried in vacuo to give 1,3-dimethyl-1H-indazole-6-carbonitrile (250 mg, 1.46 mmol, 82%) as a white solid. $^1$H NMR (400 MHz, CDCl$_3$) δ 7.78-7.71 (m, 2H), 7.34 (dd, J=1.3, 8.3 Hz, 1H), 4.07 (s, 3H), 2.61 (s, 3H).

Step 2: Preparation of (Z)—N'-hydroxy-1,3-dimethyl-1H-indazole-6-carboximidamide

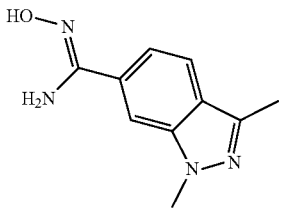

To a stirred solution of 1,3-dimethyl-1H-indazole-6-carbonitrile (100 mg, 584 μmol) in ethanol (2 mL) was added hydroxylamine hydrochloride (81 mg, 1.17 mmol), triethylamine (118 mg, 1.17 mmol, 161 μL) and water (200 μL). The mixture was heated at 75° C. for 2 h. After cooling to 20° C., water (5 mL) was added to the solution. The mixture was extracted with dichloromethane (30 mL×3). The combined organic phases were washed with saturated aqueous sodium chloride solution (5 mL) and dried over anhydrous sodium sulfate, then filtered and concentrated in vacuo to give (Z)—N'-hydroxy-1,3-dimethyl-1H-indazole-6-carboximidamide (140 mg) as a white solid. LCMS (ESI) m/z: [M+H]+=205.1.

Step 3: Preparation of N-(2-(4-(3-(1,3-dimethyl-1H-indazol-6-yl)-1,2,4-oxadiazol-5-yl)piperidin-1-yl)-2-oxoethyl)benzamide

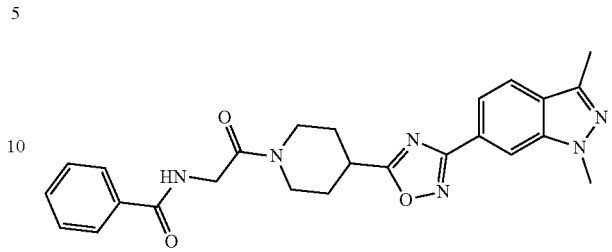

To a stirred solution of 1-(2-benzamidoacetyl)piperidine-4-carboxylic acid (120 mg, 413 μmol) in N,N-dimethylformamide (2 mL) was added (Z)—N'-hydroxy-1,3-dimethyl-1H-indazole-6-carboximidamide (101 mg, 496 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (160 mg, 1.24 mmol, 216 μL). The mixture was stirred at 20° C. for 2 h, then heated at 120° C. for 2 h. The reaction mixture cooled then purified directly by prep-HPLC (column: Waters Xbridge 150×2.5 mm 5 μm; mobile phase: [water (10 mM ammonium carbonate)-acetonitrile]; B %: 30%-65%, 12 min) to give N-(2-(4-(3-(1,3-dimethyl-1H-indazol-6-yl)-1,2,4-oxadiazol-5-yl)piperidin-1-yl)-2-oxoethyl)benzamide (46 mg, 101 μmol, 25%) as a yellow solid. $^1$H NMR (400 MHz, CDCl$_3$) δ 8.02 (s, 1H), 7.81-7.73 (m, 3H), 7.66 (dd, J=0.6, 8.4 Hz, 1H), 7.48-7.42 (m, 1H), 7.42-7.35 (m, 2H), 7.26 (br. s., 1H), 4.46 (d, J=14.1 Hz, 1H), 4.24 (d, J=3.9 Hz, 2H), 4.01 (s, 3H), 3.86 (d, J=13.7 Hz, 1H), 3.29 (ddd, J=3.6, 10.5, 14.2 Hz, 2H), 3.13-3.04 (m, 1H), 2.53 (s, 3H), 2.26-2.15 (m, 2H), 2.04-1.89 (m, 2H); LCMS (ESI) m/z: [M+H]+=459.3.

Compound 5 has the Structure:

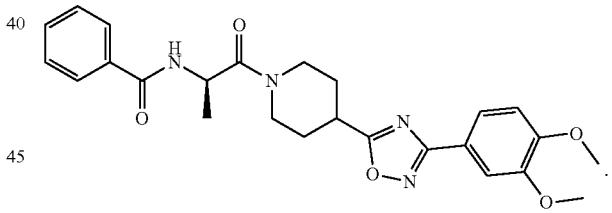

Compound 5 may be synthesized by methods known in the art. For example, Compound 5 may be synthesized as shown in the scheme below:

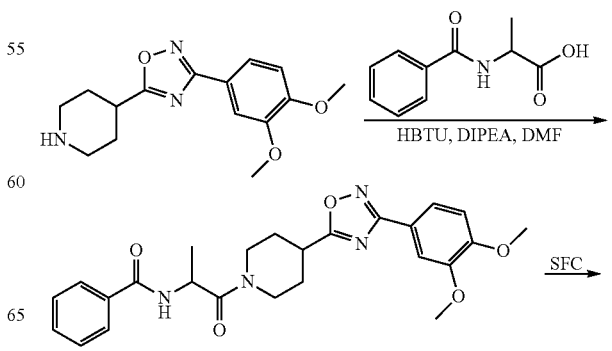

185

-continued

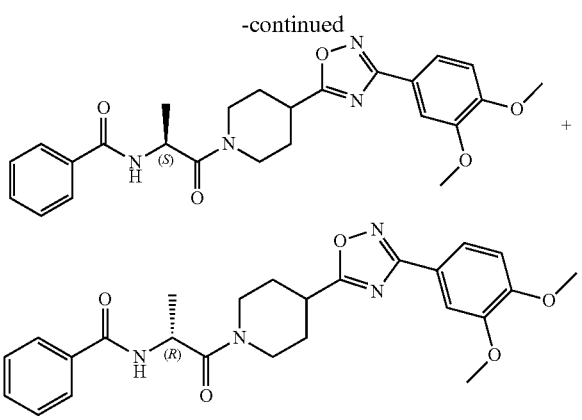

Step 1: Preparation of N—[(R)-2-[4-[3-(3,4-dimethoxyphenyl)-1,2,4-oxadiazol-5-yl]-1-piperidyl]-1-methyl-2-oxo-ethyl]benzamide and N—[(S)-2-[4-[3-(3,4-dimethoxyphenyl)-1,2,4-oxadiazol-5-yl]-1-piperidyl]-1-methyl-2-oxo-ethyl]benzamide

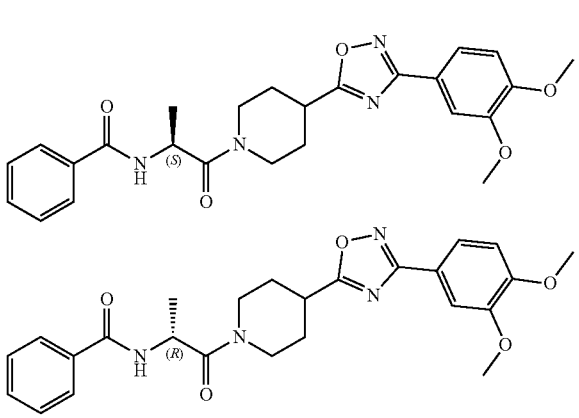

To a stirred solution of 3-(3,4-dimethoxyphenyl)-5-(4-piperidyl)-1,2,4-oxadiazole (150 mg, 518 μmol) and 2-benzamidopropanoic acid (105 mg, 544 μmol) in N,N-dimethylformamide (2 mL) was added (2-(1H-benzotriazol-1-yl)-1,1,3,3-tetramethyluronium hexafluorophosphate) (196 mg, 518 μmol) and N-ethyl-N-(propan-2-yl)propan-2-amine (201 mg, 1.56 mmol, 271 μL). The mixture was stirred at 20° C. for 5 h. The crude product was purified by prep-HPLC (column: Luna C18 150×25 5 μm; mobile phase: [water (10 mM ammonium carbonate)-acetonitrile]; B %: 35%-65%, 12 min) to give rac-N-(1-(4-(3-(3,4-dimethoxyphenyl)-1,2,4-oxadiazol-5-yl)piperidin-1-yl)-1-oxopropan-2-yl)benzamide then the product purified by SFC separation (column: AD(250×30 mm, 5 μm); mobile phase: [Neu-IPA]; B %: 42%-42%, min) to give N-[2-[4-[3-(3,4-dimethoxyphenyl)-1,2,4-oxadiazol-5-yl]-1-piperidyl]-1-methyl-2-oxo-ethyl]benzamide, Enantiomer 1 (63 mg, 134.93 μmol, 26%) as a white solid and N-[2-[4-[3-(3,4-dimethoxyphenyl)-1,2,4-oxadiazol-5-yl]-1-piperidyl]-1-methyl-2-oxo-ethyl]benzamide, Enantiomer 2 (56 mg, 120 μmol, 23% as a white solid.

186

N-[2-[4-[3-(3,4-dimethoxyphenyl)-1,2,4-oxadiazol-5-yl]-1-piperidyl]-1-methyl-2-oxo-ethyl]benzamide, Enantiomer 1

$^1$H NMR (400 MHz, DMSO-d$_6$) δ=8.63 (br dd, J=7.3, 16.1 Hz, 1H), 7.88 (br d, J=7.5 Hz, 2H), 7.62-7.41 (m, 5H), 7.11 (br d, J=8.2 Hz, 1H), 4.97 (br d, J=6.4 Hz, 1H), 4.43-4.24 (m, 1H), 4.10-3.95 (m, 1H), 3.82 (s, 6H), 3.42 (br t, J=1.8 Hz, 1H), 3.30-3.21 (m, 1H), 2.99-2.83 (m, 1H), 2.09 (br d, J=1.9 Hz, 2H), 1.83-1.60 (m, 2H), 1.30 (br s, 3H); LCMS (ESI) m/z: [M+H]+=465.3. ee=100%.

N-[2-[4-[3-(3,4-dimethoxyphenyl)-1,2,4-oxadiazol-5-yl]-1-piperidyl]-1-methyl-2-oxo-ethyl]benzamide, Enantiomer 2

$^1$H NMR (400 MHz, DMSO-d$_6$) δ=8.65 (br dd, J=7.6, 16.1 Hz, 1H), 7.98-7.86 (m, 2H), 7.70-7.41 (m, 5H), 7.13 (br d, J=8.2 Hz, 1H), 5.00 (br d, J=5.5 Hz, 1H), 4.49-4.24 (m, 1H), 4.12-3.96 (m, 1H), 3.85 (s, 6H), 3.45 (br t, J=10.7 Hz, 1H), 3.27 (br s, 1H), 3.05-2.83 (m, 1H), 2.12 (br d, J=12.5 Hz, 2H), 1.89-1.61 (m, 2H), 1.32 (br s, 3H); LCMS (ESI) m/z: [M+H]$^+$=465.3. ee=99.6 Compound 6 has the structure:

Compound 6 may be synthesized by methods known in the art. For example, Compound 6 may be synthesized as shown in the scheme below:

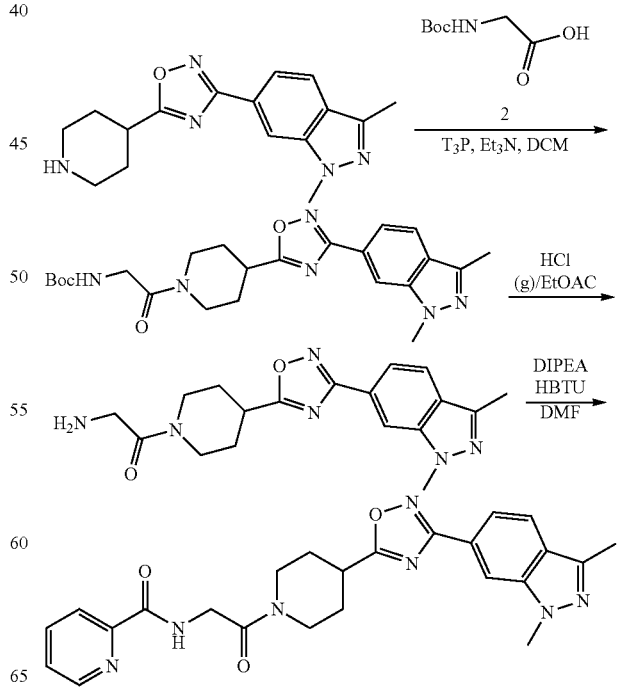

¹H NMR (400 MHz, CDCl₃) δ 8.93 (brs, 1H), 8.63 (d, J=4.0 Hz, 1H), 8.19 (d, J=7.7 Hz, 1H), 8.10 (s, 1H), 7.89-7.80 (m, 2H), 7.76-7.71 (m, 1H), 7.47-7.41 (m, 1H), 4.56 (br d, J=13.7 Hz, 1H), 4.35 (d, J=4.4 Hz, 2H), 4.09 (s, 3H), 3.96 (br d, J=13.9 Hz, 1H), 3.44-3.31 (m, 2H), 3.15 (br t, J=1.7 Hz, 1H), 2.60 (s, 3H), 2.34-2.23 (m, 2H), 2.11-1.95 (m, 2H); LCMS (ESI) m/z: [M+H]+=460.2.

Compound 7 has the Structure:

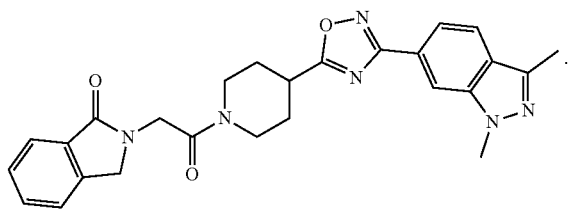 [SMILES: Cc1nn(C)c2cc(-c3noc(C4CCN(C(=O)CN5Cc6ccccc6C5=O)CC4)n3)ccc12]

Compound 7 may be synthesized by methods known in the art. For example, Compound 7 may be synthesized as shown in the scheme below:

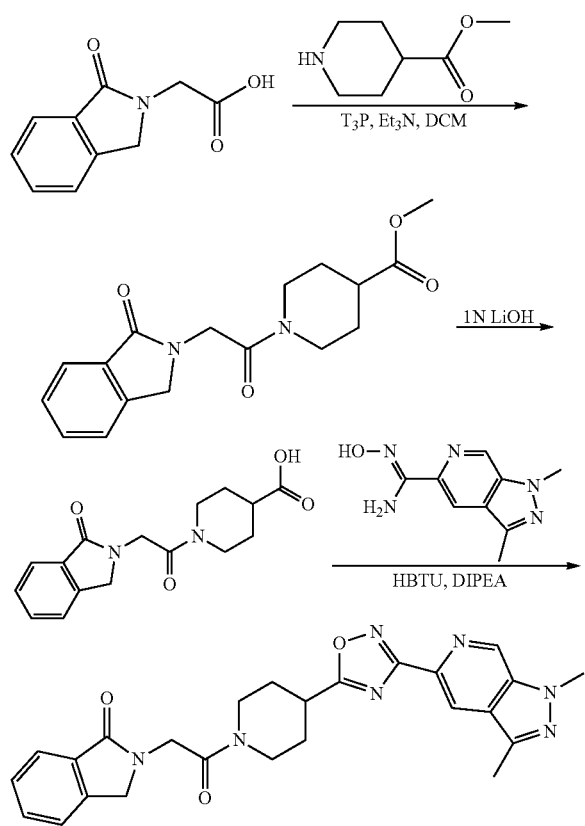

¹H NMR (400 MHz, CHLOROFORM-d) δ=8.11 (d, J=8.4 Hz, 1H), 7.89 (d, J=8.2 Hz, 1H), 7.85 (d, J=8.2 Hz, 1H), 7.56-7.50 (m, 1H), 7.47-7.41 (m, 2H), 4.60-4.41 (m, 5H), 4.16 (s, 3H), 4.12-4.05 (m, 1H), 3.41-3.31 (m, 2H), 3.06-2.98 (m, 1H), 2.62-2.57 (m, 3H), 2.25 (br t, J=14.6 Hz, 2H), 2.05-1.94 (m, 2H); LCMS(ESI) m/z: [M+H]+:472.3.

Drug Resistant Mutant Selection

Strains GMYF and W-erg3 were grown to saturation in CSM-glucose, centrifuged, resuspended in phosphate-buffered Saline (PBS), and plated at a density of $10^7$ cells/plate on solid 15 cm petri dishes containing CSM with 2% galactose (w/v), 2% (w/v) agar, and 10 µM Compound 3, and incubated at 30° C. Resistant colonies were isolated after 5-7 days, re-streaked on the same media, and resistance reconfirmed. Cultures of validated strains were then inoculated for genomic DNA isolation using a YeaStar™ yeast genomic DNA kit (Zymo Research).

Libraries were prepared for sequencing using the Illumina NEXTERA™ library prep kit and sequenced via Illumina HiSeq™ 2500 1×50 bp (single end reads). Sequences were aligned to the *S. cerevisiae* reference genome (S288CCR64-1-1, *Saccharomyces Genome* Database (SGD)) using Burrows-Wheeler Aligner (BWA, see, e.g., Li et al. *Bioinformatics* 25:1754-1760, 2009; Li et al. *Bioinformatics* 2010, Epub (PMID 20080505)). The BWA output SAI files were converted to SAM files using BWA. The SAM files were sorted using SAMtools 1.3.1 (Li et al. *Bioinformatics* 25:2079-2079, 2009). Variants (single-nucleotide polymorphisms (SNPs), indels) were identified using Freebayes (see, e.g., arXiv:1207.3907). Variant locations were summarized using snpEFF (Cingolani et al. *Fly* (Austin) 6(2):80-92, 2012).

Quantitative Lipid Profiling

Overnight cultures of yeast strain W303 pdr1Δ pdr3Δ were diluted into CSM media with 2% (w/v) raffinose, $OD_{600}$ 0.25, and grown for 4 h before resuspending at an $OD_{600}$ of 0.2 in CSM media with 2% (w/v) galactose and adding Compound 2 or DMSO at the indicated concentrations. Cells were grown for the indicated timepoints before centrifugation, washing once in PBS, and freezing pellets. Lipids were extracted from pellets by resuspending the pellets in 600 µL methanol, 300 µL water, and 400 µL chloroform, followed by cell lysis by vortexing with glass beads for 1 min. Samples were then centrifuged at 10,000×g for 10 min, and the bottom layer that formed (organic/lipids) was moved into a new tube and evaporated. Samples were then analyzed by LC/MS/MS using a Thermo Scientific Q Exactive™ Orbitrap™ coupled to a Dionex UltiMate® 3000 ultra-high performance liquid chromatography system, following the method described in Tafesse et al. *PLoS Pathog.* 11(10): e1005188, 2015.

B. Results

The effect of 1,2,4-oxiadiazoles on cell growth was assessed in a control condition and in a yeast model for ApoE4 toxicity (see International Patent Application Publication No. WO 2016/040794). The control condition was growth of the ApoE4 strain under non-inducing conditions using raffinose as the carbon source. The 1,2,4-oxadiazoles exhibited a bell-shaped rescue curve in the ApoE4 model (FIG. 1A, top panel). At higher concentrations, these compounds inhibited the growth in the control condition (FIG. 1B, bottom panel). The potency of model rescue correlated well with the potency of growth inhibition across the entire series of 1,2,4-oxadiazoles tested (FIG. 1B). These relationships indicate that the growth inhibition arises from an "on-target" activity, i.e., over activation or inhibition of a target that results in slowed growth.

Figure 9:
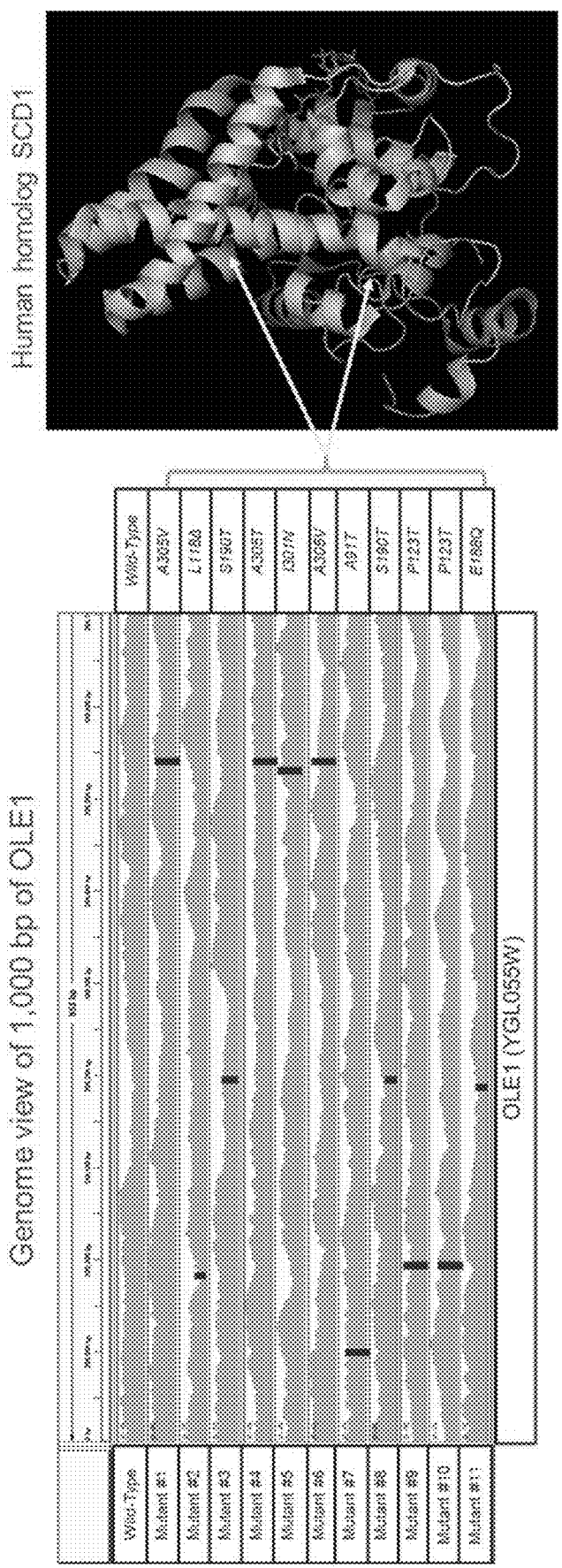
FIG. 9 shows OLE1 mutations conferring resistance to growth inhibition to 1,2,4-oxadiazoles identified by genome sequencing of resistant mutants. Cells were plated on media containing 10 μM of the 1,2,4-oxadiazole Compound 3 and resistant colonies that emerged were isolated, and genomic DNA was prepared from mutants and the parental, drug-sensitive control strain. Genomic DNA sequence was aligned to the *Saccharomyces cerevisiae* reference and unique mutations in the 1,2,4-oxadiazole-resistant mutants were identified. The position of the mutations, the amino acid changes they encode, and the fold resistance (increase in minimal inhibitory concentration) of Compound 3 are shown.

Drug-resistant mutants can be used to identify the target of the compounds, for example, by preventing or reducing drug binding, and therefore allowing growth under inhibitory doses of 1,2,4-oxadiazole concentrations. Twenty drug-resistant mutants were isolated, and the mutants were subjected to whole-genome sequencing in order to identify genetic lesions associated with the drug resistance. Surprisingly, all mutations identified in the drug resistant mutants localized to OLE1 (YGL055W), the sole stearoyl-CoA desaturase (SCD; also referred to as Δ9-desaturase) in yeast (FIG. 9). The drug resistant mutants specifically conferred resistance to 1,2,4-oxadiazoles, but were not cross-resistant to other toxic compounds. The ole1 mutations identified included indels and substitution mutations, including A305V, L118Δ, S190T, A305T, I301N, A91T, S190T, P123T, and E118Q. These mutations are relative to the wild-type OLE1 sequence provided below.

(SEQ ID NO: 1)
MPTSGTTIELIDDQFPKDDSASSGIVDEVDLTEANILATGLNKKAPRIVN

GFGSLMGSKEMVSVEFDKKGNEKKSNLDRLLEKDNQEKEEAKTKIHISEQ

PWTLNNWHQHLNWLNMVLVCGMPMIGWYFALSGKVPLHLNVFLFSVFYYA

VGGVSITAGYHRLWSHRSYSAHWPLRLFYAIFGCASVEGSAKWWGHSHRI

HHRYTDTLRDPYDARRGLWYSHMGWMLLKPNPKYKARADITDMTDDWTIR

FQHRHYILLMLLTAFVIPTLICGYFFNDYMGGLIYAGFIRVFVIQQATFC

INSLAHYIGTQPFDDRRTPRDNWITAIVTFGEGYHNFHHEFPTDYRNAIK

WYQYDPTKVIIYLTSLVGLAYDLKKFSQNAIEEALIQQEQKKINKKKAKI

NWGPVLTDLPMWDKQTFLAKSKENKGLVIISGIVHDVSGYISEHPGGELT

IKTALGKDATKAFSGGVYRHSNAAQNVLADMRVAVIKESKNSAIRMASKR

GEIYETGKFF

Figure 2A:
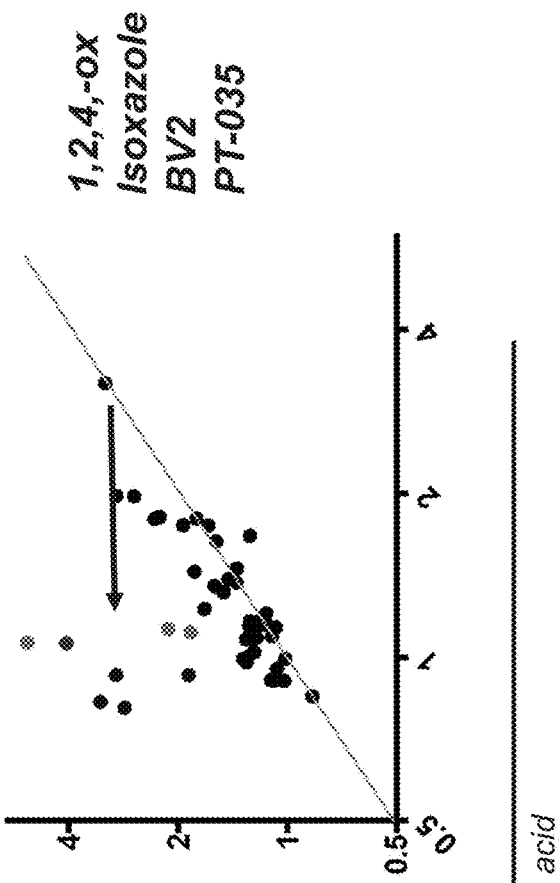
FIGS. 2A and 2B are graphs showing that exogenous oleic acid reverses growth inhibition and model rescue by Ole1/SCD-targeting 1,2,4-oxadiazoles. Growth was measured by reading $OD_{600}$ in a microplate reader and normalized to solvent control DMSO samples.
Figure 2B:
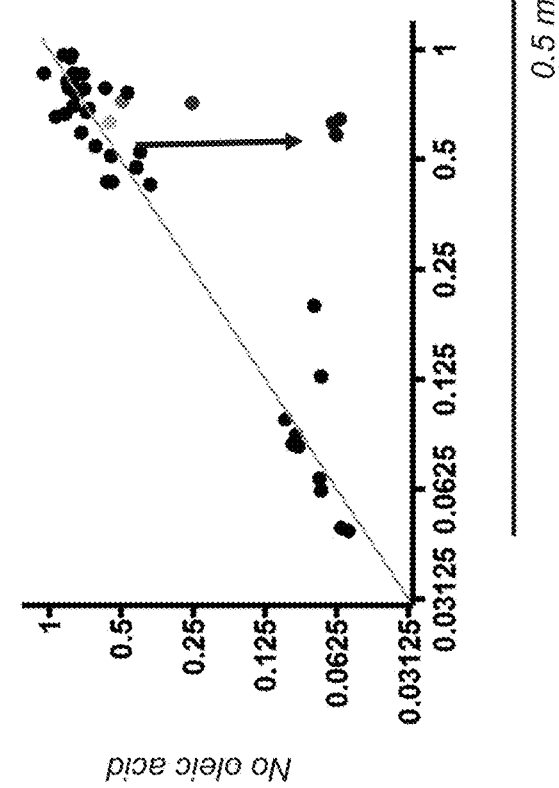

These data strongly suggest that Ole1 is the target of 1,2,4-oxadiazoles. Additionally, addition of exogenous oleic acid reversed both growth inhibition of wild-type cells and rescue of toxicity in a yeast disease model of alpha-synuclein toxicity (FIGS. 2A and 2B, respectively). Likewise, these effects were specific for 1,2,4-oxadiazoles, but not other toxic compounds.

Figure 3A:
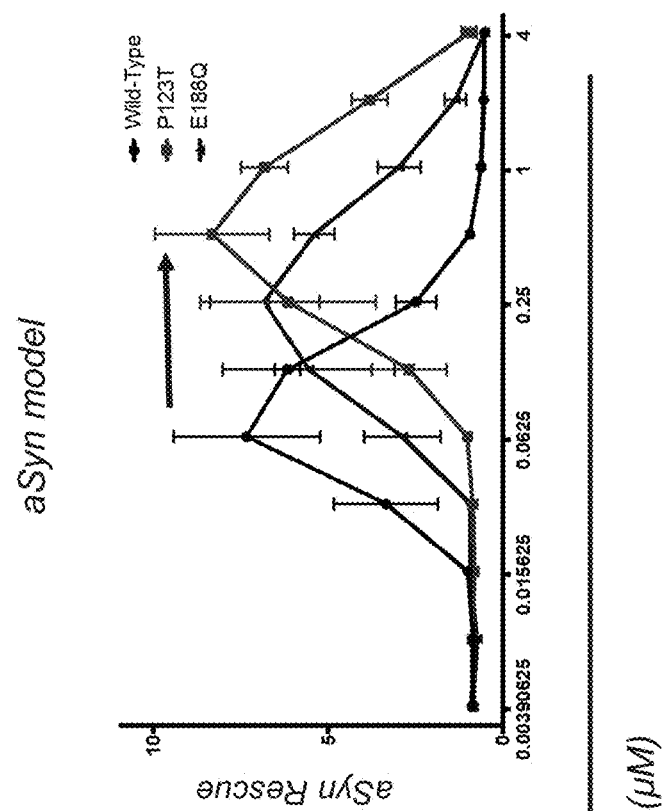
FIGS. 3A and 3B are graphs showing that point mutations in yeast OLE1 confer resistance to growth inhibition and alpha-synuclein model rescue by 1,2,4-oxadiazoles. Growth was measured by reading $OD_{600}$ in a microplate reader.
Figure 3B:
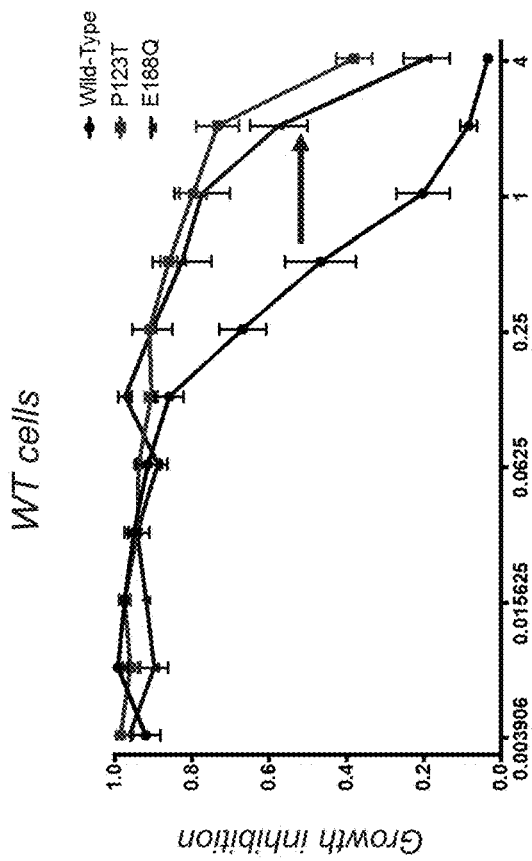

Drug-resistant Ole1 mutations reduced 1,2,4-oxadiazole-induced growth inhibition in wild-type cells (FIG. 3A). The same mutations also increased the EC50 (concentration that gives half-maximal response) in the context of the alpha-synuclein model, which is consistent with reduced binding to the target. These shifts in does response were specific for 1,2,4-oxadiazoles. These data further support that Ole1/SCD is the target for both growth inhibition and rescue of toxicity in disease models.

Figure 4:
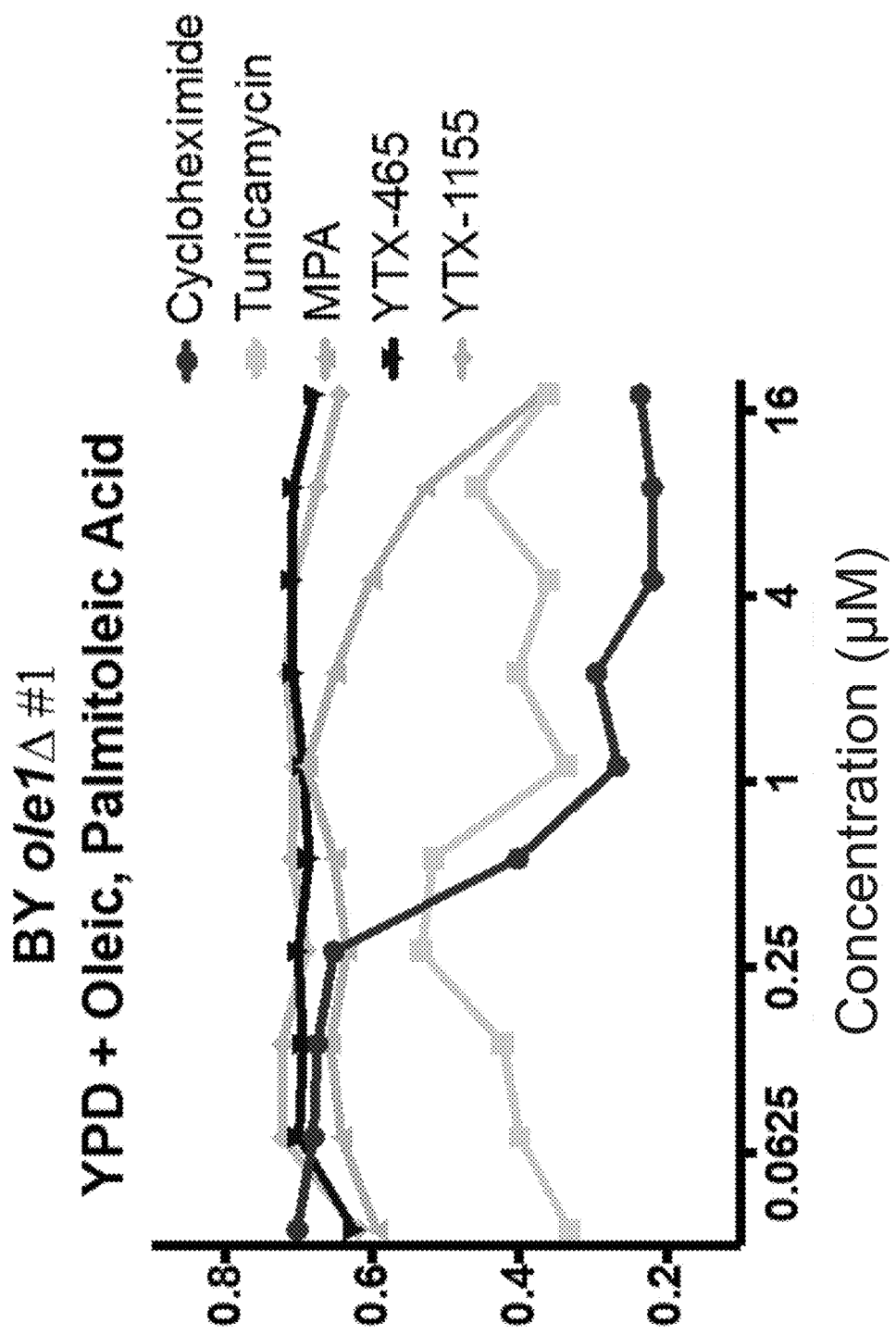
FIG. 4 is a graph showing that a ole1Δ deletion mutant is resistant to the growth-inhibitory effects of 1,2,4-oxadiazoles, but not other compounds. Twenty-four hour growth (presented as raw $OD_{600}$) of the ole1Δ deletion strain in yeast extract-peptone-dextrose (YPD) media is shown, with drugs added at the indicated concentrations.
Figure 5:
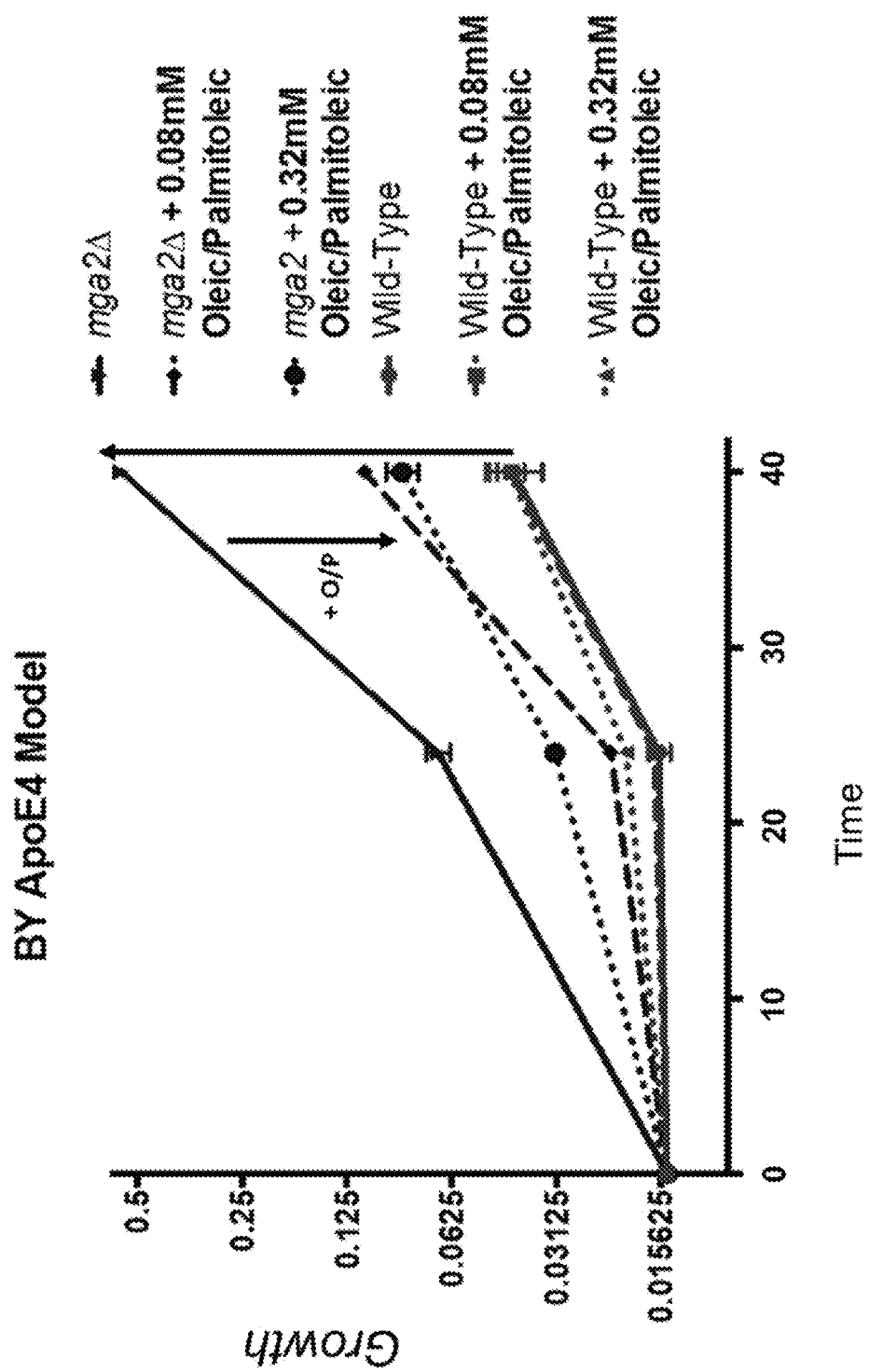
FIG. 5 is a graph showing that reducing OLE1 expression by deleting MGA2 rescues the growth of the ApoE4 yeast model. Yeast cells expressing ApoE4 were deleted for the MGA2 gene and their growth was assessed over time (compared to their isogenic, MGA2 wild-type counterpart). Growth was assessed by $OD_{600}$. Where indicated, 0.08 or 0.32 mM of oleic and palmitoleic acids (each) as added to the growth media in 0.01% tween (final).

The OLE1 gene is essential in *Saccharomyces cerevisiae*. However, strains deleted for OLE1 (ole1Δ) are viable if their growth media is supplemented with oleic/palmitoleic acid. The ole1Δ strain supplemented with exogenous fatty acids was fully resistant to 1,2,4-oxadiazoles (FIG. 4). In other words, in the absence of the target, Ole1, the 1,2,4-oxadiazoles do not have growth inhibition activity. Independently, a chemical genetics approach identified MGA2, the transcription factor that regulates Ole1. Genetic deletion of MGA2 (mga2Δ) phenocopied the effects of 1,2,4-oxadiazoles (FIG. 5). mga2Δ cells have reduced Ole1 levels, which itself rescues toxicity in the yeast disease models (e.g., the ApoE4 model). Supplementation of the growth media with oleic acid reversed this effect, similar to the results described above. Consistent with these data, treatment of yeast cells with the 1,2,4-oxadiazole Compound 2 inhibited lipid desaturation (FIGS. 8A-8D). Overall, these data provide still further evidence that Ole1/SCD is the target of 1,2,4-oxadiazoles.

Figure 6:
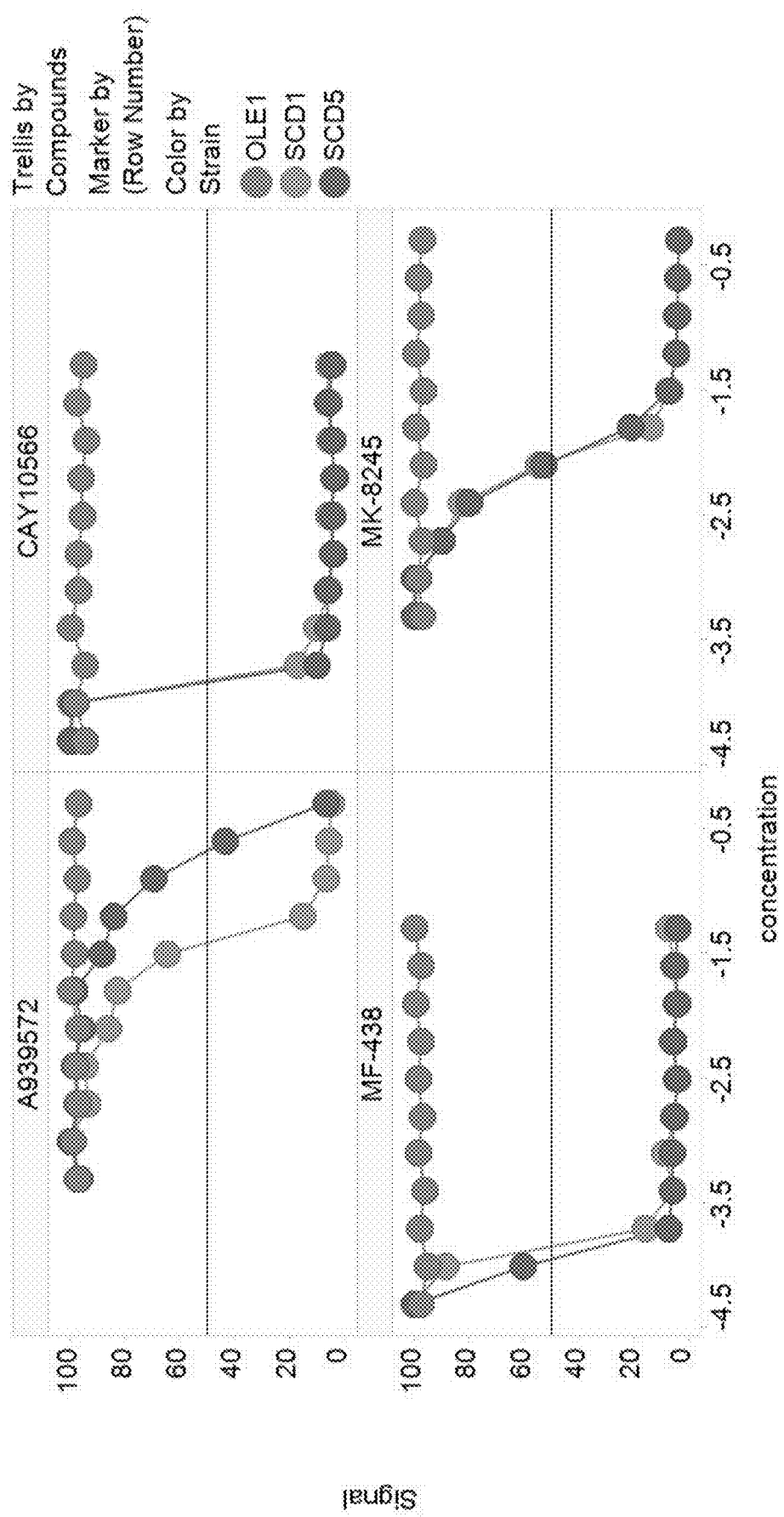
FIG. 6 is a series of graphs showing that commercial Scd inhibitors target human SCD1/SCD5 in yeast. Yeast surviving solely on yeast OLE1, or human SCD1 or SCD5, were treated with four commercial Scd inhibitors at indicated concentrations. Data are expressed as a percent of the DMSO-treated condition. All four compounds potently reduced growth of both SCD1-expressing yeast and SCD5-expressing yeast, but not the strain expressing Ole1. This growth inhibition was reversed by oleic/palmitoleic acid competition, similar to the results shown in FIGS. 2A and 2B.

Humanized yeast strains expressing the human SCD proteins SCD1 or SCD5 were generated by genetic deletion of OLE1 and expressing human SCD1 or SCD5 on a plasmid. Yeast expressing OLE1 were resistant to known SCD1/SCD5 inhibitors such as A939572, CAY10566, MF-438, and MK-8245 (FIG. 6), suggesting that they do not target the yeast enzyme. In marked contrast, in the SCD1 and SCD5 humanized strains, the known SCD1/SCD5 inhibitors were extremely potent, with low nanomolar half-maximal inhibitory concentration (IC50) values (FIG. 6).

Figure 7:
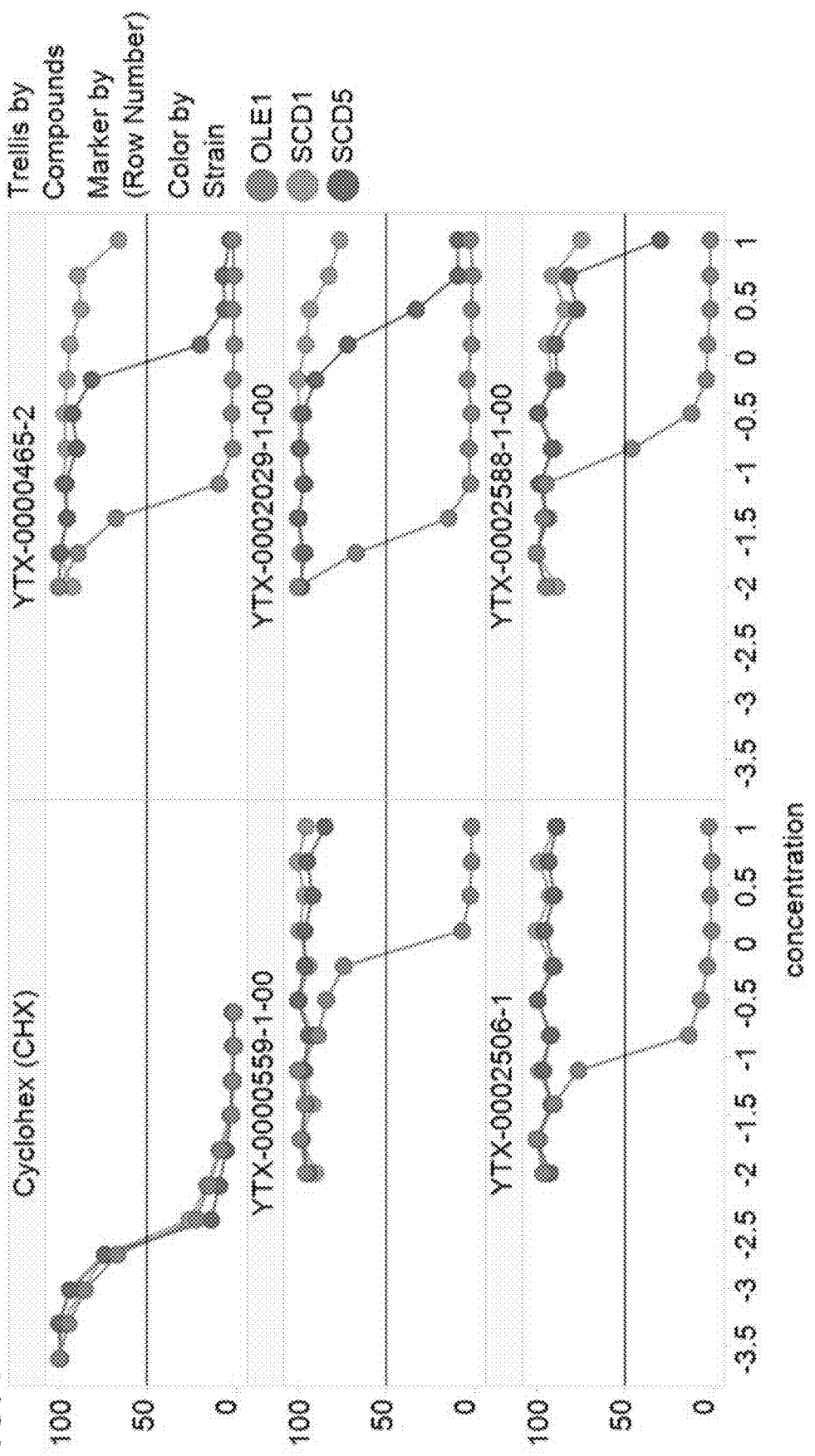
FIG. 7 is a series of graphs showing that 1,2,4-oxadiazoles target human SCD1 and SCD5. Three "SCD" strains expressing yeast OLE1 or human SCD1 or SCD5 were treated with five representative 1,2,4-oxadiazoles and a cycloheximide toxicity control at concentrations indicated on the $\log_{10}$ x-axis. The y-axis indicates the percent of the DMSO-treated condition. All of the 1,2,4-oxadiazole compounds potently inhibited Ole1-expressing yeast and showed variable growth inhibition of the SCD1 or SCD5 yeast strains. These data confirm that 1,2,4-oxadiazoles target the human protein and link Scd inhibition to rescue of neurodegenerative disease models. Approximately one half of all (250) 1,2,4-oxadiazoles tested inhibited SCD1 or SCD5 in a manner that was reversed by oleic/palmitoleic acid treatment. Cyclohexamide, a translation inhibitor (top left panel), inhibited growth of all three strains with the same potency, indicating differences in growth inhibition was due to targeting the human protein.
Figure 8A:
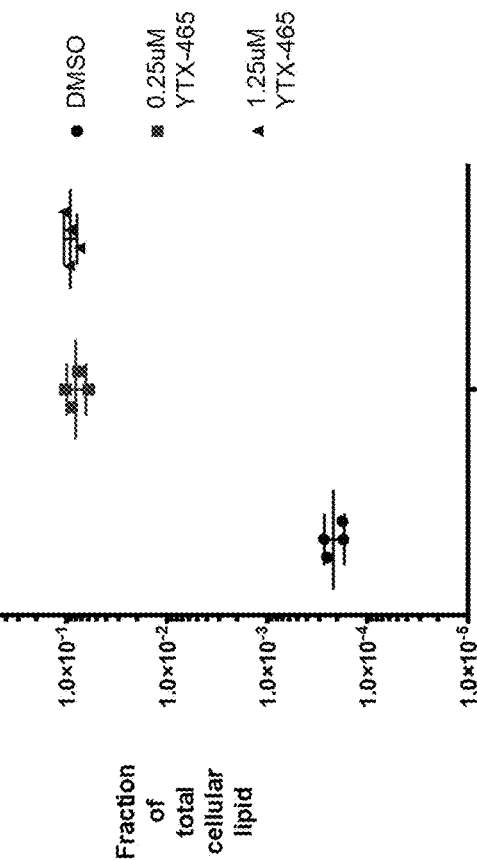
Figure 8B:
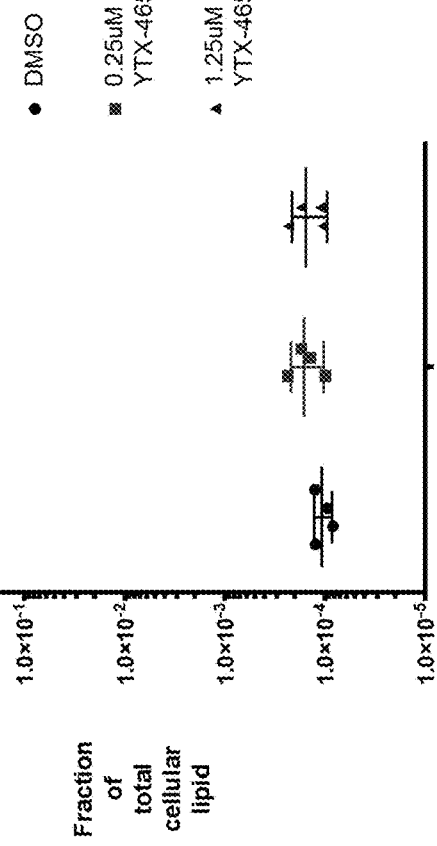

The effect of 1,2,4-oxadiazoles was also evaluated in both of the humanized SCD1 and SCD5 models. 1,2,4-oxadiazoles inhibited the growth of the SCD1 and/or SCD1 yeast strains, and differences in the structure-activity relationship (SAR) between the three SCD proteins was observed (FIG. 7). Some compounds inhibited the growth of both the SCD1 and the SCD5 strains. Other compounds appeared to target only the yeast enzyme. Out of a total of 250 1,2,4-oxadiazoles tested, 117 compounds exhibited significant activity (e.g., greater than 50% inhibition of growth) against the human enzymes, i.e., SCD1 and/or SCD5. The divergent SAR provides additional strong evidence for SCD being the target of 1,2,4-oxadiazoles.

Finally, treatment of yeast cells with the 1,2,4-oxadiazole Compound 2 inhibited lipid desaturation (FIGS. 8A-8D), providing additional confimatory evidence that SCD is the target of 1,2,4-oxadiazoles.

Taken together, these data demonstrate that Ole1/SCD is the target of 1,2,4-oxadiazoles, and that these compounds inhibit Ole1/SCD. Further, these data show that inhibition of Ole1/SCD rescues cell toxicity associated with expression of neurological disease proteins in yeast models, including ApoE4 and alpha-synuclein models, suggesting that SCD inhibition as a therapeutic approach for neurological disorders including Alzheimer's disease and Parkinson's disease.

Example 2: SCD Inhibition Rescues Alpha-Synuclein-Dependent Cell Toxicity, Neurite Degeneration, and Neuronal Cell Death A. Materials and Methods
Molecular Biology and Compound Sources Expression constructs for alpha-synuclein wild-type and A53T (SNCA), empty vector controls (pcDNA, pCAGGs), and mRab1a were obtained from the Whitehead Institute (Massachusetts Institute of Technology, Cambridge, Mass.). The pSF-CAG plasmid was obtained from Oxford Genetics (Oxford, UK). The red fluorescent protein (RFP) reporter plasmid, pSF-MAP2-mApple, was constructed by replacing the CAG promoter with human MAP2 promoter sequence, and inserting mApple coding sequence into the multiple cloning site. The RFP reporter plasmid, pSF-CAG-mKate2, was generated by inserting the mKate2 coding sequence into pSF-CAG plasmid by PCR assembly. CAY10566 was purchased from Abcam. "SMARTpool" siRNAs for SCD1 and SCD5 were purchased from GE Dharmacon.

Cell Culture

U2OS cells (Sigma-Aldrich) between passages 12 to 22 were cultured in McCoy's 5A medium (ATCC) supplemented with 10% heat inactivated fetal bovine serum (Thermo Fisher). Induced pluripotent stem cells (iPSC)-derived neurons containing a triplication in the SCNA gene (S3) were maintained in brain-derived neurotrophic factor (BDNF), cyclic adenosine monophosphate (cAMP), and glial cell-line derived neurotrophic factor (GDNF)-supplemented growth medium as previously described (Chung et al. *Science* 342(6161):983-987, 2013). Four weeks after cells were differentiated into neurons, cells were harvested and RNA was extracted. PC12 cells (ATCC) were cultured in F12K medium supplemented with 15% horse serum and 2.5% fetal bovine serum (Thermo Fisher). RNA extracted from the rat PC12 cells (passage 22) was used as a negative control for the expression of SCD1 and SCD5.

RNA Purification and Reverse Transcription-Polymerase Chain Reaction (RT-PCR)

Cells (iPSC-derived neurons, PC12 and U2OS) were rinsed with ice-cold PBS (pH 7.4). Total RNA was purified using an RNEasy® Mini Kit following the manufacturer's instructions (Qiagen). Reverse transcription was performed with 150 ng RNA using a High-Capacity cDNA Reverse Transcription Kit (Thermo Fisher) in a MASTERCYCLER® Pro thermal cycler (Eppendorf). Real-time PCR analyses of 2 µL cDNA products in a total reaction volume of 20 µL were carried out in duplicates using TaqMan® Fast Advanced Master Mix in a StepOnePlus™ Real-Time PCR System (Thermo Fisher). The primer pairs and probes for real-time amplification of SCD1 and SCD5 were predesigned TaqMan® gene expression assays (Applied Biosystems #Hs01682761_m1 and #Hs00227692_m1, respectively). Human beta-actin was used as an endogenous housekeeping control (Applied Biosystems #4310881E). The relative quantity of gene transcript abundance was calculated using the $\Delta\Delta$Ct method.

Western Immunoblotting

Cells were rinsed with ice-cold PBS and lysed in ice-cold radioimmunoassay precipitation buffer (RIPA, Thermo Fisher) containing protease and phosphatase inhibitor cocktails (Sigma-Aldrich) for 15 min on ice. The lysates were centrifuged at 10,000×g for 10 min at 4° C. Supernatant was collected and protein concentrations were measured using a bicinchoninic acid (BCA) kit (Pierce). Ten micrograms of total protein were resolved in 4-12% NuPAGE® Bis-Tris gels (Thermo Fisher) by electrophoresis then transferred to nitrocellulose membranes using the iBlot® system (Thermo Fisher). Membranes were blocked in 1:1 dilution of ODYSSEY® blocking buffer (LI-COR Biosciences) and PBS for 1 h at room temperature followed by incubation with primary anti-SCD1 (1/1000 dilution, Abcam) and anti-β-tubulin (1/4000 dilution, Sigma-Aldrich) antibodies in blocking buffer containing 0.1% of TWEEN®-20 at 4° C. overnight with gentle rocking. After three washes with PBS plus 0.1% TWEEN®-20 (PBST), blots were incubated with secondary antibodies conjugated to IRDye® 680 or 800 (1:8,000, Rockland Immunochemicals) in blocking buffer for 2 hours at room temperature. After three washes with PBST and two with water, blots were scanned in an ODYSSEY® quantitative fluorescent imaging system (LI-COR Biosciences).

U2OS Cell Transfection

U2OS cells were trypsinized using 0.25% trypsin-EDTA (Thermo Fisher) for 5 min at 37° C. followed by centrifugation at 800 rpm for 5 min at room temperature. Cell pellets were re-suspended in SE solution (Lonza Biologics, Inc.) at a density of $1\times10^4$ cells/µL. Alpha-synuclein wild-type or empty control (pcDNA) plasmids were transfected at a ratio of 10 mg per 1,000,000 cells. For genetic modifier studies, mRab1a was titrated at various concentrations in the presence of SNCA plasmids. Nucleofection was performed using 4D-NUCLEOFECTOR™ System (Lonza Biosciences, Inc.) under program code CM130 in either 20 µL Nucleocuvette™ strips or 100 µl single Nucleocuvettes™. Cells recovered at room temperature for 10-15 minutes after nucleofection before further handling. Pre-warmed medium was added and cells were thoroughly but gently mixed to a homogenous suspension before plating. Cells were seeded at $2\times10^4$ cells/100 µl/well into 96 well PLD-coated white plates (Corning, Inc.) using a customized semi-automated pipetting program (VIAFLO 384/96, Integra Biosciences).

U2OS ATP Assay

Powders of reference SCD inhibitors (CAY10566, A939572 and MF-438) were resuspended and serial diluted in DMSO. Compound treatment solutions were then prepared in complete U2OS growth medium such that compounds were held at 6-fold higher than the final intended treatment concentration. At 4 h after nucleofection, 20 µL of the 6× compound solutions were then added to wells containing SNCA transfected cells and 100 µL growth media. The final DMSO concentration was 0.3%. Plates were gently rocked to mix the drug solution into well media, and plates were incubated for 72 h with the compounds. Plates were sealed with MicroClime® lids (Labcyte Inc.) to reduce evaporation and variability. ATP content was then measured using the CellTiter-Glo® kit (Promega) with luminescence signals measured on an EnVision multimode plate reader (Perkin Elmer).

Primary Neuron Transfections

Rat primary cortical neurons cultured in 96-well plates (Greiner Bio-One) were co-transfected with a fluorescence reporter plasmid (encoding mKate2) and empty or alpha-synuclein-A53T overexpression plasmids by lipofection at 5-6 div (days in vitro). LIPOFECTAMINE® 2000 transfection reagent (Thermo Fisher) (0.5 µl/well) was diluted in NEUROBASAL® media (Thermo Fisher) and incubated for 5-10 min. The LIPOFECTAMINE®/NEUROBASAL® mixture was then added dropwise to a plasmid cocktail diluted in NEUROBASAL® media, and incubated for approximately 40 min. During this time, conditioned media on the neurons was replaced with media containing 1× kynurenic Acid (Sigma-Aldrich) in NEUROBASAL® media (NBKY). LIPOFECTAMINE®/DNA complex solutions were subsequently added dropwise to neurons in the NBKY media in the 96-well plate. Lipofection was carried out for 30-40 min in a standard cell culture incubator (37° C., 5% $CO_2$). Neurons were then washed with NEUROBASAL® media, and 50% conditioned/50% fresh NEUROBASAL® media containing B-27 supplement and GlutaMax™ (Thermo Fisher) (NBM) was applied to the cultures.

Human control and patient-derived trans-differentiated neurons were transfected with an RFP reporter driven by the human MAP2 promoter (MAP2-mApple) following the protocol for rat primary neurons as described above with the following exceptions: lipofection was carried out for approximately 1 h, and the final media replacement was with BrainPhys™ media supplemented with BDNF, GNDF, cAMP, ascorbic acid, and laminin.

Neurite Degeneration Assay

Transfected rat cortical neuron cultures were treated with DMSO or CAY10566 compound 4-6 h post-transfection. Vehicle or compound were diluted in NBM at the indicated concentrations. Culture plates were imaged at 6 h intervals in the IncuCyte® ZOOM (Essen Bioscience) incubator/imaging system for approximately 1 week. Neurite lengths of transfected neurons were tracked by an RFP reporter, mKate2, and measured by NeuroTrack™ Software Module (Essen Bioscience). Neurite lengths were normalized to the peak neurite length for each transfection group (6 replicate wells) and plotted to assess the neurite degeneration phase.

Neuron Survival Assay

Transfected neuronal cultures were imaged at 12-24 h intervals for the indicated number of days by robotic microscopy. Fluorescence images were acquired with a Nikon Eclipse Ti microscope equipped with a motorized stage, 20× extra-long working distance (ELWD) objective, and an Andor Zyla cMOS camera. During image acquisition, microplates were enclosed in an on-stage environmental chamber controlling temperature, $CO_2$, and humidity (Okolab). Images were processed and analyzed with custom-made scripts in R and ImageJ software. The lifetimes of individual neurons were determined by tracking fluorescently-labeled neurons in ImageJ. Neuronal death was determined to occur upon incidence of RFP signal loss or rupture of cell body. Cox proportional hazards analysis was used to generate cumulative hazard plots and determine the risk of neuron death. Log-rank test was used to determine statistical significance of survival curve divergence between neuron cohorts.

B. Results

Figure 10:
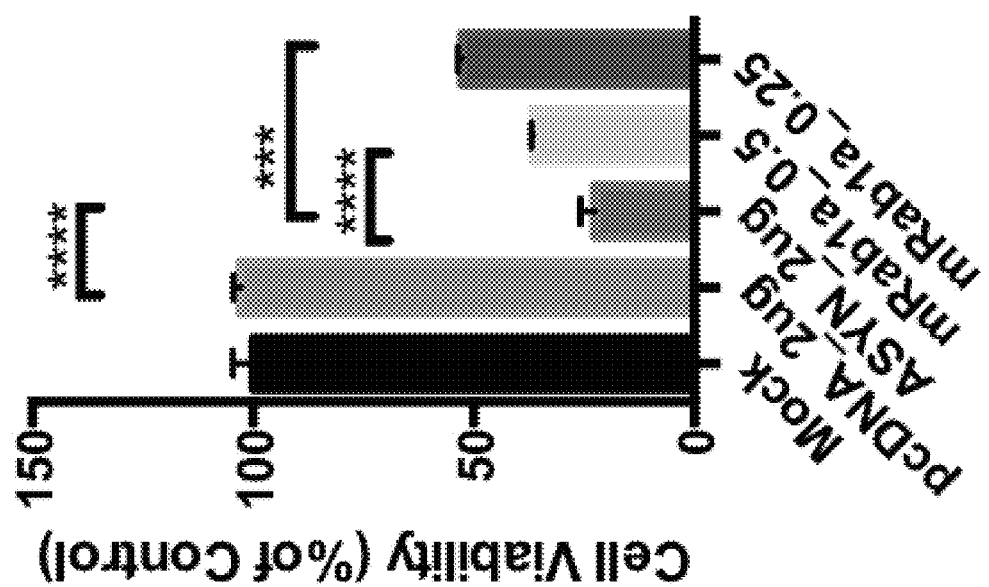
FIG. 10 is a graph showing that Rab1 co-expression in U2OS cells rescues alpha-synuclein-dependent decreases in cellular ATP levels. U2OS cells were transfected with no plasmid (Mock), 2 μg of empty plasmid control (pcDNA) or 2 μg alpha-synuclein (ASYN). U2OS cells were also co-transfected with 2 μg alpha-synuclein in combination with 0.5 or 0.25 μg of mammalian Rab1a (mRab1a). ATP levels were normalized across all samples setting the Mock control as 100%. Bars depict mean values of triplicate determinations; error bars indicate standard deviation. One-way analysis of variance (ANOVA) was utilized to evaluate differences between pcDNA alone, alpha-synuclein alone, or alpha-synuclein in combination with mRab1a, with Bonferroni post-test to adjust for multiple comparisons (*p 0.001, **p 0.0001).

To investigate the cellular events related to alpha-synuclein pathology, an assay was developed to measure the effects of alpha-synuclein expression on cellular ATP content in transfected U2OS cells, which is a general proxy for cell health and viability. U2OS cells transfected with alpha-synuclein exhibited a significant reduction in cellular ATP levels relative to cells transfected with the "empty" pCDNA vector control (FIG. 10). To evaluate the relevance of this alpha-synuclein-dependent decrease in ATP levels, U2OS were co-transfected with alpha-synuclein and mammalian Rab1a (mRab1a, a Rab GTPase family member), which is a known genetic modifier of alpha-synuclein toxicity in neurons and is involved in intracellular vesicle trafficking (Cooper et al. *Science* 313(5785):324-328, 2006). Co-transfecting mRab1a into U2OS cells with alpha-synuclein demonstrated that cellular ATP levels were significantly higher in co-transfected cells as compared to alpha-synuclein alone. This rescue of alpha-synuclein toxicity is reminiscent of that which occurs in neurons, indicating that the alpha-synuclein-dependent decrease of ATP content in U2OS cells may be recapitulating similar cellular pathological events. This indicates the U2OS model is useful for evaluating alpha-synuclein biology and toxicity.

Figure 11B:
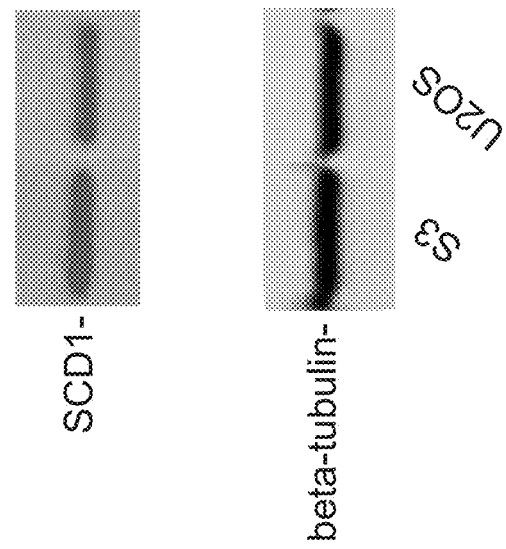
FIGS. 11A and 11B are graphs showing that U2OS cells and induced pluripotent stem cell (iPSC)-derived human neurons expressed SCD1 and SCD5.
Figure 11A:
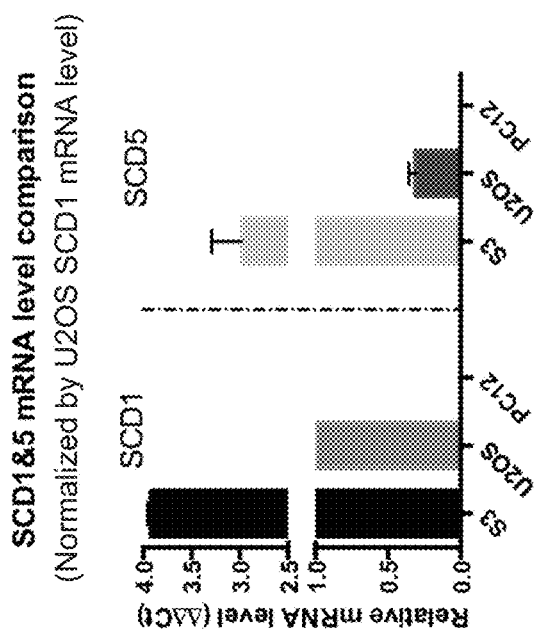

Humans are known to express two different isoforms of stearoyl-CoA desaturase, SCD1 and SCD5 (Wang et al., *Biochem. Biophys. Res. Commun.* 332(3):735-42, 2005). SCD1 and SCD5 transcript levels were first evaluated by RT-PCR to determine whether the human U2OS cell line could be used to characterize the effects of SCD inhibitors. Analysis of mRNA isolated from U2OS cells demonstrated that this cell line expressed measurable levels of both SCD1 and SCD5, with approximately 4-fold higher relative levels of SCD1 (FIG. 11A). As a positive control for the SCD1 and SCD5 RT-PCR probe sets, RNA extracted from human iPSC-derived neurons containing a triplication of the alpha-synuclein gene (S3 neurons) was also analyzed, as human brain samples have previously been shown to express both SCD1 and SCD5 (Wang et al., supra). Similar to published results, cultures of human S3 neurons were found to express both SCD1 and SCD5, with approximately 25% higher expression of SCD1. RNA extracts prepared from rat PC12 cells demonstrated the specificity of the human probe sets, as no significant amplification was detected in these samples.

To confirm and extend the RT-PCR results, cell extracts from S3 neurons and U2OS cells were analyzed for expression of SCD1 protein by Western immunoblotting. This analysis confirmed that both cell populations expressed SCD1 at similar levels, relative to a beta-tubulin loading control (FIG. 11B). Attempts to measure SCD5 protein in these cell preparations were unsuccessful, as the commercially available antibody appeared unsuitable for this purpose.

Figures 12A, 12B:
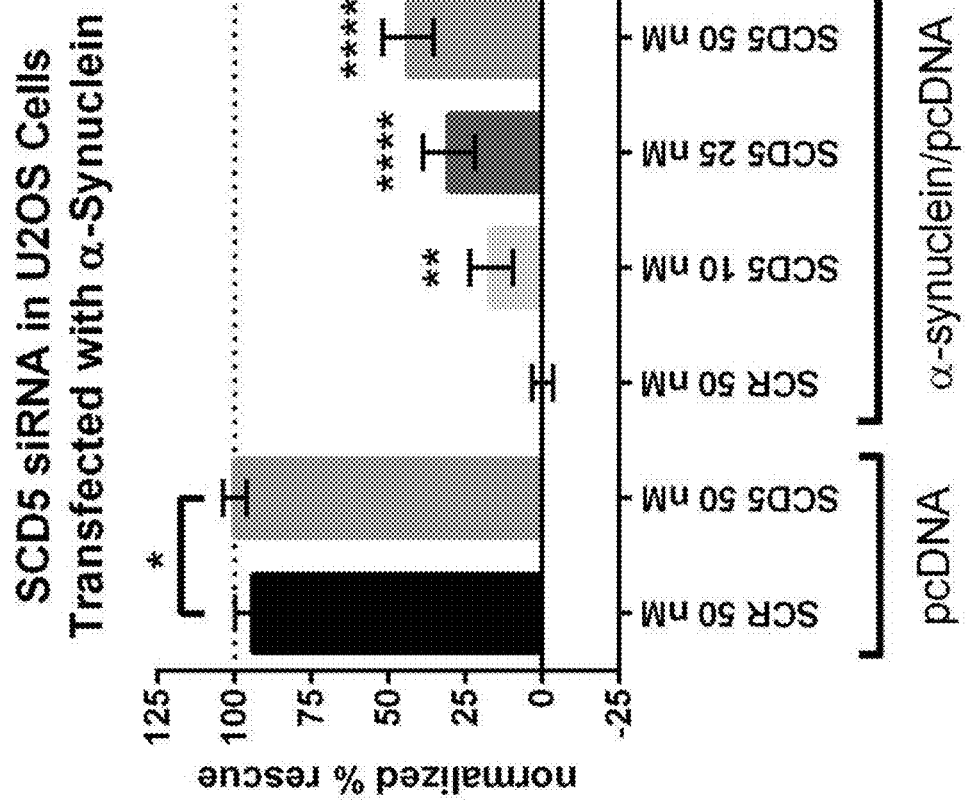
FIGS. 12A and 12B show that knocking down SCD5 expression with siRNA rescues alpha-synuclein toxicity in U2OS cells. U2OS cells were transfected with empty vector control ("pcDNA") or alpha-synuclein ("α-synuclein/pcDNA") in combination with a scrambled (SCR) siRNA control (50 nM), or human SCD5 siRNA (10, 25 or 50 nM).

The potential role of SCD in mediating alpha-synuclein-induced toxicity in U2OS cells was evaluated by siRNA knockdown of SCD1 and SCD5 expression. U2OS cells were transfected with empty vector controls, or the same plasmid containing alpha-synuclein. Cells were also co-treated with either a control scrambled siRNA, or siRNAs against human SCD1 or SCD5. Cells treated with SCD1 siRNA exhibited a general increase in ATP levels in either the presence or absence of alpha-synuclein. Thus, a specific role of SCD1 in mediating alpha-synuclein toxicity could not be evaluated under these experimental conditions. However, SCD5 knockdown resulted in a concentration-dependent rescue, which inversely correlated with levels of SCD5 mRNA (FIGS. 12A and 12B), suggesting that decreasing SCD5 transcript, and subsequently protein and activity, provided a beneficial effect.

Figure 13:
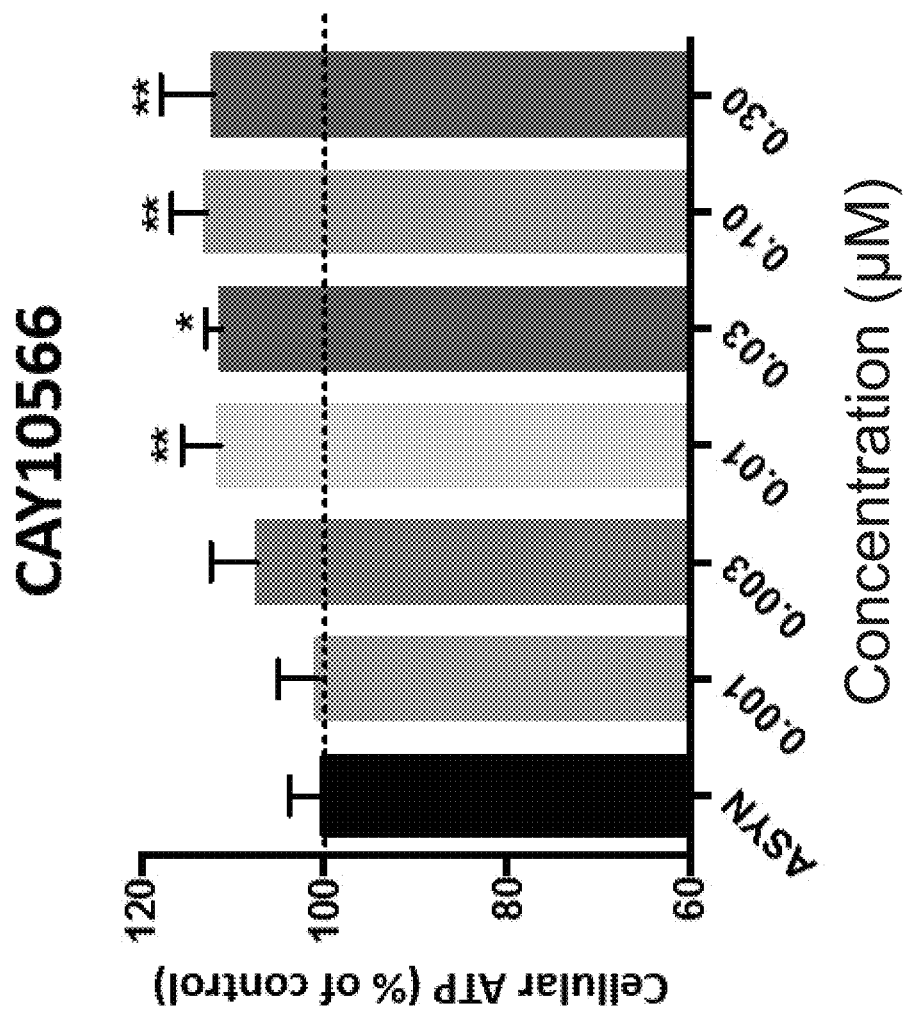
FIG. 13 is a graph showing that SCD inhibition with CAY10566 rescued alpha-synuclein-dependent decreases in cellular ATP levels. U2OS cells were transfected with alpha-synuclein, then treated with DMSO as a control (ASYN) or a titration of the commercially available SCD inhibitor CAY10566. Cellular ATP levels were assessed 72 h after transfection/treatment. ATP levels were normalized to the DMSO control which was set to 100%. Bars depict mean values of triplicate determinations; error bars indicate standard deviation. One-way ANOVA was utilized to evaluate CAY10566 treatment effects compared to DMSO controls, with Bonferroni post-test to adjust for multiple comparisons (*p 0.05, **p 0.01).

To further investigate a potential role of SCD in mediating alpha-synuclein cell toxicity, U2OS cells transfected with alpha-synuclein were also treated with a titration of a commercially available SCD inhibitor (CAY10566). ATP levels were assessed 72 h after treatment. CAY10566 significantly reversed alpha-synuclein-dependent decreases in ATP levels in a concentration-dependent fashion (FIG. 13). These data indicate that inhibiting SCD activity in U2OS cells ameliorated the pathological effects of alpha-synuclein on overall cellular health.

Figure 14:
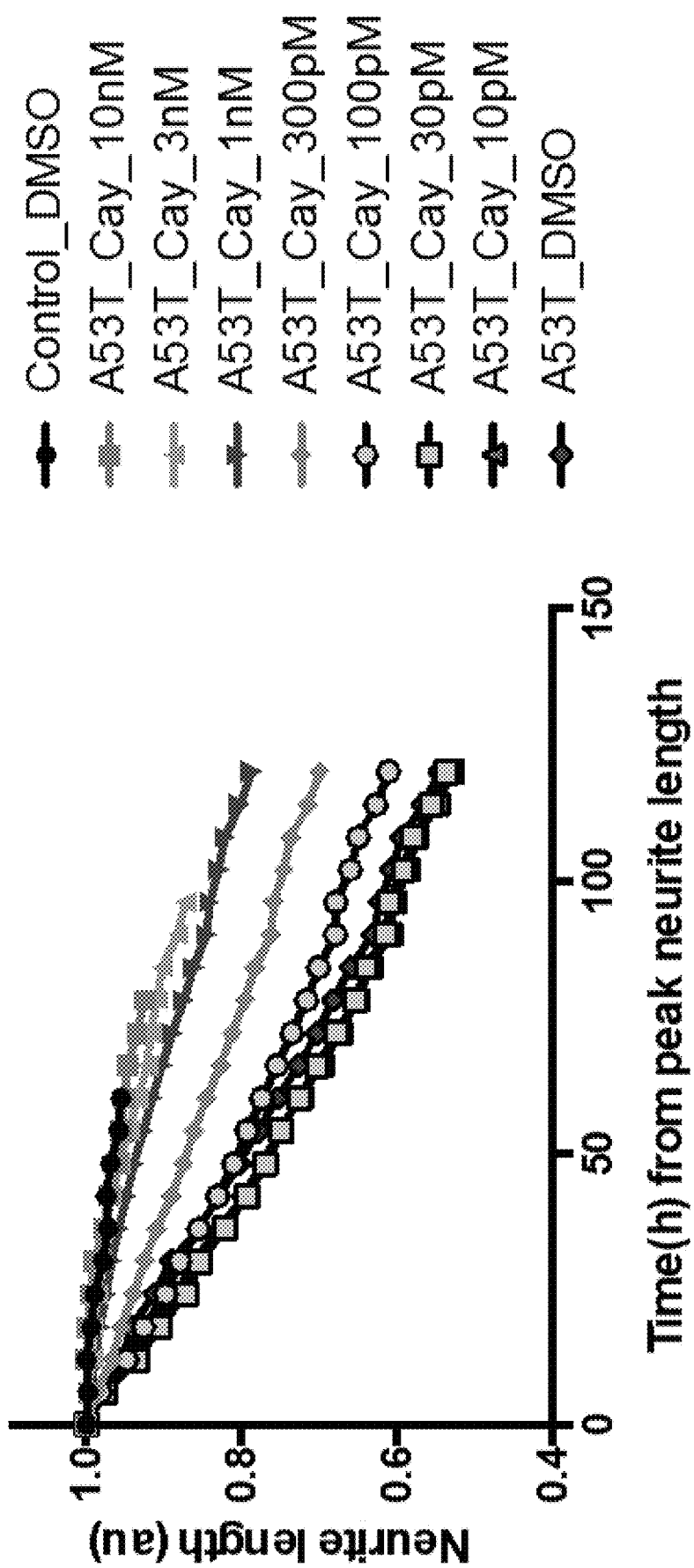
FIG. 14 is a graph showing that SCD inhibition with CAY10566 reduced alpha-synuclein (A53T)-dependent neurite degeneration in transfected rat cortical neurons. Primary cultures of rat cortical neurons were co-transfected with a fluorescence reporter plasmid encoding RFP (neurite tracer) and control plasmid (empty) or plasmid containing alpha-synuclein with an A53T mutation, and treated with vehicle (DMSO) or a titration of CAY10566 ranging from 10 nM down to 10 pM as indicated. Neurite length was tracked by RFP signal every 6 h for 7 d. To follow the degeneration phase, neurite lengths were normalized to the peak neurite length for each condition and plotted over the subsequent (up to) 120 h.

The role of SCD in mediating alpha-synuclein-dependent pathological process was next investigated in a more relevant neuronal system. Primary cultures of rat cortical neurons were transfected with α-synuclein containing the A53T mutation and also treated with a titration of CAY10566. Neurite length was measured in live cells every 6 hours after transfection for a total of 7 days. Transfected cells were tracked with a fluorescent reporter (mCherry). Relative to DMSO controls, cells transfected with α-synuclein and treated with CAY10566 exhibited a concentration-dependent decrease in neurite degeneration (FIG. 14). Cells treated with the highest concentrations of CAY10566 (10 nM and 3 nM) exhibited slower neurite degeneration that was overlapping with control cultures that were not transfected with alpha-synuclein A53T, suggesting a complete rescue of alpha-synuclein detrimental effects. These data indicate that inhibition of SCD activity with CAY10566 was sufficient to reduce the pathological effects of alpha-synuclein overexpression on neurite degeneration.

Figure 15:
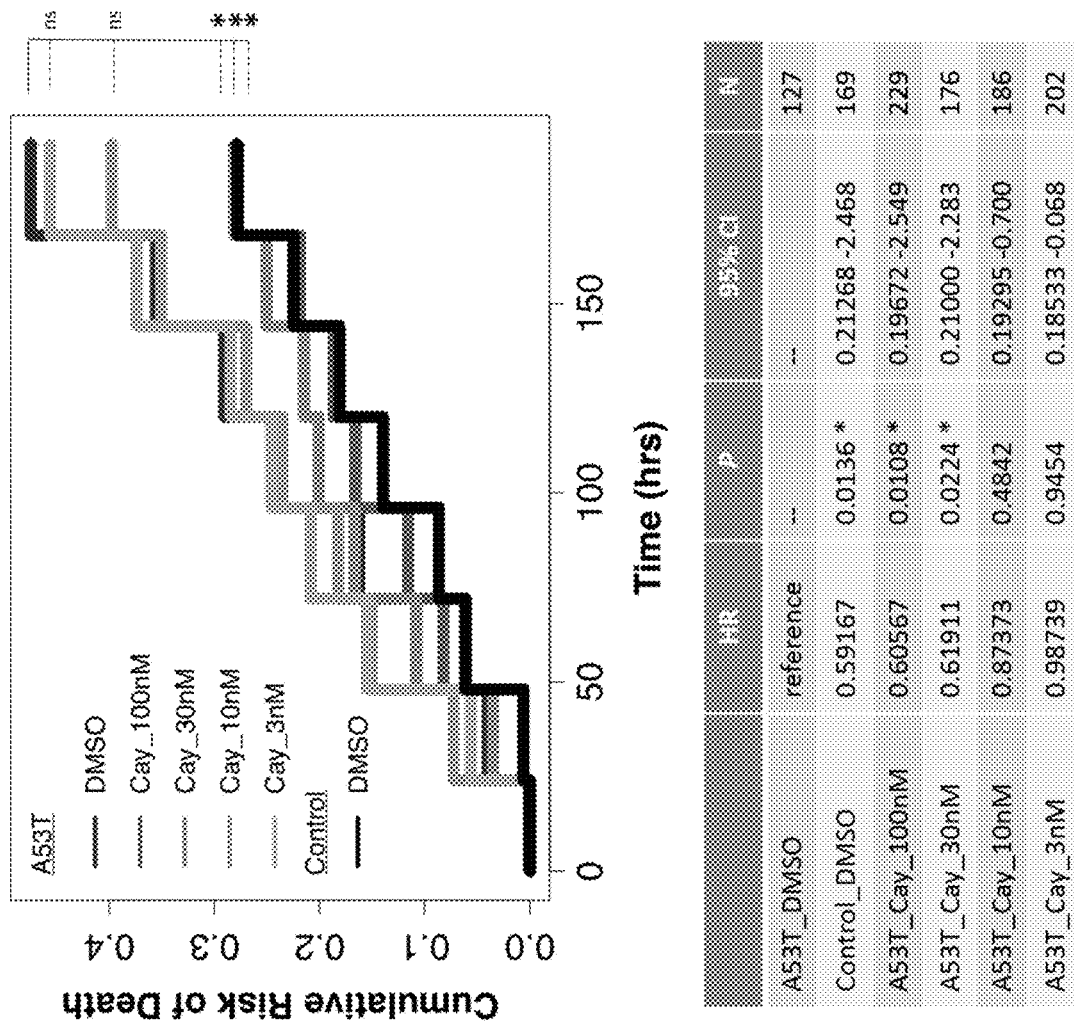
FIG. 15 is a graph showing that SCD inhibition with CAY10566 reduced the cumulative risk of death in human iPSC-derived neurons harboring the alpha-synuclein A53T mutation. Human iPSC cells harboring the alpha-synuclein A53T mutation or an isogenic control line in which the mutation was corrected to wild-type were trans-differentiated into neurons. Single cells were evaluated for survival (based on overall morphology) over the course of the 192 hour study. Cell survival data was analyzed by a non-parametric Kaplan-Meier procedure to estimate survival probability, which is shown as the cumulative risk of cell death. (HR, hazard ratio; P, p value (*<0.05, ns=not significant (>0.05)); CI, confidence interval; N, number of neurons tracked).

To evaluate the effects of SCD inhibition in human neurons, human iPSC cells harboring the alpha-synuclein A53T mutation or an isogenic control line in which the A53T mutation was corrected to wild-type, were trans-differentiated into neurons, and cell survival was monitored over the course of 8 to 10 d. Analysis of cumulative single cell survival data indicated that the risk of neuron death was significantly reduced by treatment with CAY10566 at 100 nM and 30 nM (FIG. 15) relative to DMSO controls in the A53T neurons. Interestingly, at these concentrations of CAY10566, the risk of cell death was reduced back to levels observed in the isogenic control neurons, suggesting the enhanced toxicity of alpha-synuclein A53T on cell viability was eliminated.

Taken together, these data demonstrate that SCD1 and/or SCD5 inhibition rescues a number of phenotypes associated with neurological diseases in relevant disease models, providing further evidence that SCD inhibition as a therapeutic approach for neurological diseases including Alzheimer's disease and Parkinson's disease.

Figure 16:
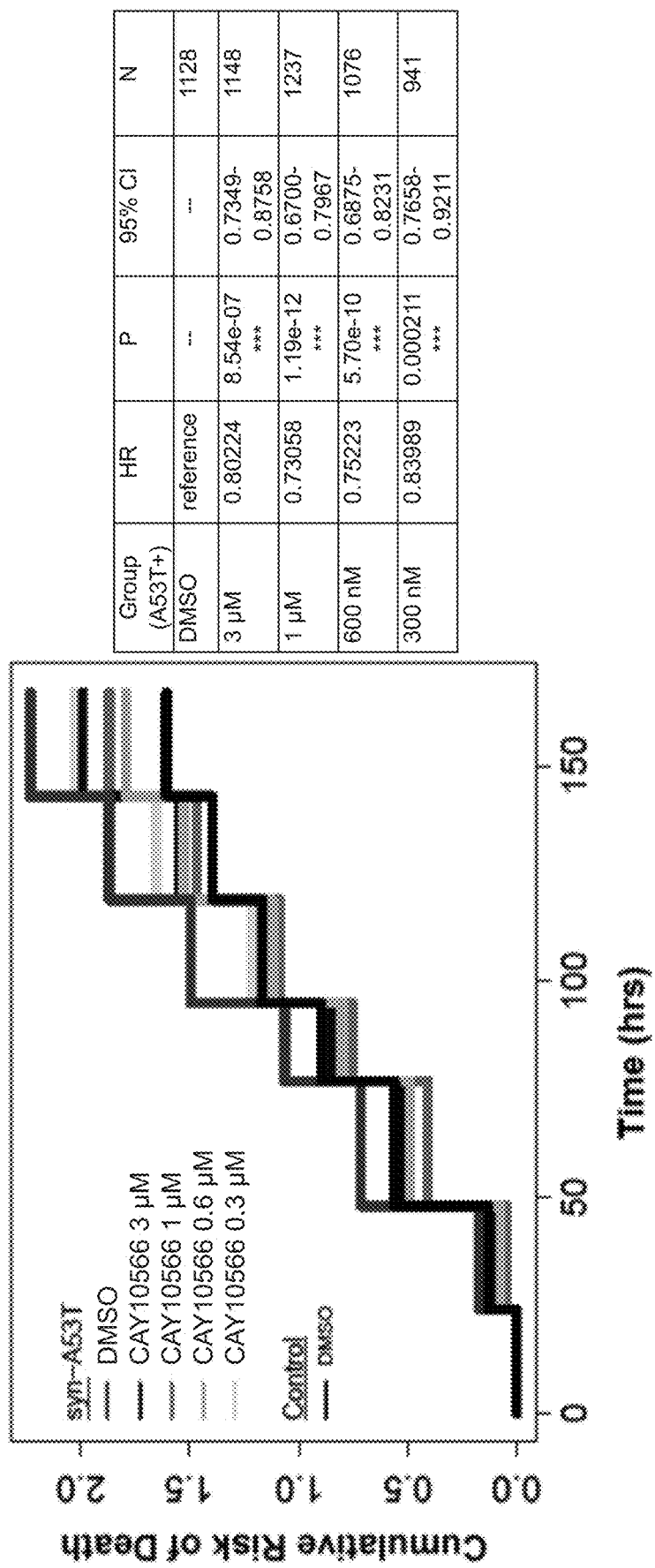
FIG. 16 is a graph illustrating that non-selective SCD reference inhibitor, CAY10566, reduces risk of death in A53T α-synuclein transfected human iPSC-derived neurons. Human iPSC-derived neurons were co-transfected with a fluorescence reporter plasmid encoding RFP (morphology tracer) and control plasmid (empty) or plasmid containing α-synuclein-A53T mutation (syn-A53T). Neuron groups as indicated were treated with either DMSO or CAY10566 at the indicated doses. The lifetimes of single neurons were tracked over time based on either loss of RFP fluorescence signal or morphological indicators of neuron death such as loss of neurites or cell blebbing. Kaplan-Meier survival analysis was used to generate cumulative risk of death plots. The cumulative risk of neuron death is plotted against time (hrs) for each group as indicated. CAY10566 treatment of the α-synuclein-A53T neurons was protective at each of the doses tested. Cox proportional hazard analysis was used to estimate relative risk of death, or hazard ratio (HR) and the P value was determined by the logrank test. CI, confidence interval; N, number of neurons.

Example 3: Selective Inhibition of SCD5, as Well as Inhibition of SCD1 and SCD5, Reduce Risk of Neuron Death from α-Synuclein Toxicity and Result in Pharmacodynamic Responses in the Brain A model of α-synuclein toxicity utilizing transient transfection into human iPSC-derived neurons was developed. In response to α-synuclein transfection, human neurons exhibit a significantly increased risk of death that can be tracked in live cells over the course of several days. This model was utilized to evaluate the role of SCD in α-synuclein-dependent neuronal toxicity. Human iPSC-derived neurons were transfected with a construct encoding A53T α-synuclein or an empty vector control. A53T α-synuclein-transfected cells were subsequently treated with a titration of the reference non-selective SCD inhibitor CAY10566 or DMSO as a vehicle control. Analysis of cumulative single cell survival data indicated that relative to DMSO controls, the risk of neuron death was significantly reduced by treatment with CAY10566 at all tested concentrations in the A53T α-synuclein neurons (FIG. 16 and Table 1). Within the relatively narrow 10-fold concentration range tested (3 µM to 0.3 µM), there was no indication of a concentration-dependent effect. This may indicate a saturation of the maximal protective effect at the tested concentrations, or that higher doses are overall less well tolerated by the cells, so any enhanced protection could be obscured by general toxicity.

Figure 17:
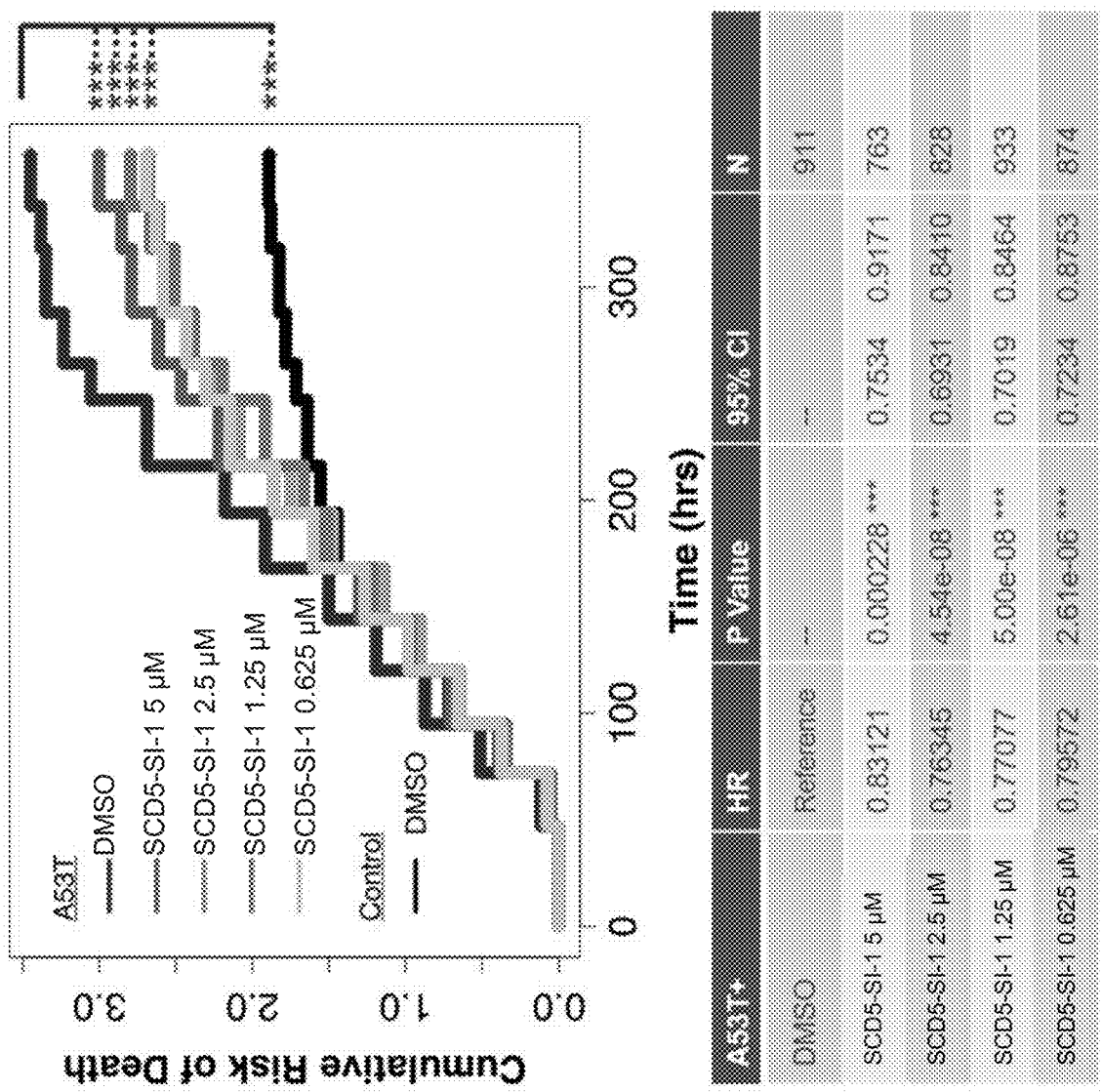
FIG. 17 is a graph illustrating that an SCD5-selective inhibitor reduces risk of death in A53T α-synuclein transfected human iPSC-derived neurons. Human iPSC-derived neurons were co-transfected with a fluorescence reporter plasmid encoding RFP (morphology tracer) and control plasmid (empty) or plasmid containing α-synuclein-A53T mutation (syn-A53T). Neuron groups as indicated were treated with either DMSO or SCD5 Selective Inhibitor 1 ("SCD5-SI-1") at the indicated doses. The lifetimes of single neurons were tracked over time based on either loss of RFP fluorescence signal or morphological indicators of neuron death such as loss of neurites or cell blebbing. Kaplan-Meier survival analysis was used to generate cumulative risk of death plots. The cumulative risk of neuron death is plotted against time (hrs) for each group as indicated. SCD5 Selective Inhibitor 1 treatment of the α-synuclein-A53T neurons was protective at each of the doses tested. Cox proportional hazard analysis was used to estimate relative risk of death, or hazard ratio (HR) and the P value was determined by the logrank test. CI, confidence interval; N, number of neurons.

To better understand the relative contributions of different SCD isoforms in promoting protection against A53T α-synuclein toxicity, tool compounds were developed that exhibited an SCD5-selective inhibitor profile. Compounds with this selectivity profile have not been previously described in the literature. SCD5 Selective Inhibitor 1 (SCD5-SI-1) is a SCD5-selective compound that exhibits sub-micromolar potency in yeast growth inhibition assays, and was selected for further study in mammalian cells. Human iPSC-derived neurons were transfected with a construct encoding A53T α-synuclein or an empty vector control. A53T α-synuclein transfected cells were subsequently treated with a titration of the SCD5-selective inhibitor SCD5 Selective Inhibitor 1 or DMSO as a vehicle control. Analysis of cumulative single cell survival data indicated that relative to DMSO controls, the risk of neuron death was significantly reduced by treatment with SCD5 Selective Inhibitor 1 at all tested concentrations in the A53T α-synuclein neurons (FIG. 17). Within the relatively narrow 10-fold concentration range tested (5 µM to 0.6 µM), there was no indication of a concentration-dependent effect. This may indicate a saturation of the maximal protective effect at the tested concentrations, or that higher doses are overall less well tolerated by the cells, so any enhanced protection could be obscured by general toxicity.

Figures 18A, 18B, 18C, 18D:
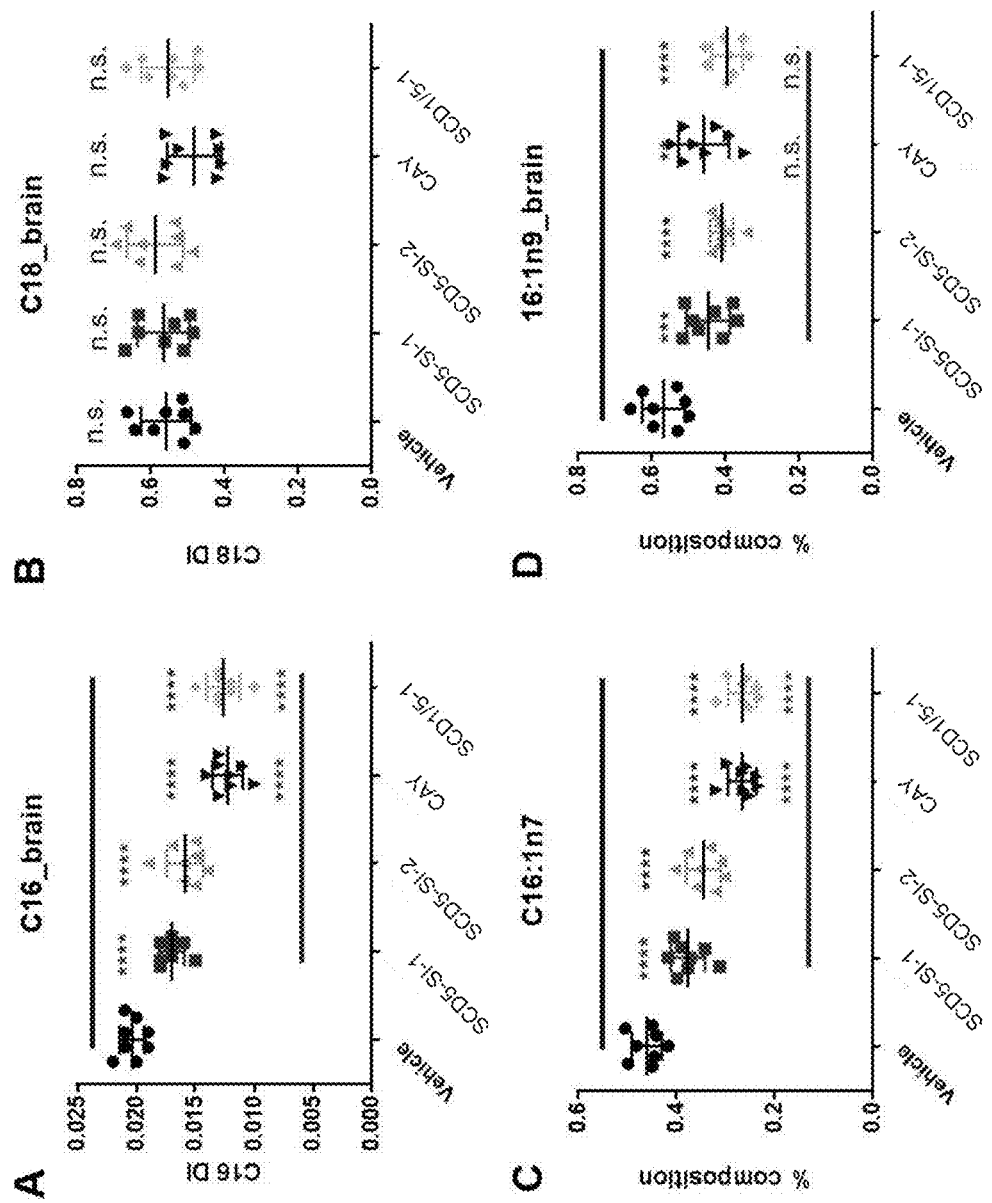
FIGS. 18A-18F are a series of graphs showing an evaluation of fatty acid saturation in guinea pig brain after oral administration of SCD inhibitors. Guinea pigs were dosed orally with SCD inhibitors twice daily (every 12 hours) for 5 days. Guinea pigs were dosed with vehicle, SCD5 Selective Inhibitor 1 ("SCD5-SI-1"), SCD5 Selective Inhibitor 2 ("SCD5-SI-2"), CAY10566 ("CAY") or SCD1/SCD5 Inhibitor 1 ("SCD1/5-1"), all compounds at 25 mg/kg with a volume-matched vehicle control. Four hours after the last dose on day 5, guinea pigs were sacrificed, and brains were removed after whole-body saline perfusion. Brains were homogenized, and fatty acids hydrolyzed from esterified lipids, which were then methylated to generate fatty acid methyl esters (FAME). Samples were evaluated on a gas chromatograph with a flame ionization detector (GC-FID) to quantify a comprehensive panel of fatty acid species. Brain samples were evaluated for levels of 16 (FIG. 18A) and 18 (FIG. 18B) carbon-containing fatty acids (C16, C18 respectively), and the desaturation index (DI) was calculated by taking the ratio of desaturated to saturated fatty acid for each species. SCD5-selective compounds SCD5-SI-1 and SCD5-SI-2, and SCD non-selective inhibitors CAY10566 and SCD1/5-1, all decreased the C16 DI, indicating they were active in modulating SCD activity in the brain and promoting a pharmacodynamic response. No significant changes were observed in the C18 DI. Brain samples were evaluated for the relative levels of the positional isomers of C16, including C16:1 n7 palmitoleic acid (FIG. 18C) or C16:1 n9 monounsaturated fatty acids (FIG. 18D). C16:1 n9 fatty acids are derived from monounsaturated C18:1 n9 fatty acids that have lost 2 carbon units due to β-oxidation. Compared to vehicle controls, all compounds decreased the levels of monounsaturated C16:1 fatty acids.
Figures 18E, 18F:
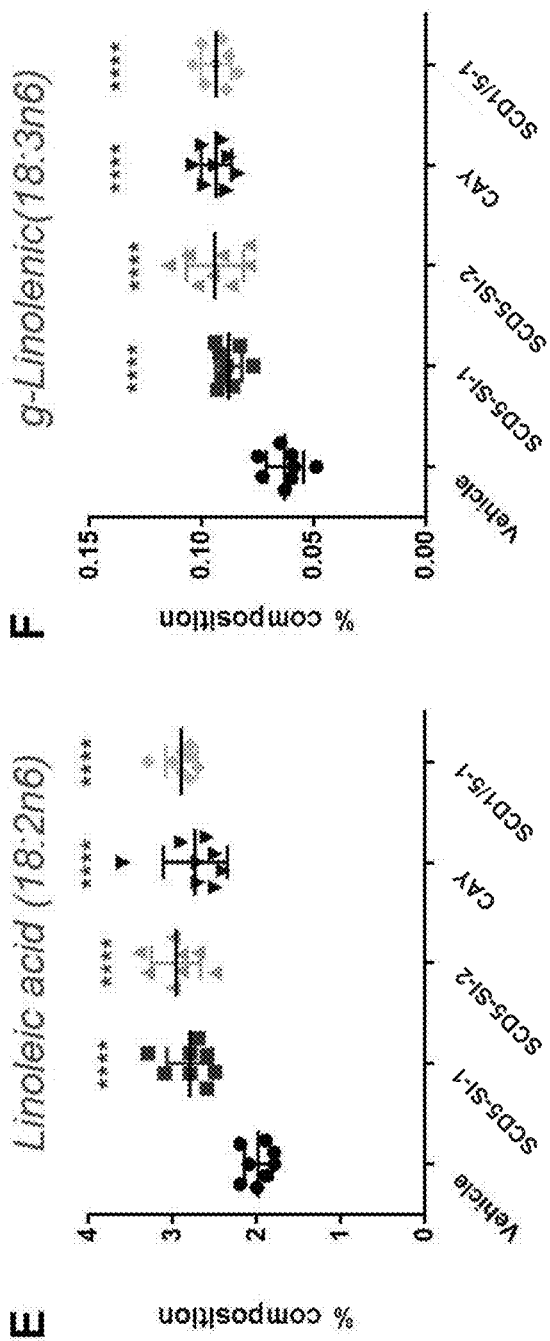

To identify potential central nervous system (CNS) pharmacodynamic markers that respond to inhibition of SCD, guinea pigs were selected as a model organism. Unlike rats and mice, guinea pigs express an SCD isoform similar to human SCD5, and expression of this isoform is enriched in the brain. For these reasons, this species was selected for evaluating both SCD5-selective and non-selective inhibitors. Potential effects of SCD inhibitors on steady state brain fatty acid saturation state, as well as all fatty acid levels, were evaluated by dosing guinea pigs orally twice a day for 5 days with either vehicle, SCD5-selective compounds (SCD5 Selective Inhibitor 1 or SCD5 Selective Inhibitor 2), or non-selective SCD inhibitors (CAY10566 or SCD1/SCD5 Inhibitor 1 ("SCD1/5-1")). SCD5 Selective Inhibitor 1 is a SCD5-selective compound with >3000-fold selectivity over SCD1 that exhibits sub-micromolar potency in yeast growth inhibition assays. SCD5 Selective Inhibitor 2 is a SCD5-selective compound with >500-fold selectivity over SCD1 that exhibits sub-micromolar potency in yeast growth inhibition assays. SCD1/SCD5 Inhibitor 1 approximately equivalent potency towards SCD1 and SCD5 that exhibits sub-micromolar potency in yeast growth inhibition assays. All compounds were evaluated at 25 mg/kg. On the last day of the study, the brains from these guinea pigs were harvested and evaluated for changes in fatty acid levels and saturation status. The desaturation index (DI) was calculated for 16 and 18 carbon chain fatty acids (C16 and C18 respectively) by taking the ratio of desaturated to saturated fatty acid of each species. Relative to vehicle, all compounds significantly reduced the C16 DI (FIG. 18A). No significant effects were observed on the C18 DI (FIG. 18B). The relative levels of individual monounsaturated C16 fatty acids (expressed as the % composition of total) was also evaluated. For both positional isomers of monounsaturated C16 fatty acids, C16:1 n7 and C16:1 n9, inhibitors of both SCD1/SCD5 selectivity profiles significantly reduced monounsaturated fatty acid levels (FIGS. 18C and 18D). The data in FIGS. 18A-18D are consistent with compounds having SCD inhibitory activity, in which there is a decrease in the levels of unsaturated fatty acids. The C16:1 n9 fatty acid is derived from C18:1 n9 through beta-oxidation. Thus, a decrease in this fatty acid indicated that although no effects were observed in the overall C18 DI, there was a reduction in the monounsaturated C18 species. Interestingly, probing brain samples for the relative levels of linoleic acid (18:2n6) (FIG. 18E) and gamma-linoleic acid (18:3n6) (FIG. 18F) revealed that levels of these essential omega-6 fatty acids both significantly increased with administration of SCD5-selective or non-selective compounds. This inverse relationship in changes to mono- and poly-unsaturated fatty acid levels is consistent with reports in the literature. These data all indicate that both selective inhibition of SCD5, as well as inhibition of both SCD isoforms, result in a measurable pharmacodynamic response in the tissue of interest for CNS indications.

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A method of treating a Parkinson's disease or Lewy body dementia in a subject in need thereof, the method comprising administering an effective amount of an SCD5 inhibitor to the subject.

2. A method of treating a Parkinson's disease or Lewy body dementia in a subject in need thereof, the method comprising administering an effective amount of an inhibitor of SCD5 and SCD1 to the subject.

3. The method of claim 1, wherein the subject carries one or two copies of the ApoE4 allele.

4. The method of claim 1, wherein the method further comprises administering an additional therapeutic agent to the subject.

5. The method of claim 4, wherein the additional therapeutic agent is a small molecule, an antibody or fragment thereof, or a nucleic acid.

6. The method of claim 4, wherein the additional therapeutic agent is a cognition-enhancing agent, an antidepressant agent, an anxiolytic agent, an antipsychotic agent, a sedative, a dopamine promoter, or an anti-tremor agent.

7. The method of claim 2, wherein the subject carries one or two copies of the ApoE4 allele.

8. The method of claim 2, wherein the method further comprises administering an additional therapeutic agent to the subject.

9. The method of claim 8, wherein the additional therapeutic agent is a small molecule, an antibody or fragment thereof, or a nucleic acid.

10. The method of claim 9, wherein the additional therapeutic agent is a cognition-enhancing agent, an antidepressant agent, an anxiolytic agent, an antipsychotic agent, a sedative, a dopamine promoter, or an anti-tremor agent.

* * * * *